US006492553B1

(12) United States Patent
Hulme et al.

(10) Patent No.: US 6,492,553 B1
(45) Date of Patent: Dec. 10, 2002

(54) METHODS FOR PREPARING N-[(ALIPHATIC OR AROMATIC)CARBONYL)]-2-AMINOAETAMIDE COMPOUNDS AND FOR CYCLIZING SUCH COMPOUNDS

(75) Inventors: Christopher Hulme, Phoenixville; George C. Morton, Collegeville; Joseph M. Salvino, Schwenksville; Richard F. Labaudiniere, Collegeville, all of PA (US); Helen J. Mason, Skillman, NJ (US); Matthew M. Morrissette, Pottstown, PA (US); Liang Ma, King of Prussia, PA (US); Marie-Pierre Cherrier, Phoenixville, PA (US)

(73) Assignee: Aventis Pharamaceuticals Inc., Bridgewater, NJ (US)

( * ) Notice: Subject to any disclaimer, the term of this patent is extended or adjusted under 35 U.S.C. 154(b) by 0 days.

(21) Appl. No.: 09/368,213

(22) Filed: Aug. 4, 1999

Related U.S. Application Data

(63) Continuation-in-part of application No. PCT/US99/01923, filed on Jan. 29, 1999.
(60) Provisional application No. 60/101,056, filed on Sep. 18, 1998, provisional application No. 60/098,708, filed on Sep. 1, 1998, provisional application No. 60/098,404, filed on Aug. 31, 1998, and provisional application No. 60/073,007, filed on Jan. 29, 1998.

(51) Int. Cl.$^7$ .................... C07C 231/02; C07C 231/06
(52) U.S. Cl. ............... 564/129; 540/200; 540/362; 540/504; 540/506; 540/507; 544/354; 544/355; 544/359; 544/360; 544/374; 544/377; 548/313.7; 548/333.5; 560/27; 564/155; 564/158; 502/159; 558/441

(58) Field of Search ................ 540/200, 362, 540/504, 506, 507; 544/354, 355, 359, 360, 370, 374, 377; 560/27; 564/115, 158, 129; 548/313.7, 333.5; 502/159; 558/441

(56) References Cited

PUBLICATIONS

Fukuyama et al, Tetrahedron Lett., vol. 22, No. 42, pp 4155–4158, 1981.*
Failli et al, Canadian J. Chem., vol. 51, pp 2769–2775, 1973.*
Boehm et al, J. Org. Chem., vol. 51, pp 2307–2314, 1986.*
Hulme et al., Improved Procedure for the Solution Phase Preparation of 1,4–Benzodiazepine–2,5–dione Libraries via Armstron'gs Convertible Isonitrile and the Ugi Reaction, J. ORg. Chem., vol. 63, No. 22, pp. 8021–8023, 1998.
Hulme et al., Novel applicatioins of ethyl glyoxalate with the Ugi MCR, Tetrahedron Letters 40 (1999) 5295–5299.
Hulme et al., Application of N–BOC–Diamines for the Solution Phase Synthesis of Ketopiperazine Libraries Utilizing a Ugi/De–BOC/Cyclization (UDC) Strategy, Tetrahedron Letters 39 (1998) 8047–8050.
Hulme et al., Remarkable three–step–one–pot solution phase preparation of novel imidzaolines utilizing a UDC (Ugi/de–Boc/cyclize) strategy, Tetrahedron Letters 40 (1999) 7925–7928.

* cited by examiner

*Primary Examiner*—Shailendra Kumar
(74) *Attorney, Agent, or Firm*—George G. Wang; Irving Newman

(57) ABSTRACT

A method for preparing a N-[(aliphatic or aromatic) carbonyl)]-2-aminoacetamide compound, and for preparing a cyclized compound therefrom, as well as novel resin bound intermediate compounds that are useful for preparing such compounds.

53 Claims, No Drawings

US 6,492,553 B1

METHODS FOR PREPARING N-[(ALIPHATIC OR AROMATIC)CARBONYL)]-2-AMINOAETAMIDE COMPOUNDS AND FOR CYCLIZING SUCH COMPOUNDS

This application is a continuation-in-part of International Patent Application No. PCT/US99/01923, filed on Jan. 29, 1999, which is, in turn, a continuation-in-part of U.S. Provisional Patent Application No. 60/101,056, filed Sep. 18, 1998, U.S. Provisional Patent Application No. 60/098,708, filed Sep. 1, 1998, U.S. Patent Application No. 60/098,404, filed Aug. 31, 1998, and U.S. Provisional Patent Application No. 60/073,007, filed Jan. 29, 1998.

This invention is directed to a method for preparing an N-[(aliphatic or aromatic)carbonyl)]-2-aminoacetamide compound, and for preparing a cyclized compound therefrom, as well as to the novel resin bound intermediate compounds that are useful for preparing such compounds.

BACKGROUND OF THE INVENTION 1,4-benzodiazepine-2,5-diones are an important class of biologically actives compounds. This class of compounds has been identified as having platelet aggregation inhibitor activity, anticonvulsant activity, anxiolytic activity and activity as anti tumor agents (Mc Dowell, R. S. et al., J. Am. Chem. Soc., 1994, 116, 5077; Cho, N. S. et al., J Heterocycl. Chem., 1989, 26, 1807; Wright, W. B. et al., J. Med. Chem., 1978, 21, 1087; Jones; G. B. et al., Anti-Cancer Drug Des. 1990, 5, 249).

Diketopiperazines are known to be ligands of neurokinin-2 receptors and neurokinin-3 receptors (Gordon, D. W.; Steele, J. Bioorg. Med. Chem. Lett., 1995, 5, 47. (b) Terrett, N. K.; Gardner, M.; Gordon, D. W.; Kobylecki, R. J.; Steele, J., Tetrahedron, 1995, 51, 8135) and are useful in the treatment of asthma, inflammation, Parkinsons disease, anxiety, psychosis, epilepsy and pain.

Reports of the biological utility of ketopiperazines have appeared in several areas, including applications as antagonists of the platelet glycoprotein IIb-IIIa (Takada, S.; Kurokawa, T.; Miyazaki, K.; Iwasa, S.; Ogawa, Y. Pharm. Res. 1997, 14, 1146), and substance P (Wright, H. B.; Martin, D. L. J. Med. Chem. 1968, 11, 390) and as hypocholesteremic agents (Piercey, M. F.; Moon, M. W.; Blinn, J. R. Brain Res., 1986, 385, 74).

Reports of the biological utility of dihydroquinoxalinones (also known as benzopiperazinones) have appeared in several areas, including applications as inhibitors of aldose reductase (Sarges, R.; Lyga, J. W. J. Heterocycl. Chem. 1988, 25, 1474), and partial agonists of the gamma-aminobutyric acid (GABA)/benzodiazepine receptor complex (Tenbrink, R. E.; Im, W. B.; Sethy, V. H.; Tang, A. H.; Carter, D. B. J. Med. Chem. 1994, 37, 758), angiotensin II receptor antagonists (Kim, K. S.; Qian, L.; Bird, J. E.; Dickinson, K. E.; Moreland, S.; Schaeffer, T. R.; Waldron, T. L.; Delaney, C. L.; Weller, H. N.; Miller, A. V. J. Med. Chem. 1993, 36, 2335); also they are known to possess antiviral activity as associated with HIV (Meichsner, C.; Riess, G.; Kleim, J. P.; Roesner, M.; Paessens, A.; Blunck, M. Eur. Pat. Appl. EP 657166 A1 950614).

Early work pioneered by Freidinger (Freidinger, R. M.; Perlow, D. S.; Veber, D. F. J. Org. Chem. 1982, 47, 104) showed g-lactams to be a useful new type of conformational constraint in peptides and useful in the synthesis of LHRH (Samenen, J.; Hempel, J. C.; Narindray, D.; Regoli, D. 'Peptides. Chemistry and Biology', Proc. 10th Am. Peptide Symp. 1988, 137), angiotensin II (Douglas, A. J.; Mulholland, G.; Walker, B.; Guthrie, D. J. S.; Elmore, D. T.; Murphy, R. F. Biochem. Soc. Trans. 1988, 16, 175), pentagastrin (Piercey, M. F.; Moon, M. W.; Blinn, J. R.; Dobry-Schreur, P. J. K. Brain Res. 1986, 385, 74), and substance P analogues. The lactams described herein, in particular those produced via cyclization of a primary amine, result in potential ATP competitive kinase inhibitors possessing functionality that may mimic the N1–N6 interaction of ATP binding to a relevant kinase (Myers, M. R.; He, W.; Hulme, C. Curr. Pharm. Design. 1997, 3, 473).

Benzodiazepines have been to shown to have utility as GPIIb/IIIa receptor antagonists (Ku, T. W.; Miller, W. H.; Bondinell, W. E.; Erhard, K. F.; Keenan, R. M.; Nichols, A. J.; Peishoff, C. E.; Samenen, J. M.; Wong, A. S.; Huffman, W. F. J. Med. Chem. 1995, 38, 9–12) and may be useful for the treatment of acute myocardial infarction, unstable angina, or thrombotic stroke. Recent developments have extended the therapeutic utility of this class of molecule to include integrin antagonists (for example antagonists of the vitronectin receptor), useful for the stimulation of bone formation and treatment of bone fractures, osteoporosis and other bone-related disorders (Drake, F. H. WO98115278-A1, 1997).

Dihydroimidazoles (or imidazolines) have been shown to have biological utility as anti-depressants and additionally imidazoline receptors are widely distributed in both the peripheral and central nervous system playing potential roles in the regulation of several physiological effects (Pigini, M.; Bousquet, P.; Carotti, A.; Dontenwill, M.; Gianella, M.; Moriconi, R.; Piergentili, A.; Quaglia, W.; Tayebati, S. K.; Brasili, L.; Bioorg. Med. Chem. 1997, 5, 833; Harfenist, M.; Heuser, D. J.; Joyner, C. T.; Batchelor, J. F.; White, H. L.; J. Med. Chem. 1996, 39, 1857; Jackson, H. C.; Griffin, I. J.; Nutt, D. J.; Br. J. Pharmacol. 1991, 104, 258; and Tibirica, E.; Feldman, J.; Mermet, C.; Gonon, F.; Bousquet, P. J. Pharmacol. 1987, 134, 1). The imidazoline moiety has also been extensively studied as an amide bond replacement in biologically active peptides (Gilbert, I.; Rees, D. C.; Richardson, R. S. Tetrahedron Lett. 1991, 32, 2277; and Jones, R. C. F.: Ward, G. J. Tetrahedron Lett. 1988, 29, 3853).

Cyclic ureas have recently shown promise as integrin receptor antagonists useful for the treatment and prevention of bone resorption, restenosis, angiogenesis and diabetic retinopathy (see M. E. Duggan et al., WO9931099-A1 and M. E. Duggan et al., WO9930713-A1).

Also, hydantoins have recently shown promise as inhibitors of luekocyte adhesion and migration and VLA-4 receptor inhibitors useful for the treatment and prevention of e.g. rheumatoid arthritis and inflammatory bowel disease (see V. Wehner et al., EP-903353-A1).

Pressures on the pharmaceutical industry have increased significantly to meet new economic challenges. As a consequence, efforts in both industrial and academic sectors are now being directed at new technologies for approaching drug discovery in a more efficient and cost-effective manner. As such, with the recent development of combinatorial chemistry and high speed parallel synthesis within the Lead Discovery arena, the multi-component reaction (MCR) has witnessed a resurgence of interest. From a practical consideration, "one-pot reactions", such as the Ugi and Passerini reactions, are easily automated, and production of diverse or directed libraries of small organic molecules is thus both facile and high-throughput. Despite this tremendous synthetic potential, the Ugi reaction is limited in that it produces products that are flexible and peptidic-like, often being classified as "non-drug-like" and exhibiting bioavailability problems. Interestingly, several novel intramolecular variations of this versatile reaction have recently been reported, wherein constrained products are achieved by intercepting the intermediate nitrilium ion of the Ugi reaction. An alternative approach, and the one described in this application, is to constrain the Ugi product via a so-called secondary reaction after initial formation of the classical Ugi product. Production of the derivatives described herein is facile and amenable to automated high throughput production, allowing production of vast arrays of biologically relevant molecules (in the range of at least 10,000 molecules/template, revealed in good purity).

SUMMARY OF THE INVENTION

The present invention relates to a method for preparing an N-[(aliphatic or aromatic)carbonyl)]-2-aminoacetamide compound of the formula

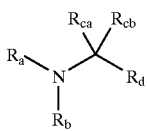

wherein $R_a$ is 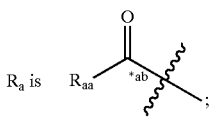;

$R_{aa}$ is hydrogen, alkoxy, an optionally substituted aliphatic moiety or an optionally substituted aromatic moiety;

$R_b$ is hydrogen, an optionally substituted aliphatic moiety or an optionally substituted aromatic moiety;

$R_{ca}$ and $R_{cb}$ are independently hydrogen, optionally substituted aliphatic or optionally substituted aromatic;

$R_d$ is 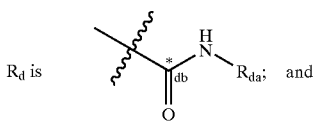 and $R_{da}$ is optionally substituted aliphatic or optionally substituted aromatic; and wherein either $R_{aa}$ is an aliphatic or aromatic moiety that is substituted with a primary or secondary protected amine that, upon deprotection, can react with the *ab or *db carbon, or with at least one $R_b$, $R_{ca}$ and $R_{cb}$, which is substituted with an activated carboxylic acid, to form a 5–7 membered cyclic ring; or $R_b$ is an aliphatic or aromatic moiety that is substituted with a primary or secondary protected amine that, upon deprotection, can react with the *ab or *db carbon, or with at least one $R_{aa}$, $R_{ca}$ and $R_{cb}$, which is substituted with an activated carboxylic acid, to form a 5–7 membered cyclic ring; or at least one of $R_{ca}$ and $R_{cb}$ is an aliphatic or aromatic moiety that is substituted with a primary or secondary protected amine that, upon deprotection, can react with the *ab or *db carbon, or with at least one $R_{aa}$, $R_b$, $R_{ca}$, $R_{cb}$ and $R_{da}$, which is substituted with an activated carboxylic acid, to form a 5–7 membered cyclic ring; or $R_{da}$ is an aliphatic or aromatic moiety that is substituted with a primary or secondary protected amine that, upon deprotection, can react with at least one of $R_{ca}$ and $R_{cb}$, which is substituted with an activated carboxylic acid, to form a 5–7 membered cyclic ring, provided that, when $R_{aa}$ is substituted with a primary or secondary protected amine that, upon deprotection, can react with $R_b$ (substituted with an activated carboxylic acid), then $R_{aa}$ is substituted aromatic, this method comprising reacting:

(i) a carbonyl compound of formula

, with (ii) an amine compound of formula

, (iii) an isonitrile compound of formula

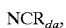, and (iv) an acid compound of formula

, to produce the N-[(aliphatic or aromatic)carbonyl)]-2-aminoacetamide compound. The invention is also directed to a method for cyclizing an N-[(aliphatic or aromatic)carbonyl)]-2-aminoacetamide compound to a cyclic compound selected from the group consisting of a 1,4-benzodiazepine-2,5-dione derivatives, diketopiperazine derivatives, ketopiperazine derivatives, lactam derivatives, 1,4-benzodiazapine derivatives and dihydroquinoxalinones derivative, cyclic ureas, hydantoins, as well as to the cyclized compound per se.

DETAILED DESCRIPTION

As used above, and throughout the description of the invention, the following terms, unless otherwise indicated, shall be understood to have the following meanings:—

"Acid bioisostere" means a group which has chemical and physical similarities producing broadly similar biological properties to a carboxy group (see Lipinski, Annual Reports in Medicinal Chemistry, 1986, 21, p.283 "Bioisosterism In Drug Design"; Yun, Hwahak Sekye, 1993, 33, p.576–579 "Application Of Bioisosterism To New Drug Design"; Zhao, Huaxue Tongbao, 1995, p.34–38 "Bioisosteric Replacement And Development Of Lead Compounds In Drug Design"; Graham, Theochem, 1995, 343, p.105–109 "Theoretical Studies Applied To Drug Design:ab initio Electronic Distributions In Bioisosteres"). Examples of suitable acid bioisosteres include: —C(=O)—NHOH, —C(=O)—CH$_2$OH, —C(=O)—CH$_2$SH, —C(=O)—NH— CN, sulpho, phosphono, alkylsulphonylcarbamoyl, tetrazolyl, arylsulphonylcarbamoyl, heteroarylsulphonylcarbamoyl, N-methoxycarbamoyl, 3-hydroxy-3-cyclobutene-1,2-dione, 3,5-dioxo-1,2,4-oxadiazolidinyl or heterocyclic phenols such as 3-hydroxyisoxazolyl and 3-hydoxy-1-methylpyrazolyl.

"Acidic functional group" means a group with an acidic hydrogen within it. The "corresponding protected derivatives" are those where the acidic hydrogen atom has been replaced with a suitable protecting group, to block or protect the acid functionality while reactions involving other functional sites of the compound are carried out. Such protecting groups are well known to those skilled in the art, having been extensively used in the protection of carboxyl groups in the penicillin and cephalosporin fields, as described in U.S. Pat. No. 3,840,556 and U.S. Pat. No. 3,719,667, the disclosures of which are hereby incorporated herein by reference. For reference to suitable protecting groups, see T. W. Green and P. G. M. Wuts in "Protective Groups in Organic Chemistry" John Wiley and Sons, 1991. Exemplary acidic functional groups include carboxyl (and acid bioisosteres), hydroxy, mercapto and imidazole. Examples of carboxylic acid protecting groups include esters, such as methoxymethyl, methylthiomethyl, tetrahydropyranyl, substituted and unsubstituted phenacyl, 2,2,2-trichloroethyl, tert-butyl, cinnamyl, dialkylaminoalkyl (e.g., dimethylaminoethyl and the like), trimethylsilyl, and the like, and amides and hydrazides including N,N-dimethyl, 7-nitroindolyl hydrazide, N-phenylhydrazine, $C_1$ to $C_8$ loweralkyl (e.g., methyl, ethyl or tertiary butyl and the like); substituted derivatives such as alkoxybenzyl or nitrobenzyl groups and the like; alkanoyloxyalkyl groups such as pivaloyloxymethyl or propionyloxymethyl and the like; aroyloxyalkyl, such as benzoyloxyethyl and the like; alkoxycarbonylalkyl, such as methoxycarbonylmethyl, cyclohexyloxycarbonylmethyl and the like; alkoxycarbonyloxyalkyl, such as t-butyloxycarbonyloxymethyl and the like; alkoxycarbonylaminoalkyl, such as t-butyloxycarbonylaminomethyl and the like; alkylaminocarbonylaminoalkyl, such as methylaminocarbonylaminomethyl and the like; alkanoylaminoalkyl, such as acetylaminomethyl and the like; heterocycliccarbonyloxyalkyl, such as 4-methylpiperazinylcarbonyloxymethyl and the like; dialkylaminocarbonylalkyl, such as dimethylaminocarbonylmethyl and the like; (5-(loweralkyl)-2-oxo-1,3-dioxolen-4-yl)alkyl, such as (5-t-butyl-2-oxo-1,3-dioxolen-4-yl)methyl and the like; and (5-phenyl-2-oxo-1,3-dioxolen-4-yl)alkyl, such as (5-phenyl-2-oxo-1,3-dioxolen-4-yl)methyl and the like.

"Acyl" means an H—CO— or alkyl—CO— group wherein the alkyl group is as herein described. Preferred acyls contain a lower alkyl. Exemplary acyl groups include formyl, acetyl, propanoyl, 2-methylpropanoyl, t-butylacetyl, butanoyl and palmitoyl.

"Aliphatic" means a radical derived from a non aromatic C—H bond by removal of the hydrogen atom. The aliphatic radical may be further substituted by additional aliphatic or aromatic radicals as defined herein. Representative aliphatic groups include alkyl, alkenyl, alkynyl, cycloalkyl, cycloalkenyl, heterocyclyl, heterocyclenyl, aralkenyl, aralkyloxyalkyl, aralkyloxycarbonylalkyl, aralkyl, aralkynyl, aralkyloxyalkenyl, heteroaralkenyl, heteroaralkyl, heteroaralkyloxyalkenyl, heteroaralkyloxyalkyl, heteroaralkynyl, fused arylcycloalkyl, fused heteroarylcycloalkyl, fused arylcycloalkenyl, fused heteroarylcycloalkenyl, fused arylheterocyclyl, fused heteroarylheterocyclyl, fused arylheterocyclenyl, fused heteroarylheterocyclenyl, and the like. "Aliphatic", as used herein, also encompasses the residual, non-carboxyl portion of natural and unnatural amino acids as defined herein. Preferred aliphatic contain from about 1 to about 20 carbon atoms.

"Aromatic" means a radical derived from an aromatic C—H bond by removal of the hydrogen atom. Aromatic includes both aryl and heteroaryl rings as defined herein. The aryl or heteroaryl ring may be further substituted by additional aliphatic or aromatic radicals as defined herein. Representative aromatic groups include aryl, fused cycloalkenylaryl, fused cycloalkylaryl, fused heterocyclylaryl, fused heterocyclenylaryl, heteroaryl, fused cycloalkylheteroaryl, fused cycloalkenylheteroaryl, fused heterocyclenylheteroaryl, fused heterocyclylheteroaryl, and the like.

"Acylamino" is an acyl-NH— group wherein acyl is as defined herein.

"Alkenoyl" means an alkenyl-CO— group wherein alkenyl is as defined herein.

"Alkenyl" means an aliphatic hydrocarbon group containing a carbon-carbon double bond, which may be straight or branched-chain, having about 2 to about 15 carbon atoms in the chain. Preferred alkenyl groups have 2 to about 12 carbon atoms in the chain; more preferably about 2 to about 5 carbon atoms in the chain. Branched means that one or more lower alkyl groups, such as methyl, ethyl or propyl are attached to a linear alkenyl chain. "Lower alkenyl" means about 2 to about 4 carbon atoms in the chain, which may be straight or branched. The alkenyl group may be substituted with one or more "alkenyl group substituents" which may be the same or different, and include halo, alkenyloxy, cycloalkyl, cyano, hydroxy, alkoxy, carboxy, alkynyloxy, aralkoxy, aryloxy, aryloxycarbonyl, alkylthio, heteroaralkyloxy, heterocyclyl, heterocyclylalkyloxy, alkoxycarbonyl, aralkoxycarbonyl, heteroaralkyloxycarbonyl or $Y^1Y^2N$—, $Y^1Y^2NCO$— or $Y^1Y^2NSO_2$—, wherein $Y^1$ and $Y^2$ are independently hydrogen, alkyl, aryl, aralkyl or heteroaralkyl, or where the substituent is $Y^1Y^2N$—, then one of $Y^1$ and $Y^2$ may be acyl or aroyl as defined herein and the other of $Y^1$ and $Y^2$ is as defined previously, or where the substituent is $Y^1Y^2NCO$— or $Y^1Y^2NSO_2$, $Y^1$ and $Y^2$ may also, taken together with the N atom through which $Y^1$ and $Y^2$ are linked, form a 4 to 7 membered heterocyclyl or heterocyclenyl group. Exemplary alkyl groups include methyl, trifluoromethyl, cyclopropylmethyl, cyclopentylmethyl, ethyl, n-propyl, i-propyl, n-butyl, t-butyl, n-pentyl, 3-pentyl, methoxyethyl, carboxymethyl, methoxycarbonylethyl, benzyloxycarbonylmethyl, and pyridylmethyloxycarbonylmethyl. Exemplary alkenyl groups include ethenyl, propenyl, n-butenyl, i-butenyl, 3-methylbut-2-enyl, n-pentenyl, heptenyl, octenyl, cyclohexylbutenyl and decenyl.

"Alkenyloxy" means an alkenyl-O— group wherein the alkenyl group is as herein described. Exemplary alkenyloxy groups include allyloxy and 3-butenyloxy.

"Alkenyloxyalkyl" means an alkenyl-O-alkyl group wherein the alkyl and alkenyl groups are as described herein.

"Alkoxy" means an alkyl-O— group wherein the alkyl group is as herein described. Exemplary alkoxy groups include methoxy, ethoxy, n-propoxy, i-propoxy, n-butoxy and heptoxy.

"Alkoxyalkyl" means an alkyl-O-alkyl- group wherein the alkyl groups are independently as herein described. Exemplary alkoxyalkyl groups include methoxyethyl, ethoxymethyl, n-butoxymethyl and cyclopentylmethyloxyethyl.

"Aminoiminomethyl" means a $NH_2C(=NH)$— group. It is known that this moiety may be mono or di-protected to afford, for example (alkoxycarbonylamino)iminomethyl and (alkoxycarbonylamino)alkoxycarbonyliminomethyl groups.

"Alkoxycarbonyl" means an alkyl-O—CO— group, wherein the alkyl group is as herein defined. Exemplary alkoxycarbonyl groups include methoxycarbonyl, ethoxycarbonyl, and t-butyloxycarbonyl.

"Alkoxycarbonylalkyl" means an alkyl-O—OC-alkyl- group wherein the alkyl groups are independently as herein defined. Preferred alkoxycarbonylalkyl groups include methoxy- and ethoxy-carbonylmethyl as well as methoxy- and ethoxy-carbonyl ethyl.

"Alkyl" means an aliphatic hydrocarbon group, which may be straight or branched-chain, having about 1 to about 20 carbon atoms in the chain. Preferred alkyl groups have 1 to about 12 carbon atoms in the chain. Branched means that one or more lower alkyl groups such as methyl, ethyl or propyl are attached to a linear alkyl chain. "Lower alkyl" means that there are about 1 to about 4 carbon atoms in the chain, which may be straight or branched. The alkyl may be substituted with one or more "alkyl group substituents", which may be the same or different, and include halo, alkenyloxy, cycloalkyl, aroyl, cyano, hydroxy, alkoxy, carboxy, alkynyloxy, aralkoxy, aryloxy, aryloxycarbonyl, alkylthio, heteroarylthio, aralkylthio, arylsulphonyl, alkylsulphonyl, alkylphosphonate, guanidino, heteroaralkyloxy, heterocyclyl, fused heteroarylcycloalkenyl, fused heteroarylcycloalkyl, fused heteroarylheterocyclenyl, fused heteroarylheterocyclyl, fused arylcycloalkenyl, fused arylcycloalkyl, fused arylheterocyclenyl, fused arylheterocyclyl, alkoxycarbonyl, aralkoxycarbonyl, (alkoxycarbonylamino)iminomethyl, (alkoxycarbonylamino)alkoxycarbonyliminomethyl, heteroaralkyloxycarbonyl, or $Y^1Y^2N$—, $Y^1Y^2NCO$— or $Y^1Y^2NSO_2$—, wherein $Y^1$ and $Y^2$ are independently hydrogen, alkyl, aryl, heteroaroyl, aralkyl or heteroaralkyl, or when the substituent is $Y^1Y^2NCO$— or $Y^1Y^2NSO_2$, $Y^1$ and $Y^2$ may also, together with the N atom through which $Y^1$ and $Y^2$ are linked, form a 4 to 7 membered heterocyclyl or heterocyclenyl ring. Exemplary alkyl groups include methyl, trifluoromethyl, cyclopropylmethyl, cyclopentylmethyl, ethyl, n-propyl, i-propyl, n-butyl, t-butyl, n-pentyl, n-nonyl, decyl, 3-pentyl, methoxyethyl, carboxymethyl, methoxycarbonylethyl, benzyloxycarbonylmethyl, and pyridylmethyloxycarbonylmethyl. Preferred alkyl group substituents are fused arylcycloalkenyl, cyano, fused arylcycloalkyl, aralkylthio, $Y^1Y^2N$—, $Y^1Y^2NCO$—, fused arylheterocyclenyl, fused arylheterocyclyl, hydroxy, heterocyclyl, aralkoxy, alkoxycarbonyl, alkylthio, aryloxy, aroyl, heteroaroyl, arylsulphonyl, heteroarylthio alkylphosphonate, alkylsulphonyl, (alkoxycarbonylamino)iminomethyl, (alkoxycarbonylamino)alkoxycarbonyliminomethyl, and cycloalkyl.

"Alkylcarbamoyl" is an alkyl-NH—CO— group wherein the alkyl group is herein defined.

"Alkylphosphonate" means an $(alkylO)_2P$=O— group wherein the alkyl groups are independently as herein defined.

"Alkylsulfinyl" means an alkyl-SO— group wherein the alkyl group is as defined herein. Preferred alkylsulfinyl groups are those wherein the alkyl group is lower alkyl.

"Alkylsulfonyl" means an alkyl-SO$_2$— group wherein the alkyl group is as defined herein. Preferred alkylsulfonyl groups are those wherein the alkyl group is lower alkyl.

"Alkylsulphonylcarbamoyl" means an alkyl-SO$_2$—NH—C(=O)— group wherein the alkyl group is as herein described. Preferred alkylsulphonylcarbamoyl groups are those wherein the alkyl group is $C_{1-4}$ alkyl.

"Alkylthio" means an alkyl-S— group wherein the alkyl group is as herein described. Exemplary alkylthio groups include methylthio, ethylthio, i-propylthio and heptylthio.

"Alkynyl" means an aliphatic hydrocarbon group containing a carbon-carbon triple bond, which may be straight or branched-chain, having about 2 to about 15 carbon atoms in the chain. Preferred alkynyl groups have 2 to about 12 carbon atoms in the chain; and, more preferably, about 2 to about 4 carbon atoms in the chain. Branched means that one or more lower alkyl groups, such as methyl, ethyl or propyl, are attached to a linear alkynyl chain. "Lower alkynyl" means 2 to about 4 carbon atoms in the chain, which may be straight or branched-chain. The alkynyl group may be substituted with one or more "alkynyl group substituents", which may be the same or different, and include halo, alkenyloxy, cycloalkyl, cyano, hydroxy, alkoxy, carboxy, alkynyloxy, aralkoxy, aryloxy, aryloxycarbonyl, alkylthio, heteroaralkyloxy, heterocyclyl, heterocyclylalkyloxy, alkoxycarbonyl, aralkoxycarbonyl, heteroaralkyloxycarbonyl or $Y^1Y^2N$—, $Y^1Y^2NCO$— or $Y^1Y^2NSO_2$—, wherein $Y^1$ and $Y^2$ are independently hydrogen, alkyl, aryl, aralkyl or heteroaralkyl, or when the substituent is $Y^1Y^2N$—, then one of $Y^1$ and $Y^2$ may be acyl or aroyl as defined herein and the other of $Y^1$ and $Y^2$ is as defined previously, or when the substituent is $Y^1Y^2NCO$— or $Y^1Y^2NSO_2$, $Y^1$ and $Y^2$ may also, taken together with the N atom through which $Y^1$ and $Y^2$ are linked, form a 4 to 7 membered heterocyclyl or heterocyclenyl ring. Exemplary alkyl groups include methyl, trifluoromethyl, cyclopropylmethyl, cyclopentylmethyl, ethyl, n-propyl, i-propyl, n-butyl, t-butyl, n-pentyl, 3-pentyl, methoxyethyl, carboxymethyl, methoxycarbonylethyl, benzyloxycarbonylmethyl, pyridyl- methyloxycarbonylmethyl. Exemplary alkynyl groups include ethynyl, propynyl, n-butynyl, 2-butynyl, 3-methylbutynyl, n-pentynyl, heptynyl, octynyl and decynyl.

"Alkynyloxy" means an alkynyl-O— group wherein the alkynyl group is as herein described. Exemplary alkynyloxy groups include propynyloxy and 3-butynyloxy.

"Amino acid" means an amino acid selected from the group consisting of natural and unnatural amino acids as defined herein. Preferred amino acids are those possessing an α-amino group. The amino acids may be neutral, positive or negative depending on the substituents in the side chain. "Neutral amino acid" means an amino acid containing uncharged side chain substituents. Exemplary neutral amino acids include alanine, valine, leucine, isoleucine, proline, phenylalanine, tryptophan, methionine, glycine, serine, threonine and cysteine. "Positive amino acid" means an amino acid in which the side chain substituents are positively charged at physiological pH. Exemplary positive amino acids include lysine, arginine and histidine. "Negative amino acid" means an amino acid in which the side chain substituents bear a net negative charge at physiological pH. Exemplary negative amino acids include aspartic acid and glutamic acid. Preferred amino acids are α-amino acids. Exemplary natural amino acids are isoleucine, proline, phenylalanine, tryptophan, methionine, glycine, serine, threonine, cysteine, tyrosine, asparagine, glutamine, lysine, arginine, histidine, aspartic acid and glutamic acid.

"Unnatural amino acid" means an amino acid for which there is no nucleic acid codon. Examples of unnatural amino acids include, for example, the D-isomers of the natural α-amino acids as indicated above; Aib (aminobutyric acid), βAib (3-aminoisobutyric acid), Nva (norvaline), β-Ala, Aad (2-aminoadipic acid), βAad (3-aminoadipic acid), Abu (2-aminobutyric acid), Gaba (γ-aminobutyric acid), Acp (6-aminocaproic acid), Dbu (2,4-diaminobutryic acid), α-aminopimelic acid, TMSA (trimethylsilyl-Ala), aIle (allo- isoleucine), Nle (norleucine), tert-Leu, Cit (citrulline), Orn, Dpm (2,2'-diaminopimelic acid), Dpr (2,3-diaminopropionic acid), α- or β-Nal, Cha (cyclohexyl-Ala), hydroxyproline, Sar (sarcosine), and the like; cyclic amino acids; N-α-alkylated amino acids such as MeGly (N-α-methylglycine), EtGly (N-α-ethylglycine) and EtAsn (N-α-ethylasparagine); and amino acids in which the α-carbon bears two side-chain substituents. The names of natural and unnatural amino acids and residues thereof used herein follow the naming conventions suggested by the IUPAC Commission on the Nomenclature of Organic Chemistry and the IUPAC-IUB Commission on Biochemical Nomenclature as set out in "Nomenclature of α-Amino Acids (Recommendations, 1974)" Biochemistry, 14(2), (1975). To the extent that the names and abbreviations of amino acids and residues thereof employed in this specification and appended claims differ from those noted, differing names and abbreviations will be made clear.

"Amino acid side chains" means the substituent found on the carbon between the amino and carboxy groups in α-amino acids. For examples of "corresponding protected derivatives" of amino acid side chains, see T. W. Green and P. G. M. Wuts in "Protective Groups in Organic Chemistry" John Wiley and Sons, 1991.

"Amine protecting group" means an easily removable group which is known in the art to protect an amino group against undesirable reaction during synthetic procedures and to be selectively removable. The use of amine protecting groups is well known in the art for protecting groups against undesirable reactions during a synthetic procedure, and many such protecting groups are known. See, for example, T. H. Greene and P. G. M. Wuts, Protective Groups in Organic Synthesis, 2nd edition, John Wiley & Sons, New York (1991), the contents of which are hereby incorporated herein by reference. Preferred amine protecting groups are acyl, including formyl, acetyl, chloroacetyl, trichloroacetyl, o-nitrophenylacetyl, o-nitrophenoxyacetyl, trifluoroacetyl, acetoacetyl, 4-chlorobutyryl, isobutyryl, o-nitrocinnamoyl, picolinoyl, acylisothiocyanate, aminocaproyl, benzoyl and the like, and acyloxy including methoxycarbonyl, 9-fluorenylmethoxycarbonyl, 2,2,2-trifluoroethoxycarbonyl, 2-trimethylsilylethxoycarbonyl, vinyloxycarbonyl, allyloxycarbonyl, t-butyloxycarbonyl (BOC), 1,1-dimethylpropynyloxycarbonyl, benzyloxycarbonyl (CBZ), p-nitrobenzyloxycarbony, 2,4-dichlorobenzyloxycarbonyl, and the like.

"Acid labile amine protecting group" means an amine protecting group as defined above which is readily removed by treatment with acid while remaining relatively stable to other reagents. Preferred acid labile amine protecting groups include tert-butoxycarbonyl (BOC), and 2-(4-biphenyl)-isopropoxy carbonyl.

"Base labile amine protecting group" means an amine protecting group as defined above which is readily removed by treatment with base while remaining relatively stable to other reagents. Preferred base labile amine protecting groups include 9-fluorenylmethoxycarbonyl (FMOC).

"Hydrogenation labile amine protecting group" means an amine protecting group as defined above which is readily removed by hydrogenation while remaining relatively stable to other reagents. A preferred hydrogenation labile amine protecting group is benzyloxycarbonyl (CBZ).

"Hydrogenation labile acid protecting group" means an acid protecting group as defined above which is readily removed by hydrogenation while remaining relatively stable to other reagents. A preferred hydrogenation labile acid protecting group is benzyl.

"Analogue" means a compound which comprises a chemically modified form of a specific compound or class thereof, and which maintains the pharmaceutical and/or pharmacological activities characteristic of said compound or class.

"Aralkenyl" means an aryl-alkenyl- group wherein the aryl and alkenyl are as herein described. Preferred aralkenyl groups contain a lower alkenyl moiety. An exemplary aralkenyl group is 2-phenethenyl.

"Aralkoxy" means an aralkyl-O— group wherein the aralkyl group is as herein described. Exemplary aralkoxy groups include benzyloxy and 1- or 2-naphthalenemethoxy.

"Aralkoxyalkyl" means an aralkyl-O-alkyl group wherein the aralkyl and alkyl groups are as herein described. An exemplary aralkyloxyalkyl group is benzyloxyethyl.

"Aralkoxycarbonyl" means an aralkyl-O—CO— group wherein the aralkyl groups is as herein described. An exemplary aralkoxycarbonyl group is benzyloxycarbonyl.

"Aralkoxycarbonylalkyl" means an aralkyl-OOC-alky-group wherein the alkyl and aralkyl groups are as herein described. Preferred aralkoxycarbonylalkyl groups include benzyloxy-carbonyl methyl and benzyloxy-carbonyl ethyl.

"Aralkyl" means an alkyl group substituted by one or more aryl groups, wherein the aryl and alkyl are as herein described. Preferred aralkyl groups contain a lower alkyl moiety. Exemplary aralkyl groups include benzyl; 2,2-diphenylethyl; 2,2-diphenylmethyl; 2-phenethyl and naphthlenemethyl.

"Aralkylamino" means an aryl-alkyl-NH— group wherein aryl and alkyl are as defined herein. Exemplary aralkylamino groups include phenethylamino.

"Aralkyloxyalkenyl" means an aralkyl-O-alkenyl group wherein the aralkyl and alkenyl groups are as herein described. An exemplary aralkyloxyalkenyl group is 3-benzyloxyallyl.

"Aralkylsulfonyl" means an aralkyl-$SO_2$— group wherein the aralkyl group is as herein described. Exemplary aralkylsulfonyl groups include phenethylsulfonyl.

"Aralkylsulfinyl" means an aralkyl-SO— group wherein the aralkyl group is as herein described. Exemplary aralkylsulfinyl groups include phenethylsulfinyl.

"Aralkylthio" means an aralkyl-S— group wherein the aralkyl group is as herein described. An exemplary aralkylthio group is benzylthio.

"Aroyl" means an aryl-CO— group wherein the aryl group is as herein described. Exemplary aroyl groups include benzoyl and 1- and 2-naphthoyl.

"Aroylamino" is an aroyl-NH— group wherein aroyl is as defined herein. Exemplary aroylamino gorups include benzoylamino groups.

"Aryl" means an aromatic monocyclic or multicyclic ring system of about 6 to about 14 carbon atoms, preferably of about 6 to about 10 carbon atoms. The aryl is optionally substituted with one or more "ring system substituents" which may be the same or different, and are as defined herein. Representative aryl groups include phenyl, naphthyl, substituted phenyl and substituted naphthyl groups. Preferred aryl groups are phenyl and naphthyl.

"Aralkenyl" means an aryl-alkenyl- group wherein the aryl and alkenyl moieties are as described herein. Preferred aralkenyl groups contain a $C_{2-12}$ alkenyl moiety. Exemplary aralalkenyl groups include styryl; 4-phenyl-1,3-pentadienyl; and 2,5-dimethyl-2-phenyl-4-hexenyl.

"Aralkynyl" means an aryl-alkynyl- group wherein the aryl and alkynyl moieties are as described herein. Exemplary arylalkynyl groups include phenylacetylenyl and 3-phenylbut-2-ynyl.

"Arylazo" means an aryl-azo- group wherein the aryl and azo groups are as defined herein. Exemplary arylazo compounds include naphthalene-2-azo.

"Arylcarbamoyl" is an aryl-NHCO— group, wherein the aryl group is as defined herein. Exemplary arylcarbamoyl compounds include benzaryl.

"Fused arylcycloalkenyl" means a fused aryl and cycloalkenyl wherein the aryl and cycloalkenyl groups are as defined herein. Preferred fused arylcycloalkenyl groups are those wherein the aryl thereof is phenyl and the cycloalkenyl consists of about 5 to 6 ring atoms. A fused arylcycloalkenyl group may be bonded through any atom of the ring system thereof capable of such bonding. The fused arylcycloalkenyl group may be optionally substituted by one or more ring system substituents, wherein the "ring system substituent" is as defined herein. Representative fused arylcycloalkenyl groups include 1,2-dihydronaphthylene, indene, and the like.

"Fused arylcycloalkyl" means a fused aryl and cycloalkyl wherein the aryl and cycloalkyl groups are as defined herein. Preferred fused arylcycloalkyl groups are those wherein the aryl thereof is phenyl and the cycloalkyl consists of about 5 to 6 ring atoms. A fused arylcycloalkyl group may be bonded through any atom of the ring system thereof capable of such bonding. The fused arylcycloalkyl group may be optionally substituted by one or more ring system substituents, wherein the "ring system substituent" is as defined herein. Representative fused arylcycloalkyl groups includes 1,2,3,4-tetrahydronaphthyl; 5,6,7,8-tetrahydronaphth-1-yl, and the like.

"Fused arylheterocyclenyl" means a fused aryl and heterocyclenyl wherein the aryl and heterocyclenyl groups are as defined herein. Preferred fused arylheterocyclenyl groups are those wherein the aryl thereof is phenyl and the heterocyclenyl consists of about 5 to 6 ring atoms. A fused arylheterocyclenyl group may be bonded through any atom of the ring system thereof capable of such bonding. The designation of aza, oxa or thia as a prefix before heterocyclenyl portion of the fused arylheterocyclenyl means that at least a nitrogen, oxygen or sulfur atom is present, respectively, as a ring atom. The fused arylheterocyclenyl group may be optionally substituted by one or more ring system substituent, wherein the "ring system substituent" is as defined herein. The nitrogen atom of a fused arylheterocyclenyl group may be a basic nitrogen atom. The nitrogen or sulphur atom of the heterocyclenyl portion of the fused arylheterocyclenyl group may also be optionally oxidized to the corresponding N-oxide, S-oxide or S,S-dioxide. Representative fused arylheterocyclenyl groups include 3H-indolinyl; 1H-2-oxoquinolyl; 2H-1-oxoisoquinolyl; 1,2-dihydroquinolinyl; 3,4-dihydroquinolinyl; indazolyl; 1,2-dihydroisoquinolinyl; benzotriazolyl; ,3,4-dihydroisoquinolinyl, and the like.

"Fused arylheterocyclyl" means a fused aryl and heterocyclyl wherein the aryl and heterocyclyl groups are as defined herein. Preferred fused arylheterocyclyl groups are those wherein the aryl thereof is phenyl and the heterocyclyl consists of about 5 to 6 ring atoms. A fused arylheterocyclyl group may be bonded through any atom of the ring system thereof capable of such bonding. The designation of aza, oxa or thia as a prefix before heterocyclyl portion of the fused arylheterocyclyl means that at least a nitrogen, oxygen or sulfur atom is present, respectively, as a ring atom. The fused arylheterocyclyl group may be optionally substituted by one or more ring system substituent, wherein the "ring system substituent" is as defined herein. The nitrogen atom of a fused arylheteroaryl group may be a basic nitrogen atom. The nitrogen or sulphur atom of the heterocyclyl portion of the fused arylheterocyclyl may also be optionally oxidized to the corresponding N-oxide, S-oxide or S,S-dioxide. Representative preferred fused arylheterocyl ring systems include indolinyl, phthalimide; 1,2,3,4-tetrahydroisoquinoline; 1,2,3,4-tetrahydroquinoline 1H-2,3-dihydroisoindol-2-yl; 2,3-dihydrobenz[f]isoindol-2-yl; 1,2,3,4-tetrahydrobenz[g]isoquinolin-2-yl; 1,3-benzodioxole, and the like.

"Aryloxy" means an aryl-O— group wherein the aryl group is as defined herein. Exemplary aryloxy groups include phenoxy and 2-naphthyloxy.

"Aryloxyalkyl" means an aryl-O-alkyl- group wherein the aryl and alkyl groups are as herein described. An exemplary aryloxyalkyl group is phenoxypropyl.

"Aryloxyalkenyl" means an aryl-O-alkenyl- group wherein the aryl and alkenyl groups are as herein described. An exemplary aryloxyalkenyl group is phenoxyallyl.

"Aryloxycarbonyl" means an aryl-O—CO— group wherein the aryl group is as defined herein. Exemplary aryloxycarbonyl groups include phenoxycarbonyl and naphthoxycarbonyl.

"Aryloxycarbonylalkyl" means an aryl-O—OC-alky- group. Preferred groups include phenoxycarbonyl-methyl and phenoxycarbonyl-ethyl.

"Arylsulfonyl" means an aryl-$SO_2$— group wherein the aryl group is as defined herein.

"Arylsulfinyl" means an aryl-SO— group wherein the aryl group is as defined herein.

"Arylthio" means an aryl-S— group wherein the aryl group is as herein described. Exemplary arylthio groups include phenylthio and naphthylthio.

"Basic nitrogen atom" means an $sp^2$ or $sp^3$ hybridized nitrogen atom having a non-bonded pair of electrons which is capable of being protonated. Examples of groups that contain basic nitrogen atoms include optionally substituted imino, optionally substituted amino and optionally substituted amidino groups.

"Carbamoyl" is an $NH_2$—CO— group.

"Carboxy" means an HO(O)C— (carboxylic acid) group.

"Carboxyalkyl" means an HOOC-alkyl- group wherein the alkyl group is as defined herein. Preferred carboxyalkyl groups include carboxymethyl and carboxyethyl.

"Compounds of the invention", and equivalent expressions, are meant to embrace compounds of general formula (I), and compounds of formula (II), as hereinbefore described, and to include their prodrugs, their pharmaceutically acceptable salts, and their solvates, e.g. hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and their use is not intended to exclude other instances when the context so permits.

"Cycloalkoxy" means an cycloalkyl-O— group wherein the cycloalkyl group is as herein described. Exemplary cycloalkoxy groups include cyclopentyloxy and cyclohexyloxy.

"Cycloalkyl" means a non-aromatic mono- or multicyclic ring system of about 3 to about 10 carbon atoms. Preferred ring sizes of rings of the ring system include about 5 to 6 ring atoms. The cycloalkyl group is optionally substituted with one or more "ring system substituents", which may be the same or different, and are as defined herein. Representative monocyclic cycloalkyl groups include cyclopropyl, cyclopentyl, cyclohexyl, cycloheptyl, and the like. Representative multicyclic cycloalkyl groups include 1-decalin, norbornyl, adamant-(1- or 2-)yl, 6,6-dimethylbicyclo[3.1.1] heptane, and the like. Preferred ring system substituents for a cycloalkyl include alkyl, aralkoxy, amidino, hydroxy, and $Y^1Y^2N$— as defined herein.

"Cycloalkylcarbonyl" means a cycloalkyl-CO— group, wherein the cycloalkyl group is as hereinbefore defined. Exemplary cycloalkylcarbonyl groups include cyclopropylcarbonyl, and the like.

"Cycloalkenyl" means a non-aromatic mono- or multicyclic ring system of about 3 to about 10 carbon atoms, preferably of about 5 to about 10 carbon atoms, which contains at least one carbon-carbon double bond. Preferred ring sizes of rings of the ring system include about 5 to 6 ring atoms. The cycloalkenyl is optionally substituted with one or more "ring system substituents", which may be the same or different, and are as defined herein. Representative monocyclic cycloalkenyl groups include cyclopentenyl, cyclohexenyl, cycloheptenyl, and the like. A representative multicyclic cycloalkenyl group is norbornylenyl. Preferred ring system substituents for a cycloalkyl group are amidino and $Y^1Y^2N$— as defined herein.

"Derivative" means a chemically modified compound wherein the modification is considered routine by the ordinary skilled chemist, such as an ester or an amide of an acid, protecting groups, such as a benzyl group for an alcohol or thiol, and tert-butoxycarbonyl group for an amine.

"Azo" means a bivalent —N=N— radical.

"Effective amount" is means an amount of a compound/composition according to the present invention effective in producing the desired therapeutic effect.

"Electron donating group" means a group that will release or donate electrons more than hydrogen would if it occupied the same position in the molecule. See J. March, Advanced Organic Chemistry, 3rd Ed., John Wiley & Sons p. 238 (1985). These types of groups are well known in the art. Examples include alkyl, aralkyl, cycloalkyl, heteroaralkyl, heteroaryl, or heterocyclyl.

"Formulations suitable for nasal or inhalational administration" means formulations which are in a form suitable to be administered nasally or by inhalation to a patient. The formulation may contain a carrier, in a powder form, having a particle size, for example, in the range 1 to 500 microns (including particle sizes in a range between 20 and 500 microns in increments of 5 microns such as 30 microns, 35 microns, etc.) Suitable formulations wherein the carrier is a liquid, for administration as, for example, a nasal spray or as nasal drops, include aqueous or oily solutions of the active ingredient. Formulations suitable for aerosol administration may be prepared according to conventional methods and may be delivered with other therapeutic agents. Inhalational therapy is readily administered by metered dose inhalers.

"Formulations suitable for oral administration" means formulations which are in a form suitable to be administered orally to a patient. The formulations may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

"Formulations suitable for parenteral administration" means formulations which are in a form suitable to be administered parenterally to a patient. The formulations are sterile and include emulsions, suspensions, aqueous and non-aqueous injection solutions, which may contain suspending agents, thickening agents, anti-oxidants, buffers, bacteriostats, and solutes which render the formulation isotonic with the blood of the intended recipient and have a suitably adjusted pH.

"Formulations suitable for rectal administrations" means formulations which are in a form suitable to be administered rectally to a patient. The formulation is preferably in the form of suppositories which can be prepared by mixing the compounds of this invention with suitable non-irritating excipients or carriers such as cocoa butter, polyethylene glycol or a suppository wax, which are solid at ordinary temperatures but liquid at body temperature and, therefore, melt in the rectum and release the active component.

"Formulations suitable for systemic administration" means formulations which are in a form suitable to be administered systemically to a patient. The formulation is preferably administered by injection, including transmuscular, intravenous, intraperitoneal, and subcutaneous. For injection, the compounds of the invention are formulated in liquid solutions, preferably in physiologically compatible buffers such as Hank's solution or Ringer's solution. In addition, the compounds may be formulated in solid form and redissolved or suspended immediately prior to use. Lyophilized forms are also included. Systemic administration also can be by transmucosal or transdermal means, or the compounds can be administered orally. For transmucosal or transdermal administration, penetrants appropriate to the barrier to be permeated are used in the formulation. Such penetrants are generally known in the art, and include, for example, bile salts and fusidic acid derivatives for transmucosal administration. In addition, detergents may be used to facilitate permeation. Transmucosal administration may be through use of nasal sprays, for example, or suppositories. For oral administration, the compounds are formulated into conventional oral administration forms such as capsules, tablets, and tonics.

"Formulations suitable for topical administration" means formulations which are in a form suitable to be administered to a patient. The formulation may be presented as a topical ointment, salve, powder, spray and inhalant, gel (water or alcohol based), creams, as is generally known in the art, or incorporated into a matrix base for application in a patch, which would allow a controlled release of compound through the dermal barrier. When formulated in an ointment, the active ingredients may be employed with either a paraffinic or a water-miscible ointment base. Alternatively, the active ingredients may be formulated in a cream with an oil-in-water cream base. Formulations suitable for topical administration in the eye include eye drops wherein the active ingredient is dissolved or suspended in a suitable carrier, especially an aqueous solvent for the active ingredient. Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

"Formulations suitable for vaginal administration" means formulations which are in a form suitable to be administered vaginally to a patient. The formulation may be presented as pessaries, tampons, creams, gels, pastes, foams or spray formulations containing in addition to the active ingredient such carriers as are known in the art to be appropriate.

"Guanidino" or "guanidine" means a group of formula

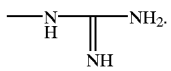

"Halo" means fluoro, chloro, bromo, or iodo. Preferred halo are fluoro, chloro or bromo, and more preferred are fluoro or chloro.

"Heteroaralkenyl" means an heteroaryl-alkenyl- group wherein the heteroaryl and alkenyl moieties are as herein described. Preferred heteroaralkenyl groups contain a lower alkenyl moiety. Exemplary heteroaralkenyl groups are 4-pyridylvinyl, thienylethenyl, pyridylethenyl, imidazolylethenyl and pyrazinylethenyl.

"Heteroaralkyl" means a heteroaryl-alkyl- group wherein the heteroaryl and alkyl moieties are as herein described. Preferred heteroaralkyl groups contain a lower alkyl moiety. Exemplary heteroaralkyl groups include thienylmethyl, pyridylmethyl, imidazolylmethyl and pyrazinylmethyl.

"Heteroaralkyloxy" means an heteroaralkyl-O— group wherein the heteroaralkyl group is as herein described. An exemplary heteroaralkyloxy group is 4-pyridylmethyloxy.

"Heteroaralkyloxyalkenyl" means an heteroaralkyl-O-alkenyl group wherein the heteroaralkyl and alkenyl groups are as herein described. An exemplary heteroaralkyloxyalkenyl group is 4-pyridylmethyloxyallyl.

"Heteroaralkyloxyalkyl" means an heteroaralkyl-O-alkyl group wherein the heteroaralkyl and alkyl groups are as herein described. An exemplary heteroaralkyloxy group is 4-pyridylmethyloxyethyl.

"Heteroaralkynyl" means an heteroaryl-alkynyl- group wherein the heteroaryl and alkynyl groups are as herein described. Preferred heteroaralkynyl groups contain a lower alkynyl moiety. Exemplary heteroaralkynyl groups are pyrid-3-ylacetylenyl, quinolin-3-ylacetylenyl and 4-pyridylethynyl.

"Heteroaroyl" means an means an heteroaryl-CO— group wherein the heteroaryl group is as herein described. Exemplary heteroaroyl groups include thiophenoyl, nicotinoyl, pyrrol-2-ylcarbonyl and 1- and 2-naphthoyl and pyridinoyl.

"Heteroaryl" means an aromatic monocyclic or multicyclic ring system of about 5 to about 14 carbon atoms, preferably about 5 to about 10 carbon atoms, in which at least one of the atoms in the ring system is an (hetero) element(s) other than carbon, for example nitrogen, oxygen or sulfur. Preferred ring sizes of rings of the ring system include about 5 to 6 ring atoms. The heteroaryl group may also be substituted by one or more "ring system substituents", which may be the same or different, and are as defined herein. The designation of aza, oxa or thia as a prefix before heteroaryl means that at least a nitrogen, oxygen or sulfur atom is present, respectively, as a ring atom. A nitrogen atom of an heteroaryl may be a basic nitrogen atom and may also be optionally oxidized to the corresponding N-oxide. Representative heteroaryl and substituted heteroaryl groups include pyrazinyl, furanyl, thienyl, pyridyl, pyrimidinyl, isoxazolyl, isothiazolyl, tetrazolyl, oxazolyl, thiazolyl, pyrazolyl, furazanyl, pyrrolyl, pyrazolyl, triazolyl, 1,2,4-thiadiazolyl, pyridazinyl, quinoxalinyl, phthalazinyl, imidazo[1,2-a]pyridine, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindole, 1,2,4-triazinyl, Preferred heteroaryl groups include pyrazinyl, thienyl, pyridyl, pyrimidinyl, quinolinyl, tetrazolyl, imidazolyl, thiazolyl, benzothienyl, isoxazolyl and isothiazolyl.

"Heteroarylalkenyl" means a heteroaryl-alkenyl-group wherein the heteroaryl and alkenyl moieties are as described herein. Preferred heteroarylalkenyl groups contain a $C_{2-12}$ alkenyl moiety. Exemplary heteroarylalkenyl groups include pyridylpentenyl, pyridylhexenyl and pyridylheptenyl.

"Heteroarylalkynyl" means a heteroaryl-alkynyl- group wherein the heteroaryl and alkynyl moieties are as herein described. Preferred heteroarylalkynyl groups contain a $C_{2-12}$ alkynyl moiety. Exemplary heteroarylalkynyl groups include 3-pyridyl-but-2-ynyl and pyridylpropynyl.

"Heteroarylazo" means an heteroaryl-azo- group wherein the heteroaryl and azo groups are as defined herein.

"Fused heteroarylcycloalkenyl" means a fused heteroaryl and cycloalkenyl group wherein the heteroaryl and cycloalkenyl moieties are as defined herein. Preferred fused heteroarylcycloalkenyl groups are those wherein the heteroaryl thereof is phenyl and the cycloalkenyl portion consists of about 5 to 6 ring atoms. A fused heteroarylcycloalkenyl as a variable may be bonded through any atom of the ring system thereof capable of such. The designation of aza, oxa or thia as a prefix before the heteroaryl portion of the fused heteroarylcycloalkenyl means that at least a nitrogen, oxygen or sulfur atom is present respectively as a ring atom. The fused heteroarylcycloalkenyl group may be optionally substituted by one or more ring system substituents, wherein the "ring system substituent" is as defined herein. The nitrogen atom of a fused heteroarylcycloalkenyl group may be a basic nitrogen atom. The nitrogen atom of the heteroaryl portion of the fused heteroarylcycloalkenyl group may also be optionally oxidized to the corresponding N-oxide. Representative fused heteroarylcycloalkenyl grjoups include 5,6-dihydroquinolyl; 5,6-dihydroisoquinolyl; 5,6-dihydroquinoxalinyl; 5,6-dihydroquinazolinyl; 4,5-dihydro-1H-benzimidazolyl; 4,5-dihydrobenzoxazolyl, and the like.

"Fused heteroarylcycloalkyl" means a fused heteroaryl and cycloalkyl group wherein the heteroaryl an cycloalkyl moieties are as defined herein. Preferred fused heteroarylcycloalkyl groups are those wherein the heteroaryl portion thereof consists of about 5 to 6 ring atoms and the cycloalkyl consists of about 5 to about 6 ring atoms. A fused heteroarylcycloalkyl group may be bonded through any atom of the ring system thereof capable of such. The designation of aza, oxa or thia as a prefix before the heteroaryl portion of the fused heteroarylcycloalkyl group means that at least a nitrogen, oxygen or sulfur atom is present, respectively, as a ring atom. The fused heteroarylcycloalkyl group may be optionally substituted by one or more ring system substituents, wherein the "ring system substituent" is as defined herein. The nitrogen atom of a fused heteroarylcycloalkyl group may be a basic nitrogen atom. The nitrogen atom of the heteroaryl portion of the fused heteroarylcycloalkyl group may also be optionally oxidized to the corresponding N-oxide. Representative fused heteroarylcycloalkyl groups include 5,6,7,8-tetrahydroquinolinyl; 5,6,7,8-tetrahydroisoquinolyl; 5,6,7,8-tetrahydroquinoxalinyl; 5,6,7,8-tetrahydroquinazolyl; 4,5,6,7-tetrahydro-1H-benzimidazolyl; 4,5,6,7-tetrahydrobenzoxazolyl; 1H-4-oxa-1,5-diazanaphthalen-2-only; 1,3-dihydroimidizole-[4,5]-pyridin-2-onyl, and the like.

"Fused heteroarylheterocyclenyl" means a fused heteroaryl and heterocyclenyl group wherein the heteroaryl and heterocyclenyl moieties are as defined herein. Preferred fused heteroarylheterocyclenyl groups are those wherein the heteroaryl portion thereof consists of about 5 to 6 ring atoms and the heterocyclenyl portion consists of about 5 to 6 ring atoms. A fused heteroarylheterocyclenyl group may be bonded through any atom of the ring system thereof capable of such. The designation of aza, oxa or thia as a prefix before the heteroaryl or heterocyclenyl portion of the fused heteroarylheterocyclenyl group means that at least a nitrogen, oxygen or sulfur atom is present, respectively, as a ring atom. The fused heteroarylheterocyclenyl group may be optionally substituted by one or more ring system substituents, wherein the "ring system substituent" is as defined herein. The nitrogen atom of a fused heteroarylazaheterocyclenyl group may be a basic nitrogen atom. The nitrogen or sulphur atom of the heteroaryl or heterocyclyl portion of the fused heteroarylheterocyclyl group may also be optionally oxidized to the corresponding N-oxide, S-oxide or S,S-dioxide. Representative fused heteroarylheterocyclenyl groups include 7,8-dihydro[1,7]naphthyridinyl; 1,2-dihydro[2,7]naphthyridinyl; 6,7-dihydro-3H-imidazo[4,5-c]pyridyl; 1,2-dihydro-1,5-naphthyridinyl; 1,2-dihydro-1,6-naphthyridinyl; 1,2-dihydro-1,7-naphthyridinyl; 1,2-dihydro-1,8-naphthyridinyl; 1,2-dihydro-2,6-naphthyridinyl, and the like.

"Fused heteroarylheterocyclyl" means a fused heteroaryl and heterocyclyl group wherein the heteroaryl and heterocycly moieties are as defined herein. Preferred fused heteroarylheterocyclyl groups are those wherein the heteroaryl portion thereof consists of about 5 to 6 ring atoms and the heterocyclyl portion consists of about 5 to 6 ring atoms. A fused heteroarylheterocyclyl group may be bonded through any atom of the ring system thereof capable of such. The designation of aza, oxa or thia as a prefix before the heteroaryl or heterocyclyl portion of the fused heteroarylheterocyclyl group means that at least a nitrogen, oxygen or sulfur atom is present, respectively, as a ring atom. The fused heteroarylheterocyclyl group may be optionally substituted by one or more ring system substituents, wherein the "ring system substituent" is as defined herein. A nitrogen atom of a fused heteroarylheterocyclyl group may be a basic nitrogen atom. A nitrogen or sulphur atom of the heteroaryl or heterocyclyl portion of the fused heteroarylheterocyclyl group may also be optionally oxidized to the corresponding N-oxide, S-oxide or S,S-dioxide. Representative fused heteroarylheterocyclyl groups include 2,3-dihydro-1H pyrrol[3,4-b]quinolin-2-yl; 1,2,3,4-tetrahydrobenz[b][1,7]naphthyridin-2-yl; 1,2,3,4-tetrahydrobenz[b][1,6]naphthyridin-2-yl; 1,2,3,4-tetrahydro-9H-pyrido[3,4-b]indol-2yl; 1,2,3,4-tetrahydro-9H-pyrido[4,3-b]indol-2yl; 2,3,-dihydro-1H-pyrrolo[3,4-b]indol-2-yl; 1H-2,3,4,5-tetrahydroazepino[3,4-b]indol-2-yl; 1H-2,3,4,5-tetrahydroazepino[4,3-b]indol-3-yl, 1H-2,3,4,5-tetrahydroazepino[4,5-b]indol-2yl; 5,6,7,8-tetrahydro[1,7]napthyridinyl, 1,2,3,4-tetrhydro[2,7]naphthyridinyl, 2,3-dihydro[1,4]dioxino[2,3-b]pyridyl; 2,3-dihydro[1,4]dioxino[2,3-b]pryidyl; 3,4-dihydro-2H-1-oxa[4,6]diazanaphthalenyl; 4,5,6,7-tetrahydro-3H-imidazo[4,5-c]pyridyl; 6,7-dihydro[5,8]diazanaphthalenyl; 1,2,3,4-tetrahydro[1,5]napthyridinyl; 1,2,3,4-tetrahydro[1,6]napthyridinyl; 1,2,3,4-tetrahydro[1,7]napthyridinyl; 1,2,3,4-tetrahydro[1,8]napthyridinyl; 1,2,3,4-tetrahydro[2,6]napthyridinyl, and the like.

"Heteroarylsulphonylcarbamoyl" means a heteroaryl-SO$_2$—NH—C(=O)— group wherein the heteroaryl group is as herein described.

"Heterocyclenyl" means a non-aromatic monocyclic or multicyclic hydrocarbon ring system of about 3 to about 13 carbon atoms, preferably about 5 to about 13 carbon atoms, in which one or more of the carbon atoms in the ring system is/are replaced by an atome of an element other than carbon (i.e., a "heteroatom"), for example nitrogen, oxygen or sulfur, and which contains at least one carbon-carbon double bond or carbon-nitrogen double bond. Preferred ring sizes of rings of the ring system include about 5 to 6 ring atoms. The designation of aza, oxa or thia as a prefix before the heterocyclenyl means that at least a nitrogen, oxygen or sulfur atom is present, respectively, as a ring atom. The heterocyclenyl group may be optionally substituted by one or more ring system substituents, wherein the "ring system substituent" is as defined herein. The nitrogen atom of an heterocyclenyl group may be a basic nitrogen atom. A nitrogen or sulphur atom of the heterocyclenyl group may also be optionally oxidized to the corresponding N-oxide, S-oxide or S,S-dioxide. Representative monocyclic azaheterocyclenyl groups include 1,2,3,4-tetrahydrohydropyridine; 1,2-dihydropyridyl; 1,4-dihydropyridyl; 1,2,3,6-tetrahydropyridine; 1,4,5,6-tetrahydropyrimidine; 2-pyrrolinyl; 3-pyrrolinyl; 2-imidazolinyl; 2-pyrazolinyl; 1,4,4a,5a,6,9,9a,9b-octahydro-dibenzofuran, and the like. Exemplary oxaheterocyclenyl groups include 3,4-dihydro-2H-pyran, dihydrofuranyl, and fluorodihydrofuranyl. Preferred is dihydrofuranyl. An exemplary multicyclic oxaheterocyclenyl group is 7-oxabicyclo[2.2.1]heptenyl. Preferred monocyclic thiaheterocycleny groups include dihydrothiophenyl and dihydrothiopyranyl; more preferred is dihydrothiophenyl. Preferred ring system substituents include amidino, halogen, hydroxy, alkoxycarbonylalkyl, carboxyalkyl and Y$^1$Y$^2$N— as defined herein.

"Heterocyclyl" means a non-aromatic saturated monocyclic or multicyclic ring system of about 3 to about 10 carbon atoms, preferably about 5 to about 10 carbon atoms, in which one or more of the carbon atoms in the ring system is/are replaced by an atom of an element other than carbon (i.e., a "heteratom"), for example nitrogen, oxygen or sulfur. Preferred ring sizes of rings of the ring system include about 5 to 6 ring atoms. The designation of aza, oxa or thia as a prefix before the heterocyclyl means that at least a nitrogen, oxygen or sulfur atom is present, respectively, as a ring atom. The heterocyclyl group may be optionally substituted by one or more "ring system substituents" which may be the same or different, and are as defined herein. The nitrogen atom(s) of an heterocyclyl may be a basic nitrogen atom. The nitrogen or sulphur atom(s) of the heterocyclyl may also be optionally oxidized to the corresponding N-oxide, S-oxide or S,S-dioxide. Representative monocyclic heterocyclyl groups include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, 2-thioxo-4-thiazolidinonyl, tetrahydrothiopyranyl, and the like. Preferred heterocyclyl groups include pyrrolidinyl, tetrahydrofuranyl, morpholinyl, piperidyl, Preferred heterocyclyl group substituents include alkyl, aralkyl, amidino, halogen, hydroxy, aralkoxycarbonyl, alkoxycarbonylalkyl, carboxyalkyl and Y$^1$Y$^2$N— as defined herein.

"Heterocyclylalkyl" means an heterocyclyl-alkyl- group wherein the heterocyclyl and alkyl portions are as herein described. Preferred heterocyclylalkyl groups contain a lower alkyl moiety. An exemplary heteroaralkyl group is tetrahydropyranylmethyl.

"Heterocyclylalkyloxyalkyl" means an heterocyclyl-alkyl-O-alkyl- group wherein the heterocyclyl and alkyls groups independently are as herein described. An exemplary heteroaralkyl group is tetrahydropyranylmethyloxymethyl.

"Heterocyclyloxy" means a heterocyclyl-O— group in which the heterocyclyl group is as defined herein. Exemplary heterocyclyloxy groups include quinuclidyloxy, pentamethylenesulfideoxy, tetrahydropyranyloxy, tetrahydrothiophenyloxy, pyrrolidinyloxy, tetrahydrofuranyloxy, 7-oxabicyclo[2.2.1]heptanyloxy, hydroxytetrahydropyranyloxy and hydroxy-7-oxabicyclo[2.2.1]heptanyloxy.

"Hydrate" means a solvate wherein the solvent molecules are $H_2O$.

"Hydroxyalkyl" means a HO-alkyl- group wherein alkyl is as herein defined. Preferred hydroxyalkyls contain lower alkyl. Exemplary preferred hydroxyalkyl groups include hydroxymethyl and 2-hydroxyethyl.

"Hygroscopicity" means sorption, implying an acquired amount or state of water sufficient to affect the physical or chemical properties of the substance (Eds. J. Swarbrick and J. C. Boylan, Encyclopedia of Pharmaceutical Technology, Vol. 10, p. 33).

"Liquid dosage form" means that the dose of the active compound to be administered to the patient is in liquid form, for example, a pharmaceutically acceptable emulsion, solution, suspension, syrup and elixir. In addition to the active compounds, the liquid dosage forms may contain inert diluents commonly used in the art, such as water or other solvents, solubilizing agents and emulsifiers, as, for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil and sesame oil, glycerol, tetrahydrofurfuryl alcohol, polyethylene glycols and fatty acid esters of sorbitan, or mixtures of these substances, and the like.

"Modulate" refers to the ability of a compound to either directly (by binding to the receptor as a ligand) or indirectly (as a precursor for a ligand or an inducer which promotes production of a ligand from a precursor) induce expression of a gene maintained under hormone control, or to repress expression of a gene maintained under such control.

"Patient" includes both human and other mammals.

"Pharmaceutical composition" refers to a composition comprising an active compound and at least one component selected from pharmaceutically acceptable carriers, diluents, adjuvants, excipients, vehicles, preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Examples of suspending agents include ethoxylated isostearyl alcohols, polyoxyethylene sorbitol and sorbitan esters, microcrystalline cellulose, aluminum metahydroxide, bentonite, agar-agar and tragacanth, and mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents that delay absorption, for example, aluminum monosterate and gelatin. Examples of suitable carriers, diluents, solvents or vehicles include water, ethanol, polyols, suitable mixtures thereof, vegetable oils (such as olive oil) and injectable organic esters such as ethyl oleate. Examples of excipients include lactose, sodium citrate, calcium carbonate, and dicalcium phosphate. Examples of disintegrating agents include starch, alginic acids and certain complex silicates. Examples of lubricants include magnesium stearate, sodium lauryl sulphate, talc, and high molecular weight polyethylene glycols.

"Pharmaceutically acceptable" means that, within the scope of sound medical judgment, the item is suitable for use in contact with the cells of humans and lower animals without causing undue toxicity, irritation, allergic response and the like, and is commensurate with a reasonable risk/benefit analysis.

"Pharmaceutically acceptable dosage forms" refers to dosage forms of the compound of the invention, and includes, for example, tablets, dragees, powders, elixirs, syrups, liquid preparations, including suspensions, sprays, inhalants tablets, lozenges, emulsions, and solutions, granules, capsules and suppositories, as well as liquid preparations for injections, including liposome preparations. Techniques and formulations generally may be found in Remington's Pharmaceutical Sciences, Mack Publishing Co., Easton, Pa., latest edition.

"Pharmaceutically acceptable ester" refers to esters which hydrolyze in vivo and include those that break down readily in the patient's body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

"Pharmaceutically acceptable prodrugs" as used herein refers to those prodrugs of the compounds of the present invention which are, within the scope of sound medical judgment, suitable for use in contact with the tissues of humans and lower animals without causing undue toxicity, irritation, allergic response, and the like, commensurate with a reasonable risk/benefit analysis, and are effective for their intended use, as well as the zwitterionic forms, where possible, of the compounds of the invention. The term "prodrug" refers to compounds that are rapidly transformed in vivo to yield the parent compound, for example by hydrolysis in blood. Functional groups which may be rapidly transformed, by metabolic cleavage, in vivo, may be formed by reaction with the carboxyl group of the compounds of this invention. They include, but are not limited to such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), and the like. Because of the ease with which the metabolically cleavable groups of the compounds of this invention are cleaved in vivo, compounds bearing such groups act as pro-drugs. The compounds bearing the metabolically cleavable groups have the advantage that they may exhibit improved bioavailability as a result of enhanced solubility and/or rate of absorption conferred upon the parent compound by virtue of the presence of the metabolically cleavable group. A thorough discussion of prodrugs is provided in Design of Prodrugs, H. Bundgaard, ed., Elsevier, 1985; Methods in Enzymology, K. Widder et al, Ed., Academic Press, 42, p.309–396, 1985; A Textbook of Drug Design and Developement, Krogsgaard-Larsen and H. Bundgaard, ed., Chapter 5; "Design and Applications of Prodrugs" p.113–191, 1991; Advanced Drug Delivery Reviews, H. Bundgard, 8, p.1–38, 1992; Journal of Pharmaceutical Sciences, 77, p. 285, 1988; Chem. Pharm. Bull., N. Nakeya et al, 32, p. 692, 1984; Pro-drugs as Novel Delivery Systems, T. Higuchi and V. Stella, Vol. 14 of the A.C.S. Symposium Series, and Bioreversible Carriers in Drug Design, Edward B. Roche, ed., American Pharmaceutical Association and Pergamon Press, 1987, the contents of all of which are hereby incorporated herein by reference.

"Pharmaceutically acceptable salts" refers to the relatively non-toxic, inorganic and organic acid addition salts, and base addition salts, of compounds of the present invention. These salts can be prepared in situ during the final isolation and purification of the compounds. In particular, acid addition salts can be prepared by separately reacting the purified compound in its free base form with a suitable organic or inorganic acid and isolating the salt thus formed. Representative acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactobionate, sulphamates, malonates, salicylates, propionates, methylene-bis-β-hydroxynaphthoates, gentisates, isothionates, di-p-toluoyltartrates, methane-sulphonates, ethanesulphonates, benzenesulphonates, p-toluenesulphonates, cyclohexylsulphamates, quinates, laurylsulphonate salts, and the like. (See, for example S. M. Berge, et al., "Pharmaceutical Salts," J. Pharm. Sci., 66: p.1–19 (1977) the contents of which are hereby incorporated herein by reference.) Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases, which include sodium hydride, sodium hydroxide, potassium hydroxide, calcium hydroxide, aluminium hydroxide, lithium hydroxide, magnesium hydroxide, and zinc hydroxide. Suitable amine base addition salts are prepared from amines which have sufficient basicity to form a stable salt, and preferably include those amines which are frequently used in medicinal chemistry because of their low toxicity and acceptability for medical use, such as ammonia, ethylenediamine, N-methylglucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

"Solid dosage form" means that the dosage form of the compound of the invention is in solid form, for example, as capsules, tablets, pills, powders, dragees or granules. In such solid dosage forms, the compound of the invention is admixed with at least one inert customary excipient (or carrier), such as sodium citrate or dicalcium phosphate or one or more (a) fillers or extenders, for example, starches, lactose, sucrose, glucose, mannitol and silicic acid, (b) binders, for example, carboxymethylcellulose, alignates, gelatin, polyvinylpyrrolidone, sucrose and acacia, (c) humectants, as, for example, glycerol, (d) disintegrating agents, for example, agar-agar, calcium carbonate, potato or tapioca starch, alginic acid, certain complex silicates and sodium carbonate, (e) solution retarders, for example, paraffin, (f) absorption accelerators, for example, quaternary ammonium compounds, (g) wetting agents, for example, cetyl alcohol and glycerol monostearate, (h) adsorbents, for example, kaolin and bentonite, (i) lubricants, for example, talc, calcium stearate, magnesium stearate, solid polyethylene glycols, and sodium lauryl sulfate, (j) opacifying agents, (k) buffering agents, and agents which release the compound (s) of the invention in a certain part of the intestinal tract in a delayed manner.

"Solid support" is represented as "◉" and means a substrate which is inert to the reagents and reaction conditions described herein, as well as being substantially insoluble in the media used. Representative solid supports include inorganic substrates such as kieselguhr, silica gel, and controlled pore glass; organic polymers including polystyrene, including 1–2% copolystyrene divinyl benzene (gel form) and 20–40% copolystyrene divinyl benzene (macro porous form), polypropylene, polyethylene glycol, polyacrylamide, cellulose, and the like; and composite inorganic/polymeric compositions such as polyacrylamide supported within a matrix of kieselguhr particles. See J. M. Stewart and J. D. Young, *Solid-phase Peptide Synthesis*, 2nd. Ed., Pierce Chemical Co. (Chicago, Ill., 1984).

In addition, "solid support" includes a solid support as described above which is affixed to a second inert support such as the pins described in Technical Manual, Multipin™ SPOC, Chiron Technologies (1995) and references therein which comprise a detachable polyethylene- or polyproylene-based head grafted with an amino functionalized methacrylate copolymer and an inert stem.

In addition, "solid support" includes polymeric supports such as the polyethylene glycol supports described by Janda et al., *Proc. Natl. Acad. Sci. USA*, 92, 6419–6423 (1995) and S. Brenner, WO 95/16918, which are soluble in many solvents but can be precipitated by the addition of a precipitating solvent.

"Solvate" means a physical association of a compound of this invention with one or more solvent molecules. This physical association involves varying degrees of ionic and covalent bonding, including hydrogen bonding. In certain instances, the solvate will be capable of isolation, for example, when one or more solvent molecules are incorporated in the crystal lattice of the crystalline solid. "Solvate" encompasses both solution-phase and isolable solvates. Representative solvates include ethanolates, methanolates, and the like.

"Ring system substituents" mean substituents attached to aromatic or non-aromatic ring systems, and includes hydrogen, alkyl, alkenyl, alkynyl, aryl, heteroaryl, aralkyl, heteroaralkyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, aryldiazo, heteroaryldiazo, amidino, $Y^1Y^2N-$, $Y^1Y^2N$-alkyl-, $Y^1Y^2NCO-$ and $Y^1Y^2NSO_2-$, wherein $Y^1$ and $Y^2$ are independently selected from hydrogen, optionally substituted alkyl, optionally substituted aryl, optionally substituted aralkyl and optionally substituted heteroaralkyl, or, where the substituent is $Y^1Y^2N-$, then one of $Y^1$ and $Y^2$ may be acyl or aroyl as defined herein and the other of $Y^1$ and $Y^2$ is as defined previously, or where the substituent is $Y^1Y^2NCO$— or $Y^1Y^2NSO_2$—, $Y^1$ and $Y^2$ may also be taken together with the N atom through which $Y^1$ and $Y^2$ are linked to form a 4 to 7 membered heterocyclyl or heterocyclenyl. Preferred ring system substituents are alkoxycarbonyl, alkoxy, halo, aryl, aralkoxy, alkyl, hydroxy, aryloxy, nitro, alkylsulfonyl, heteroaryl, $Y^1Y^2N$—. Most preferred ring system substituents are selected from alkoxycarbonyl, halo, aryl, aralkoxy, aralkyl, alkyl, hydroxy, aryloxy, $Y^1Y^2N$—, oxo, cyano, nitro, and arylsulfinyl. When a ring system is saturated or partially saturated, the "ring system substituents" further include, methylene ($H_2C=$), oxo ($O=$), thioxo ($S=$).

"$Y^1Y^2N$—" means a substituted or unsubstituted amino group, wherein $Y^1$ and $Y^2$ are as herein described. Exemplary groups include amino ($H_2N$—), methylamino, dimethylamino, diethylamino, pyrrolidine, piperidine, benzylamino, or phenethylamino.

"$Y^1Y^2NCO$—" means a substituted or unsubstituted carbamoyl group, wherein $Y^1$ and $Y^2$ are as herein described. Exemplary groups are carbamoyl ($H_2NCO$—) and dimethylaminocarbamoyl ($Me_2NCO$—).

"$Y^1Y^2NSO_2$—" means a substituted or unsubstituted sulfamoyl group, wherein $Y^1$ and $Y^2$ are as herein described. Exemplary groups are aminosulfamoyl ($H_2NSO_2$—) and dimethylaminosulfamoyl ($Me_2NSO_2$—).

"Primary or secondary protected amine" means a group of the following formula $Y^aY^bN$— wherein one of $Y^a$ and $Y^b$ is $P^a$, a nitrogen protecting group, and the other of $Y^a$ and $Y^b$ is hydrogen, alkenyl, alkyl, aralkyl, aryl, fused arylcycloalkenyl, fused arylcycloalkyl, fused arylheterocyclenyl, fused arylheterocyclyl, cycloalkyl, cycloalkenyl, heteroaralkyl, heteroaryl, fused heteroarylcycloalkenyl, fused heteroarylcycloalkyl, fused heteroarylheterocyclenyl, fused heteroarylheterocyclyl, heterocyclenyl or heterocyclyl.

"Activated carboxylic acid" means a group of the formula LO—CO— wherein L is an aliphatic, aromatic or a resin moiety.

In a specific embodiment, the term "about" or "approximately" means within 20%, preferably within 10%, and more preferably within 5% of a given value or range.

Preferred Embodiments

One particular aspect of the present invention is directed to a method for preparing a cyclized compound selected from group of formulae consisting of 1,4-benzodiazepine-2,5-dione derivatives of general formulae (I), and (VII), diketopiperazine derivatives of general formula (II), ketopiperazine derivatives and dihydroquinoxalinone derivatives of general formula (III) and (VIII), dihydroimidazole derivatives of general formula (IV), lactam derivatives of general formula (V), 1,4-benzodiazepine-2,5-dione diketopiperazine derivatives of formula (VI), ketopiperazine derivatives of formula (XLII), cyclic urea derivatives of general formulae (L) and (LIII), and hydantoin derivatives of general formula (LV):—.

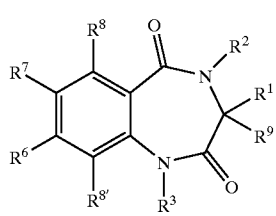
(I)

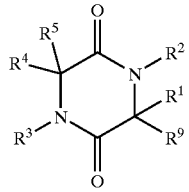
(II)

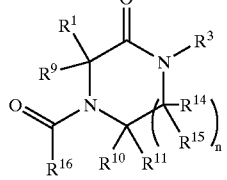
(III)

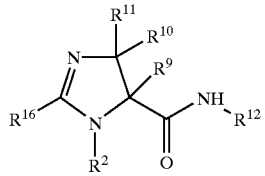
(IV)

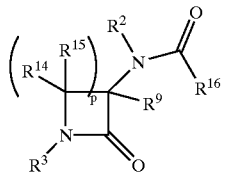
(V)

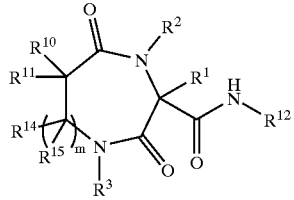
(VI)

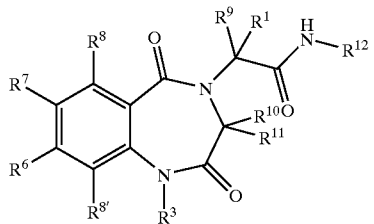
(VII)

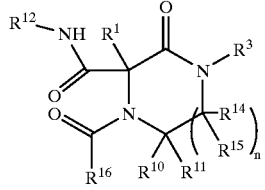
(VIII)

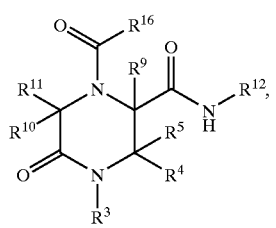
(XLII)

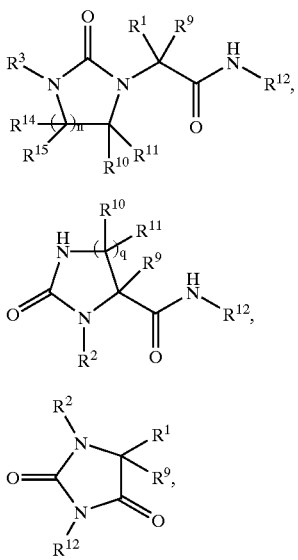

(L)

(LIII)

(LV)

wherein:

n=1 or 2;

m=0 or 1;

p=2;

q=1 or 2;

$R^1$ and $R^9$ independently are selected from hydrogen, alkenyl, alkyl, aralkenyl, aralkyl, aryl, fused arylcycloalkenyl, fused arylcycloalkyl, fused arylheterocyclenyl, fused arylheterocyclyl, cycloalkyl, cycloalkenyl, heteroaralkenyl, heteroaralkyl, heteroaryl, fused heteroarylcycloalkenyl, fused heteroarylcycloalkyl, fused heteroarylheterocyclenyl, fused heteroarylheterocyclyl, heterocyclenyl, and heterocyclyl;

$R^2$ is selected from hydrogen, alkenyl, alkyl, aralkyl, aryl, fused arylcycloalkenyl, fused arylcycloalkyl, fused arylheterocyclenyl, fused arylheterocyclyl, cycloalkyl, cycloalkenyl, heteroaralkyl, heteroaryl, fused heteroarylcycloalkenyl, fused heteroarylcycloalkyl, fused heteroarylheterocyclenyl, fused heteroarylheterocyclyl, heterocyclenyl and heterocyclyl, or $R^1$ and $R^2$ taken together with the nitrogen atom and carbon atoms through which $R^1$ and $R^2$ are linked form a 6 membered heterocyclyl;

$R^3$ is selected from hydrogen, alkenyl, alkyl, aralkyl, aryl, fused arylcycloalkenyl, fused arylcycloalkyl, fused arylheterocyclenyl, fused arylheterocyclyl, cycloalkyl, cycloalkenyl, heteroaralkyl, heteroaryl, fused heteroarylcycloalkenyl, fused heteroarylcycloalkyl, fused heteroarylheterocyclenyl, fused heteroarylheterocyclyl, heterocyclenyl and heterocyclyl.

$R^4$ or $R^5$ independently are selected from hydrogen, alkenyl, alkyl, aryl, alkynyl, aralkenyl, aralkynyl, fused arylcycloalkenyl, fused arylcycloalkyl, fused arylheterocyclenyl, fused arylheterocyclyl, heteroaralkenyl, heteroaralkynyl, fused heteroarylcycloalkenyl, fused heteroarylcycloalkyl, fused heteroarylheterocyclenyl, fused heteroarylheterocyclyl, heteroaryl, aralkyl, heteroaralkyl, cycloalkyl, cycloalkenyl, heterocyclyl and heterocyclenyl, or $R^4$ and $R^5$ taken together with the carbon atom through which $R^4$ and $R^5$ are linked form a 3 to 7 membered cycloalkyl or cycloalkenyl;

$R^6$, $R^7$, $R^8$ and $R^{8'}$ independently are selected from hydrogen, alkenyl, alkenyloxy, alkoxy, alkyl, aryl, alkylsulfinylcarbamoyl, alkynyl, alkynyloxy, aralkenyl, aralkylsulfonyl, aralkynyl, fused arylcycloalkenyl, fused arylcycloalkyl, fused arylheterocyclenyl, fused arylheterocyclyl, aryloxycarbonyl, cycloalkyloxy, heteroaralkenyl, heteroaralkyloxy, heteroaralkynyl, heteroaroyl, fused heteroarylcycloalkenyl, fused heteroarylcycloalkyl, fused heteroarylheterocyclenyl, fused heteroarylheterocyclyl, heteroarylsulphonylcarbamoyl, heterocyclyloxy, heteroaryl, aralkyl, heteroaralkyl, hydroxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, aryldiazo, heteroaryldiazo, amidino, $Y^1Y^2N—$, $Y^1Y^2NCO—$ and $Y^1Y^2NSO_2—$, wherein $Y^1$ and $Y^2$ are independently hydrogen, alkyl, aryl, aralkyl or heteroaralkyl, or, where the substituent is $Y^1Y^2N—$, then one of $Y^1$ and $Y^2$ may be acyl or aroyl and the other of $Y^1$ and $Y^2$ is as defined previously, or, where the substituent is $Y^1Y^2NCO—$ or $Y^1Y^2NSO_2—$, $Y^1$ and $Y^2$ may also be taken together with the N atom through which $Y^1$ and $Y^2$ are linked form a 4 to 7 membered heterocyclyl or heterocyclenyl, or $R^3$ and $R^{8'}$ taken together with the nitrogen atom and carbon atoms through which $R^3$ and $R^{8'}$ are linked form a 5 to 7 membered heterocyclyl or heterocyclenyl, or two adjacent substituents selected from the substituents $R^6$, $R^7$, $R^{8'}$ and $R^8$ taken together with the aryl carbon atoms through which the two adjacent substituents are linked form a 5 to 7 membered cycloalkyl or a cycloalkenyl, heterocyclyl or heterocyclenyl, or 6 membered aryl or 5 or 6 membered heteroaryl;

$R^{14}$, $R^{15}$, $R^{10}$ and $R^{11}$ independently are selected from hydrogen, alkenyl, alkyl, aryl, alkynyl, aralkenyl, aralkynyl, fused arylcycloalkenyl, fused arylcycloalkyl, fused arylheterocyclenyl, fused arylheterocyclyl, heteroaralkenyl, heteroaralkynyl, fused heteroarylcycloalkenyl, fused heteroarylcycloalkyl, fused heteroarylheterocyclenyl, fused heteroarylheterocyclyl, heteroarylsulphonylcarbamoyl, heteroaryl, aralkyl, heteroaralkyl, cycloalkyl, cycloalkenyl, heterocyclyl, heterocyclenyl, or, when n=1, $R^{11}$ and $R^{14}$ are absent and $R^{10}$ and $R^{15}$ taken together with the adjacent carbon atoms through which they are linked, form a 6 membered aryl or 5 or 6 membered heteroaryl;

or, when n=1, and $R^{11}$ and $R^{14}$ are present, $R^{10}$ and $R^{15}$ taken together with the adjacent carbon atoms through which they are linked form a 5 to 7 membered cycloalkyl or a cycloalkenyl, heterocyclyl or heterocyclenyl;

or, when n=2, adjacent $R^{11}$ and $R^{14}$ are absent and $R^{10}$ and adjacent $R^{15}$ taken together with the adjacent carbon atoms through which they are linked form a 6 membered aryl or 5 to 6 membered heteroaryl;

or when n=2, and $R^{11}$ and $R^{14}$ are present, $R^{10}$ and adjacent $R^{15}$ taken together with the adjacent carbon atoms through which they are linked form a 5 to 7 membered cycloalkyl or a cycloalkenyl, heterocyclyl or heterocyclenyl; or when n or p=2, the adjacent $R^{14}$ and $R^{14}$ are absent and the adjacent $R^{15}$ and $R^{15}$ taken together with the adjacent carbon atoms through which they are linked, form a 6 membered aryl or 5 or 6 membered heteroaryl;

or when n or p=2, and the adjacent $R^{14}$ and $R^{14}$ are present, adjacent $R^{15}$ and $R^{15}$ taken together with the adjacent carbon atoms through which they are linked form a 5 to 7 membered cycloalkyl or a cycloalkenyl, heterocyclyl or heterocyclenyl; or when m=1, $R^{11}$ and $R^{14}$ are absent and $R^{10}$ and $R^{15}$, taken together with the adjacent carbon atoms through which they are linked, form a 6 membered aryl or 5 or 6 membered heteroaryl;

or when m=1, and $R^{11}$ and $R^{14}$ are present, $R^{10}$ and $R^{15}$, taken together with the adjacent carbon atoms through which they are linked, form a 5 to 7 membered cycloalkyl or a cycloalkenyl, heterocyclyl or heterocyclenyl;

$R^{12}$ is selected from alkenyl, alkyl, aralkyl, aryl, fused arylcycloalkenyl, fused arylcycloalkyl, fused arylheterocyclenyl, fused arylheterocyclyl, cycloalkyl, cycloalkenyl, heteroaralkyl, heteroaryl, fused heteroarylcycloalkenyl, fused heteroarylcycloalkyl, fused heteroarylheterocyclenyl, fused heteroarylheterocyclyl, heterocyclenyl and heterocyclyl; and $R^{16}$ is selected from hydrogen, alkenyl, alkyl, aralkyl, aryl, fused arylcycloalkenyl, fused arylcycloalkyl, fused arylheterocyclenyl, heteroaralkenyl, fused arylheterocyclyl, cycloalkyl, cycloalkenyl, heteroaralkyl, heteroaryl, fused heteroarylcycloalkenyl, fused heteroarylcycloalkyl, fused heteroarylheterocyclenyl, fused heteroarylheterocyclyl, heterocyclenyl and heterocyclyl, or $R^9$ and $R^{16}$ together with the carbon atoms and nitrogen atom though which they are attached form a 5–8 membered heterocyclyl group.

In one aspect, this invention is directed to a solution phase synthesis of a compound of formula (I) via a '3-step, one pot' procedure, employing the Ugi multi-component reaction (MCR) (Ugi, I., Angew. Chem. Int. Ed. Engl., 1962, 1, 8) comprising reacting a nitrogen-protected amino acid of formula (XIV) with an aldehyde or ketone of formula (XV), an amine of formula (XVI), and a non resin bound isonitrile of formula (IX) to form an intermediate compound of formula (XVII), and nitrogen-deprotection of the intermediate compound, and cyclization to form the compound of formula (I). Hulme, C.; Tang, S-Y.; Burns, C. J.; Morize, I,; Labaudiniere, R. J. Org. Chem. 1998, 63, 8021.

In another aspect, this invention is directed to a solid phase synthesis of a compound of formula (I) via a '3-step, one pot' procedure, employing the Ugi multi-component reaction (MCR) (Ugi, I., Angew. Chem. Int. Ed. Engl., 1962, 1, 8) comprising reacting a nitrogen-protected amino acid of formula (XIV) with an aldehyde or ketone of formula (XV), an amine of formula (XVI), and a resin bound isonitrile selected from (IXa) and (XVIII) to form the respective intermediate resin bound compound, nitrogen-deprotection of the intermediate compound, and cyclization and decoupling of the resin to form the compound of formula (I).

In one aspect, this invention is directed to a solution phase synthesis of a compound of formula (Ia) via a '3-step, one pot' procedure, employing the Ugi multi-component reaction (MCR) (Ugi, I., Angew. Chem. Int. Ed. Engl., 1962, 1, 8) comprising reacting a nitrogen-protected amino acid of formula (XIV) with an aldehyde or ketone of formula (XVa), an amine of formula (XVIa), and a non resin bound isonitrile of formula (IX) to form an intermediate compound of formula (XVIIa), and nitrogen-deprotection of the intermediate compound, and cyclization to form the compound of formula (Ia).

In another aspect, this invention is directed to a solid phase synthesis of a compound of formula (Ia) via a '3-step, one pot' procedure, employing the Ugi multi-component reaction (MCR) (Ugi, I., Angew. Chem. Int. Ed. Engl., 1962, 1, 8) comprising reacting a nitrogen-protected amino acid of formula (XIV) with an aldehyde or ketone of formula (XVa), an amine of formula (XVIa), and a resin bound isonitrile selected from (IXa) and (XVIII) to form the respective intermediate resin bound compound, nitrogen-deprotection of the intermediate compound, and cyclization and decoupling of the resin to form the compound of formula (Ia).

In another aspect, this invention is directed to a solution phase synthesis of a compound of formula (II) via a '3-step, one pot' procedure, employing the Ugi multi-component reaction (MCR) (Ugi, I., Angew. Chem. Int. Ed. Engl., 1962, 1, 8) comprising a nitrogen-protected amino acid of formula (XXII) with an aldehyde or ketone of formula (XV), an amine of formula (XVI), and a non resin bound isonitrile of formula (IX) to form an intermediate compound of formula (XXIII), and nitrogen-deprotection of the intermediate compound and cyclization to form the compound of formula (II). Hulme, C.; Morrissette, M. M.; Volz, F. A.; Burns, C. J. Tetrahedron Lett. 1998, 39, 113.

In another aspect, this invention is directed to a solid phase synthesis of a compound of formula (II) via a '3-step, one pot' procedure, employing the Ugi multi-component reaction (MCR) (Ugi, I., Angew. Chem. Int. Ed. Engl., 1962, 1, 8) comprising reacting a nitrogen-protected amino acid of formula (XXII) with an aldehyde or ketone of formula (XV), an amine of formula (XVI), and a resin bound isonitrile selected from (IXa) and (XVIII) to form the respective intermediate resin bound compound, nitrogen-deprotection of the intermediate compound, and cyclization and decoupling of the resin to form the compound of formula (II).

In another aspect, this invention is directed to a solution phase synthesis of a compound of formula (IIa) via a '3-step, one pot' procedure, employing the Ugi multi-component reaction (MCR) (Ugi, I., Angew. Chem. Int. Ed. Engl., 1962, 1, 8) comprising a nitrogen-protected amino acid of formula (XXII) with an aldehyde or ketone of formula (XVa), an amine of formula (XVIa), and a non resin bound isonitrile of formula (IX) to form an intermediate compound of formula (XXIIIa), and nitrogen-deprotection of the intermediate compound and cyclization to form the compound of formula (IIa).

In another aspect, this invention is directed to a solid phase synthesis of a compound of formula (IIa) via a '3-step, one pot' procedure, employing the Ugi multi-component reaction (MCR) (Ugi, I., Angew. Chem. Int. Ed. Engl., 1962, 1, 8) comprising reacting a nitrogen-protected amino acid of formula (XXII) with an aldehyde or ketone of formula (XVa), an amine of formula (XVIa), and a resin bound isonitrile selected from (IXa) and (XVIII) to form the respective intermediate resin bound compound (XXIIIa), nitrogen-deprotection of the intermediate compound, and cyclization and decoupling of the resin to form the compound of formula (IIa).

In another aspect, this invention is directed to a solution phase synthesis of a compound of formula (III) via a '3-step, one pot' procedure, employing the Ugi multi-component reaction (MCR) (Ugi, I., Angew. Chem. Int. Ed. Engl., 1962, 1, 8) comprising reacting an acid of formula (XXVI) with an aldehyde or ketone of formula (XV), a diamine of formula (XXVII), and a non resin bound isonitrile of formula (IX) to form an intermediate compound of formula (XXVIII) and nitrogen-deprotection of the intermediate compound and cyclization to form a compound of formula (III). Hulme, C.; Peng, J.; Louridas, B.; Menard, P.; Krolikowski, P.; Kumar, N. V. *Tetrahedron Lett.* 39, 7227.

In another aspect, this invention is directed to a solid phase synthesis of a compound of formula (III) via a '3-step, one pot' procedure, employing the Ugi multi-comprising reaction (MCR) (Ugi, I., Angew. Chem. Int. Ed. Engl., 1962, 1, 8) combining reacting an acid of formula (XXVI) with an aldehyde or ketone of formula (XV), a diamine of formula (XXVII), and a resin bound isonitrile selected from (IXa) and (XVIII) to form the respective intermediate resin bound compound, nitrogen-deprotection of the intermediate compound and cyclization and decoupling of the resin to form the compound of formula (III).

In another aspect, this invention is directed to a solution phase synthesis of a compound of formula (IIIa) via a '3-step, one pot' procedure, employing the Ugi multi-component reaction (MCR) (Ugi, I., Angew. Chem. Int. Ed. Engl., 1962, 1, 8) comprising reacting an acid of formula (XXVIa) with a diamine of formula (XXVII), and a non resin bound isonitrile of formula (IX) to form an intermediate compound of formula (XXVIIIa) and nitrogen-deprotection of the intermediate compound and cyclization to form a compound of formula (IIIa).

In another aspect, this invention is directed to a solid phase synthesis of a compound of formula (IIIa) via a '3-step, one pot' procedure, employing the Ugi multi-comprising reaction (MCR) (Ugi, I., Angew. Chem. Int. Ed. Engl., 1962, 1, 8) combining reacting an acid of formula (XXVIa) with a diamine of formula (XXVII), and a resin bound isonitrile selected from (IXa) and (XVIII) to form the respective intermediate resin bound compound (XXVIII), nitrogen-deprotection of the intermediate compound and cyclization and decoupling of the resin to form the compound of formula (IIIa).

In another aspect, this invention is directed to a solution phase synthesis of a compound of formula (IV) via a '3-step, one pot' procedure, employing the Ugi multi-component reaction (MCR) (Ugi, I., Angew. Chem. Int. Ed. Engl., 1962, 1, 8) comprising reacting a nitrogen-protected amino aldehyde of formula (XXXIII) with acid of formula (XXVI), an amine of formula (XVI), and a non resin bound isonitrile of formula (IX) to form an intermediate compound of formula (XXXIV), and nitrogen-deprotection of the intermediate compound and cyclization to form a compound of formula (IV). The non-cyclized amines are removed via a solution phase scavenging step with the simultaneous addition of PS-DIEA or PS-tris(2-aminoethyl)amine (6 equiv.) and PS-NCO (3 equiv.) in dichloroethane. (Booth, R. J.; Hodges, J. C. *J. Am. Chem. Soc.*1997, 119, 4882. Flynn, D. L.; Crich, J. Z.; Devraj, R. V.; Hockerman, S. L.; Parlow, J. J.; South, M. S.; Woodward, S. *J. Am. Chem. Soc.* 1997, 119, 4874. Purchased from Argonaut® technologies (PS-DIEA= polystyrene bound disopropylethylamine)).

In another aspect, this invention is directed to a solid phase synthesis of a compound of formula (V) via a '3-step, one pot' procedure, employing the Ugi multi-component reaction (MCR) (Ugi, I., Angew. Chem. Int. Ed. Engl., 1962, 1, 8) comprising reacting a nitrogen-protected amino aldehyde or ketone of formula (XXXV), an amine of formula (XVI), an acid of formula (XXVI) and a resin bound isonitrile selected from (IXa) or (XVIII) to form the respective intermediate resin bound compound, nitrogen-deprotection of the intermediate compound, and cyclization and decoupling of the resin to form the compound of formula (V).

In another aspect, this invention is directed to a solution phase synthesis of a compound of formula (VI) via a '3-step, one pot' procedure, employing the Ugi multi-component reaction (MCR) (Ugi, I., Angew. Chem. Int. Ed. Engl., 1962, 1, 8) comprising a nitrogen-protected amino acid of formula (XIV) with an aldehyde or ketone of formula (XXXVII), an amine of formula (XVI), and a non resin bound isonitrile of formula (IX) to form an intermediate compound of formula (XXXVIII) and nitrogen-deprotection of the intermediate compound and cyclization to form a compound of formula (VI).

In another aspect, this invention is directed to a solid phase synthesis of a compound of formula (VI) via a '3-step, one pot' procedure, employing the Ugi multi-component reaction (MCR) (Ugi, I., Angew. Chem. Int. Ed. Engl., 1962, 1, 8) comprising reacting a nitrogen-protected amino acid of formula (XIV) with an aldehyde or ketone of formula (XXXVII), an amine of formula (XVI), and a resin bound isonitrile of formula (XVIII) to form an intermediate compound and nitrogen-deprotection of the intermediate compound, and cyclization and decoupling of the resin to form a compound of formula (VI).

In another aspect, this invention is directed to a solution phase synthesis of a compound of formula (VII) via a '3-step, one pot' procedure, employing the Ugi multi-component reaction (MCR) (Ugi, I., Angew. Chem. Int. Ed. Engl., 1962, 1, 8) comprising reacting a nitrogen-protected amino acid of formula (XIV), a suitable non-resin bound α-amino ester, a non-resin bound isonitrile (IX), and an aldehyde or ketone of formula (XV), to form an intermediate compound and nitrogen-deprotection of the intermediate compound and cyclization to form a compound of formula (VII).

In another aspect, this invention is directed to a solid phase synthesis of a compound of formula (VII) via a '3-step, one pot' procedure, employing the Ugi multi-component reaction (MCR) (Ugi, I., Angew. Chem. Int. Ed. Engl., 1962, 1, 8) comprising reacting a nitrogen-protected amino acid of formula (XIV), a resin bound α-amino ester of formula (XXXIX), and a non-resin bound isonitrile (IX) and an aldehyde or ketone of formula (XV), to form the intermediate resin bound compound (XL) and nitrogen-deprotection of the intermediate compound, and cyclization and decoupling of the resin to form the compound of formula (VII).

In another aspect, this invention is directed to a solution phase synthesis of a compound of formula (VIII) via a '3-step, one pot' procedure, employing the Ugi multi-component reaction (MCR) (Ugi, I., Angew. Chem. Int. Ed. Engl., 1962, 1, 8) comprising reacting an acid of formula (XXVI) with a compound of formula (XXXVII), a diamine of formula (XXVII), and a non resin bound isonitrile of formula (IX) to form an intermediate compound of formula (XLI), nitrogen-deprotection of the intermediate compound and cyclization to form a compound of formula (VIII).

In another aspect, this invention is directed to a solution phase synthesis of a compound of formula (VIII) via a '3-step, one pot' procedure, employing the Ugi multi-component reaction (MCR) (Ugi, I., Angew. Chem. Int. Ed. Engl., 1962, 1, 8) comprising an acid of formula (XXVI) with a compound of formula (XXXVII), a diamine of formula (XXVIIa), and a non resin bound isonitrile of formula (IX) to form an intermediate compound of formula (XLI), nitrogen-deprotection of the intenrediate compound and cyclization to form a compound of formula (VIII).

In another aspect, this invention is directed to a solid phase synthesis of a compound of formula (VIII) via a '3-step, one pot' procedure, employing the Ugi multi-component reaction (MCR) (Ugi, I., Angew. Chem. Int. Ed. Engl., 1962, 1, 8) comprising reacting an acid of formula (XXVI) with (XXXVII), a diamine of formula (XXVII), and a resin bound isonitrile of formula (IXa) or (XVIII) to form an intermediate, nitrogen-deprotection of the intermediate compound and cyclization to form a compound of formula (VIII), wherein $R^{12}$ represents the resin portion of the resin bound isonitrile derivative.

In another aspect, this invention is directed to a solid phase synthesis of a compound of formula (XLII) via a '3-step, one pot' procedure, employing the Ugi multi-component reaction (MCR) (Ugi, I., Angew. Chem. Int. Ed. Engl., 1962, 1, 8) comprising reacting a nitrogen-protected amino acid of formula (XLIII), a resin bound α-amino ester of formula (XXXIX), a non-resin bound isonitrile (IX) and an acid of formula (XXVI), to form the intermediate resin bound compound (XLIX), nitrogen-deprotection of the intermediate compound and cyclization and decoupling of the resin to form the compound of formula (XLII).

In another aspect, this invention is directed to a solution phase synthesis of a compound of formula (L) via a '3-step, one pot' procedure, employing the Ugi multi-component reaction (MCR) (Ugi, I., Angew. Chem. Int. Ed. Engl., 1962, 1, 8) comprising an acid of formula (LI) with an aldehyde or ketone of formula (XV), a diamine of formula (XXVII), and a non resin bound isonitrile of formula (IX) to form an intermediate compound of formula (LII), nitrogen-deprotection of the intermediate compound and cyclization to form a compound of formula (L).

In another aspect, this invention is directed to a solid phase synthesis of a compound of formula (L) via a '3-step, one pot' procedure, employing the Ugi multi-component reaction (MCR) (Ugi, I., Angew. Chem. Int. Ed. Engl., 1962, 1, 8) comprising reacting an acid of formula (LI) with an aldehyde or ketone of formula (XV), a diamine of formula (XXVII), and a resin bound isonitrile of formula (IXa) or (XVIII) to form an intermediate, nitrogen-deprotection of the intermediate compound and cyclization to form a compound of formula (L).

In another aspect, this invention is directed to a solution phase synthesis of a compound of formula (LIII) via a '3-step, one pot' procedure, employing the Ugi multi-component reaction (MCR) (Ugi, I., Angew. Chem. Int. Ed. Engl., 1962, 1, 8) comprising an acid of formula (LI) with an aldehyde or ketone of formula (XXXIII), an amine of formula (VI), and a non resin bound isonitrile of formula (IX) to form an intermediate compound of formula (LIV), nitrogen-deprotection of the intermediate compound and cyclization to form a compound of formula (LIII).

In another aspect, this invention is directed to a solid phase synthesis of a compound of formula (LIII) via a '3-step, one pot' procedure, employing the Ugi multi-component reaction (MCR) (Ugi, I., Angew. Chem. Int. Ed. Engl., 1962, 1, 8) comprising reacting an acid of formula (LI) with an aldehyde or ketone of formula (XXXIII), an amine of formula (XVI), and a resin bound isonitrile of formula (IXa) or (XVIII) to form an intermediate of formula (LIV), nitrogen-deprotection of the intermediate compound (LIV) and cyclization to form a compound of formula (LIII).

In another aspect, this invention is directed to a solid phase synthesis of a compound of formula (LV) via a '3-step, one pot' procedure, employing the Ugi multi-component reaction (MCR) (Ugi, I., Angew. Chem. Int. Ed. Engl., 1962, 1, 8) comprising reacting an acid of formula (LI) with an aldehyde or ketone of formula (XV), an amine of formula (XVI), and a resin bound isonitrile of formula (IXa) or (XVIII) to form an intermediate of formula (LVI), nitrogen-deprotection of the intermediate compound (LVI) and cyclization to form a compound of formula (LV).

In another aspect, this invention is directed to a solution phase synthesis of a compound of formula (LV) via a '3-step, one pot' procedure, employing the Ugi multi-component reaction (MCR) (Ugi, I., Angew. Chem. Int. Ed. Engl., 1962, 1, 8) comprising an acid of formula (LI) with an aldehyde or ketone of formula (XV), an amine of formula (XVI), and a non resin bound isonitrile of formula (IX) to form an intermediate compound of formula (LVI), nitrogen-deprotection of the intermediate compound and cyclization to form a compound of formula (LV).

In another aspect, this invention is directed to the preparation of 1,4-benzodiazepine-2,5-dione derivatives of general formulae (I) and (VI), diketopiperazine derivatives of general formula (II), ketopiperazine derivatives and dihydroquinoxalinone derivatives of general formula (III) and (VIII), dihydroimidazole derivatives of general formula (IV), lactam derivatives of general formula (V), cyclic urea derivatives of general formulae (L) and (LIII), and hydantoin derivatives of general formula (LV), by solid phase synthesis employing the Ugi multi-component reaction (MCR) (Ugi, I., Angew. Chem. Int. Ed. Engl., 1962, 1, 8) using an isonitrile functionalized polymer resin linker (IXa) as described herein, followed by amine deprotection, cleavage from the resin and cyclization. The alkoxide and hydroxide safety-catch clipping strategy and subsequent solution phase cyclization offers similar advantages to a traceless linker (Plunkett, M. J.; Ellman, J. A. *J. Org Chem.* 1995, 60, 6006; Hulme, C.; Peng, J.; Morton, G.; Salvino, J. M.; Herpin, T.; Labaudiniere, R. *Tetrahedron Let.* 1998, 39,) in that no constant functionality derived from clipping remains at the end of the synthetic protocol.

In another aspect, this invention is directed to the preparation of ketopiperazine derivatives of general formula (XLII) and 1,4-benzodiazepine-2,5-dione derivatives of general formula (VII), by solid phase synthesis employing the Ugi multi-component reaction (MCR) (Ugi, I., Angew. Chem. Int. Ed. Engl., 1962, 1, 8) using an amino ester bound polymer resin linker (XXXIX) as described herein, followed by amine deprotection, cleavage from the resin and cyclization.

In another aspect, this invention is directed to the preparation and use of a novel resin bound isonitrile (IXa), deployed as a novel safety catch linker (Backes, B. J., Virgilio, A. A., Ellman, J. A. J. Am. Chem. Soc. 1996, 118, 3055; Kenner, G. W., McDermott, J. R., Sheppard, R. C. J. Chem. Soc., Chem. Commun. 1971, 636.) in the preparation of 1,4-benzodiazepine-2,5-dione derivatives of general formulae (I), (VI) and (VII), diketopiperazine derivatives of general formula (II), ketopiperazine derivatives and dihydroquinoxalinone derivatives of general formula (III) and (VIII), dihydroimidazole or imidazoline derivatives of general formula (IV), and lactam derivatives of general formula (V).

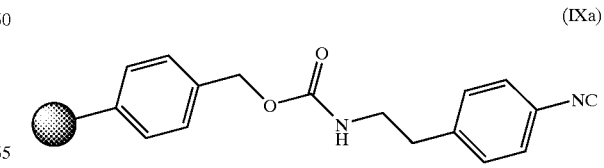

(IXa)

A preferred aspect of the compounds produced by the methods of the invention are those wherein:

n=1 or 2.

A preferred aspect of the compounds prepared by the methods of the invention is those compounds wherein:

m=0 or 1.

A preferred aspect of the compounds prepared by the methods of the invention is those compounds wherein:

$R^1$ is aralkyl, alkyl, aryl, heteroaryl, cycloalkyl, aralkenyl, heterocyclenyl or heterocyclyl.

A preferred aspect of the compounds prepared by the methods of the invention is those compounds wherein:

$R^1$ is hydrogen or alkyl.

A preferred aspect of the compounds prepared by the methods of the invention is those compounds wherein:

$R^2$ is selected from heteroaralkyl, aralkyl, alkyl, fused arylcycloalkyl, cycloalkyl, heterocyclyl, aryl, fused arylheterocyclenyl, and fused arylheterocyclyl.

A preferred aspect of the compounds prepared by the methods of the invention is those compounds wherein:

$R^3$ is selected from hydrogen, alkyl, aralkyl, aryl, fused arylcycloalkenyl, fused aralkylcycloalkyl, fused arylheterocyclenyl, fused arylheterocyclyl, cycloalkyl, cycloalkenyl, heteroaralkyl, heteroaryl, fused heteroarylcycloalkenyl, fused heteroarylcycloalkyl, fused heteroarylheterocyclenyl, fused heteroarylheterocyclyl, heterocyclenyl, and heterocyclyl.

A preferred aspect of the compounds prepared by the methods of the invention is those compounds wherein:

$R^4$ and $R^5$ independently are selected from hydrogen, alkyl, aralkyl, aryl, cycloalkyl, cycloalkenyl, heteroaralkyl, heteroaryl, heterocyclenyl or heterocyclyl.

A preferred aspect of the compounds prepared by the methods of the invention is those compounds wherein:

$R^6$, $R^7$ $R^8$ and $R^{8'}$ independently selected from hydrogen, alkenyl, alkyl, aryl, aralkyl, heteroaralkyl, hydroxy, aryloxy, alkoxy, aralkoxy, halo, nitro, cyano, alkylsulfonyl, arylsulfonyl, heteroarylsulfonyl, alkylthio, arylthio, heteroarylthio, heteroaralkylthio, cycloalkyl, heterocyclyl, fused arylcycloalkenyl, fused arylcycloalkyl, fused arylheterocyclenyl, fused arylheterocyclyl, fused heteroarylcycloalkenyl, fused heteroarylcycloalkyl, fused heteroarylheterocyclenyl, fused heteroarylheterocyclyl, heteroarylsulphonylcarbamoyl, heteroaryl, $Y^1Y^2N-$, or $Y^1Y^2NSO_2-$.

A preferred aspect of the compounds prepared by the methods of the invention is those compounds wherein:

$R^{15}$ is absent and $R^3$ and $R^{14}$ taken together with the nitrogen atom and carbon atom through which $R^3$ and $R^{14}$ are linked form a 6 membered aryl or 5 to 6 membered heteroaryl ring.

A preferred aspect of the compounds prepared by the methods of the invention is those compounds wherein:

$R^4$ and $R^5$ taken together with the carbon atom through which $R^4$ and $R^5$ are linked form a 3 to 7 membered cycloalkyl or cycloalkenyl ring.

A preferred aspect of the compounds prepared by the methods of the invention is those compounds wherein:

two adjacent substituents selected from the substituents $R^6$, $R^7$, $R^{8'}$ and $R^8$ taken together with the aryl carbon atoms through which the two adjacent substituents are linked form a 5 to 7 membered cycloalkyl or a cycloalkenyl, heterocyclyl or heterocyclenyl, or 6 membered aryl or 5 to 6 membered heteroaryl ring.

A preferred aspect of the compounds prepared by the methods of the invention is those compounds wherein:

$R^{10}$, $R^{11}$, $R^{14}$ and $R^{15}$ independently are selected from hydrogen, alkyl, heteroaralkyl, cycloalkyl, cycloalkenyl, heterocyclyl, heterocyclenyl, and aralkyl.

A preferred aspect of the compounds prepared by the methods of the invention is those compounds wherein:

n=1, $R^{11}$ and $R^{14}$ are absent and $R^{10}$ and $R^{15}$ taken together with the adjacent carbon atoms through which they are linked form a 6 membered aryl or 5 to 6 membered heteroaryl ring.

A preferred aspect of the compounds prepared by the methods of the invention is those compounds wherein:

n=1, $R^{10}$ and $R^{15}$ taken together with the adjacent carbon atoms through which they are linked form a 5 to 7 membered cycloalkyl or a cycloalkenyl, heterocyclyl or heterocyclenyl ring.

A preferred aspect of the compounds prepared by the methods of the invention is those compounds wherein:

n=2, adjacent $R^{11}$ and $R^{14}$ are absent, and $R^{10}$ and adjacent $R^{15}$ taken together with the adjacent carbon atoms through which they are linked form a 6 membered aryl or 5 to 6 membered heteroaryl ring.

A preferred aspect of the compounds prepared by the methods of the invention is those compounds wherein:

n=2, $R^{11}$ and $R^{14}$ are present, and $R^{10}$ and adjacent $R^{15}$ taken together with the adjacent carbon atoms through which they are linked form a 5 to 7 membered cycloalkyl or a cycloalkenyl, heterocyclyl or heterocyclenyl ring.

A preferred aspect of the compounds prepared by the methods of the invention is those compounds wherein:

n or p=2, adjacent $R^{14}$ and $R^{14}$ are absent, and adjacent $R^{15}$ and $R^{15}$ taken together with the adjacent carbon atoms through which they are linked form a 6 membered aryl or 5 to 6 membered heteroaryl ring.

A preferred aspect of the compounds prepared by the methods of the invention is those compounds wherein:

n or p=2, and adjacent $R^{14}$ and $R^{14}$ are present, and adjacent $R^{15}$ and $R^{15}$ taken together with the adjacent carbon atoms through which they are linked form a 5 to 7 membered cycloalkyl or a cycloalkenyl, heterocyclyl or heterocyclenyl ring.

A preferred aspect of the compounds prepared by the methods of the invention is those compounds wherein:

m=1, $R^{11}$ and $R^{14}$ are absent and $R^{10}$ and $R^{15}$ taken together with the adjacent carbon atoms through which they are linked form a 6 membered aryl or 5 to 6 membered heteroaryl ring.

A preferred aspect of the compounds prepared by the methods of the invention is those compounds wherein:

m=1, $R^{11}$ and $R^{14}$ are present, and $R^{10}$ and $R^{15}$ taken together with the adjacent carbon atoms through which they are linked form a 5 to 7 membered cycloalkyl or a cycloalkenyl, heterocyclyl or heterocyclenyl.

A preferred aspect of the compounds prepared by the methods of the invention is those compounds wherein:

$R^{16}$ is selected from hydrogen, alkenyl, alkyl, aralkyl, aryl, fused arylcycloalkenyl, fused arylcycloalkyl, fused arylheterocyclenyl, heteroaralkenyl, fused arylheterocyclyl, cycloalkyl, cycloalkenyl, heteroaralkyl, heteroaryl, fused heteroarylcycloalkenyl, fused heteroarylcycloalkyl, fused heteroarylheterocyclenyl, fused arylcycloalkyl, fused heteroarylheterocyclyl, heterocyclenyl and heterocyclyl.

A preferred aspect of the compounds prepared by the methods of the invention is those compounds wherein:

$R^{16}$ is selected from alkenyl, alkyl, aralkyl, aryl, fused arylcycloalkenyl, fused arylcycloalkyl, heteroaralkenyl, fused arylheterocyclenyl, fused arylheterocyclyl, cycloalkyl, cycloalkenyl, heteroaralkyl, heteroaryl, fused heteroarylcycloalkenyl, fused heteroarylcycloalkyl, fused heteroarylheterocyclenyl, fused heteroarylheterocyclyl, heterocyclenyl or heterocyclyl.

A more preferred aspect of the compounds prepared by the methods of the invention is those compounds wherein:

$R^6$, $R^7$ $R^8$ and $R^{8'}$ independently are selected from hydrogen, halo, alkoxy, alkyl, fused arylcycloalkenyl, fused arylcycloalkyl, fused arylheterocyclenyl, fused arylheterocyclyl, fused heteroarylcycloalkenyl, fused heteroarylcycloalkyl, fused heteroarylheterocyclenyl, fused heteroarylheterocyclyl, or heteroaryl.

A more preferred aspect of the compounds prepared by the methods of the invention is those compounds wherein:

$R^{10}$, $R^{11}$, $R^{14}$ and $R^{15}$ independently are selected from hydrogen, alkyl, and aralkyl.

A more preferred aspect of the compounds prepared by the methods of the invention is those compounds wherein:

$R^{12}$ is selected from alkyl, aralkyl, aryl, cycloalkyl, and heterocyclyl.

A more preferred aspect of the compounds prepared by the methods of the invention is those compounds wherein:

$R^{16}$ is selected from alkyl, fused arylheterocyclyl, aralkyl, cycloalkyl, heteroaryl, aryl, heteroaralkyl, alkenyl, heteroaralkenyl, fused arylcycloalkyl, fused arylheterocyclenyl, fused heteroarylcycloalkenyl, fused heteroarylheterocyclyl, heterocyclenyl and heterocyclyl.

A preferred compound prepared according to the invention is selected from the group of compounds having the following formulae:

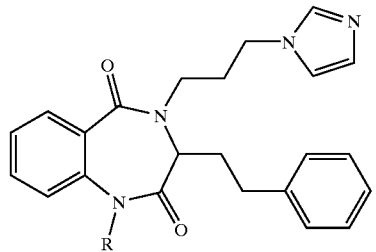

for R=H, or CH3

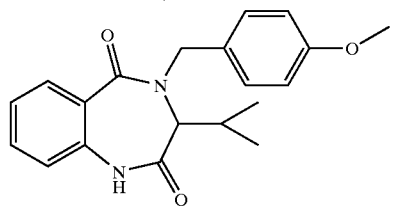

-continued

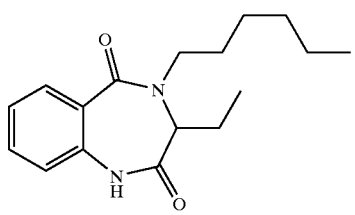

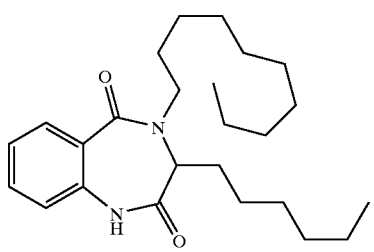

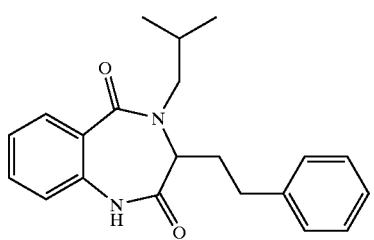

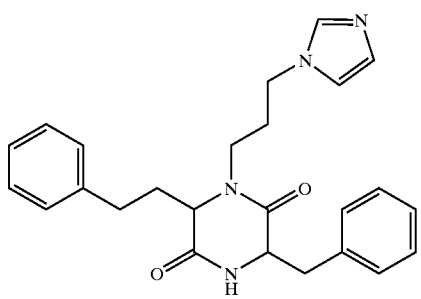

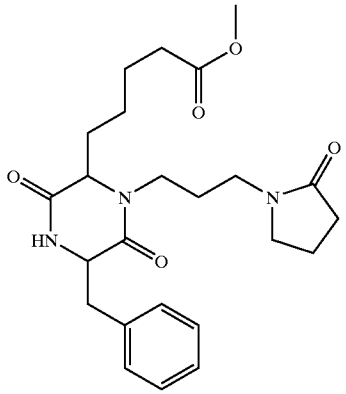

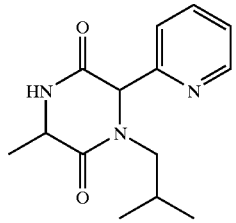

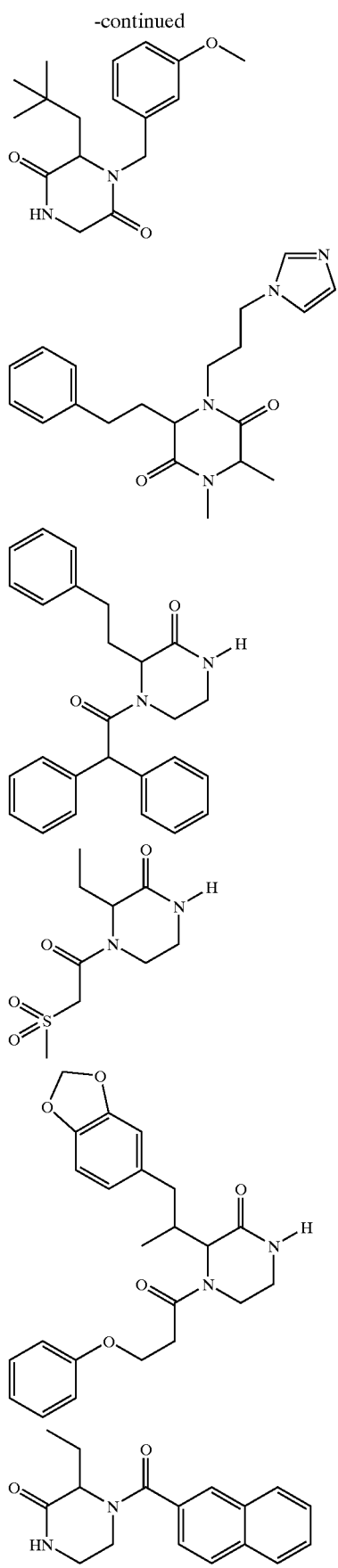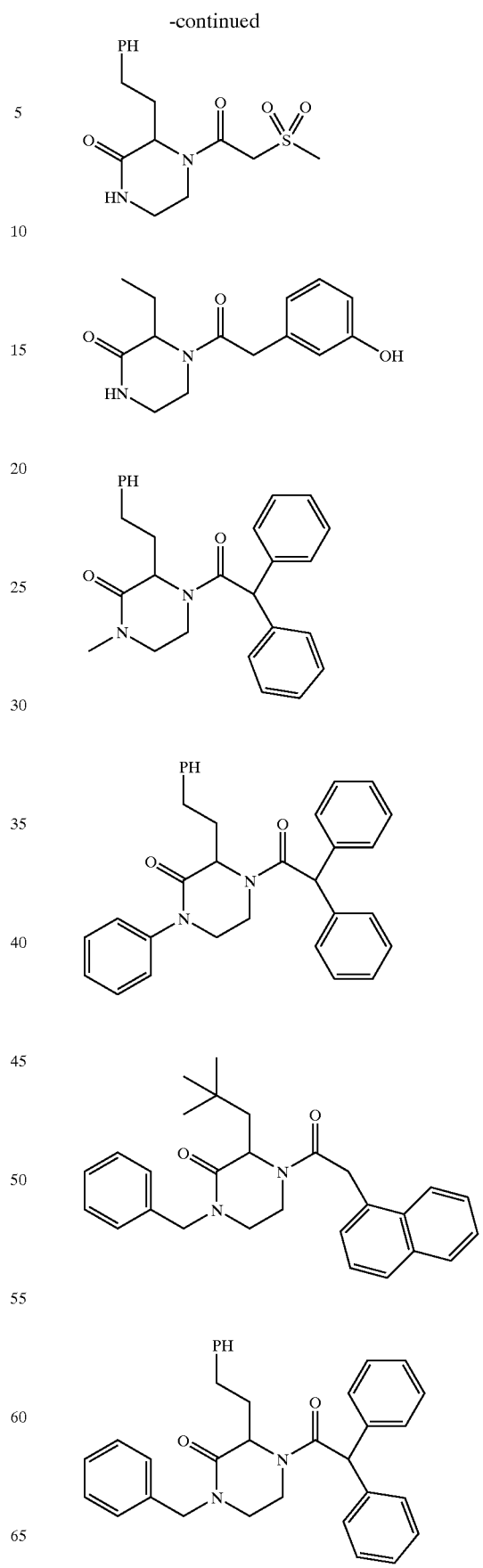

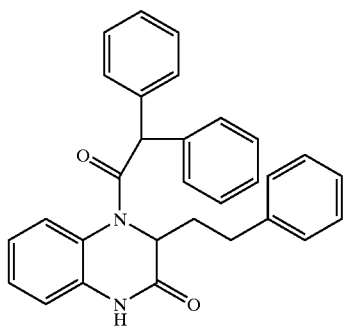
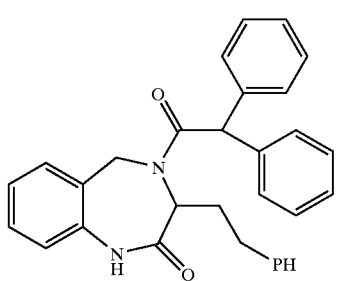
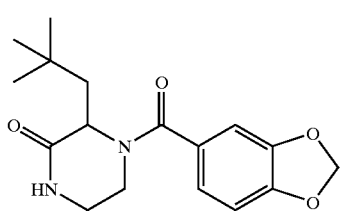
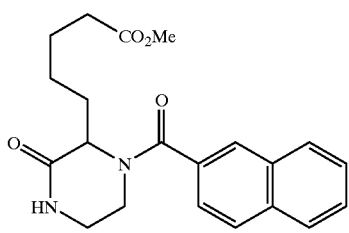
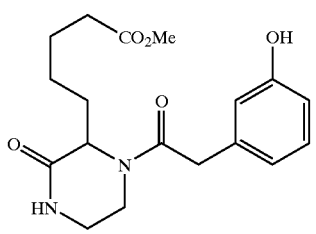
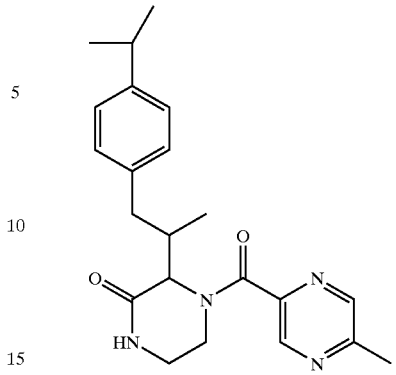
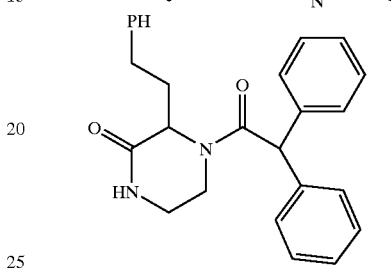
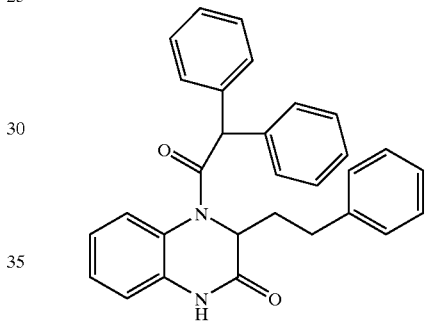
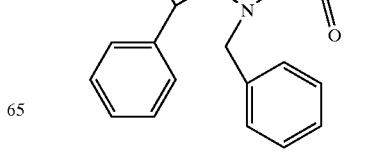

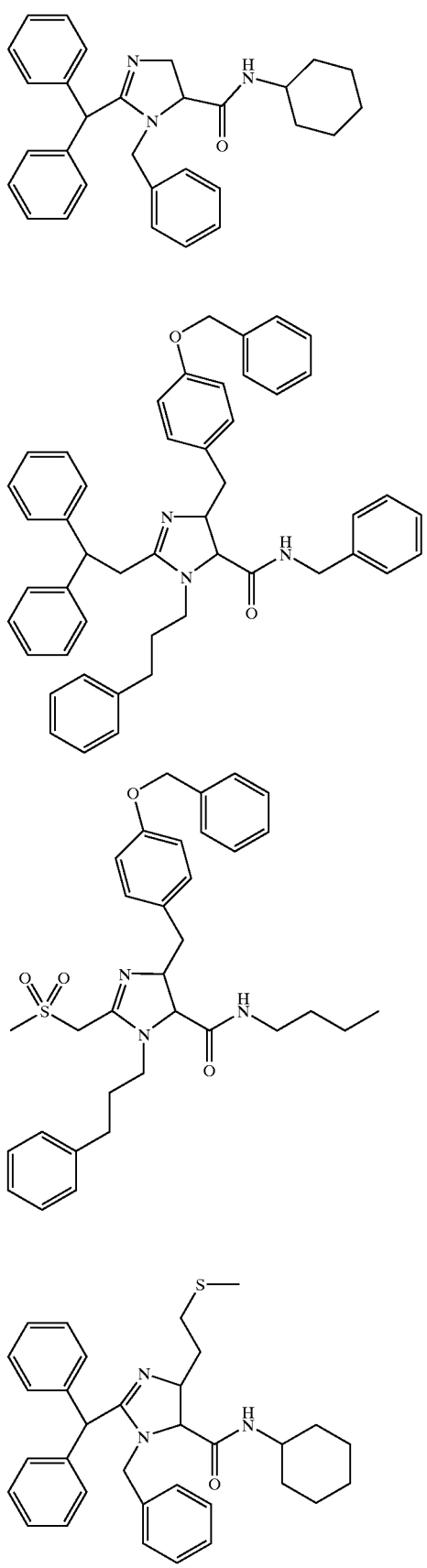
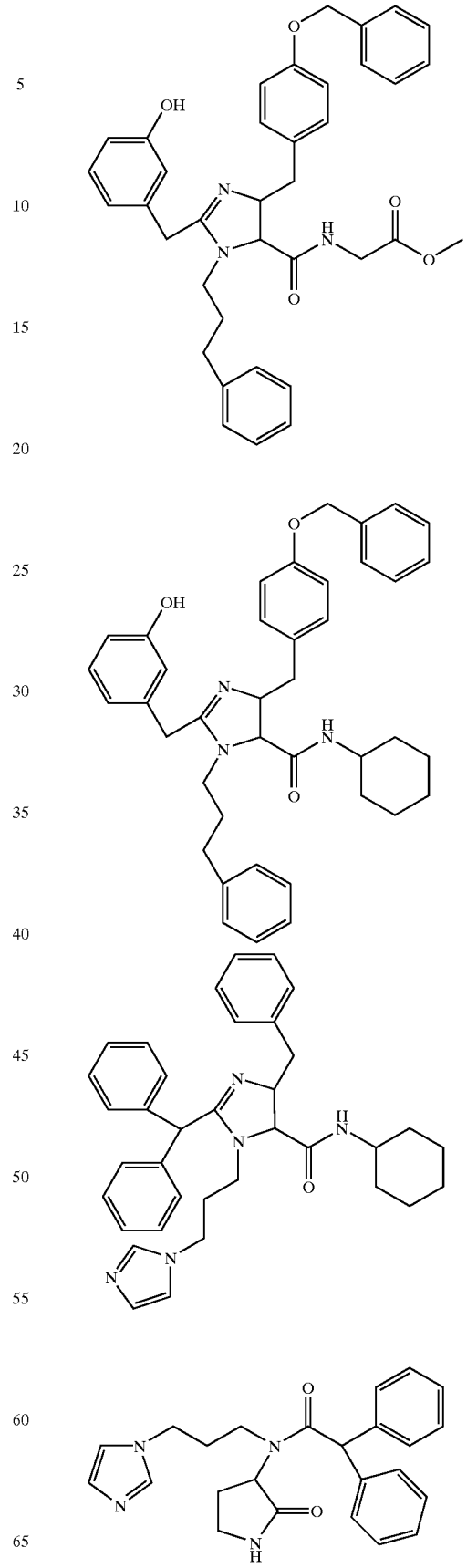

-continued
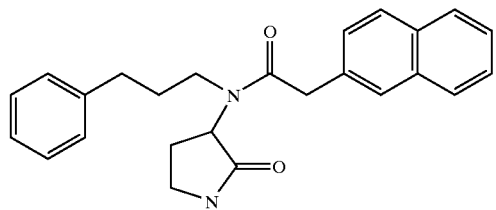
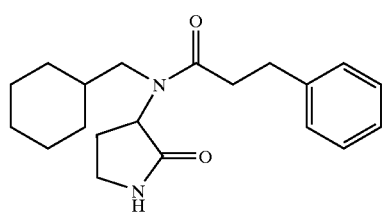
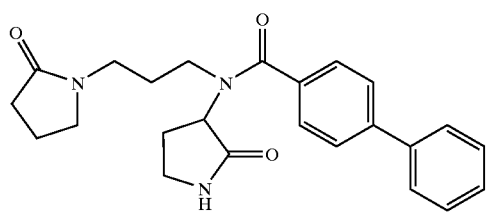
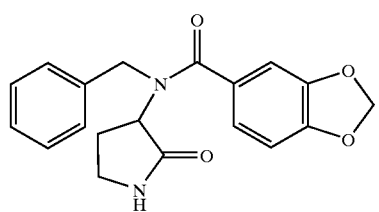
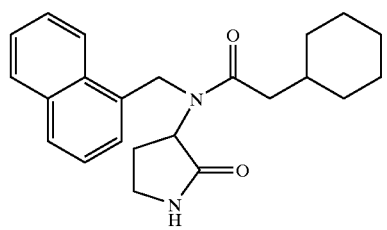
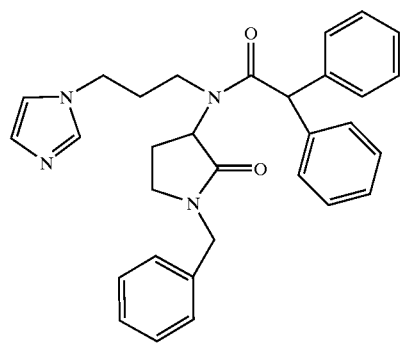
-continued
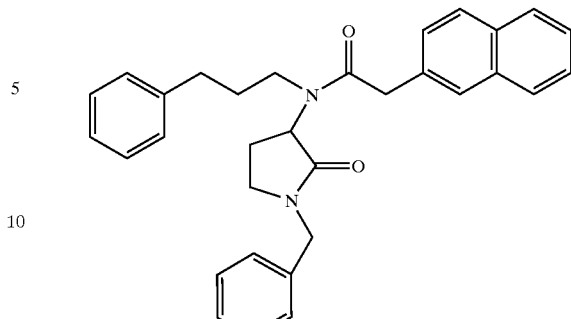
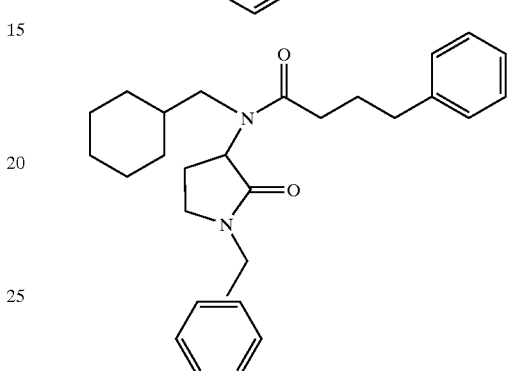
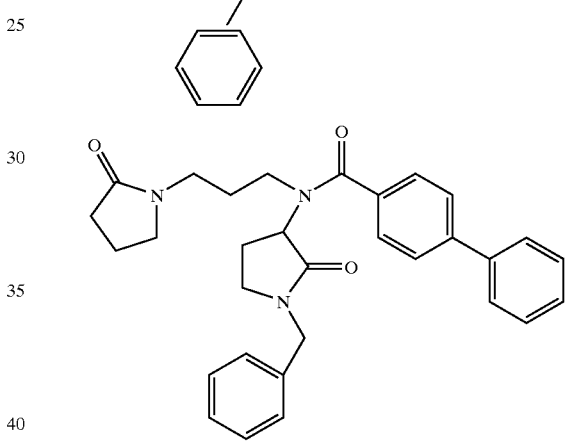
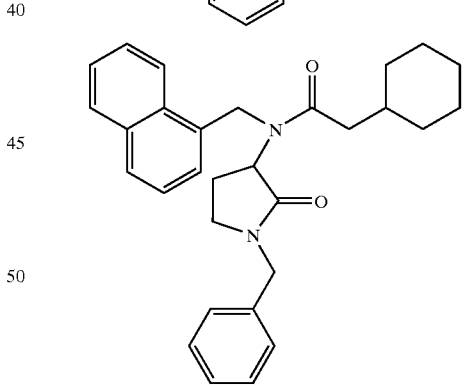
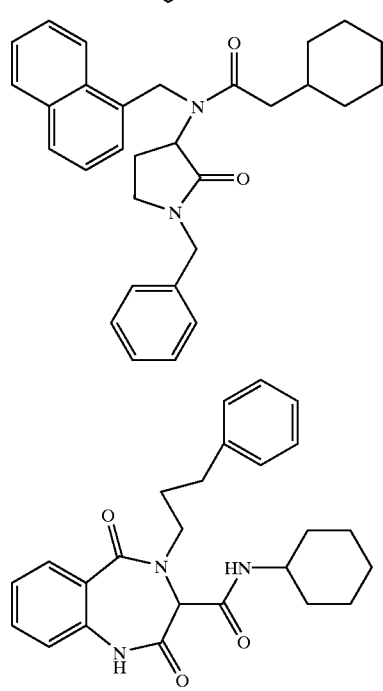

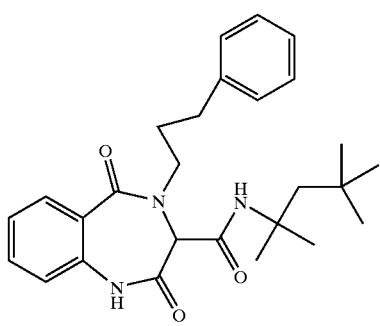
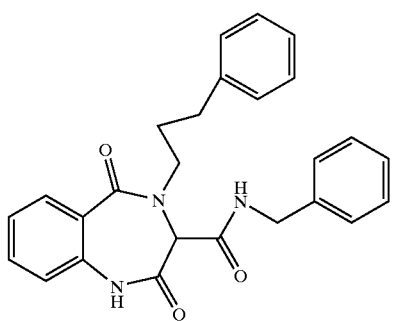
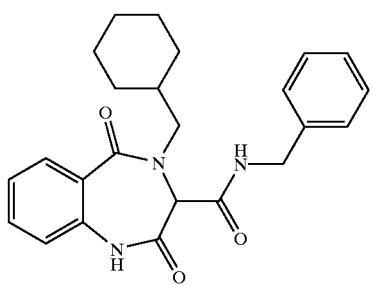
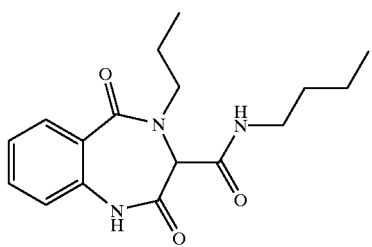
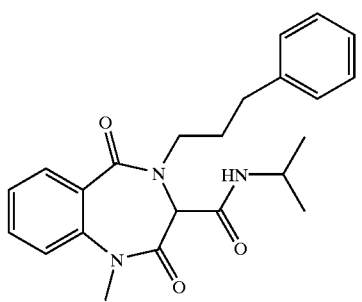
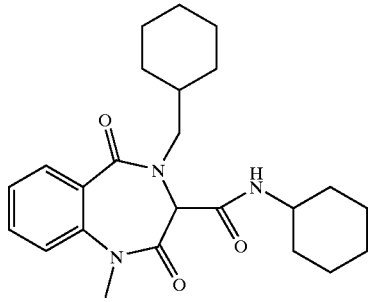
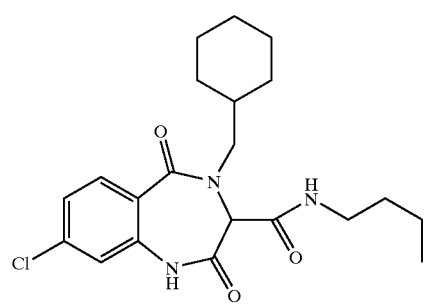
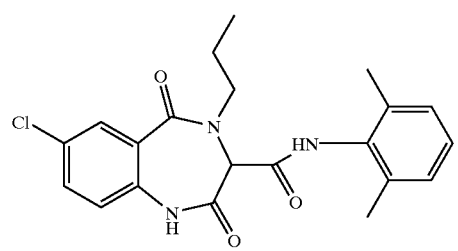
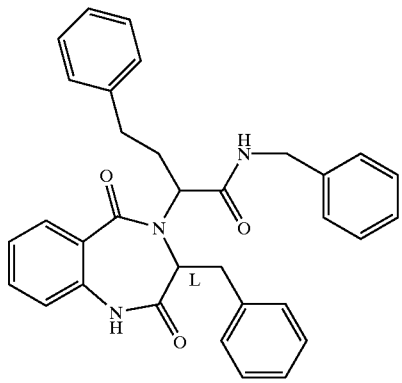
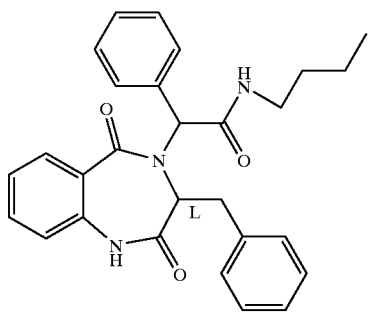

-continued
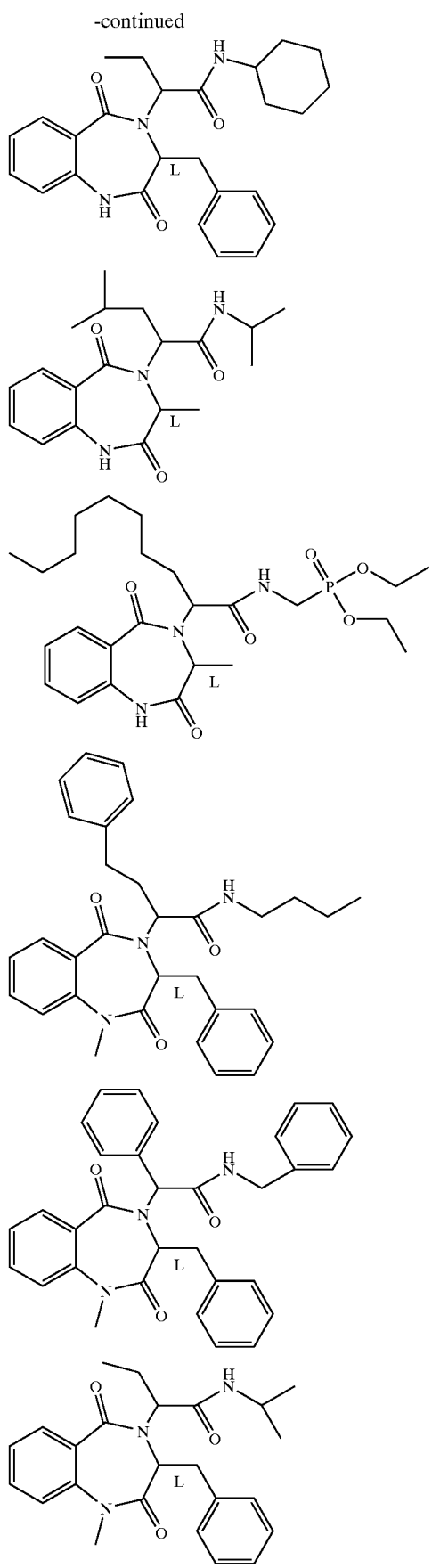
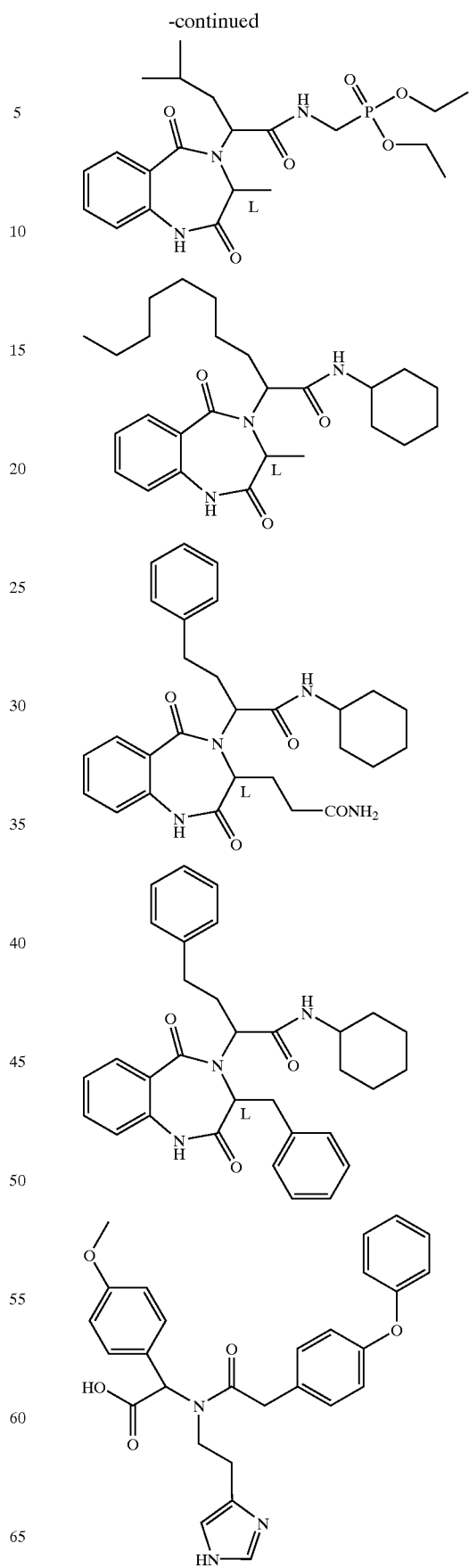

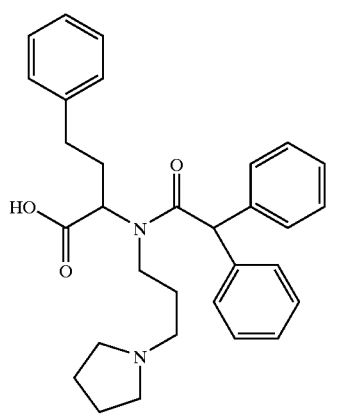
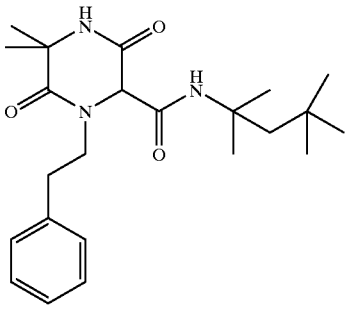
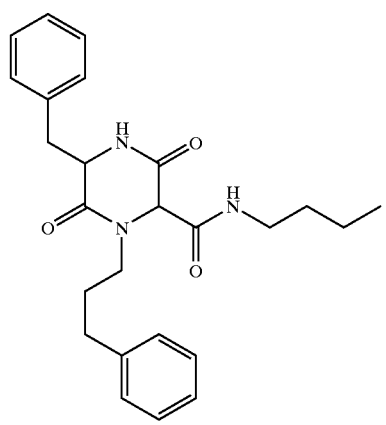
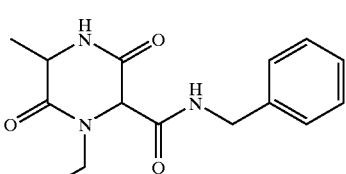
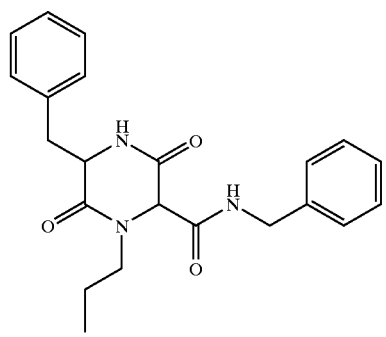
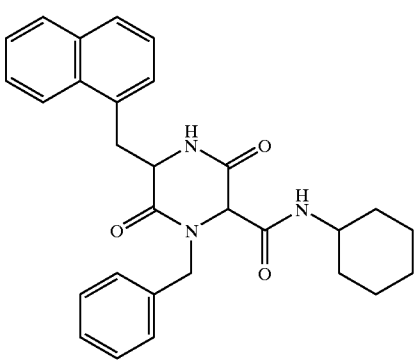
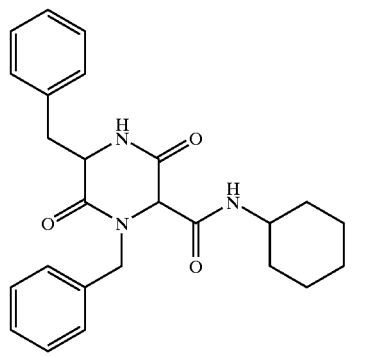
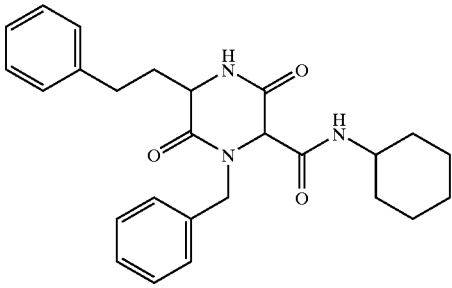

-continued
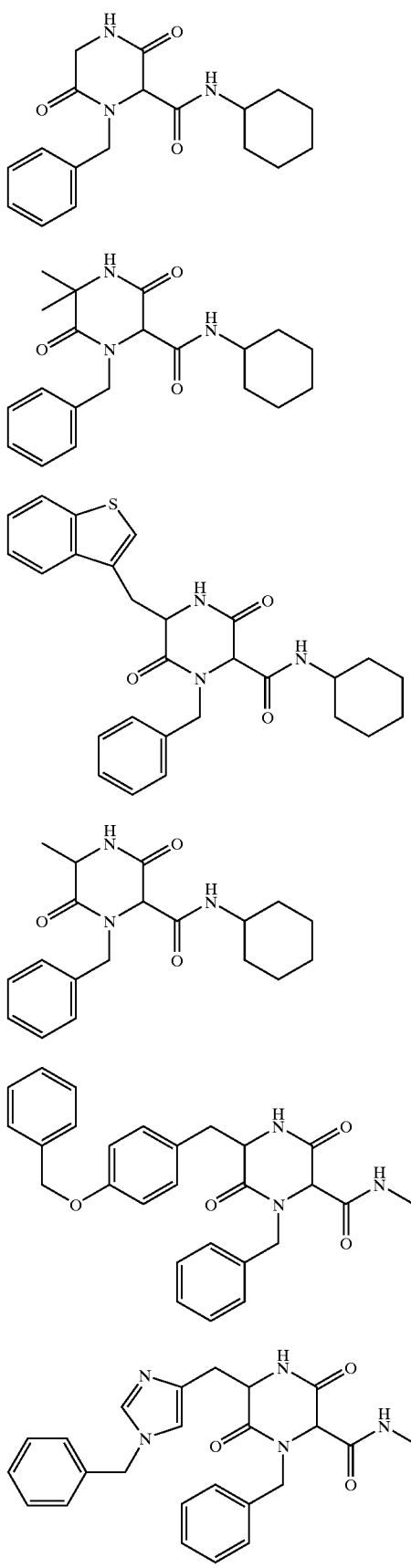
-continued
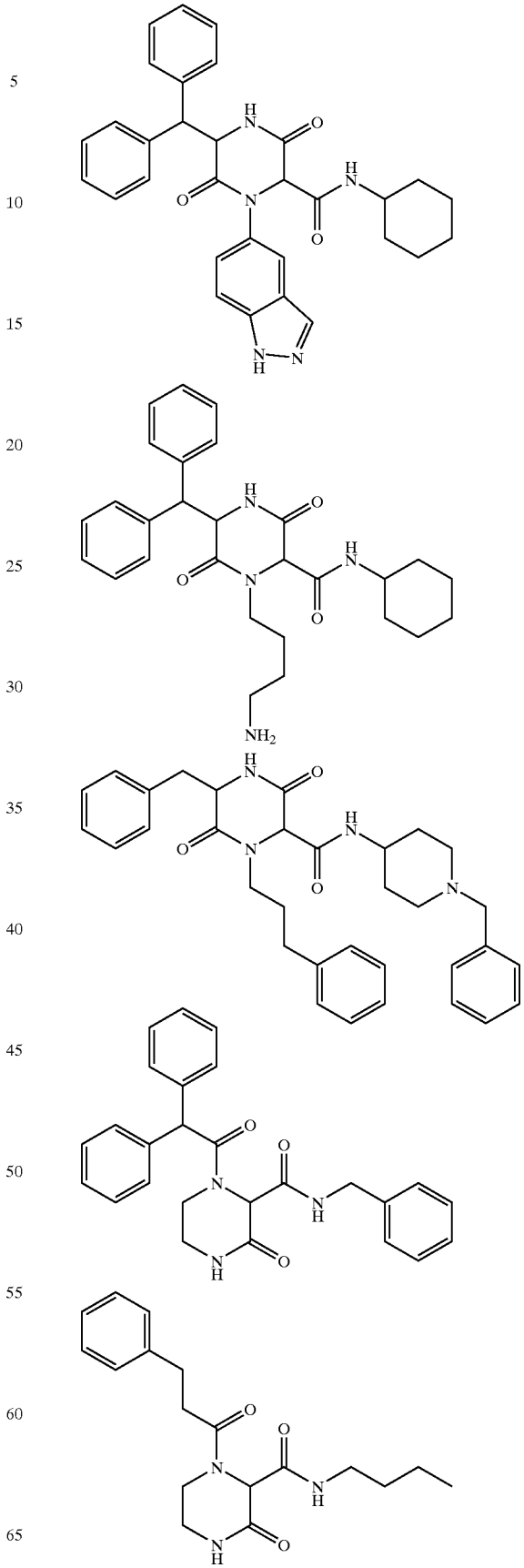

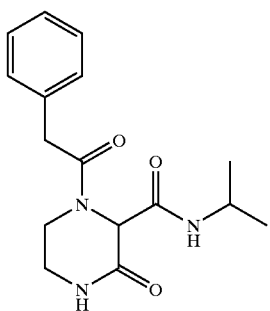
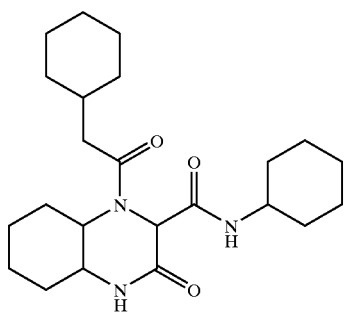
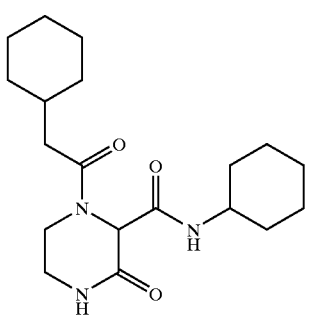
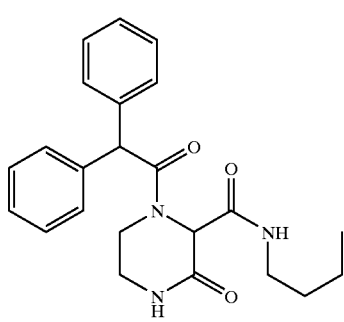
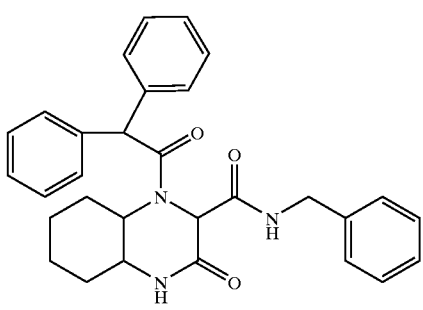
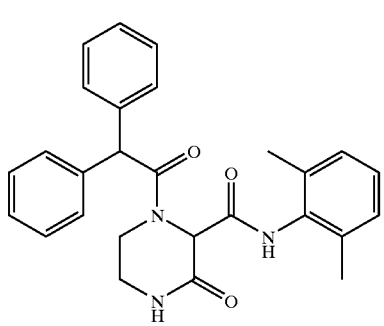
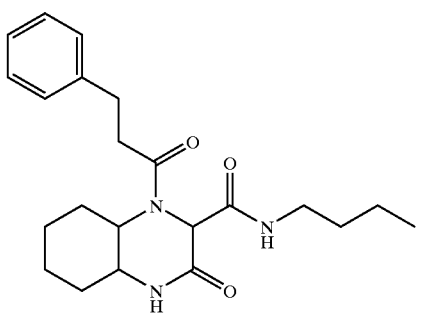
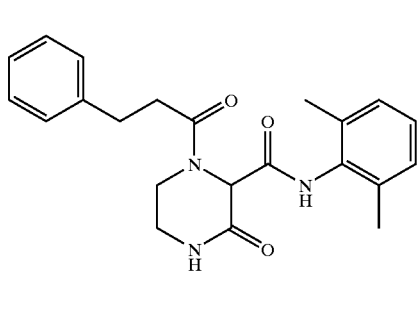
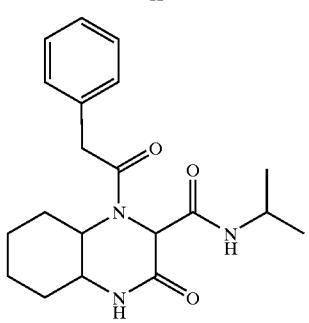
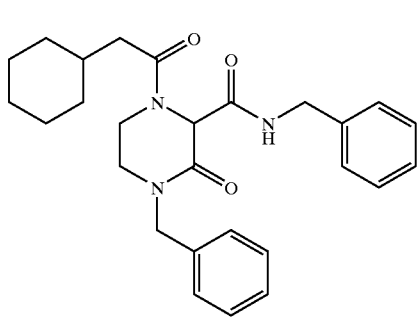

-continued
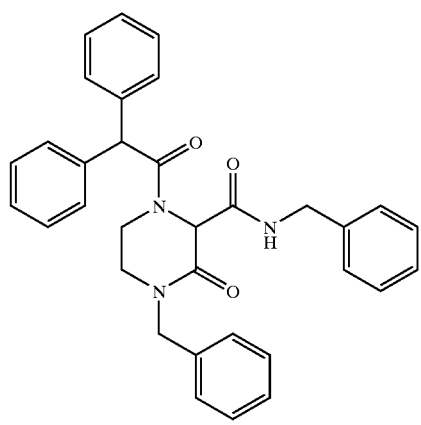
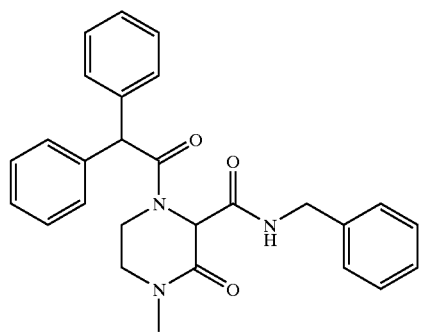
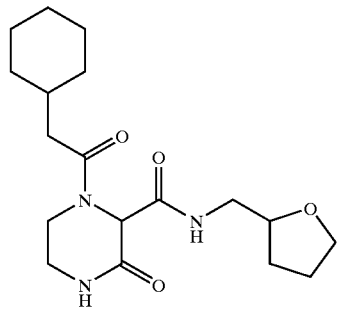
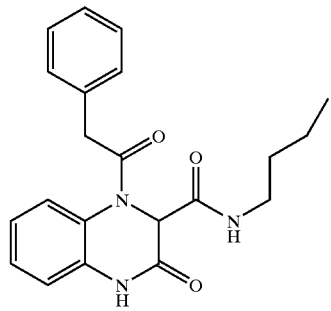
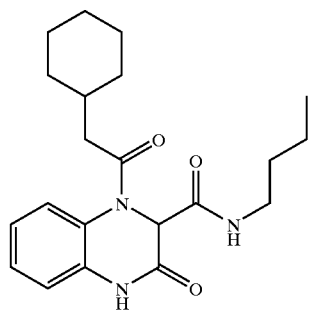
-continued
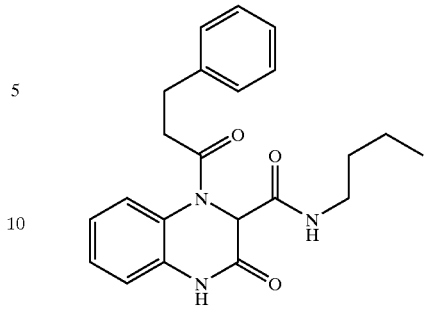
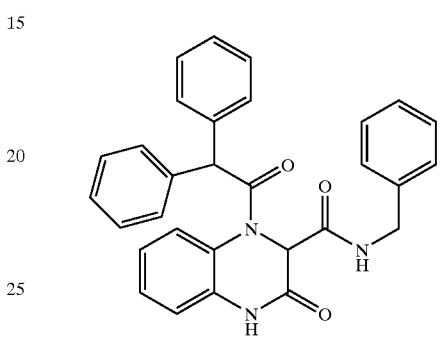
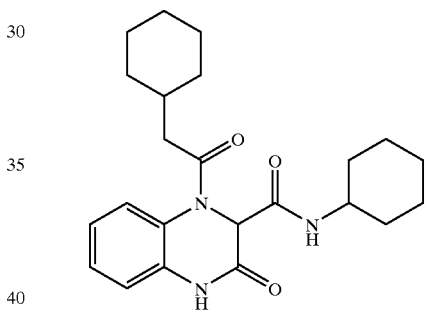
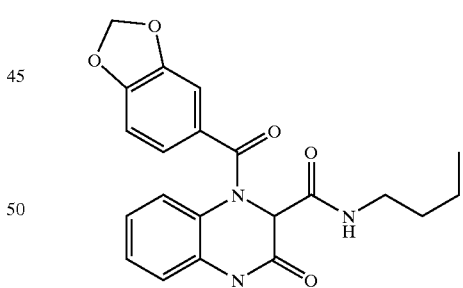
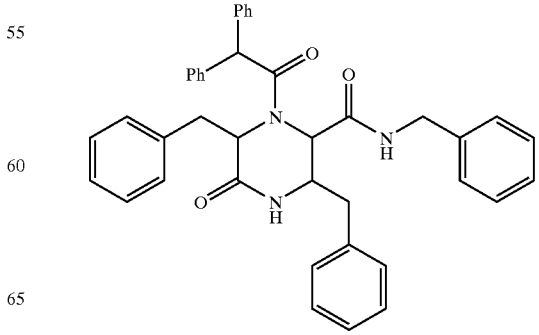

-continued
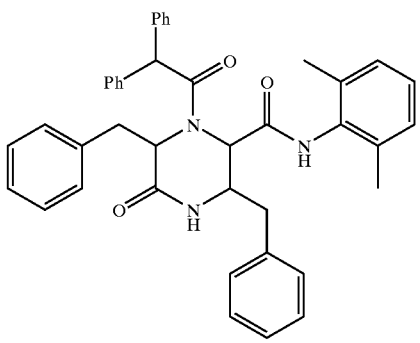
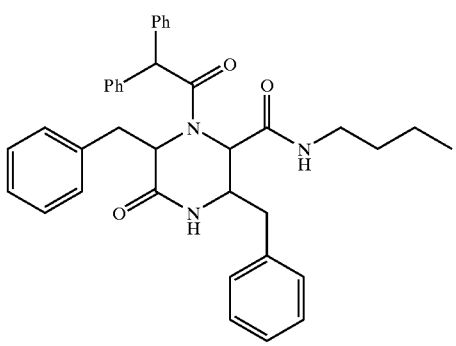
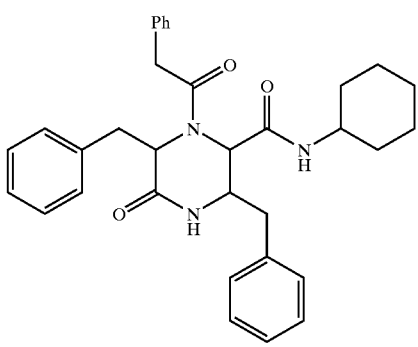
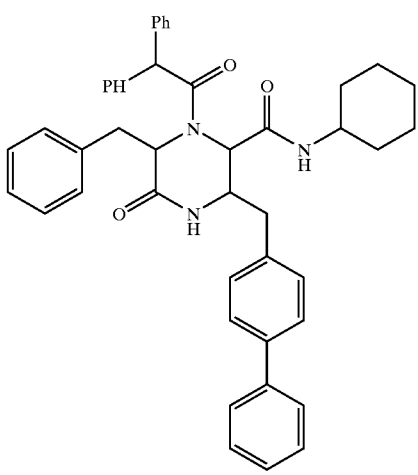
-continued
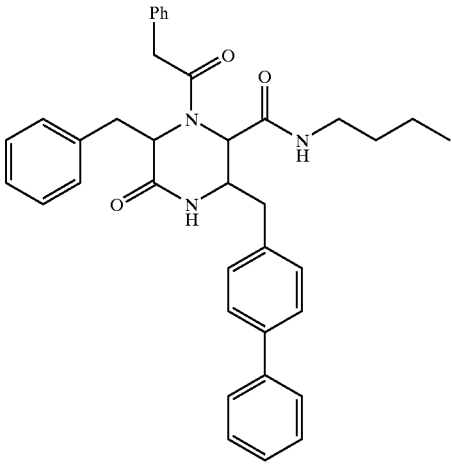
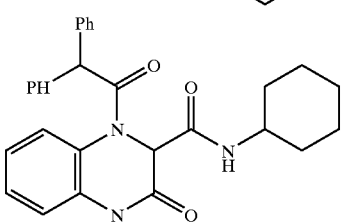
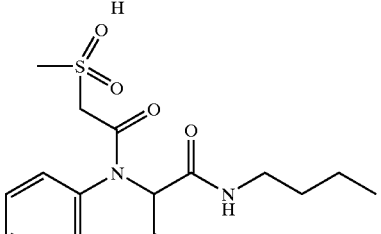
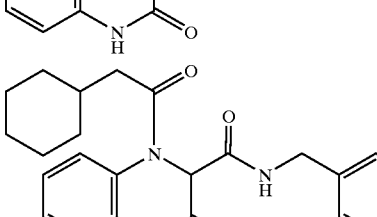
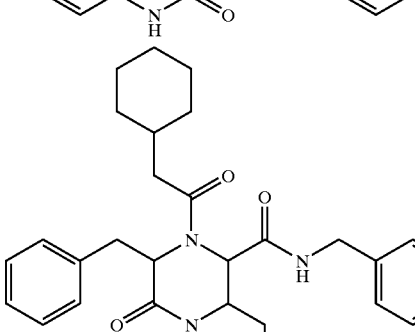
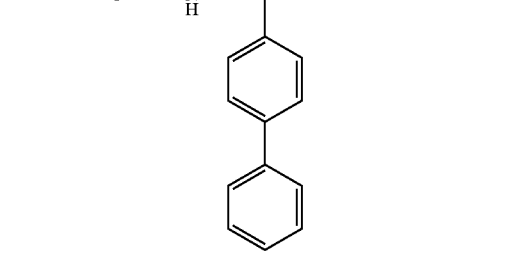 and -continued

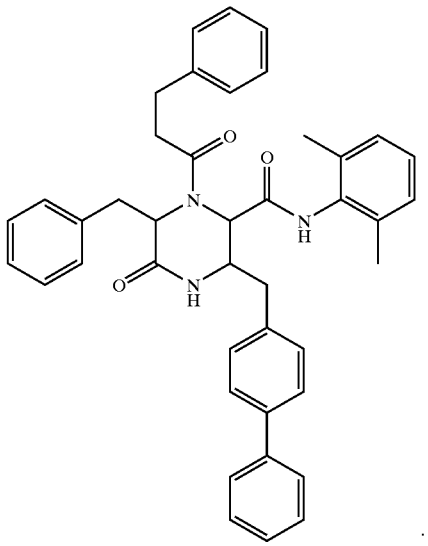

It is to be understood that this invention covers all appropriate combinations of the particular and preferred groupings referred to herein.

The compounds prepared by the methods of the invention optionally are supplied as salts. Those salts which are pharmaceutically acceptable are of particular interest since they are useful in administering the foregoing compounds for medical purposes. Salts which are not pharmaceutically acceptable are useful in manufacturing processes, for isolation and purification purposes, and in some instances, for use in separating stereoisomeric forms of the compounds of this invention. The latter is particularly true of amine salts prepared from optically active amines.

Where the compound of the invention contains a carboxy group, or a sufficiently acidic bioisostere, base addition salts may be formed and are simply a more convenient form for use; and in practice, use of the salt form inherently amounts to use of the free acid form.

Also, where the compound of the invention contains a basic group, or a sufficiently basic bioisostere, acid addition salts may be formed and are simply a more convenient form for use; and in practice, use of the salt form inherently amounts to use of the free base form.

While it is possible for the compounds of the invention to be administered alone, it is preferably to present them as pharmaceutical compositions. The pharmaceutical compositions, both for veterinary and for human use, of the present invention comprise at lease one compound of the invention, as above defined, together with one or more acceptable carriers therefor and optionally other therapeutic ingredients.

The choice of vehicle and the content of active substance in the vehicle are generally determined in accordance with the solubility and chemical properties of the active compound, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulphate and talc may be used for preparing tablets. To prepare a capsule, it is advantageous to use lactose and high molecular weight polyethylene glycols. When aqueous suspensions are used, they can contain emulsifying agents or agents which facilitate suspension. Diluents such as sucrose, ethanol, polyethylene glycol, propylene glycol, glycerol and chloroform or mixtures thereof may also be used.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the emulsifying wax, and the wax together with the oil and fat make up the emulsifying ointment base which forms the oily dispersed phase of the cream formulations. Emulgents and emulsion stabilizers suitable for use in the formulation of the present invention include Tween® 60, Span® 80, cetostearyl alcohol, benzyl alcohol, myristyl alcohol, glyceryl monostearate and sodium lauryl sulfate.

If desired, the aqueous phase of the cream base may include, for example, a least 30% w/w of a polyhydric alcohol, i.e. an alcohol having two or more hydroxyl groups, such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The choice of suitable oils or fats for the formulation is based on achieving the desired cosmetic properties. Thus the cream should preferably be a non-greasy, non-staining and washable product with suitable consistency to avoid leakage from tubes or other containers. Straight or branched chain, mono- or dibasic alkyl esters, such as di-isopropyl myristate, decyl oleate, isopropyl palmitate, butyl stearate, 2-ethylhexyl palmitate or a blend of branched chain esters known as Crodamol CAP, may be used, the last three being preferred esters. These may be used alone or in combination depending on the properties required. Alternatively, high melting point lipids such as white soft paraffin and/or liquid paraffin or other mineral oils can be used.

Solid compositions may also be employed as fillers in soft and hard-filled gelatin capsules using such excipients as lactose or milk sugar as well as high molecular weight polyethylene glycols, and the like.

The pharmaceutical compositions can be administered in a suitable formulation to humans and animals by topical or systemic administration, including oral, inhalational, rectal, nasal, buccal, sublingual, vaginal, parenteral (including subcutaneous, intramuscular, intravenous, intradermal, intrathecal and epidural), intracisternal and intraperitoneal. It will be appreciated that the preferred route may vary with, for example, the condition of the recipient.

The formulations can be prepared in unit dosage form by any of the methods well known in the art of pharmacy. Such methods include the step of bringing into association the active ingredient with the carrier, which may constitute one or more accessory ingredients. In general, the formulations are prepared by uniformly and intimately bringing into association the active ingredient with liquid carriers or finely divided solid carriers or both, and then, if necessary, shaping the product.

A tablet may be made by compression or moulding, optionally with one or more accessory ingredients. Compressed tablets may be prepared by compressing, in a suitable machine, the active ingredient in a free-flowing form, such as a powder or granules, optionally mixed with one or more of a binder, lubricant, inert diluent, preservative, surface active or dispersing agent. Moulded tablets may be made by moulding, in a suitable machine, a mixture of the powdered compounds moistened with an inert liquid diluent. The tablets may optionally be coated or scored and may be formulated so as to provide slow or controlled release of the active ingredient.

Solid compositions for rectal administration include suppositories formulated in accordance with known methods and containing at least one compound of the invention.

If desired, and for more effective distribution, the compounds can be microencapsulated in, or attached to, a slow release or targeted delivery system, such as a biocompatible, biodegradable polymer matrix (e.g. poly(d,1-lactide co-glycolide)), liposomes, and microspheres, and subcutaneously or intramuscularly injected by a technique called subcutaneous or intramuscular depot, to provide continuous slow release of the compound(s) for a period of 2 weeks or longer. The compounds may be sterilized, for example, by filtration through a bacteria retaining filter, or by incorporating sterilizing agents in the form of sterile solid compositions which can be dissolved in sterile water, or some other sterile injectable medium immediately before use.

Actual dosage levels of active ingredient in the compositions of the invention may be varied so as to obtain an amount of active ingredient that is effective to obtain a desired therapeutic response for a particular composition and method of administration. The selected dosage level, therefore, depends upon the desired therapeutic effect, on the route of administration, on the desired duration of treatment and other factors.

Total daily dose of the compounds of this invention administered to a host in single or divided doses may be in amounts, for example, of from about 0.001 to about 100 mg/kg body weight daily, and preferably 0.01 to 10 mg/kg/day. Dosage unit compositions may contain such amounts or such submultiples thereof as may be used to make up the daily dose. It will be understood, however, that the specific dose level for any particular patient will depend upon a variety of factors, including the body weight, general health, sex, diet, time and route of administration, rates of absorption and excretion, combination with other drugs and the severity of the particular disease being treated.

The amount of each component administered is determined by the attending clinicians taking into consideration the etiology and severity of the disease, the patient's condition and age, the potency of each component and other factors.

The formulations may be presented in unit-dose or multi-dose containers, for example, sealed ampoules and vials with elastomeric stoppers, and may be stored in a freeze-dried (lyophilized) condition, requiring only the addition of the sterile liquid carrier, for example, water for injections, immediately prior to use. Extemporaneous injection solutions and suspensions may be prepared from sterile powders, granules and tablets of the kind previously described.

Preparation of Compounds of the Invention

The starting materials and intermediates used in the preparation of compounds according to the invention may be prepared by the application or adaptation of known methods, for example, methods described in the Reference Examples or their obvious chemical equivalents.

In the reactions described hereinafter, it may be necessary to protect reactive functional groups, for example hydroxy, amino, imino, thio or carboxy groups, particularly where these are desired in the final product, to avoid their unwanted participation in the reactions. Conventional protecting groups may be used in accordance with standard practice. For examples, see T. W. Green and P. G. M. Wuts in "Protective Groups in Organic Chemistry" John Wiley and Sons, 1991; J. F. W. McOmie in "Protective Groups in Organic Chemistry" Plenum Press, 1973.

General Methodology for the Preparation the Isonitrile Resin Linker of Formula (IXa)

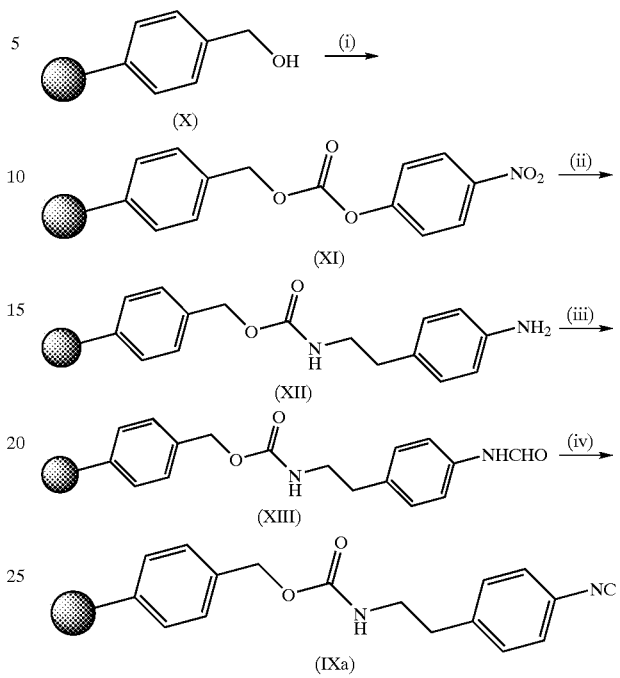

Reagents and Conditions:—(i) Wang resin, 4-nitrophenylchloroformate (5 equiv.), n-methyl morpholine (10 equiv.), THF. (ii) 2-(4 amino phenyl)ethylamine (5 equiv.), DMF. (iii) Formic acid (excess), acetic anhydride (excess), $CH_2Cl_2$ (iv) $Ph_3P$ (5 equiv.), $CCl_4$ (5 equiv.), $Et_3N$ (5 equiv.), $CH_2Cl_2$.

Experimental Procedures

Nitrocarbonate Resin of Formula (XI)

Wang resin (X) (100.0 g, 109.0 mmol) is swelled in anhydrous THF (1500 ml). N-methyl morpholine (119.8 ml, 1090.0 mmol) and 4-nitrophenyl chloroformate (109.86 g, 545 mmol) are added sequentially. The reaction is cooled in an ice bath for several minutes to quench the slightly exothermic reaction. The ice bath is then removed and the reaction is allowed to warm to room temperature. It is mixed on an orbital shaker at RT overnight. The reaction solution is drained off and the resin is ished with THF (5×), 20% $H_2O$ in DMF (5×), DMF (5×), THF (5×), and $Et_2O$ (5×). The resin product (XI) is then placed in a vacuum oven at RT overnight to dry. IR analysis showed two sharp peaks at 1520 $cm^{-1}$ and 1350 $cm^{-1}$ for the $NO_2$ group.

Aniline Resin of Formula (XII)

The nitrocarbonate resin (XI) (115.0 g, 125.35 mmol) is swelled in anhydrous DMF (1250 ml). 2-(4-Aminophenyl) ethylamine (82.6 ml, 626.75 mmol) is added to the resin slurry. The reaction mixture is mixed on an orbital shaker at RT overnight. The reaction solution is drained off and the resin is washed with DMF (8×). The still swollen resin is suspended in anhydrous DMF (1000 ml) and a second coupling of the amine (82.6 ml) is run overnight. After draining and washing with DMF (8×) a third coupling is run overnight. The final reaction solution is drained off and the resin product (XII) is washed with DMF (10×), THF (10×), and $Et_2O$ (10×). The resin is then dried in a vacuum oven at RT overnight. IR analysis showed loss of the $NO_2$ peaks.

Formamide Resin (XIII)

The aniline resin (XII) (109.0 g, 86.1 mmol) is swelled in anhydrous $CH_2Cl_2$ (1000 ml). Formic acid (500 ml) and acetic anhydride (500 ml) are combined, and the resulting exothermic reaction is cooled in an ice bath. Once at RT, the resulting solution is allowed to sit at RT for 40 minutes. This mixed anhydride solution is then added to the resin slurry. The reaction mixture is mixed on an orbital shaker at RT overnight. The reaction solution is drained off, and the resin is washed with $CH_2Cl_2$ (10x). To remove any remaining acetic acid, the resin is washed with 20% $H_2O$ in THF (6x) until the washings are neutral to litmus paper. The resin product (XIII) is finally washed with THF (10x) and $Et_2O$ (8x) and then dried in a vacuum oven at RT overnight. IR analysis shows a strong carbonyl stretch for the formamide at 1698 $cm^{-1}$.

Isonitrile Resin of Formula (IXa)

The formamide resin (XIII) (50.0 g, 44.5 mmol) is swelled in anhydrous $CH_2Cl_2$ (500 ml). Triphenylphosphine (58.4 g, 222.5 mmol), carbon tetrachloride (21.5 ml, 222.5 mmol), and triethylamine (31.0 ml, 222.5 mmol) are added sequentially at RT. The reaction mixture is mixed on an orbital shaker for 4.5 hours at RT. The reaction solution is drained off and the resin product (IXa) is washed with $CH_2Cl_2$ (20x), THF (10x), and $Et_2O$ (10x). The resin is then placed in a vacuum oven at RT overnight to dry. IR analysis shows a sharp peak for the isonitrile at 2121 $cm^{-1}$.

General methodology for the preparation of 1,4-Benzodiazepine-2,5-diones

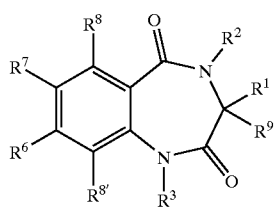

(I)

In general terms, compounds of formula (I) wherein $R^1$, $R^2$, $R^3$, $R^{8'}$ $R^6$, $R^7$, $R^8$ and $R^9$ are as hereinbefore defined, may be synthesized by reacting a compound of formula (XIV) wherein $R^3$, $R^{8'}$, $R^6$, $R^7$ and $R^8$ are as hereinbefore defined and $Z^1$ is a suitable amine protecting group, with a compound of formula (XV) wherein $R^1$ and $R^9$ are as hereinbefore defined, a compound of formula (XVI) wherein $R^2$ is as hereinbefore defined, and a compound of formula (IX) wherein $R^{12}$ represents alkyl, aralkyl, aryl, fused arylcycloalkyl, fused arylheterocyclyl, cycloalkyl, heteroaralkyl, heteroaryl, fused heteroarylcycloalkyl, fused heteroarylheterocyclyl, or heterocyclyl; in a suitable solvent at about room temperature, to afford the intermediate compound (XVII), wherein $R^1$, $R^2$, $R^3$, $R^{8'}$ $R^6$, $R^7$, $R^8$, $R^9$, $R^{12}$ and $Z^1$ are as hereinbefore defined.

The general reaction is illustrated in scheme 1 below:

Scheme 1

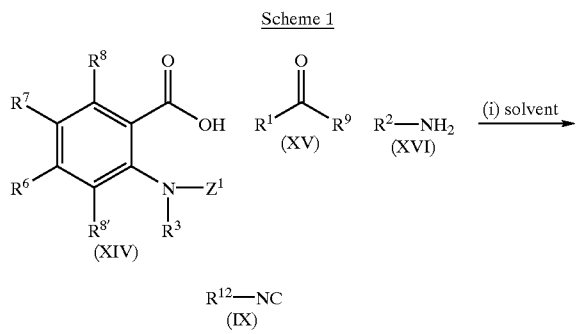

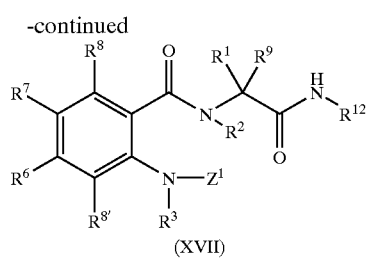

(XVII)

The conversion of the compound (XVII) to the compound of formula I is described hereinafter with reference to Scheme 2. There is no particular restriction on the nature of the solvent to be employed, provided that it has no adverse effect on the reaction or on the reagents involved (See Waki et al. J. Am. Chem. Soc., 1977, 6075–6077, the contents of which are hereby incorporated herein by reference). Examples of suitable solvents include: alcohols, such as methanol, 1-butanol, phenol, trifluoroethanol, and hexafluoro-2-propanol; hydrocarbons, such as benzene and toluene; amides, such as dimethyl acetamide, and dimethylformamide; halides, such as dichloromethane, and dichloroethane; and ethers, such as tetrahydrofuran and dioxane; other solvents include water, 1-methyl-2-pyrrolidine, diethyl phosphite, tetramethylsulphone, dimethyl sulphoxide, acetonitrile and pyridine. Of these solvents, the alcohols are preferred.

There is no restriction on the isonitrile of formula (IX) used in the reaction scheme 1 above, provided that it has no adverse effect on the reaction involved. Examples of suitable isonitriles include, 1-isocyanocyclohexene, benzyl isocyanide, n-butyl isocyanide, diethyl isocyanomethyl phosphonate, cyclohexyl isocyanide, 2,6-dimethylphenyl isocyanide, methyl isocyanoacetate, isopropyl isocyanide and 1,1,3,3-tetramethylbutyl isocyanide also the isonitrile described in Ugi et al., Tetrahedron, 1999, 55, 7411–7420, the content s of which are hereby incorporated herein by reference. Preferable isonitriles include the isonitrile functionalized polymer resin of formula (IXa) or of formula (XVIII), 1-isocyanocyclohexene of formula (IXb), benzyl isocyanide, n-butyl isocyanide, diethyl isocyanomethyl phosphonate. More preferably, isonitriles used in the reaction are isonitrile functionalized polymer resin of formula (IXa)

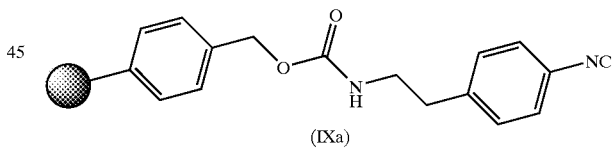

(IXa)

or the isonitrile functionalized polymer resin of formula (XVIII) (A. Piscopio, ORG Poster 232, American Chemical Society Meeting, Las Vegas, Nev., Sep. 7–10, 1997):

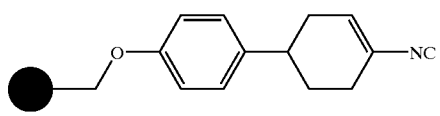

(XVIII) or 1-isocyanocyclohexene of formula (IXb):

(IXb)

The use of resin bound isonitriles of formula (IXa) or of formula (XVIII) in the synthesis of compounds of the formula (I), (II), (III) (IV), (V), (VI), (VII), (VIII), (XLII), (L), (LIII), and (LV) is advantageous over the use of other non-resin bound isonitriles. The use of the resin bound isonitriles allow excess amount of reagents to be used in the reaction to drive the Ugi reaction forward. Also, unlike solution phase procedures, these reagents can be easily removed by subsequent washing of the resin, leaving the Ugi product clean and resin bound.

The reaction can take place over a wide range of temperatures, and the precise reaction temperature is not critical to the invention. In general, we find it convenient to carry out the reaction at a temperature of from about 0° C. to about 150° C., preferably from room temperature to about 100° C., more preferably at about room temperature. The time required for the reaction may also vary widely, depending on many factors, notably the reaction temperature and the nature of the reagents. However, provided that the reaction is effected under the preferred conditions outlined above, a period of from 3 hours to 36 hours will usually suffice.

The intermediate compound of the formula (XVII) thus prepared may be recovered from the reaction mixture by conventional means. For example, the compounds may be recovered by distilling off the solvent in vacuo from the reaction mixture or, if necessary after distilling off the solvent from the reaction mixture, pouring the residue into water followed by extraction with a water-immiscible organic solvent and distilling off the solvent from the extract. Additionally, the product can, if desired, be further purified by various well known techniques, such as recrystallization, reprecipitation or the various chromatography techniques, notably column chromatography or preparative thin layer chromatography. The intermediate compound is preferably recovered from the reaction mixture by distilling off the solvent in vacuo.

The intermediate compound (XVII) may be converted to a compound of formula (I) by reacting with acid and optionally base, in a suitable solvent and appropriate temperature, to effect removal of the amine protecting group ($Z^1$), followed by cyclization. This reaction is illustrated in Scheme 2.

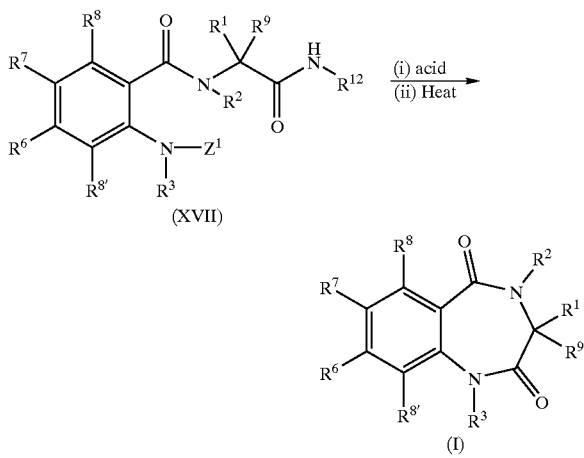

Scheme 2

This reaction is carried out in the presence of an acid. There is no particular restriction on the nature of the acid to be used in this reaction, and any acid conventionally used to facilitate removal of an acid labile amine protecting group $Z^1$ and cyclization, may equally be used here, provided that it has no adverse effect on other parts of the molecule. Examples of suitable acids include: mineral acids such as hydrochloric acid or sulfuric acid; organic acids such as trifluoroacetic acid. Acids to be used in the reaction can also be generated in situ, for example by the addition of acetyl chloride in methanol, to generate hydrochloric acid. Preferably, anhydrous acids are used.

In addition to carrying out the reaction in scheme 2 in the presence of acid, a reaction step involving basic conditions can also be optionally carried out so as to facilitate the removal of the amine protecting group $Z^1$, wherein $Z^1$ is a base labile amine protecting group. There is no particular restriction on the nature of the base to be used in this reaction, and any base conventionally used to facilitate removal of a base labile amine protecting group $Z^1$, may equally be used here, provided that it has no adverse effect on other parts of the molecule. Examples of suitable bases include: organic bases such as ammonia, piperidine, morpholine, ethanolamine and diethylamine.

In situations where acidic conditions are used to remove the amine protecting group in intermediate compound of formula (XVII) it may also be necessary to treat the deprotected intermediate, which is present as an acid salt, with base so as to convert the acid addition salt to its corresponding free base. There is no particular restriction on the nature of the base to be used. A base conventionally used to convert an acid addition salt to its corresponding free base form may be used here, provided that it has no adverse effect on other parts of the molecule. Examples of suitable bases include ammonia, piperidine, morpholine, ethanolamine, diethylamine, polystyrene bound di-isopropylethylamine or basic DOWEX. Preferably diethylamine, basic DOWEX or polystyrene bound di-isopropylethylamine.

This reaction can take place over a wide range of temperatures, and the precise reaction temperature is not critical to the invention. In general, we find it convenient to carry out the reaction at a temperature of from about 0° C. to about 150° C., preferably from room temperature to about 100° C., more preferably at about room temperature. The time required for the reaction may also vary widely, depending on many factors, notably the reaction temperature and the nature of the reagents. However, provided that the reaction is effected under the preferred conditions outlined above, a period of from 3 hours to 36 hours will usually suffice.

There is no particular restriction on the amine protecting group ($Z^1$) employed. However, amino acid protecting groups which allow removal of the protecting group and cyclization of the deprotected intermediate, without purification or isolation of intermediates, are preferred. Examples of amine protecting groups include both acid labile amine protecting groups and base labile protecting groups. Preferred acid labile amine protecting group include tert-butoxycarbonyl (BOC) and 2-(4-biphenylyl)-isopropoxy carbonyl (BPOC). Preferred base labile amine protecting group include 9-fluoroenylmethyl carbamate (FMOC).

Furthermore, a piperazinyl intermediate of formula (XVIIa); i.e. an intermediate of formula (XVII) wherein $R^1$ and $R^2$ together with the nitrogen and carbon atoms through which $R^1$ and $R^2$ are attached form a piperazinyl group; is formed by reacting an amine of formula (XVIa); i.e. an amine of formula (XVI) wherein $R^2$ is $C(R^{19}R^{19'})C(R^{20}R^{20'})NY^1Y^2$, and $Y^1$ is hydrogen, $Y^2$ is independently, hydrogen, alkyl, aryl, heteroaryl, aralkyl, or heteroaralkyl, and $R^{19}$, $R^{19'}$, $R^{20}$, and $R^{20'}$ are independently optionally substituted alkyl; with an aldehyde or ketone of formula (XVa); i.e. an amine of formula (XV) wherein $R_1$ is a $CR^{21}R^{21'}X'$ and $R^{21}$ and $R^{2'}$ are independently optionally substituted alkyl and X' is an appropriate leaving, for example a halogen atom; an N-protected amino acid of formula (XIV) and an isonitrile of formula (IX), under conditions analogous to those described for synthesizing intermediate of formula (XVII) in scheme 1 and as described in Rossen et al., Tetrahedron et Lett. 1997, 38, 3183, the contents of which are hereby incorporated by reference.

Scheme 2a

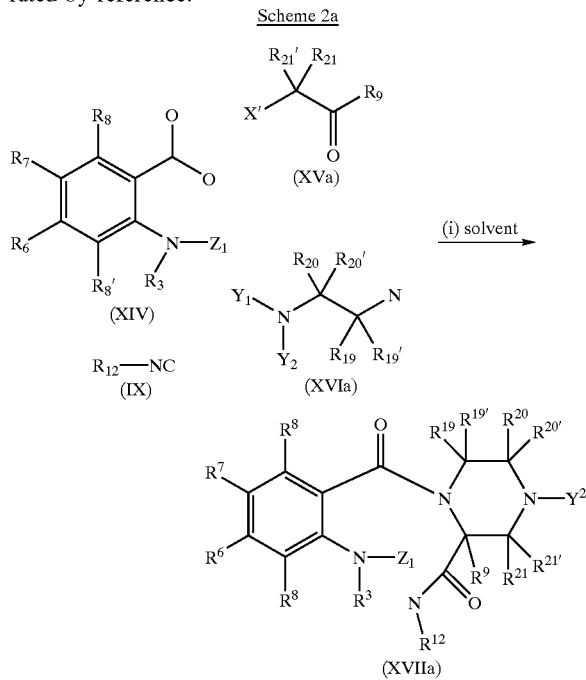

The piperazinyl intermediate of formula (XVIIa) can then undergo further cyclisation to afford compounds of formula (Ia) i.e. compounds of formula I, wherein $R^1$ and $R^2$ together with the nitrogen and carbon atoms through which $R^1$ and $R^2$ are attached form a piperazinyl group. The cyclisation of piperazinyl intermediate of formula (XVIIa) to afford the compound of formula (Ia) is carried out under conditions analogous to those described for synthesizing compound of formula (I) in scheme 2 above.

Scheme 2b

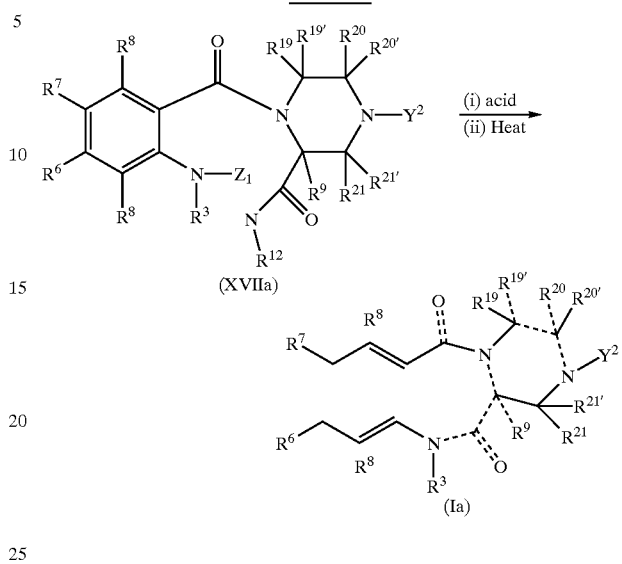

The use of the novel resin bound isonitrile of formula (IXa) in the synthesis of compounds of the formula (I), wherein $R^{12}$ is the novel resin bound isonitrile derivative of formula (IXa), is advantageous over other non-resin bound isonitriles. However, use of a compound of formula (IXa) in the synthesis of a compound of formula (I) involves activation of the resin linker to facilitate cleavage of the resin linkage and cyclization to afford a compound of formula (I). An illustration of the use of the novel resin bound isonitrile of formula (IXa) in the synthesis of the intermediate formula (XIX) is illustrated in Scheme 3.

Scheme 3

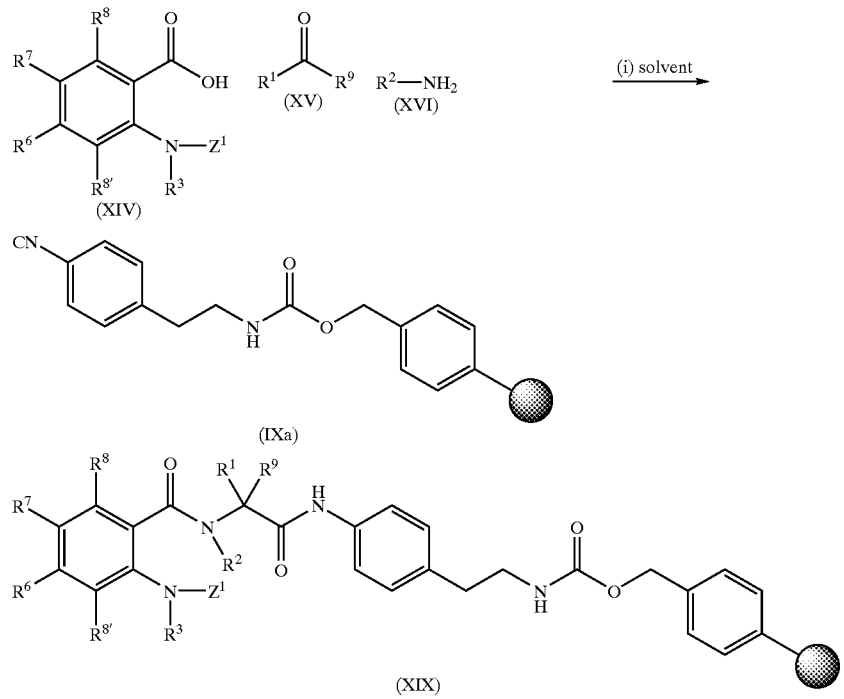

Activation of the benzamide carbonyl of (XIX) to give the intermediate of formula (XX), wherein $Z^2$ is a carbamate protective group promotes facile cleavage from the resin. Examples of carbamate protective groups which may activate cleavage of the benzamide group, provided that they have no adverse effect on the reaction involved are, for example, t-butyl-O—CO— (BOC), benzyl-O—CO— (CBZ), $Cl_3CCH_2$—O—CO— (Troc), $(CH_3)_3SiCH_2CH_2$—O—CO— (TEOC), 1-methyl-1-(4-biphenylyl)ethyl-O—CO— (BPOC) and cycloalkyl-O—CO—. Other carbamate protective groups include those described in 'Protecting groups in Organic Synthesis' Greene, 1981, p. 223–49. An example of the activation of the benzamide group is illustrated in Scheme 4, wherein $Z^2X$ a suitable carbamate protective group reagent, for example $(BOC)_2O$.

for the conversion of an amine to a carbamate group. This sort of reaction is usually carried out in dichloromethane, in the presence of a base, for example $Et_3N$, and a catalytic amount of DMAP. (For other suitable reaction conditions, see 'Protecting groups in Organic Synthesis' Greene, 1981, p. 223–49).

The resin "safety catch" linker is then cleaved, to facilitate the removal of the resin, by reacting the activated benzamide compound of formula (XX) with an appropriate alkoxide, or hydroxide, to afford the corresponding alkyl ester or carboxylic acid derivative of formula (XXI) respectively, wherein $R^{13}$ is, for example, H, alkyl, phenyl or cycloalkyl (Mjalli, A. M. M., Sarshar, S., Baiga, T. J. *Tetrahedron Lett.* 1996, 37, 2943; Flynn, D. L., Zelle, R. E., Grieco, P. A. *J.*

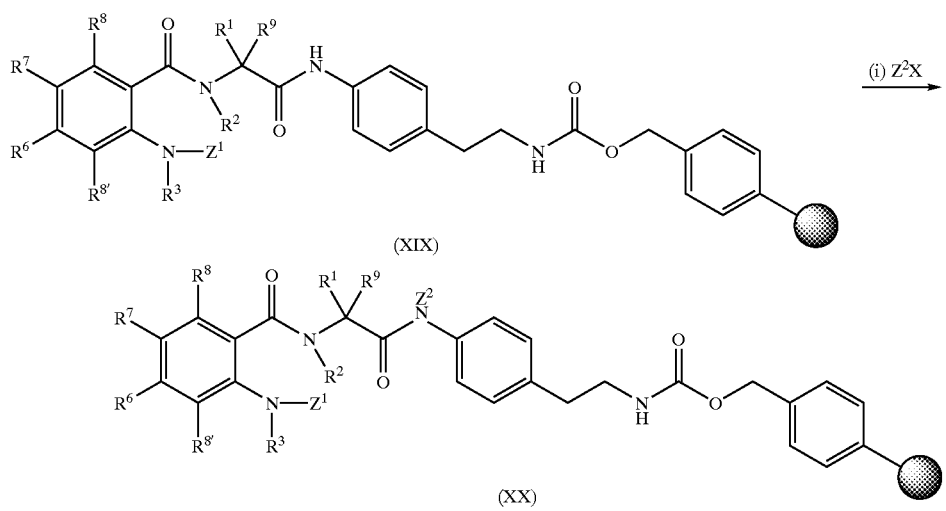

The reaction conditions and reagents used in the activation of the benzamide, are ones that are known in the art of

*Org. Chem.* 1983, 48, 2424.) An example of the cleavage from the resin is illustrated in reaction Scheme 5:

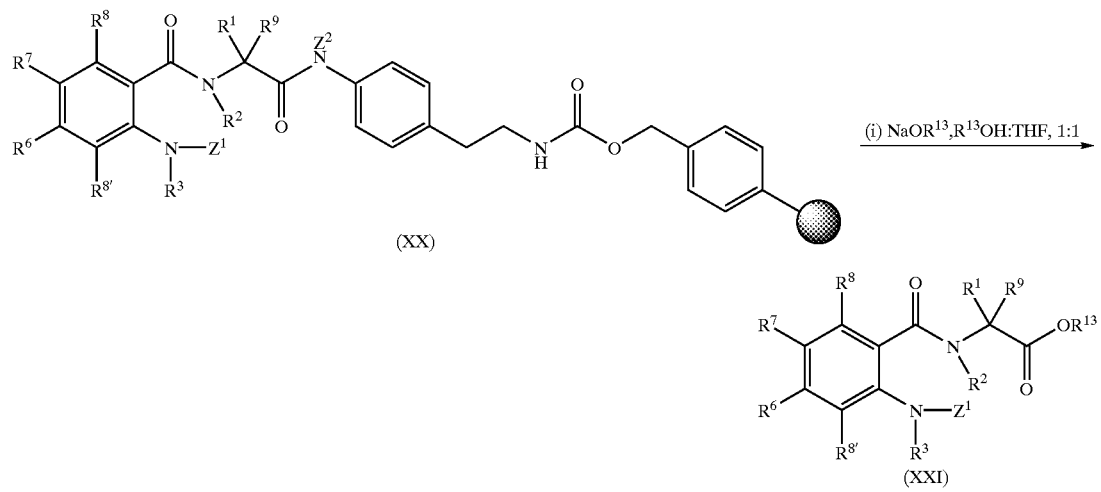

The intermediate compound of formula (XXI) may be converted to a compound of formula (I) by reacting with acid, in a suitable solvent and at an appropriate temperature, to effect removal of the amine protecting group ($Z^1$), followed by cyclization. This reaction is illustrated in Scheme 6.

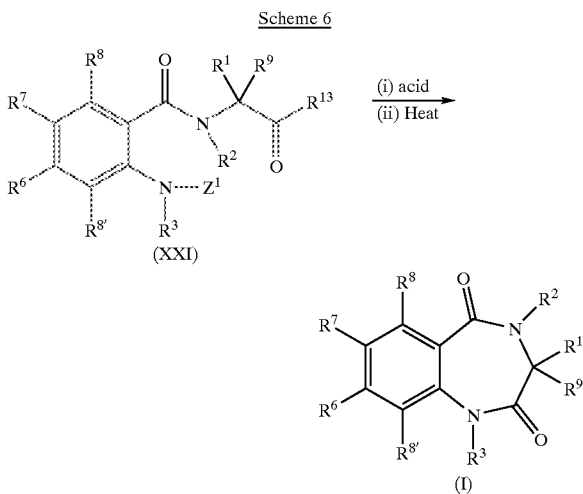

This reaction is carried out in the presence of an acid. There is no particular restriction on the nature of the acid to be used in this reaction, and any acid conventionally used to facilitate removal of an acid labile amine protecting group $Z^1$ and cyclization, may equally be used here, provided that it has no adverse effect on other parts of the molecule. Examples of suitable acids include: mineral acids such as hydrochloric acid or sulfuric acid; organic acids such as trifluoroacetic acid. Acids to be used in the reaction can also be generated in situ, for example by the addition of acetyl chloride in methanol, to generate hydrochloric acid. Preferably, anhydrous acids are used.

In addition to carrying out the reaction in scheme 6 in the presence of acid, a reaction step involving basic conditions can also be optionally carried out so as to facilitate the removal of the amine protecting group $Z^1$, wherein $Z^1$ is a base labile amine protecting group. There is no particular restriction on the nature of the base to be used in this reaction, and any base conventionally used to facilitate removal of an base labile amine protecting group $Z^1$, may equally be used here, provided that it has no adverse effect on other parts of the molecule. Examples of suitable bases include: organic bases such as ammonia, piperidine, morpholine, ethanolamine and diethylamine.

This reaction can take place over a wide range of temperatures, and the precise reaction temperature is not critical to the invention. In general, we find it convenient to carry out the reaction at a temperature of from about 0° C. to about 150° C., preferably from room temperature to about 100° C., more preferably at about room temperature. The time required for the reaction may also vary widely, depending on many factors, notably the reaction temperature and the nature of the reagents. However, provided that the reaction is effected under the preferred conditions outlined above, a period of from 3 hours to 36 hours will usually suffice.

There is no particular restriction on the amine protecting group ($Z^1$) employed. However, amino acid protecting groups which allow removal of the protecting group and cyclization of the deprotected intermediate, without purification or isolation of intermediates, are preferred. Examples of amine protecting groups include both acid labile amine protecting groups and base labile protecting groups. Preferred acid labile amine protecting group include tert-butoxycarbonyl (BOC) and 2-(4-biphenylyl)-isopropoxy carbonyl (BPOC). Preferred base labile amine protecting group include 9-fluoroenylmethyl carbamate (FMOC).

In situations where acidic conditions are used to remove the amine protecting group in intermediate compound of formula (XXI) it may also be necessary to treat the deprotected intermediate, which is present as an acid salt, with base so as to convert the acid addition salt to its corresponding free base. There is no particular restriction on the nature of the base to be used. A base conventionally used to convert an acid addition salt to its corresponding free base form may be used here, provided that it has no adverse effect on other parts of the molecule. Examples of suitable bases include ammonia, piperidine, morpholine, ethanolamine, diethylamine, polystyrene bound di-isopropylethylamine or basic DOWEX. Preferably diethylamine, basic DOWEX or polystyrene bound di-isopropylethylamine.

Similarly, solid phase synthesis of a compound of formula (I) can be carried out using the resin bound isonitrile of formula (XVIII) using reaction conditions similar to those described for scheme 1 and scheme 2.

General methodology for the preparation of diketopiperazines (II)

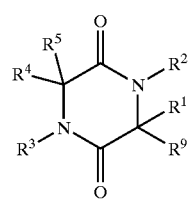

(II)

Compounds of formula II may be prepared by the application or adaptation of known methods, by which is meant methods used heretofore or described in the literature, or by methods according to this invention described and claimed herein.

In general terms, compounds of formula (II) wherein $R^1$, $R^2$, $R^3$, $R^4$ $R^5$ and $R^9$ are as hereinbefore defined and $Z^1$ is a suitable amine protecting group, may be synthesized by reacting an amino acid of formula (XXII), wherein $R^3$, $R^4$, $R^5$ and $Z^1$ are as hereinbefore defined, with compounds of formula (XV) wherein $R^1$ and $R^9$ are as hereinbefore defined, a compound of formula (XVI) wherein $R^2$ is as hereinbefore defined, and a compound of formula (IX) wherein $R^{12}$ is as hereinbefore defined, in a suitable solvent at about room temperature, to afford the intermediate compound of formula (XXIII). This reaction is illustrated in Scheme 7 below:

Scheme 7

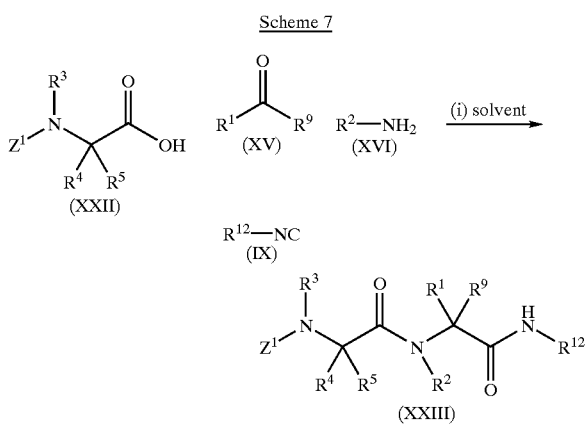

The reaction conditions used for the synthesis of intermediate of formula (XXIII), illustrated in Scheme 7, are similar to those described for the synthesis of intermediate of formula (XVII) illustrated in Scheme 1.

The intermediate compound of formula (XXIII) may be converted to a compound of formula (II) by reacting with acid, in a suitable solvent and appropriate temperature, to effect removal of the amine protecting group ($Z^1$), followed by cyclization. This reaction is illustrated in Scheme 8 below.

Scheme 8

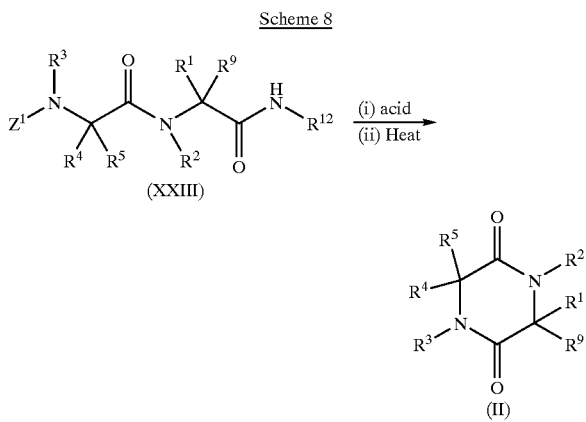

This reaction is carried out in the presence of an acid. There is no particular restriction on the nature of the acid to be used in this reaction, and any acid conventionally used to facilitate removal of an acid labile amine protecting group $Z^1$ and cyclization, may equally be used here, provided that it has no adverse effect on other parts of the molecule. Examples of suitable acids include: mineral acids such as hydrochloric acid or sulfuric acid; organic acids such as trifluoroacetic acid. Acids to be used in the reaction can also be generated in situ, for example by the addition of acetyl chloride in methanol, to generate hydrochloric acid. Preferably, anhydrous acids are used.

In addition to carrying out the reaction in scheme 8 in the presence of acid, a reaction step involving basic conditions can also be optionally carried out so as to facilitate the removal of the amine protecting group $Z^1$, wherein $Z^1$ is a base labile amine protecting group. There is no particular restriction on the nature of the base to be used in this reaction, and any base conventionally used to facilitate removal of an base labile amine protecting group $Z^1$, may equally be used here, provided that it has no adverse effect on other parts of the molecule. Examples of suitable bases include: organic bases such as ammonia, piperidine, morpholine, ethanolamine and diethylamine.

This reaction can take place over a wide range of temperatures, and the precise reaction temperature is not critical to the invention. In general, we find it convenient to carry out the reaction at a temperature of from about 0° C. to about 150° C., preferably from room temperature to about 100° C., more preferably at about room temperature. The time required for the reaction may also vary widely, depending on many factors, notably the reaction temperature and the nature of the reagents. However, provided that the reaction is effected under the preferred conditions outlined above, a period of from 3 hours to 36 hours will usually suffice.

There is no particular restriction on the amine protecting group ($Z^1$) employed. However, amine protecting groups which allow removal of the protecting group and cyclization of the deprotected intermediate, without purification or isolation of intermediates, are preferred. Examples of amine protecting groups include both acid labile amine protecting groups and base labile protecting groups. Preferred acid labile amine protecting group include tert-butoxycarbonyl (BOC) and 2-(4-biphenylyl)-isopropoxy carbonyl (BPOC). Preferred base labile amine protecting group include 9-fluoroenylmethyl carbamate (FMOC).

In situations where acidic conditions are used to remove the amine protecting group in intermediate compound of formula (XXIII) it may also be necessary to treat the deprotected intermediate, which is present as an acid salt, with base so as to convert the acid addition salt to its corresponding free base. There is no particular restriction on the nature of the base to be used. A base conventionally used to convert an acid addition salt to its corresponding free base form may be used here, provided that it has no adverse effect on other parts of the molecule. Examples of suitable bases include ammonia, piperidine, morpholine, ethanolamine, diethylamine, polystyrene bound di-isopropylethylamine or basic DOWEX. Preferably diethylamine, basic DOWEX or polystyrene bound di-isopropylethylamine.

Furthermore, a piperazinyl intermediate of formula (XXIIIa); i.e. an intermediate of formula (XXIII) wherein $R^1$ and $R^2$ together with the nitrogen and carbon atoms through which $R^1$ and $R^2$ are attached form a piperazinyl group; is formed by reacting an amine of formula (XVIa); i.e. an amine of formula (XVI) wherein $R^2$ is $C(R^{19}R^{19'})C(R^{20}R^{20'})NY^1Y^2$, and $Y^1$ is hydrogen, $Y^2$ is independently, hydrogen, alkyl, aryl, heteroaryl, aralkyl, or heteroaralkyl, and $R^{19}$, $R^{19'}$, $R^{20}$, and $R^{20'}$ are independently optionally substituted alkyl; with an aldehyde or ketone of formula (XVa); i.e. aldehyde or ketone of formula (XV) wherein $R_1$ is a $CR^{21}R^{21'}X'$ and $R^{21}$ and $R^{21'}$ are independently optionally substituted alkyl and X is an appropriate leaving, for example a halogen atom; an N-protected amino acid of formula (XXII) and an isonitrile of formula (IX), under conditions analogous to those described for synthesizing intermediate of formula (XXIII) in scheme 7 and as described in Rossen et al., Tetrahedron et Lett. 1997, 38, 3183, the contents of which are hereby incorporated by reference. This reaction is illustrated in Scheme 8a.

Scheme 8a

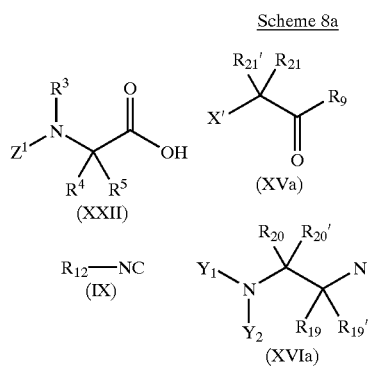

analogous to those described for synthesizing compound of formula (II) in scheme 8 above.

Scheme 8b

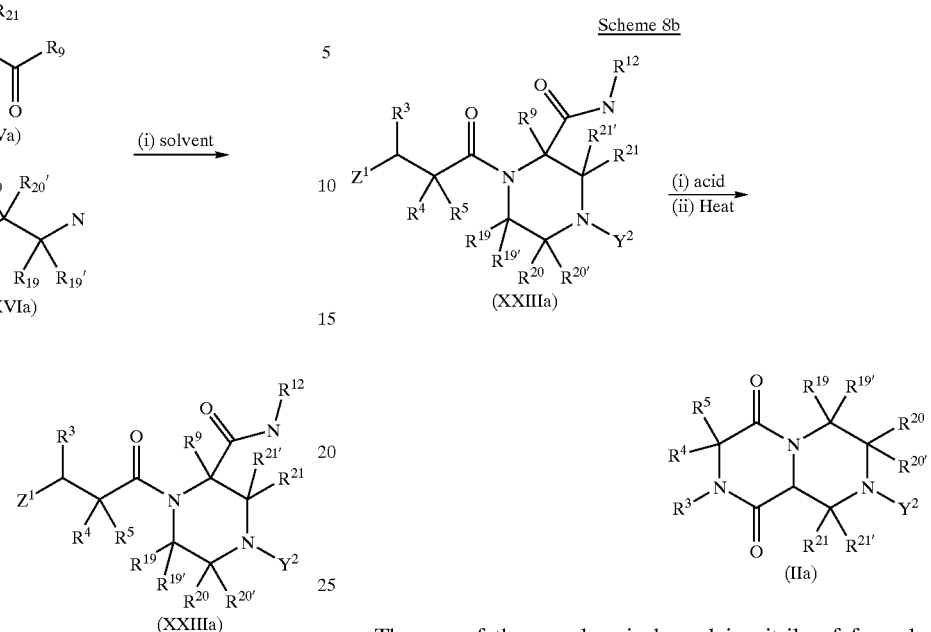

The piperazinyl intermediate of formula (XXIIIa) can then undergo further cyclisation to afford compounds of formula (IIa) i.e. compounds of formula II, wherein $R^1$ and $R^2$ together with the nitrogen and carbon atoms through which $R^1$ and $R^2$ are attached form a piperazinyl group. This reaction is illustrated in Scheme 8b. The cyclisation of piperazinyl intermediate of formula (XXIIIa) to afford the compound of formula (IIa) is carried out under conditions The use of the novel resin bound isonitrile of formula (IXa) in the synthesis of compounds of the formula (XXIII), wherein $R^{12}$ is the novel resin bound isonitrile derivative, is advantageous over other non-resin bound isonitriles. However, use of (IXa) in the synthesis of a compound of formula (II) involves activation of the resin linker to facilitate cleavage of the resin linkage and cyclization to afford a compound of formula (II). An illustration of the use of the novel resin bound isonitrile (IXa) in the synthesis of the intermediate of the formula (XXIII) is illustrated in Scheme 9.

Scheme 9

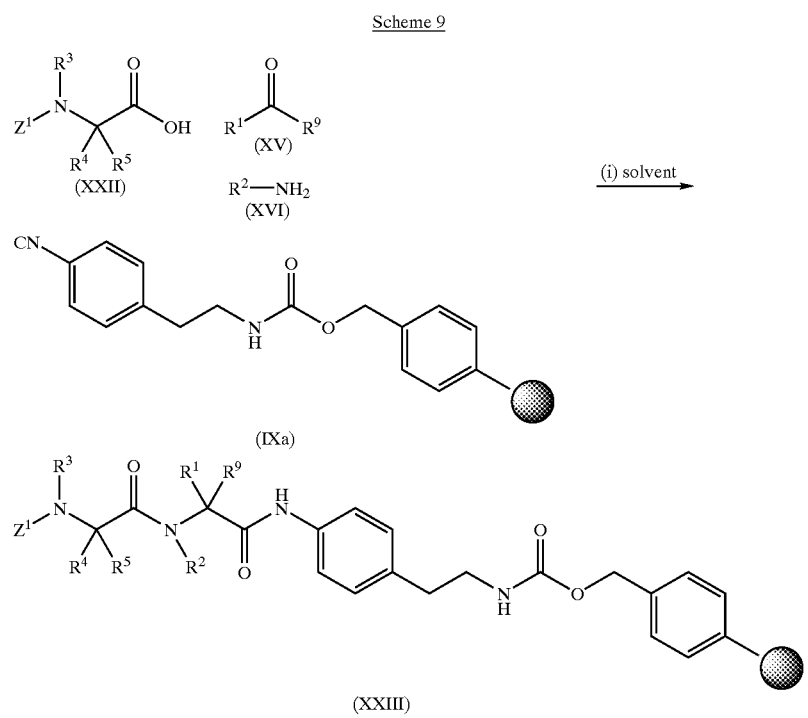

The reaction conditions, and isolation of the product, of the reaction illustrated in Scheme 9 are similar to those described for the synthesis of compound of formula(XIX) illustrated in Scheme 3 above.

The benzamide compound of formula (XXIII) is then activated for nucleophilic cleavage by conversion to intermediate of formula (XXIV) under similar conditions to that described for synthesis of the intermediate of formula (XX). The conversion of (XXIII) to a compound of formula (XXIV) is illustrated in Scheme 10.

The intermediate compound of formula (XXV), may be converted to a compound of formula (II) by reacting with acid, in a suitable solvent and appropriate temperature, to effect removal of the amine protecting group ($Z^1$) and, wherein $R^3$ is an amine protecting group, removal of this amine protecting group also. The deprotected intermediate is then cyclized. This reaction is illustrated in Scheme 12.

Scheme 10

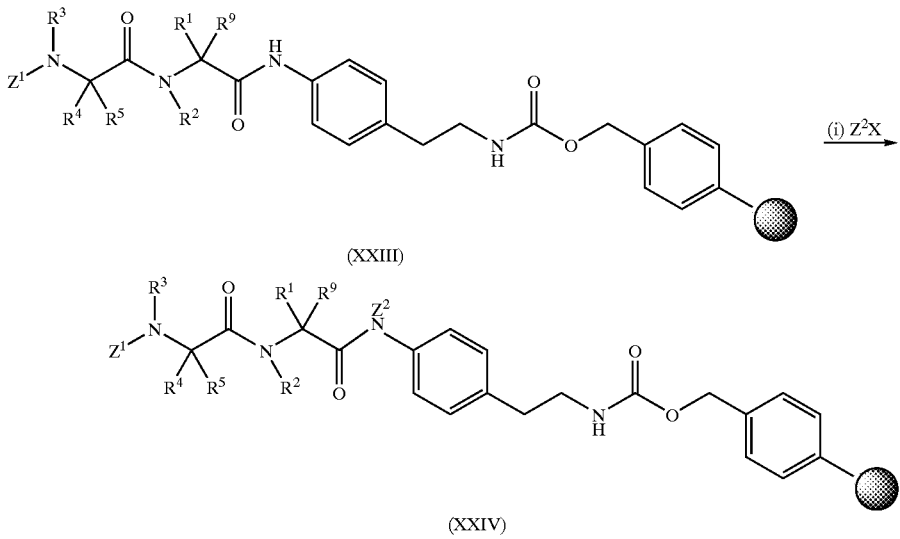

The resin "safety catch" linker is then cleaved, to facilitate the removal of the resin, by reacting the activated benzamide compound of formula (XXIV) with an appropriate alkoxide, or hydroxide, affording the corresponding alkyl esters or carboxylic acids derivative of formula (XXV) respectively, wherein $R^{13}$ is, for example, H, alkyl, phenyl or cycloalkyl (Mjalli, A. M. M., Sarshar, S., Baiga, T. J. *Tetrahedron Lett.* 1996, 37, 2943; Flynn, D. L., Zelle, R. E., Grieco, P. A. *J. Org. Chem.* 1983, 48, 2424). An example of the cleavage from the resin is illustrated in reaction Scheme 11:

Scheme 12

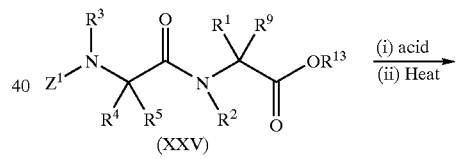

Scheme 11

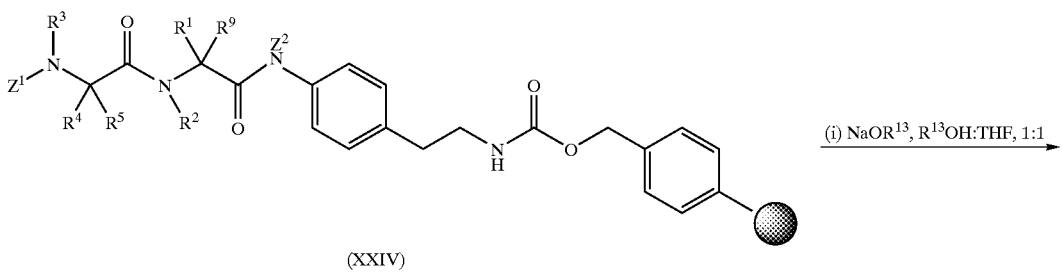

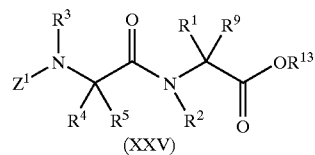

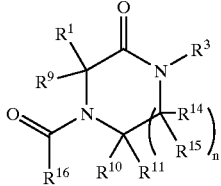
(II)

The reaction conditions and reagents used for the synthesis of compounds of formula (II), illustrated in Scheme 12, are similar to those described for the synthesis of compounds of formula (I) illustrated in Scheme 6.

In situations where acidic conditions are used to remove the amine protecting group in intermediate compound of formula (XXV) it may also be necessary to treat the deprotected intermediate, which is present as an acid salt, with base so as to convert the acid addition salt to its corresponding free base. There is no particular restriction on the nature of the base to be used. A base conventionally used to convert an acid addition salt to its corresponding free base form may be used here, provided that it has no adverse effect on other parts of the molecule. Examples of suitable bases include ammonia, piperidine, morpholine, ethanolamine, diethylamine, polystyrene bound di-isopropylethylamine or basic DOWEX. Preferably diethylamine, basic DOWEX or polystyrene bound di-isopropylethylamine.

General methodology for the preparation of ketopiperazines and dihydroquinoxalinone derivatives of general formula (III):-

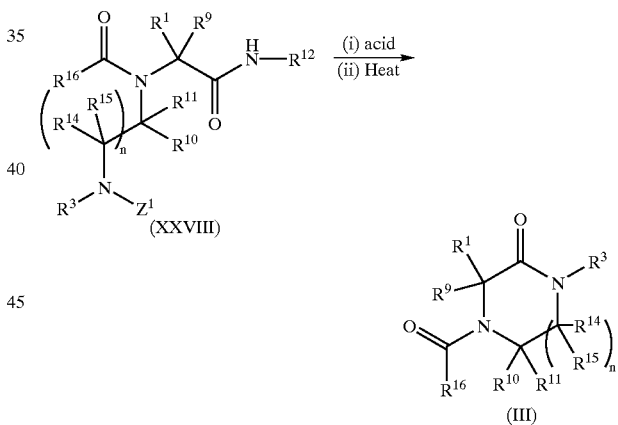
(III)

Compounds of formula (III) may be prepared by the application or adaptation of known methods, by which is meant methods used heretofore or described in the literature, or by methods according to the present invention.

In general terms, compounds of formula (III) wherein n, $R^1$, $R^3$, $R^9$, $R^{10}$, $R^{11}$, $R^{14}$, $R^{15}$ and $R^{16}$ are as hereinbefore defined, may be synthesized according to the present invention via a '3-step, 1-pot' procedure by reacting a compound of formula (XXVI) wherein $R^{16}$ is as hereinbefore defined, with a compound of formula (XXVII) wherein n, $R^3$, $R^{10}$, $R^{11}$, $R^{14}$ and $R^{15}$ are as hereinbefore defined and $Z^1$ is a suitable amine protecting group, (XV) wherein $R^1$ and $R^9$ are as hereinbefore defined, and a compound of formula (IX) wherein $R^{12}$ is as hereinbefore defined, in a suitable solvent at about room temperature, to afford the intermediate compound of formula (XXVIII), wherein n, $R^1$, $R^3$, $R^9$, $R^{10}$, $R^{11}$, $R^{12}$, $R^{14}$, $R^{15}$, $R^{16}$ and $Z^1$ are as hereinbefore defined. The general reaction is illustrated in Scheme 13 below:

Scheme 13

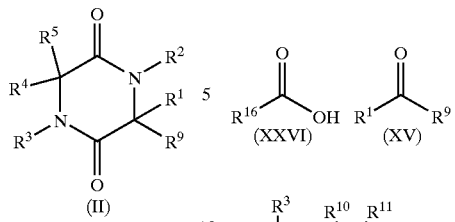

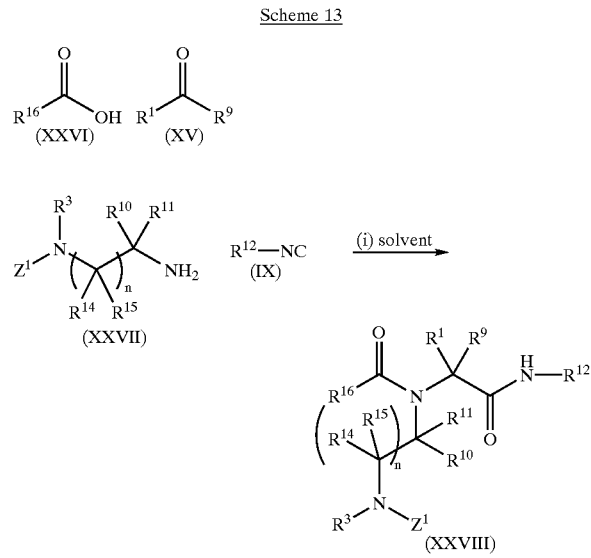

The reaction conditions used for the synthesis of compounds of formula (XXVIII), illustrated in Scheme 13, are similar to those described for the synthesis of compounds of formula (XVII) illustrated in Scheme 1.

The intermediate compound of formula (XXVIII) may be converted to a compound of formula (III) by reacting with acid, in a suitable solvent and appropriate temperature, to effect removal of the amine protecting group ($Z^1$), followed by cyclization. This reaction is illustrated in Scheme 14 below.

Scheme 14

This reaction is carried out in the presence of an acid. There is no particular restriction on the nature of the acid to be used in this reaction, and any acid conventionally used to facilitate removal of an acid labile amine protecting group $Z^1$ and cyclization, may equally be used here, provided that it has no adverse effect on other parts of the molecule. Examples of suitable acids include: mineral acids such as hydrochloric acid or sulfuric acid; organic acids such as trifluoroacetic acid. Acids to be used in the reaction can also be generated in situ, for example by the addition of acetyl chloride in methanol, to generate hydrochloric acid. Preferably, anhydrous acids are used.

In addition to carrying out the reaction in scheme 14 in the presence of acid, a reaction step involving basic conditions can also be optionally carried out so as to facilitate the removal of the amine protecting group $Z^1$, wherein $Z^1$ is a base labile amine protecting group. There is no particular restriction on the nature of the base to be used in this reaction, and any base conventionally used to facilitate removal of an base labile amine protecting group $Z^1$, may equally be used here, provided that it has no adverse effect on other parts of the molecule. Examples of suitable bases include: organic bases such as ammonia, piperidine, morpholine, ethanolamine and diethylamine.

This reaction can take place over a wide range of temperatures, and the precise reaction temperature is not critical to the invention. In general, we find it convenient to carry out the reaction at a temperature of from about 0° C. to about 150° C., preferably from room temperature to about 100° C., more preferably at about room temperature. The time required for the reaction may also vary widely, depending on many factors, notably the reaction temperature and the nature of the reagents. However, provided that the reaction is effected under the preferred conditions outlined above, a period of from 3 hours to 36 hours will usually suffice.

There is no particular restriction on the amine protecting group ($Z^1$) employed. However, amine protecting groups which allow removal of the protecting group and cyclization of the deprotected intermediate, without purification or isolation of intermediates, are preferred. Examples of amine protecting groups include both acid labile amine protecting groups and base labile protecting groups. Preferred acid labile amine protecting group include tert-butoxycarbonyl (BOC) and 2-(4-biphenylyl)-isopropoxy carbonyl (BPOC). Preferred base labile amine protecting group include 9-fluoroenylmethyl carbamate (FMOC).

In situations where acidic conditions are used to remove the amine protecting group in intermediate compound of formula (XXVIII) it may also be necessary to treat the deprotected intermediate, which is present as an acid salt, with base so as to convert the acid addition salt to its corresponding free base. There is no particular restriction on the nature of the base to be used. A base conventionally used to convert an acid addition salt to its corresponding free base form may be used here, provided that it has no adverse effect on other parts of the molecule. Examples of suitable bases include ammonia, piperidine, morpholine, ethanolamine, diethylamine, polystyrene bound di-isopropylethylamine or basic DOWEX. Preferably diethylamine, basic DOWEX or polystyrene bound di-isopropylethylamine.

Furthermore, a lactam intermediate of formula of formula (XXVIIIa); i.e. an intermediate of formula of formula (XXVIII) wherein $R^9$ and $R^{16}$ together with the carbon atoms and nitrogen atom though which they are attached form a 5–8 membered heterocyclyl group; is formed by reacting an N-protected amine of formula of formula (XXVII) with an aldehyde-acid of formula (XXVIa) wherein r is 1, 2, 3, or 4; i.e. an acid of formula (XXVI) wherein $R^{16}$ is C-3 to C-5 alkyl substituted by an acyl group; and an isonitrile of formula (IX), under conditions analogous to those described for synthesizing intermediate (XXVIII) in scheme 13. This reaction is illustrated in Scheme 13a.

Scheme 13a

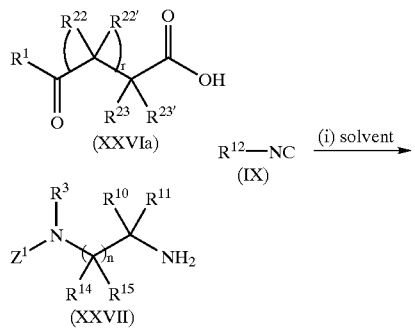

-continued

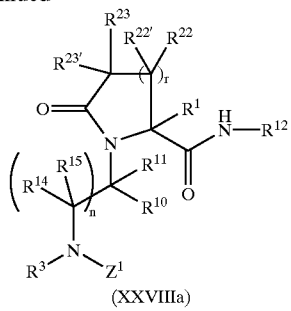

(XXVIIIa)

The lactam intermediate of formula (XXVIIIa) can then undergo further cyclisation to afford compounds of formula (IIIa) i.e. compounds of formula III, wherein $R^9$ and $R^{16}$ together with the carbon atoms and nitrogen atom though which they are attached form a 5–8 membered heterocyclyl group. This reaction is illustrated in Scheme 13b. The cyclisation of the lactam intermediate of formula (XXVIIIa) to afford the compound of formula (IIIa) wherein r is 1, 2, 3, or 4, is carried out under conditions analogous to those described for synthesizing compound of formula (II) in scheme 14 above.

scheme 13b

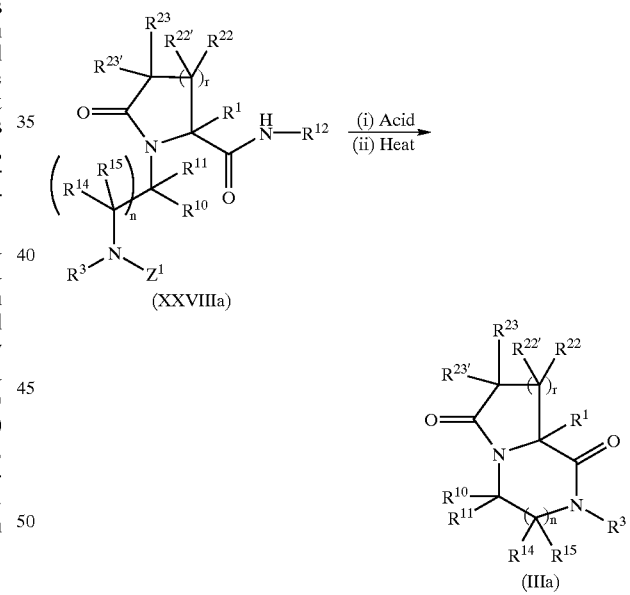

The use of the novel resin bound isonitrile (IXa) in the synthesis of intermediate compounds of the formula (XXVIII) wherein $R^{12}$ is a novel resin bound isonitrile derivative (IXa) is advantageous over other non-resin bound isonitriles. However, use of an isonitrile of formula (IXa) in the synthesis of compounds of formula (III) involves activation of the resin linker to facilitate cleavage of the resin linkage and cyclization to afford a compound of formula (III). An illustration of the use of the novel resin bound isonitrile of formula (IXa) in the synthesis of the intermediate of formula (XXIX) is illustrated in Scheme 15 below.

Scheme 15

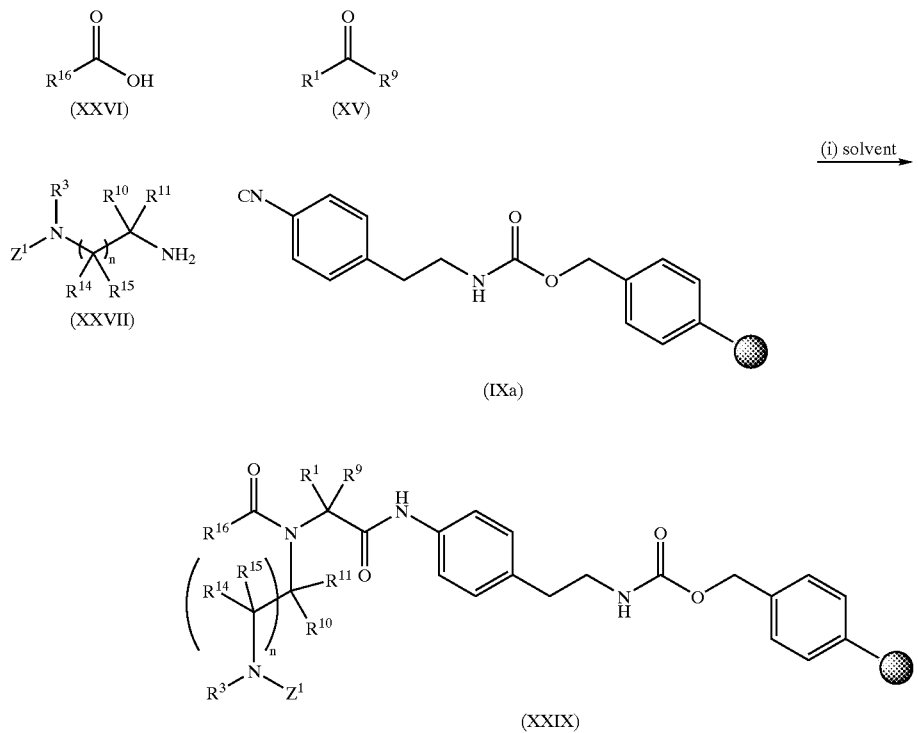

The reaction conditions, and isolation of the product, of the reaction illustrated in Scheme 15 are similar to those described for the synthesis of compound of formula (XIX) illustrated in Scheme 3 above.

The benzamide compound of formula (XXIX) is then activated for nucleophilic cleavage by conversion to intermediate of formula (XXX) under similar conditions to that described for synthesis of the intermediate of formula (XX). The conversion of a compound of formula (XXIX) to a compound of formula (XXX) is illustrated in Scheme 16.

Scheme 16

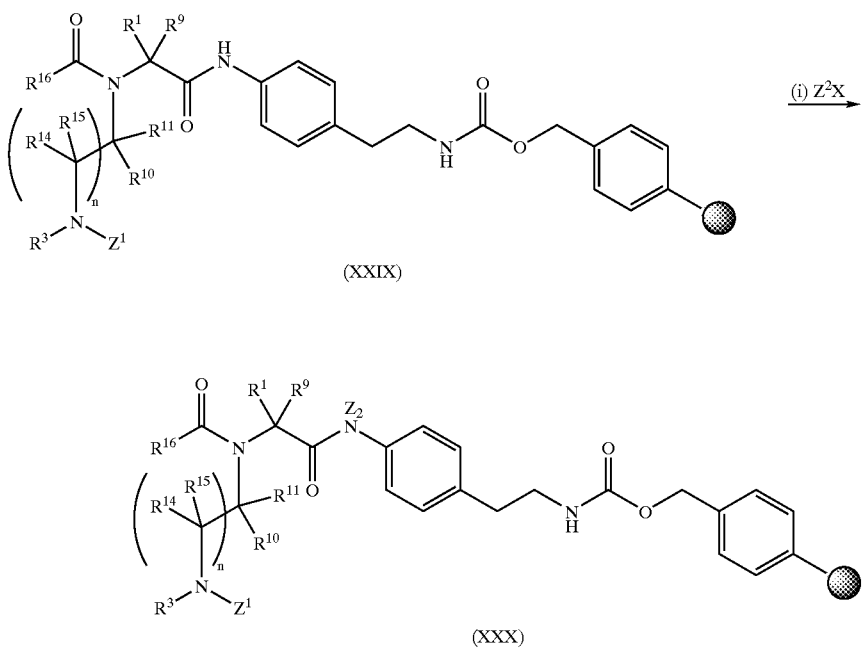

The resin "safety catch" linker is then cleaved, to facilitate the removal of the resin, by reacting the activated benzamide compound of formula (XXX) with an appropriate alkoxide, or hydroxide, affording the corresponding alkyl esters or carboxylic acids derivative of formula (XXXI) respectively, by the same procedure as described for the synthesis of compounds of formula (XXV) above. An example of the cleavage from the resin is illustrated in reaction Scheme 17:

The reaction conditions and reagents used for the synthesis of compounds of formula (III), illustrated in Scheme 18, are similar to those described for the synthesis of compounds of formula (I) illustrated in Scheme 6.

In situations where acidic conditions are used to remove the amine protecting group in intermediate compound of formula (XXXI) it may also be necessary to treat the Scheme 17

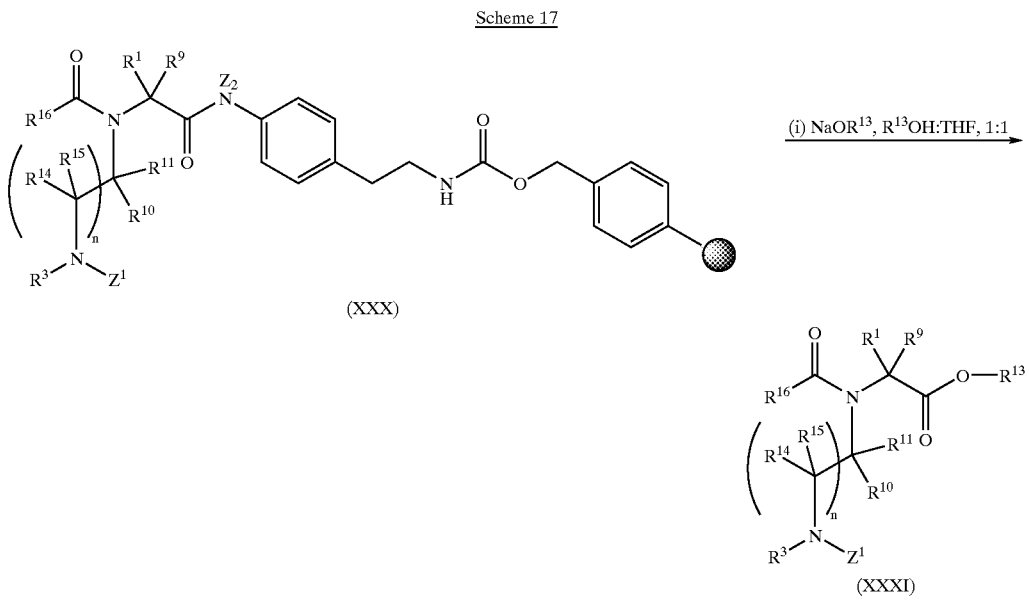

The intermediate compound of formula (XXXI), may be converted to a compound of formula (III) by reacting with acid, in a suitable solvent and appropriate temperature, to effect removal of the amine protecting group ($Z^1$) and, wherein $R^3$ is an amine protecting group, removal of this amine protecting group also. The deprotected intermediate is then cyclized to afford the product of formula (III). This reaction is illustrated in Scheme 18.

Scheme 18

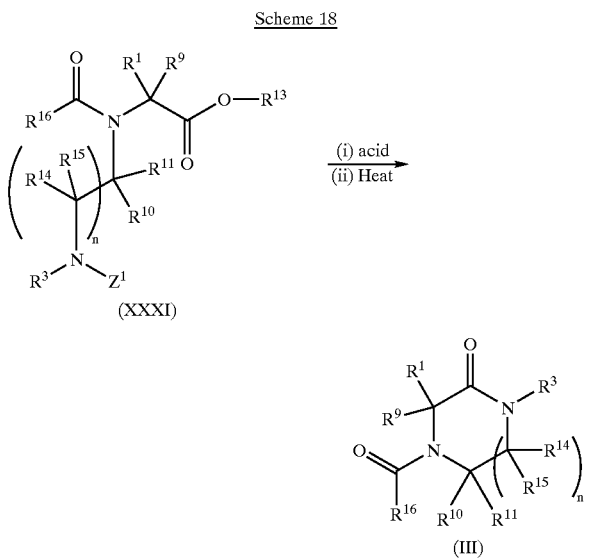

deprotected intermediate, which is present as an acid salt, with base so as to convert the acid addition salt to its corresponding free base. There is no particular restriction on the nature of the base to be used. A base conventionally used to convert an acid addition salt to its corresponding free base form may be used here, provided that it has no adverse effect on other parts of the molecule. Examples of suitable bases include ammonia, piperidine, morpholine, ethanolamine, diethylamine, polystyrene bound di-isopropylethylamine or basic DOWEX. Preferably diethylamine, basic DOWEX or polystyrene bound di-isopropylethylamine.

The use of the resin bound isonitrile of formula (XVIII) in the synthesis of compounds of the formula (XXXII), wherein $R^{12}$—NC is the resin bound isonitrile derivative of formula (XVIII), is advantageous over other non-resin bound isonitriles. However, use of an isonitrile of formula (IXa) in the synthesis of compounds of formula (III) involves activation of the resin linker to facilitate cleavage of the resin linkage and cyclization to afford a compound of formula (III). An illustration of the use of the novel resin bound isonitrile of formula (XVIII) in the synthesis of the intermediate of the formula (XXXII) is illustrated in Scheme 19.

Scheme 19

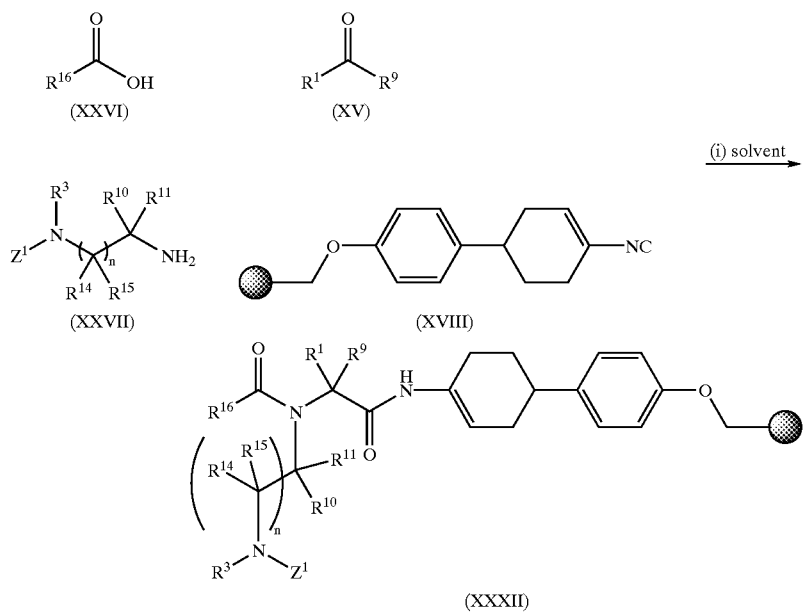

The reaction conditions used for the synthesis of compounds of formula (XXXII), illustrated in Scheme 19, are similar to those described for the synthesis of compounds of formula (XVII) illustrated in Scheme 1.

The intermediate compound of formula (XXXII) may be converted to a compound of formula (III) by reacting with acid, in a suitable solvent and appropriate temperature, to effect removal of the amine protecting group, followed by cyclization. This reaction is illustrated in Scheme 20.

removal of the amine protecting group $Z^1$, wherein $Z^1$ is a base labile amine protecting group. There is no particular restriction on the nature of the base to be used in this reaction, and any base conventionally used to facilitate removal of an base labile amine protecting group $Z^1$, may equally be used here, provided that it has no adverse effect on other parts of the molecule. Examples of suitable bases include: organic bases such as ammonia, piperidine, morpholine, ethanolamine and diethylamine.

Scheme 20

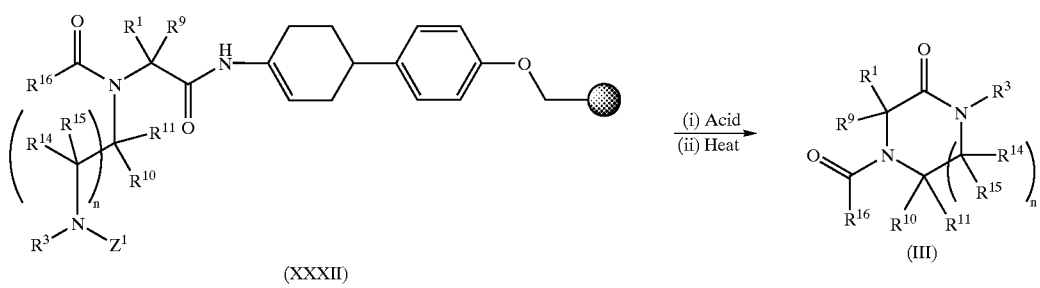

This reaction is carried out in the presence of an acid. There is no particular restriction on the nature of the acid to be used in this reaction, and any acid conventionally used to facilitate removal of an acid labile amine protecting group $Z^1$ and cyclization, may equally be used here, provided that it has no adverse effect on other parts of the molecule. Examples of suitable acids include: mineral acids such as hydrochloric acid or sulfuric acid; organic acids such as trifluoroacetic acid. Acids to be used in the reaction can also be generated in situ, for example by the addition of acetyl chloride in methanol, to generate hydrochloric acid. Preferably, anhydrous acids are used.

In addition to carrying out the reaction in scheme 20 in the presence of acid, a reaction step involving basic conditions can also be optionally carried out so as to facilitate the This reaction can take place over a wide range of temperatures, and the precise reaction temperature is not critical to the invention. In general, we find it convenient to carry out the reaction at a temperature of from about 0° C. to about 150° C., preferably from room temperature to about 100° C., more preferably at about room temperature. The time required for the reaction may also vary widely, depending on many factors, notably the reaction temperature and the nature of the reagents. However, provided that the reaction is effected under the preferred conditions outlined above, a period of from 3 hours to 36 hours will usually suffice.

There is no particular restriction on the amine protecting group ($Z^1$) employed. However, amine protecting groups which allow removal of the protecting group and cyclization of the deprotected intermediate, without purification or isolation of intermediates, are preferred. Examples of amine protecting groups include both acid labile amine protecting groups and base labile protecting groups. Preferred acid labile amine protecting group include tert-butoxycarbonyl (BOC) and 2-(4-biphenylyl)-isopropoxy carbonyl (BPOC). Preferred base labile amine protecting group include 9-fluoroenylmethyl carbamate (FMOC).

In situations where acidic conditions are used to remove the amine protecting group in intermediate compound of formula (XXXII) it may also be necessary to treat the deprotected intermediate, which is present as an acid salt, with base so as to convert the acid addition salt to its corresponding free base. There is no particular restriction on the nature of the base to be used. A base conventionally used to convert an acid addition salt to its corresponding free base form may be used here, provided that it has no adverse effect on other parts of the molecule. Examples of suitable bases include ammonia, piperidine, morpholine, ethanolamine, diethylamine, polystyrene bound di-isopropylethylamine or basic DOWEX. Preferably diethylamine, basic DOWEX or polystyrene bound di-isopropylethylamine.

General methodology for the preparation of dihydroimidazole derivatives of general formula (IV)

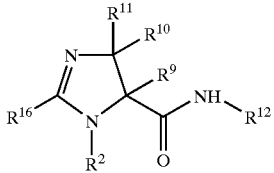

(IV)

In general terms, compounds of formula (IV) wherein $R^2$, $R^9$, $R^{10}$, $R^{11}$, $R^{12}$ and $R^{16}$ are as hereinbefore defined, may be synthesized according to the present invention via a '3-step, 1-pot' procedure by reacting a compound of formula (XXVI) wherein $R^{16}$ is as hereinbefore defined with compound of formula (XXXIII) wherein $R^9$, $R^{10}$ and $R^{11}$ are as hereinbefore defined and $Z^1$ is a amine protecting group, (IX) wherein $R^{12}$ is as hereinbefore defined, and (XVI) wherein $R^2$ is as hereinbefore defined, in a suitable solvent at about room temperature, to afford the intermediate compound of formula (XXXIV), wherein $R^2$, $R^9$, $R^{10}$, $R^{11}$, $R^{12}$, $Z^1$ and $R^{16}$, are as hereinbefore. The general reaction is illustrated in scheme 21 below:

Scheme 21

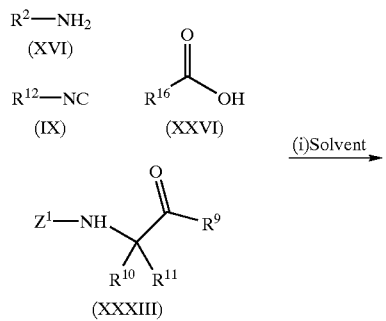

-continued

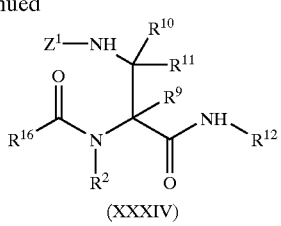

(XXXIV)

The conversion of the compound of formula (XXXIV) to the compound of formula IV is described hereinafter with reference to Scheme 22. There is no particular restriction on the nature of the solvent to be employed, provided that it has no adverse effect on the reaction or on the reagents involved (See Waki et al. J. Am. Chem. Soc., 1977, 6075–6077, the contents of which are hereby incorporated herein by reference). Examples of suitable solvents include: alcohols, such as methanol, 1-butanol, phenol, trifluoroethanol, and hexafluoro-2-propanol; hydrocarbons, such as benzene and toluene; amides, such as dimethyl acetamide, and dimethylformamide; halides, such as dichloromethane, and dichloroethane; and ethers, such as tetrahydrofuran and dioxane; other solvents include water, 1-methyl-2-pyrrolidine, diethyl phosphite, tetramethylsulphone, dimethyl sulphoxide, acetonitrile and pyridine. Of these solvents, the alcohols are preferred.

There is no restriction on the isonitrile used in the reaction scheme 21 above. Examples of suitable isonitriles include, benzyl isocyanide, n-butyl isocyanide, diethyl isocyanomethyl phosphonate, cyclohexyl isocyanide, 2,6-dimethylphenyl isocyanide, methyl isocyanoacetate, isopropyl isocyanide and 1,1,3,3-tetramethylbutyl isocyanide. Preferable isocyanides include, benzyl isocyanide, n-butyl isocyanide, diethyl isocyanomethyl phosphonate.

The reaction can take place over a wide range of temperatures, and the precise reaction temperature is not critical to the invention. In general, we find it convenient to carry out the reaction at a temperature of from about 0° C. to about 150° C., preferably from room temperature to about 100° C., more preferably at about room temperature. The time required for the reaction may also vary widely, depending on many factors, notably the reaction temperature and the nature of the reagents. However, provided that the reaction is effected under the preferred conditions outlined above, a period of from 3 hours to 36 hours will usually suffice.

The intermediate compound of the formula (XXXIV) thus prepared may be recovered from the reaction mixture by conventional means. For example, the compounds may be recovered by distilling off the solvent in vacuo from the reaction mixture or, if necessary after distilling off the solvent from the reaction mixture, pouring the residue into water followed by extraction with a water-immiscible organic solvent and distilling off the solvent from the extract. Additionally, the product can, if desired, be further purified by various well known techniques, such as recrystallization, reprecipitation or the various chromatography techniques, notably column chromatography or preparative thin layer chromatography. The intermediate compound is preferably recovered from the reaction mixture by distilling off the solvent in vacuo.

The intermediate compound of formula (XXXIV) may be converted to a compound of formula (IV) by reacting with acid, in a suitable solvent and appropriate temperature, to effect removal of the amine protecting group, followed by cyclization. This reaction is illustrated in scheme 22.

Scheme 22

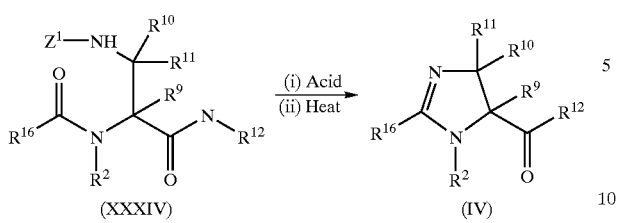

(XXXIV) → (IV)

(i) Acid
(ii) Heat

Cyclization of the deprotected amine to dihydroimidazole proceeded an average of 66% of possible dihydroimidazole product. The remaining no-cyclized amines are removed via a solution phase scavenging step with the simultaneous addition of PS-DIEA or PS-tris(2-aminoethyl)amine (6 equiv.) and PS-NCO (3 equiv.) in dichloroethane. (Booth, R. J.; Hodges, J. C. *J. Am. Chem. Soc.*1997, 119, 4882. Flynn, D. L.; Crich, J. Z.; Devraj, R. V.; Hockerman, S. L.; Parlow, J. J.; South, M. S.; Woodward, S. *J. Am. Chem. Soc.* 1997, 119, 4874. Purchased from Argonaut® technologies (PS-DIEA—polystyrene bound disopropylethylamine)).

This reaction is carried out in the presence of an acid. There is no particular restriction on the nature of the acid to be used in this reaction, and any acid conventionally used to facilitate removal of an acid labile amine protecting group $Z^1$ and cyclization, may equally be used here, provided that it has no adverse effect on other parts of the molecule. Examples of suitable acids include: mineral acids such as hydrochloric acid or sulfuric acid; organic acids such as trifluoroacetic acid. Acids to be used in the reaction can also be generated in situ, for example by the addition of acetyl chloride in methanol, to generate hydrochloric acid. Preferably, anhydrous acids are used.

In addition to carrying out the reaction in scheme 22 in the presence of acid, a reaction step involving basic conditions can also be optionally carried out so as to facilitate the removal of the amine protecting group $Z^1$, wherein $Z^1$ is a base labile amine protecting group. There is no particular restriction on the nature of the base to be used in this reaction, and any base conventionally used to facilitate removal of an base labile amine protecting group $Z^1$, may equally be used here, provided that it has no adverse effect on other parts of the molecule. Examples of suitable bases include: organic bases such as ammonia, piperidine, morpholine, ethanolamine and diethylamine.

This reaction can take place over a wide range of temperatures, and the precise reaction temperature is not critical to the invention. In general, we find it convenient to carry out the reaction at a temperature of from about 0° C. to about 150° C., preferably from room temperature to about 100° C., more preferably at about room temperature. The time required for the reaction may also vary widely, depending on many factors, notably the reaction temperature and the nature of the reagents. However, provided that the reaction is effected under the preferred conditions outlined above, a period of from 3 hours to 36 hours will usually suffice.

There is no particular restriction on the amine protecting group ($Z^1$) employed. However, acid labile amine protecting groups which allow removal of the protecting group and cyclization of the deprotected intermediate, without purification or isolation of intermediates, are preferred. Preferred acid labile amine protecting group include tert-butoxycarbonyl (BOC) and 2-(4-biphenylyl)-isopropoxy carbonyl (BPOC).

It is also envisaged that a solid phase synthesis of compounds of formula (IV) could be carried out using a resin bound Ugi component of formulae (XII), (IXa), (XV) or (XXXIII) using similar reaction conditions as described herein.

General methodology for the preparation of lactam derivatives of general formula (V)

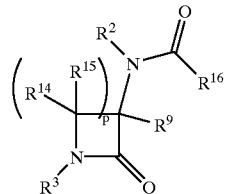

(V)

In general terms, compounds of formula (V) wherein p, $R^2$, $R^3$, $R^9$, $R^{14}$, $R^{15}$ and $R^{16}$ are as hereinbefore defined, may be synthesized according to the present invention via a '3-step, 1-pot' procedure by reacting a compound of formula (XXVI) wherein $R^{16}$ is as hereinbefore defined, with a compound of formula (XXXV) wherein p, $R^3$, $R^9$, $R^{14}$, $R^{15}$ and $Z^1$ are as hereinbefore defined, an amine of formula (XVI) wherein $R^2$ is as hereinbefore defined, and a resin bound isonitrile of formula (XVIII) in a suitable solvent at about room temperature, to afford the intermediate compound of formula (XXXVI), wherein p, $R^2$, $R^3$, $R^9$, $R^{14}$, $R^{15}$, $R^{16}$ and $Z^1$ are as hereinbefore defined. The general reaction is illustrated in Scheme 23 below:

Scheme 23

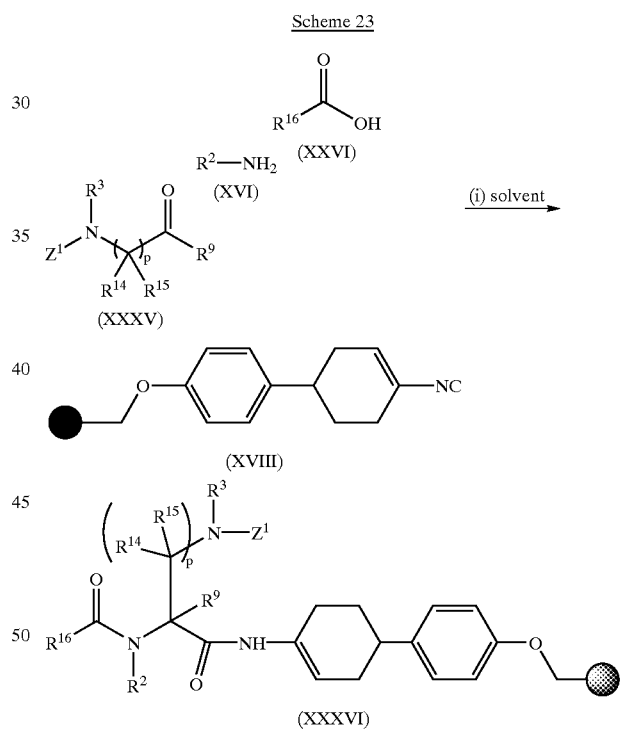

The conversion of the compound of formula (XXXVI) to the compound of formula V is described hereinafter with reference to Scheme 24. There is no particular restriction on the nature of the solvent to be employed, provided that it has no adverse effect on the reaction or on the reagents involved (See Waki et al. J. Am. Chem. Soc., 1977, 6075–6077, the contents of which are hereby incorporated herein by reference). Examples of suitable solvents include: alcohols, such as methanol, 1-butanol, phenol, trifluoroethanol, and hexafluoro-2-propanol; hydrocarbons, such as benzene and toluene; amides, such as dimethyl acetamide, and dimethylformamide; halides, such as dichloromethane, and dichloroethane; and ethers, such as tetrahydrofuran and dioxane;

other solvents include water, 1-methyl-2-pyrrolidine, diethyl phosphite, tetramethylsulphone, dimethyl sulphoxide, acetonitrile and pyridine. Of these solvents, the alcohols are preferred.

The reaction can take place over a wide range of temperatures, and the precise reaction temperature is not critical to the invention. In general, we find it convenient to carry out the reaction at a temperature of from about 0° C. to about 150° C., preferably from room temperature to about 100° C., more preferably at about room temperature. The time required for the reaction may also vary widely, depending on many factors, notably the reaction temperature and the nature of the reagents. However, provided that the reaction is effected under the preferred conditions outlined above, a period of from 3 hours to 36 hours will usually suffice.

The intermediate compound of formula (XXXVI) may be converted to a compound of formula (V) by reacting with acid or base, in a suitable solvent and appropriate temperature, to effect removal of the amine protecting group, followed by cyclization. This reaction is illustrated in scheme 24 below:

Scheme 24

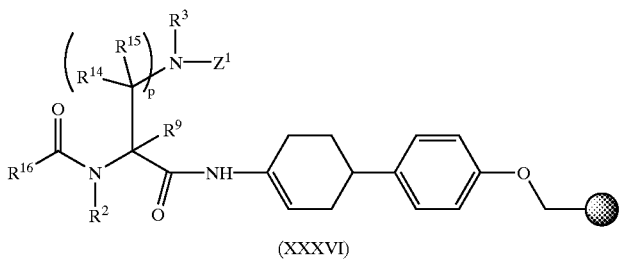

(XXXVI)    (V)

This reaction is carried out in the presence of an acid. There is no particular restriction on the nature of the acid to be used in this reaction, and any acid conventionally used to facilitate removal of an acid labile amine protecting group $Z^1$ and cyclization, may equally be used here, provided that it has no adverse effect on other parts of the molecule. Examples of suitable acids include: mineral acids such as hydrochloric acid or sulfuric acid; organic acids such as trifluoroacetic acid. Acids to be used in the reaction can also be generated in situ, for example by the addition of acetyl chloride in methanol, to generate hydrochloric acid. Preferably, anhydrous acids are used.

This reaction can take place over a wide range of temperatures, and the precise reaction temperature is not critical to the invention. In general, we find it convenient to carry out the reaction at a temperature of from about 0° C. to about 150° C., preferably from room temperature to about 100° C., more preferably at about room temperature. The time required for the reaction may also vary widely, depending on many factors, notably the reaction temperature and the nature of the reagents. However, provided that the reaction is effected under the preferred conditions outlined above, a period of from 3 hours to 36 hours will usually suffice.

There is no particular restriction on the amine protecting group ($Z^1$) employed. However, amine protecting groups which allow removal of the protecting group and cyclization of the deprotected intermediate, without purification or isolation of intermediates, are preferred. Examples of amine protecting groups include both acid labile amine protecting groups and base labile protecting groups. Preferred acid labile amine protecting group include tert-butoxycarbonyl (BOC) and 2-(4-biphenylyl)-isopropoxy carbonyl (BPOC). Preferred base labile amine protecting group include 9-fluoroenylmethyl carbamate (FMOC).

Similarly, the synthesis of compounds of formula (V) can be carried out in solid phase using a resin bound isonitrile of formula (IXa) and using reaction conditions similar to those described for schemes 15–18.

Alternatively, the synthesis of compounds of formula (V) can be carried out in solution phase using a non resin bound isonitrile.

General methodology for the preparation of 1,4-benzodiazepine-2,5-dione and diketopiperazine derivatives of general formula (VI),:-.

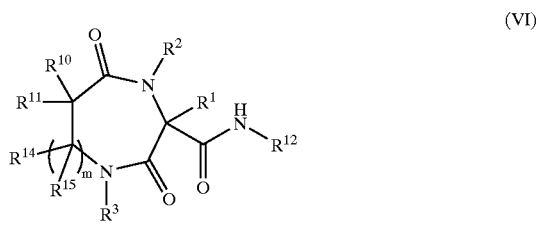

(VI)

In general terms, compounds of formula (VI) wherein m, $R^1$, $R^2$, $R^3$, $R^{10}$, $R^{11}$, $R^{12}$, $R^{14}$ and $R^{15}$ are hereinbefore defined, may be synthesized by reacting a compound of formula (XIV wherein m, $R^3$, $R^{10}$, $R^{11}$, $R^{14}$ and $R^{15}$ are hereinbefore defined and $Z^1$ is a suitable amine protecting group, with compound of formula (XXXVII) wherein $R^1$ and $R^9$ are hereinbefore defined, a compound of formula (XVI) wherein $R^2$ is hereinbefore defined, and an isonitrile of formula (IX) wherein $R^{12}$ represents hydrogen, alkyl, aroyl, aralkyl, aryl, fused arylcycloalkyl, fused arylheterocyclyl, cycloalkyl, heteroaralkyl, heteroaryl, fused heteroarylcycloalkyl, fused heteroarylheterocyclyl, heterocyclyl; in a suitable solvent at about room temperature, to afford the intermediate compound of formula (XXXVIII) wherein m, $R^1$, $R^2$, $R^3$, $R^9$, $R^{10}$, $R^{11}$, $R^{12}$, $R^{14}$, $R^{15}$, and $Z^1$ are hereinbefore defined. The general reaction is illustrated in scheme 25 below:

Scheme 25

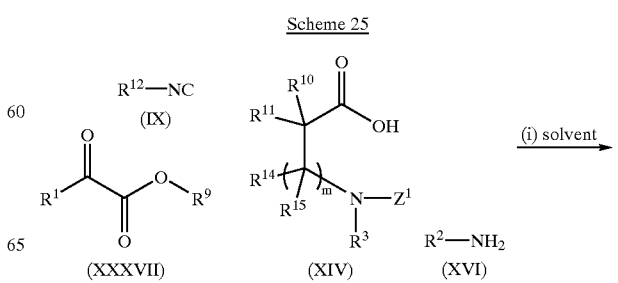

(IX)    (XXXVII)    (XIV)    (XVI)

-continued

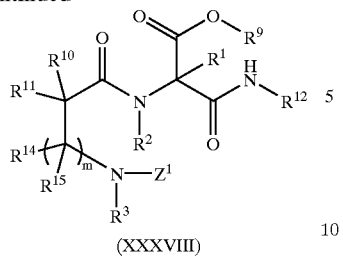

(XXXVIII)

The conversion of the compound of formula (XXXVIII) to the compound of formula VI is described hereinafter with reference to Scheme 26. There is no particular restriction on the nature of the solvent to be employed, provided that it has no adverse effect on the reaction or on the reagents involved (See Waki et al. J. Am. Chem. Soc., 1977, 6075–6077, the contents of which are hereby incorporated herein by reference). Examples of suitable solvents include: alcohols, such as methanol, 1-butanol, phenol, trifluoroethanol, and hexafluoro-2-propanol; hydrocarbons, such as benzene and toluene; amides, such as dimethyl acetamide, and dimethylformamide; halides, such as dichloromethane, and dichloroethane; and ethers, such as tetrahydrofuran and dioxane; other solvents include water, 1-methyl-2-pyrrolidine, diethyl phosphite, tetramethylsulphone, dimethyl sulphoxide, acetonitrile and pyridine. Of these solvents, the alcohols are preferred.

There is no restriction on the isonitrile ($R^{12}$—NC) used in the reaction scheme above, provided that it has no adverse effect on the reaction involved. Examples of suitable isonitriles include, benzyl isocyanide, n-butyl isocyanide, diethyl isocyanomethyl phosphonate, cyclohexyl isocyanide, 2,6-dimethylphenyl isocyanide, methyl isocyanoacetate, isopropyl isocyanide and 1,1,3,3-tetramethylbutyl isocyanide. Preferable isocyanides include cyclohexyl isocyanide, 2,6-dimethylphenyl isocyanide, isopropyl isocyanide and 1,1,3,3-tetramethylbutyl isocyanide.

The reaction can take place over a wide range of temperatures, and the precise reaction temperature is not critical to the invention. In general, we find it convenient to carry out the reaction at a temperature of from about 0° C. to about 150° C., preferably from room temperature to about 100° C., more preferably at about room temperature. The time required for the reaction may also vary widely, depending on many factors, notably the reaction temperature and the nature of the reagents. However, provided that the reaction is effected under the preferred conditions outlined above, a period of from 3 hours to 36 hours will usually suffice.

The intermediate compound of the formula (XXXVIII) thus prepared may be recovered from the reaction mixture by conventional means. For example, the compounds may be recovered by distilling off the solvent in vacuo from the reaction mixture or, if necessary after distilling off the solvent from the reaction mixture, pouring the residue into water followed by extraction with a water-immiscible organic solvent and distilling off the solvent from the extract. Additionally, the product can, if desired, be further purified by various well known techniques, such as recrystallization, reprecipitation or the various chromatography techniques, notably column chromatography or preparative thin layer chromatography. The intermediate compound is preferably recovered from the reaction mixture by distilling off the solvent in vacuo.

The intermediate compound of formula (XXXVIII) may be converted to a compound of formula (VI) by reacting with acid, in a suitable solvent and appropriate temperature, to effect removal of the amine protecting group, followed by cyclization. This reaction is illustrated in scheme 26.

Scheme 26

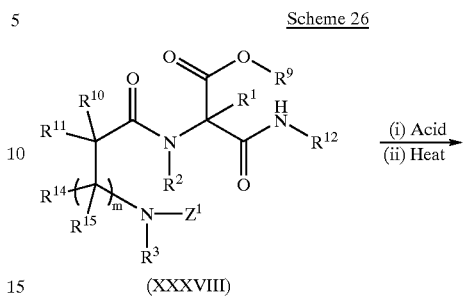

(XXXVIII)

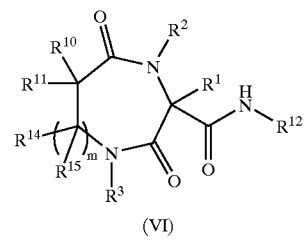

(VI)

This reaction is carried out in the presence of an acid. There is no particular restriction on the nature of the acid to be used in this reaction, and any acid conventionally used to facilitate removal of an acid labile amine protecting group $Z^1$ and cyclization, may equally be used here, provided that it has no adverse effect on other parts of the molecule. Examples of suitable acids include: mineral acids such as hydrochloric acid or sulfuric acid; organic acids such as trifluoroacetic acid. Acids to be used in the reaction can also be generated in situ, for example by the addition of acetyl chloride in methanol, to generate hydrochloric acid. Preferably, anhydrous acids are used.

In addition to carrying out the reaction in scheme 26 in the presence of acid, a reaction step involving basic conditions can also be optionally carried out so as to facilitate the removal of the amine protecting group $Z^1$, wherein $Z^1$ is a base labile amine protecting group. There is no particular restriction on the nature of the base to be used in this reaction, and any base conventionally used to facilitate removal of an base labile amine protecting group $Z^1$, may equally be used here, provided that it has no adverse effect on other parts of the molecule. Examples of suitable bases include: organic bases such as ammonia, piperidine, morpholine, ethanolamine and diethylamine.

This reaction can take place over a wide range of temperatures, and the precise reaction temperature is not critical to the invention. In general, we find it convenient to carry out the reaction at a temperature of from about 0° C. to about 150° C., preferably from room temperature to about 100° C., more preferably at about room temperature. The time required for the reaction may also vary widely, depending on many factors, notably the reaction temperature and the nature of the reagents. However, provided that the reaction is effected under the preferred conditions outlined above, a period of from 3 hours to 36 hours will usually suffice.

There is no particular restriction on the amine protecting group ($Z^1$) employed. However, amine protecting groups which allow removal of the protecting group and cyclization of the deprotected intermediate, without purification or isolation of intermediates, are preferred. Examples of amine protecting groups include both acid labile amine protecting groups and base labile protecting groups. Preferred acid labile amine protecting group include tert-butoxycarbonyl (BOC) and 2-(4-biphenylyl)-isopropoxy carbonyl (BPOC). Preferred base labile amine protecting group include 9-fluoroenylmethyl carbamate (FMOC).

General methodology for the preparation of 1,4-benzodiazepine-2,5-dione derivatives of general formula (VII)

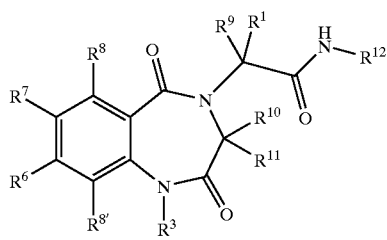

(VII)

Compounds of formula (VII) may be synthesized according to the present invention via a '3-step, 1-pot' procedure by the application or adaptation of known methods, by which is meant methods used heretofore or described in the literature, or by methods according to the present invention.

In general terms, compounds of formula (VII) wherein $R^1$, $R^3$, $R^{8'}$, $R^6$, $R^7$, $R^8$, $R^9$ $R^{10}$, $R^{11}$ and $R^{12}$ are hereinbefore defined, and $Z^1$ is a suitable amine protecting group, may be synthesized by reacting an isonitrile compound of formula (IX), wherein $R^{12}$, is hereinbefore defined, with compound of formula (XV) wherein $R^1$ and $R^9$ are hereinbefore defined, a compound of formula (XIV) wherein $R^3$, $R^{8'}$ $R^6$ $R^7$ and $R^8$ are hereinbefore defined and resin bound amino ester compound of formula (XXXIX) wherein $R^{10}$, $R^{11}$ are as hereinbefore defined, $R^{17}$ and $R^{18}$ independently represent hydrogen, alkyl, aralkyl, aryl, fused arylcycloalkyl, fused arylheterocyclyl, aryloxy, cycloalkyl, heteroaralkyl, heteroaryl, fused heteroarylcycloalkyl, fused heteroarylheterocyclyl, or heterocyclyl, most preferably, alkyl or hydrogen; and q is 1, 2 or 3, in a suitable solvent at about room temperature, to afford the intermediate compound of formula (XL). This reaction is illustrated in scheme 27 below:

Scheme 27

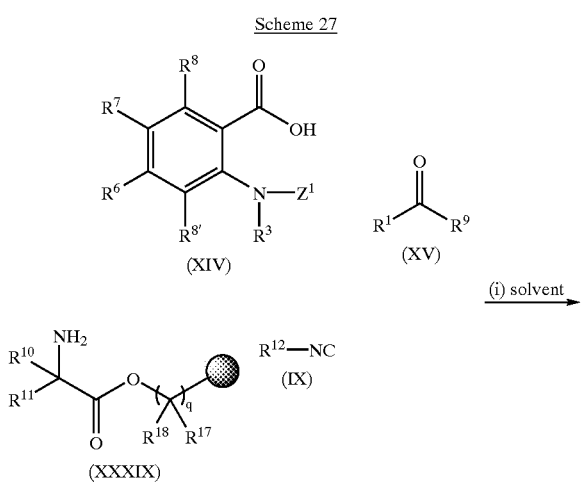

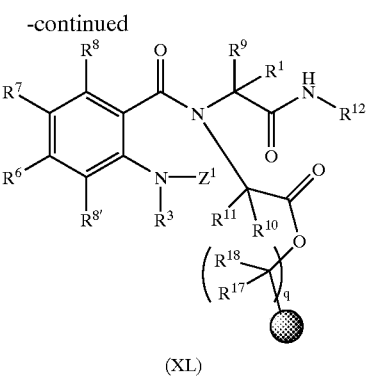

(XL)

There is no restriction on the isonitrile used in the reaction scheme 27 above. Examples of suitable isonitriles include, benzyl isocyanide, n-butyl isocyanide, diethyl isocyanomethyl phosphonate, cyclohexyl isocyanide, 2,6-dimethylphenyl isocyanide, methyl isocyanoacetate, isopropyl isocyanide and 1,1,3,3-tetramethylbutyl isocyanide. Preferable isonitriles include benzyl isocyanide, n-butyl isocyanide, diethyl isocyanomethyl phosphonate. More preferably is 1-isocyanocyclohexene.

There is no particular restriction on the nature of the solvent to be employed, provided that it has no adverse effect on the reaction or on the reagents involved. Examples of suitable solvents include: alcohols, such as methanol, 1-butanol, phenol, trifluoroethanol, hexafluoro-2-propanol; hydrocarbons, such as benzene and toluene; amides, such as dimethyl acetamide, dimethylformamide; halides, such as dichloromethane, dichloroethane; and ethers, such as tetrahydrofuran and dioxane; other solvents include water, 1-methyl-2-pyrrolidine, diethyl phosphite, tetramethylsulphone, dimethyl sulphoxide, acetonitrile and pyridine. Of these solvents, the alcohols are preferred.

The reaction can take place over a wide range of temperatures, and the precise reaction temperature is not critical to the invention. In general, we find it convenient to carry out the reaction at a temperature of from about 0° C. to about 150° C., preferably from room temperature to about 100° C., more preferably at about room temperature. The time required for the reaction may also vary widely, depending on many factors, notably the reaction temperature and the nature of the reagents. However, provided that the reaction is effected under the preferred conditions outlined above, a period of from 3 hours to 36 hours will usually suffice.

The intermediate compound of formula (XL) may be converted to a compound of formula (VII) by reacting with acid, in a suitable solvent and appropriate temperature, to effect removal of the amine protecting group, followed by cyclization. This reaction is illustrated in scheme 28 below:

Scheme 28

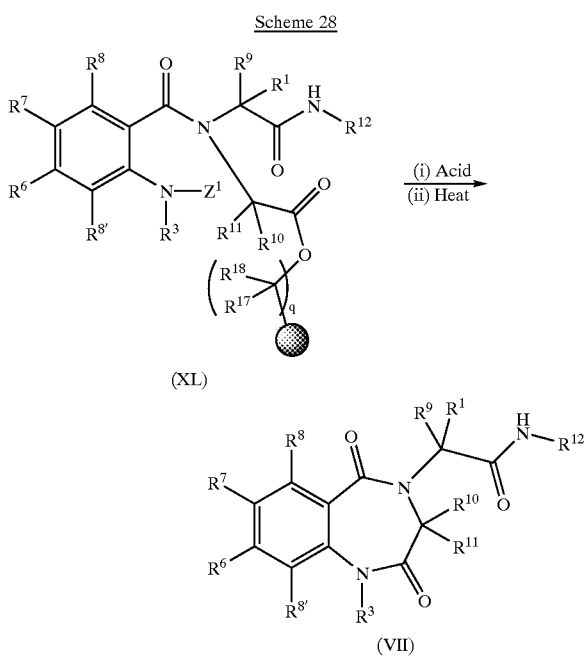

(XL)

(i) Acid
(ii) Heat (VII)

This reaction is carried out in the presence of an acid. There is no particular restriction on the nature of the acid to be used in this reaction, and any acid conventionally used to facilitate removal of an acid labile amine protecting group $Z^1$ and cyclization, may equally be used here, provided that it has no adverse effect on other parts of the molecule. Examples of suitable acids include: mineral acids such as hydrochloric acid or sulfuric acid; organic acids such as trifluoroacetic acid. Acids to be used in the reaction can also be generated in situ, for example by the addition of acetyl chloride in methanol, to generate hydrochloric acid. Preferably, anhydrous acids are used.

In addition to carrying out the reaction in scheme 28 in the presence of acid, a reaction step involving basic conditions can also be optionally carried out so as to facilitate the removal of the amine protecting group $Z^1$, wherein $Z^1$ is a base labile amine protecting group. There is no particular restriction on the nature of the base to be used in this reaction, and any base conventionally used to facilitate removal of an base labile amine protecting group $Z^1$, may equally be used here, provided that it has no adverse effect on other parts of the molecule. Examples of suitable bases include: organic bases such as ammonia, piperidine, morpholine, ethanolamine and diethylamine.

This reaction can take place over a wide range of temperatures, and the precise reaction temperature is not critical to the invention. In general, we find it convenient to carry out the reaction at a temperature of from about 0° C. to about 150° C., preferably from room temperature to about 100° C., more preferably at about room temperature. The time required for the reaction may also vary widely, depending on many factors, notably the reaction temperature and the nature of the reagents. However, provided that the reaction is effected under the preferred conditions outlined above, a period of from 3 hours to 36 hours will usually suffice.

There is no particular restriction on the amine protecting group ($Z^1$) employed. However, amine protecting groups which allow removal of the protecting group and cyclization of the deprotected intermediate, without purification or isolation of intermediates, are preferred. Examples of amine protecting groups include both acid labile amine protecting groups and base labile protecting groups. Preferred acid labile amine protecting group include tert-butoxycarbonyl (BOC) and 2-(4-biphenylyl)-isopropoxy carbonyl (BPOC). Preferred base labile amine protecting group include 9-fluoroenylmethyl carbamate (FMOC).

Alternatively, the synthesis of compounds of formula (VII) can be carried out in solution phase using a non resin bound amino ester.

General methodology for the preparation of Ketopiperazine and Dihydroquinoxalinone derivatives of general formula (VIII)

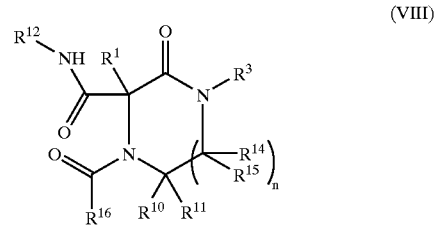

(VIII)

In general terms, compounds of formula (VIII) wherein n, $R^1$, $R^3$, $R^{10}$, $R^{11}$, $R^{12}$, $R^{14}$, $R^{15}$ and $R^{16}$ are hereinbefore defined, may be synthesized according to the present invention via a '3-step, 1-pot' procedure by reacting a compound of formula (XXVI) wherein $R^{16}$ is hereinbefore defined, with a compound of formula (XXVII) wherein n, $R^3$, $R^{10}$, $R^{11}$, $R^{14}$ and $R^{15}$ are hereinbefore defined and $Z^1$ is a suitable amine protecting group, a compound of formula (XXXVII) wherein $R^1$ and $R^9$ are hereinbefore defined, and an isonitrile of formula (IX) wherein $R^{12}$ is hereinbefore defined, in a suitable solvent at about room temperature, to afford the intermediate compound of formula (XLI), wherein n, $R^1$, $R^3$, $R^9$, $R^{10}$, $R^{11}$, $R^{14}$, $R^{15}$, $R^{16}$ and $Z^1$ are hereinbefore defined. The general reaction is illustrated in Scheme 29 below:

Scheme 29

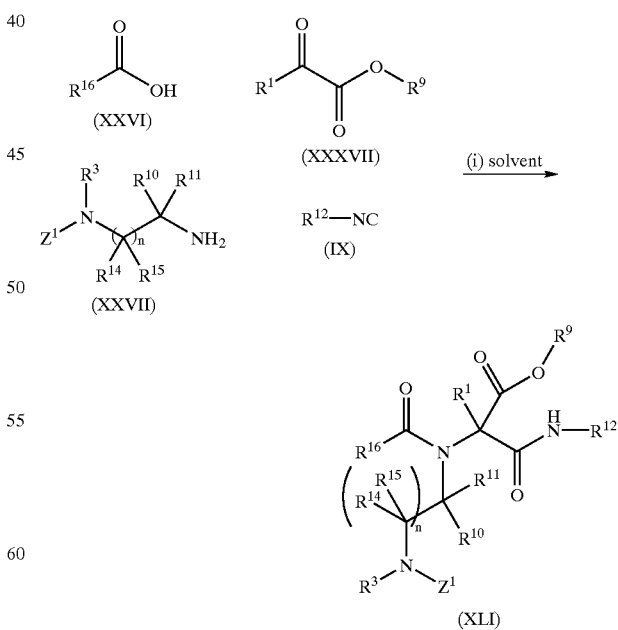

(XLI)

It is known that when the nucleophilicity of the nitrogen atom adjacent to $R^{10}$ and $R^{11}$ is poor, the Passerini reaction (See J. March, Advanced Organic Chemistry, 3rd Ed., John Wiley & Sons p. 870–871 (1985)) predominates and the yields of the desired cyclized product of formula (VIII) is lowered. Therefore, it is preferred that at least one of $R^{10}$ and $R^{11}$, is an electron donating group, or when n=1, and $R^{11}$ and $R^{14}$ are absent and $R^{10}$ and $R^{15}$ taken together with the adjacent carbon atoms through which they are linked form an electron donating 6 membered aryl or 5 to 6 membered an electron donating heteroaryl; or when n=1, $R^{10}$ and $R^{15}$ taken together with the adjacent carbon atoms through which they are linked form a 5 to 7 membered an electron donating cycloalkyl group or an electron donating heterocyclyl group; or when n=2, and adjacent $R^{11}$ and $R^{14}$ are absent, $R^{10}$ and adjacent $R^{15}$ taken together with the adjacent carbon atoms through which they are linked form a 6 membered electron donating aryl group or 5 to 6 membered electron donating heteroaryl group; or when n=2, $R^{10}$ and adjacent $R^{15}$ taken together with the adjacent carbon atoms through which they are linked form a 5 to 7 membered electron donating cycloalkyl group or an electron donating heterocyclyl group; so as to increase the nucleophilicity of the adjacent nitrogen atom and give higher yields of the desired product of formula (VIII).

There is no particular restriction on the nature of the solvent to be employed, provided that it has no adverse effect on the reaction or on the reagents involved (See Waki et al. J. Am. Chem. Soc., 1977, 6075–6077, the contents of which are hereby incorporated herein by reference). Examples of suitable solvents include: alcohols, such as methanol, 1-butanol, phenol, trifluoroethanol, and hexafluoro-2-propanol; hydrocarbons, such as benzene and toluene; amides, such as dimethyl acetamide, and dimethylformamide; halides, such as dichloromethane, and dichloroethane; and ethers, such as tetrahydrofuran and dioxane; other solvents include water, 1-methyl-2-pyrrolidine, diethyl phosphite, tetramethylsulphone, dimethyl sulphoxide, acetonitrile and pyridine. Of these solvents, the alcohols are preferred.

There is no restriction on the isonitrile ($R^{12}$—NC) used in the reaction scheme above, provided that it has no adverse effect on the reaction involved. Examples of suitable isonitriles include, benzyl isocyanide, n-butyl isocyanide, diethyl isocyanomethyl phosphonate, cyclohexyl isocyanide, 2,6-dimethylphenyl isocyanide, methyl isocyanoacetate, isopropyl isocyanide and 1,1,3,3-tetramethylbutyl isocyanide. Preferable isonitriles include cyclohexyl isocyanide, 2,6-dimethylphenyl isocyanide, isopropyl isocyanide and 1,1,3,3-tetramethylbutyl isocyanide.

The reaction can take place over a wide range of temperatures, and the precise reaction temperature is not critical to the invention. In general, we find it convenient to carry out the reaction at a temperature of from about 0° C. to about 150° C., preferably from room temperature to about 100° C., more preferably at about room temperature. The time required for the reaction may also vary widely, depending on many factors, notably the reaction temperature and the nature of the reagents. However, provided that the reaction is effected under the preferred conditions outlined above, a period of from 3 hours to 36 hours will usually suffice.

The intermediate compound of the formula (XLI) thus prepared may be recovered from the reaction mixture by conventional means. For example, the compounds may be recovered by distilling off the solvent in vacuo from the reaction mixture or, if necessary after distilling off the solvent from the reaction mixture, pouring the residue into water followed by extraction with a water-immiscible organic solvent and distilling off the solvent from the extract. Additionally, the product can, if desired, be further purified by various well known techniques, such as recrystallization, reprecipitation or the various chromatography techniques, notably column chromatography or preparative thin layer chromatography. The intermediate compound is preferably recovered from the reaction mixture by distilling off the solvent in vacuo.

The intermediate compound of formula (XLI) may be converted to a compound of formula (VIII) by reacting with acid, in a suitable solvent and appropriate temperature, to effect removal of the amine protecting group, followed by cyclization. This reaction is illustrated in scheme 30.

Scheme 30

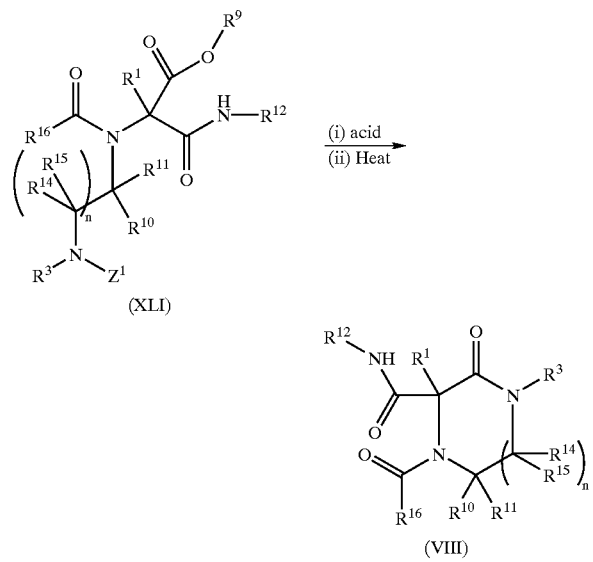

This reaction is carried out in the presence of an acid. There is no particular restriction on the nature of the acid to be used in this reaction, and any acid conventionally used to facilitate removal of an acid labile amine protecting group $Z^1$ and cyclization, may equally be used here, provided that it has no adverse effect on other parts of the molecule. Examples of suitable acids include: mineral acids such as hydrochloric acid or sulfuric acid; organic acids such as trifluoroacetic acid. Acids to be used in the reaction can also be generated in situ, for example by the addition of acetyl chloride in methanol, to generate hydrochloric acid. Preferably, anhydrous acids are used.

In addition to carrying out the reaction in scheme 30 in the presence of acid, a reaction step involving basic conditions can also be optionally carried out so as to facilitate the removal of the amine protecting group $Z^1$, wherein $Z^1$ is a base labile amine protecting group. There is no particular restriction on the nature of the base to be used in this reaction, and any base conventionally used to facilitate removal of an base labile amine protecting group $Z^1$, may equally be used here, provided that it has no adverse effect on other parts of the molecule. Examples of suitable bases include: organic bases such as ammonia, piperidine, morpholine, ethanolamine and diethylamine.

This reaction can take place over a wide range of temperatures, and the precise reaction temperature is not critical to the invention. In general, we find it convenient to carry out the reaction at a temperature of from about 0° C. to about 150° C., preferably from room temperature to about 100° C., more preferably at about room temperature. The time required for the reaction may also vary widely, depending on many factors, notably the reaction temperature and the nature of the reagents. However, provided that the reaction is effected under the preferred conditions outlined above, a period of from 3 hours to 36 hours will usually suffice.

There is no particular restriction on the amine protecting group ($Z^1$) employed. However, amine protecting groups which allow removal of the protecting group and cyclization of the deprotected intermediate, without purification or isolation of intermediates, are preferred. Examples of amine protecting groups include both acid labile amine protecting groups and base labile protecting groups. Preferred acid labile amine protecting group include tert-butoxycarbonyl (BOC) and 2-(4-biphenylyl)-isopropoxy carbonyl (BPOC). Preferred base labile amine protecting group include 9-fluoroenylmethyl carbamate (FMOC).

Alternatively, a compound of the formula (VIII) wherein n, $R^1$, $R^{10}$, $R^{11}$, $R^{12}$, $R^{14}$, $R^{15}$ and $R^{16}$ are hereinbefore defined and $R^3$ is hydrogen, may be prepared by '2-step, one pot' method by reacting a compound of formula (XXVI) wherein $R^{16}$ is hereinbefore defined, with a compound of formula (XXVIIa) wherein n, $R^{10}$, $R^{11}$, $R^{14}$ and $R^{15}$ are hereinbefore defined and $R^3$ is hydrogen, a compound of formula (XXXVII) wherein $R^1$ and $R^9$ are hereinbefore defined, and an isonitrile of formula (IX) wherein $R^{12}$ is hereinbefore defined, in a suitable solvent and appropriate temperature to effect cyclization and afford a compound of formula (VIII). The general reaction is illustrated in Scheme 31 below:

Scheme 31

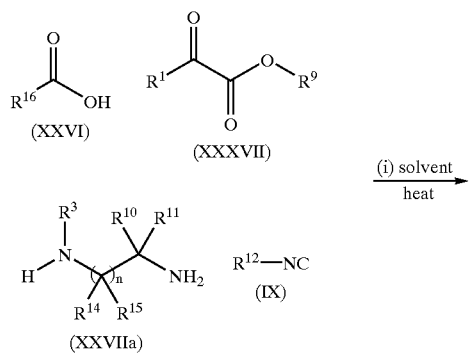

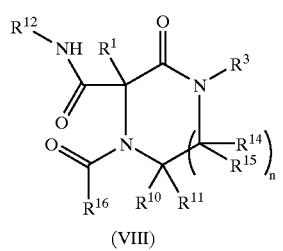

(VIII)

The solvent and isonitrile used in this reaction are similar to those used for the synthesis of a compound of formula (XLI) illustrated in Scheme 30. The reaction temperature used in this reaction is similar to that used for the cyclization of a compound of formula (XLI) illustrated in Scheme 30.

It would also be understood by a skilled person in the art that use of a diamino compound of formula (XXVIIa) wherein $R^{10}$, $R^{11}$, $R^{14}$ and $R^{15}$ are identical to each other would produce a single compound of formula (VIII).

General methodology for the preparation of ketoiperzine derivatives of general formula (XLII)

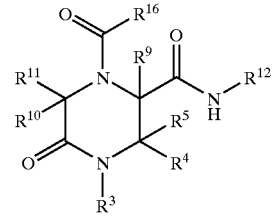

(XLII)

Compounds of formula (XLII) may be synthesized according to the present invention via a '3-step, 1-pot' procedure by the application or adaptation of known methods, by which is meant methods used heretofore or described in the literature, or by methods according to the present invention.

In general terms, compounds of formula (XLII) wherein $R^3$, $R^4$, $R^5$, $R^9$, $R^{10}$, $R^{11}$, $R^{12}$ and $R^{16}$, are hereinbefore defined, may be synthesized by reacting an isonitrile compound of formula (IX), wherein $R^{12}$, is hereinbefore defined, with compounds of formula (XLIII) wherein $R^3$, $R^4$ $R^5$, $R^9$ and $Z^1$ are hereinbefore defined, a compound of formula (XXVI) wherein $R^{16}$ is hereinbefore defined and amino ester bound resin compound of formula (XXXIX) wherein $R^{10}$, $R^{11}$ are as hereinbefore defined, $R^{17}$ and $R^{18}$ independently represent hydrogen, alkoxycarbonyl, alkyl, arylalkoxycarbonyl, aralkyl, aroyl, aryl, fused arylcycloalkyl, fused arylheterocyclyl, aryloxy, aryloxycarbonyl, cycloalkyl, heteroaralkyl, heteroaroyl, heteroaryl, fused heteroarylcycloalkyl, fused heteroarylheterocyclyl, or heterocyclyl; and q is 1, 2 or 3, in a suitable solvent at about room temperature, to afford the intermediate compound of formula (XLIX). This reaction is illustrated in scheme 32 below:

Scheme 32

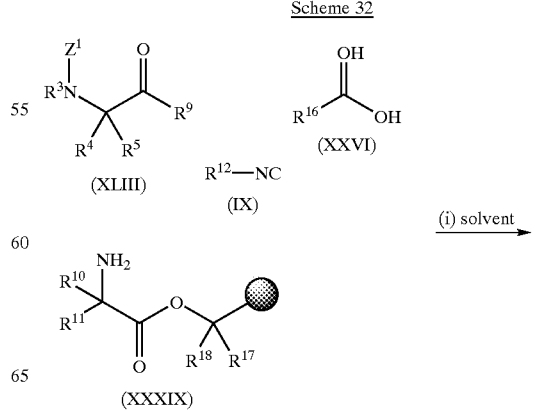

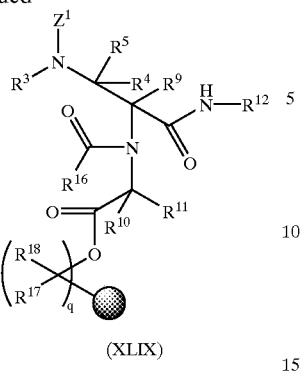

(XLIX)

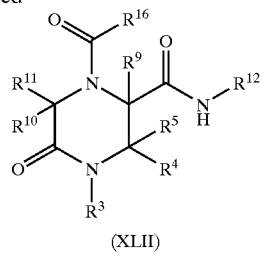

(XLII)

There is no restriction on the isonitrile used in the reaction scheme 32 above. Examples of suitable isonitriles include, benzyl isocyanide, n-butyl isocyanide, diethyl isocyanomethyl phosphonate, cyclohexyl isocyanide, 2,6-dimethylphenyl isocyanide, methyl isocyanoacetate, isopropyl isocyanide and 1,1,3,3-tetramethylbutyl isocyanide. Preferable isonitriles include benzyl isocyanide, n-butyl isocyanide, diethyl isocyanomethyl phosphonate. More preferred is 1-isocyanocyclohexene.

There is no particular restriction on the nature of the solvent to be employed, provided that it has no adverse effect on the reaction or on the reagents involved. Examples of suitable solvents include: alcohols, such as methanol, 1-butanol, phenol, trifluoroethanol, hexafluoro-2-propanol; hydrocarbons, such as benzene and toluene; amides, such as dimethyl acetamide, dimethylformamide; halides, such as dichloromethane, dichloroethane; and ethers, such as tetrahydrofuran and dioxane; other solvents include water, 1-methyl-2-pyrrolidine, diethyl phosphite, tetramethylsulphone, dimethyl sulphoxide, acetonitrile and pyridine. Of these solvents, the alcohols are preferred.

The reaction can take place over a wide range of temperatures, and the precise reaction temperature is not critical to the invention. In general, we find it convenient to carry out the reaction at a temperature of from about 0° C. to about 150° C., preferably from room temperature to about 100° C., more preferably at about room temperature. The time required for the reaction may also vary widely, depending on many factors, notably the reaction temperature and the nature of the reagents. However, provided that the reaction is effected under the preferred conditions outlined above, a period of from 3 hours to 36 hours will usually suffice.

The intermediate compound of formula (XLIX) may be converted to a compound of formula (XLII) by reacting with acid, in a suitable solvent and appropriate temperature, to effect removal of the amine protecting group, followed by cyclization. This reaction is illustrated in scheme 33 below:

Scheme 33

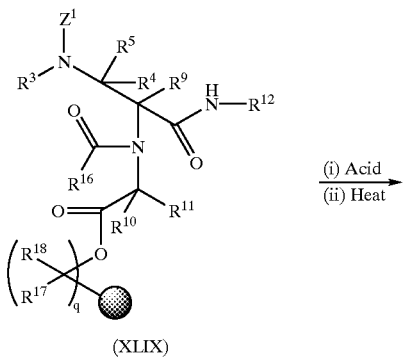

(XLIX)

(i) Acid
(ii) Heat

This reaction is carried out in the presence of an acid. There is no particular restriction on the nature of the acid to be used in this reaction, and any acid conventionally used to facilitate removal of an acid labile amine protecting group $Z^1$ and cyclization, may equally be used here, provided that it has no adverse effect on other parts of the molecule. Examples of suitable acids include: mineral acids such as hydrochloric acid or sulfuric acid; organic acids such as trifluoroacetic acid. Acids to be used in the reaction can also be generated in situ, for example by the addition of acetyl chloride in methanol, to generate hydrochloric acid. Preferably, anhydrous acids are used.

In addition to carrying out the reaction in scheme 33 in the presence of acid, a reaction step involving basic conditions can also be optionally carried out so as to facilitate the removal of the amine protecting group $Z^1$, wherein $Z^1$ is a base labile amine protecting group. There is no particular restriction on the nature of the base to be used in this reaction, and any base conventionally used to facilitate removal of an base labile amine protecting group $Z^1$, may equally be used here, provided that it has no adverse effect on other parts of the molecule. Examples of suitable bases include: organic bases such as ammonia, piperidine, morpholine, ethanolamine and diethylamine.

This reaction can take place over a wide range of temperatures, and the precise reaction temperature is not critical to the invention. In general, we find it convenient to carry out the reaction at a temperature of from about 0° C. to about 150° C., preferably from room temperature to about 100° C., more preferably at about room temperature. The time required for the reaction may also vary widely, depending on many factors, notably the reaction temperature and the nature of the reagents. However, provided that the reaction is effected under the preferred conditions outlined above, a period of from 3 hours to 36 hours will usually suffice.

There is no particular restriction on the amine protecting group ($Z^1$) employed. However, amine protecting groups which allow removal of the protecting group and cyclization of the deprotected intermediate, without purification or isolation of intermediates, are preferred. Examples of amine protecting groups include both acid labile amine protecting groups and base labile protecting groups. Preferred acid labile amine protecting group include tert-butoxycarbonyl (BOC) and 2-(4-biphenylyl)-isopropoxy carbonyl (BPOC). Preferred base labile amine protecting group include 9-fluoroenylmethyl carbamate (FMOC).

Similarly, the synthesis of compounds of formula (XLII) can be carried out in solution phase using a non resin bound amino ester.

General methodology for the preparation of cyclic ureas derivatives of general formula (L)

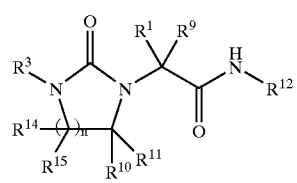

(L)

Compounds of formula (L) may be synthesized according to the present invention via a '3-step, 1-pot' procedure by the application or adaptation of known methods, by which is meant methods used heretofore or described in the literature, or by methods according to the present invention.

In general terms, compounds of formula (L) wherein $R^1$, $R^3$, $R^9$, $R^{10}$, $R^{11}$, $R^{12}$, $R^{14}$ and $R^{15}$ are hereinbefore defined and n is 1 or 2, may be synthesized by generating the acid of formula (LI) in situ (by bubbling $CO_2$ through methanol at 0° C. for 5 minutes), reacting the acid of formula (LI) with an isonitrile compound of formula (IX), wherein $R^{12}$, is hereinbefore defined, with compounds of formula (XXVII) wherein $R^3$, $R^{10}$, $R^{11}$, $R^{14}$, $R^{15}$, $Z^1$ and n are hereinbefore defined, and with an aldehyde or ketone of formula (XV) wherein $R^1$, $R^9$ are as hereinbefore defined; and n is 1 or 2, in a suitable solvent at about room temperature, to afford the intermediate compound of formula (LII). This reaction is illustrated in scheme (34) below:

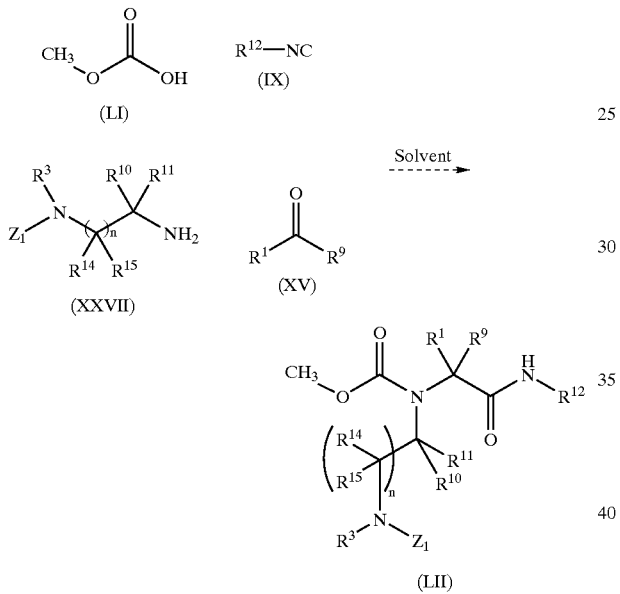

There is no restriction on the isonitrile used in the reaction scheme 34 above. Examples of suitable isonitriles include, benzyl isocyanide, n-butyl isocyanide, diethyl isocyanomethyl phosphonate, cyclohexyl isocyanide, 2,6-dimethylphenyl isocyanide, methyl isocyanoacetate, isopropyl isocyanide and 1,1,3,3-tetramethylbutyl isocyanide. Preferable isonitriles include benzyl isocyanide, n-butyl isocyanide, diethyl isocyanomethyl phosphonate. More preferred is 1-isocyanocyclohexene.

There is no particular restriction on the nature of the solvent to be employed, provided that it has no adverse effect on the reaction or on the reagents involved. Examples of suitable solvents include: alcohols, such as methanol, 1-butanol, phenol, trifluoroethanol, hexafluoro-2-propanol; hydrocarbons, such as benzene and toluene; amides, such as dimethyl acetamide, dimethylformamide; halides, such as dichloromethane, dichloroethane; and ethers, such as tetrahydrofuran and dioxane; other solvents include water, 1-methyl-2-pyrrolidine, diethyl phosphite, tetramethylsulphone, dimethyl sulphoxide, acetonitrile and pyridine. Of these solvents, the alcohols are preferred.

The reaction can take place over a wide range of temperatures, and the precise reaction temperature is not critical to the invention. In general, we find it convenient to carry out the reaction at a temperature of from about 0° C. to about 150° C., preferably from room temperature to about 100° C., more preferably at about room temperature. The time required for the reaction may also vary widely, depending on many factors, notably the reaction temperature and the nature of the reagents. However, provided that the reaction is effected under the preferred conditions outlined above, a period of from 3 hours to 36 hours will usually suffice.

The intermediate compound of formula (LII) may be converted to a compound of formula (L) by reacting with acid, in a suitable solvent and appropriate temperature, to effect removal of the amine protecting group, followed by cyclization. This reaction is illustrated in scheme 35 below:

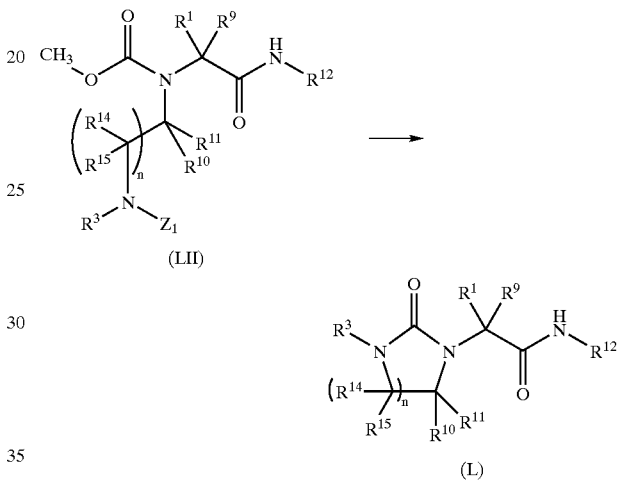

This reaction is carried out in the presence of an acid. There is no particular restriction on the nature of the acid to be used in this reaction, and any acid conventionally used to facilitate removal of an acid labile amine protecting group $Z^1$ and cyclization, may equally be used here, provided that it has no adverse effect on other parts of the molecule. Examples of suitable acids include: mineral acids such as hydrochloric acid or sulfuric acid; organic acids such as trifluoroacetic acid. Acids to be used in the reaction can also be generated in situ, for example by the addition of acetyl chloride in methanol, to generate hydrochloric acid. Preferably, anhydrous acids are used.

In addition to carrying out the reaction in scheme 35 in the presence of acid, a reaction step involving basic conditions can also be optionally carried out so as to facilitate the removal of the amine protecting group $Z^1$, wherein $Z^1$ is a base labile amine protecting group. There is no particular restriction on the nature of the base to be used in this reaction, and any base conventionally used to facilitate removal of an base labile amine protecting group $Z^1$, may equally be used here, provided that it has no adverse effect on other parts of the molecule. Examples of suitable bases include: organic bases such as ammonia, piperidine, morpholine, ethanolamine and diethylamine.

This reaction can take place over a wide range of temperatures, and the precise reaction temperature is not critical to the invention. In general, we find it convenient to carry out the reaction at a temperature of from about 0° C. to about 150° C., preferably from room temperature to about 100° C., more preferably at about room temperature. The time required for the reaction may also vary widely, depending on many factors, notably the reaction temperature and the nature of the reagents. However, provided that the reaction is effected under the preferred conditions outlined above, a period of from 3 hours to 36 hours will usually suffice.

There is no particular restriction on the amine protecting group ($Z^1$) employed. However, amine protecting groups which allow removal of the protecting group and cyclization of the deprotected intermediate, without purification or isolation of intermediates, are preferred. Examples of amine protecting groups include both acid labile amine protecting groups and base labile protecting groups. Preferred acid labile amine protecting group include tert-butoxycarbonyl (BOC) and 2-(4-biphenylyl)-isopropoxy carbonyl (BPOC). Preferred base labile amine protecting group include 9-fluoroenylmethyl carbamate (FMOC).

Alternatively, the synthesis of compounds of formula (L) can be carried out in solid phase using a resin bound isonitrile, for example, isonitrile functionalized polymer resin (IXa), 1-isocyanocyclohexene (IXb), or (XVIII).

General methodology for the preparation of cyclic urea derivatives of general formula (LIII)

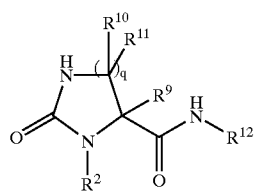

(LIII)

Compounds of formula (LIII) may be synthesized according to the present invention via a '3-step, 1-pot' procedure by the application or adaptation of known methods, by which is meant methods used heretofore or described in the literature, or by methods according to the present invention.

In general terms, compounds of formula (LIII) wherein $R^2$, $R^9$, $R^{10}$, $R^{11}$ and $R^{12}$, are hereinbefore defined and q is 1 or 2, may be synthesized by generating the acid of formula (LI) in situ (by reacting $CO_2$ in the presence of methanol ($CO_2$ is bubbled through the reaction solution for 5 minutes at 0° C.), reacting the acid of formula (LI) with an isonitrile compound of formula (IX), wherein $R^{12}$, is hereinbefore defined, an aldehyde or ketone of formula (XXXIII) wherein $R^9$, $R^{10}$ $R^{11}$ $Z^1$ and q are hereinbefore defined, and an amine of formula (XVI) wherein $R^2$,is as hereinbefore defined; in a suitable solvent at about room temperature, to afford the intermediate compound (LIV). This reaction is illustrated in scheme 36 below:

Scheme 36

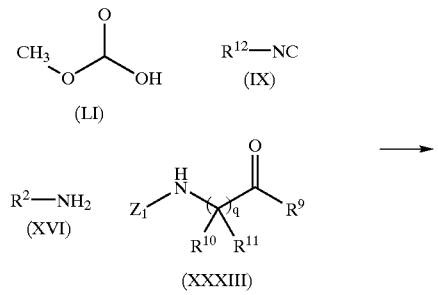

-continued

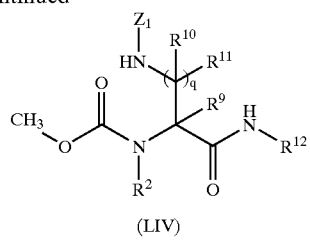

(LIV)

There is no restriction on the isonitrile used in the reaction scheme 36 above. Examples of suitable isonitriles include, benzyl isocyanide, n-butyl isocyanide, diethyl isocyanomethyl phosphonate, cyclohexyl isocyanide, 2,6-dimethylphenyl isocyanide, methyl isocyanoacetate, isopropyl isocyanide and 1,1,3,3-tetramethylbutyl isocyanide. Preferable isonitriles include benzyl isocyanide, n-butyl isocyanide, diethyl isocyanomethyl phosphonate. More preferred is 1-isocyanocyclohexene.

There is no particular restriction on the nature of the solvent to be employed, provided that it has no adverse effect on the reaction or on the reagents involved. Examples of suitable solvents include: alcohols, such as methanol, 1-butanol, phenol, trifluoroethanol, hexafluoro-2-propanol; hydrocarbons, such as benzene and toluene; amides, such as dimethyl acetamide, dimethylformamide; halides, such as dichloromethane, dichloroethane; and ethers, such as tetrahydrofuran and dioxane; other solvents include water, 1-methyl-2-pyrrolidine, diethyl phosphite, tetramethylsulphone, dimethyl sulphoxide, acetonitrile and pyridine. Of these solvents, the alcohols are preferred.

The reaction can take place over a wide range of temperatures, and the precise reaction temperature is not critical to the invention. In general, we find it convenient to carry out the reaction at a temperature of from about 0° C. to about 150° C., preferably from room temperature to about 100° C., more preferably at about room temperature. The time required for the reaction may also vary widely, depending on many factors, notably the reaction temperature and the nature of the reagents. However, provided that the reaction is effected under the preferred conditions outlined above, a period of from 3 hours to 36 hours will usually suffice.

The intermediate compound (LIV) may be converted to a compound of formula (LIII) by reacting with acid, in a suitable solvent and appropriate temperature, to effect removal of the amine protecting group, followed by cyclization. This reaction is illustrated in scheme 37 below:

Scheme 37

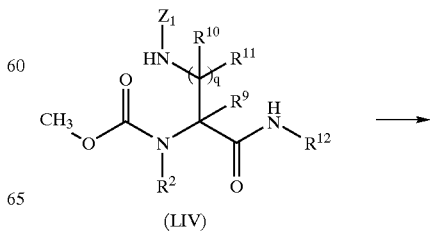

(LIV)

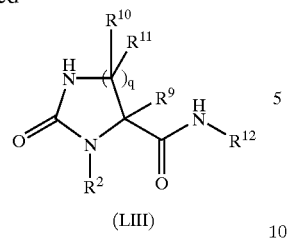

(LIII)

This reaction is carried out in the presence of an acid. There is no particular restriction on the nature of the acid to be used in this reaction, and any acid conventionally used to facilitate removal of an acid labile amine protecting group and cyclization, may equally be used here, provided that it has no adverse effect on other parts of the molecule. Examples of suitable acids include: mineral acids such as hydrochloric acid or sulfuric acid; organic acids such as trifluoroacetic acid. Acids to be used in the reaction can also be generated in situ, for example by the addition of acetyl chloride in methanol, to generate hydrochloric acid. Preferably, anhydrous acids are used.

In addition to carrying out the reaction in scheme 37 in the presence of acid, a reaction step involving basic conditions can also be optionally carried out so as to facilitate the removal of the amine protecting group $Z^1$, wherein $Z^1$ is a base labile amine protecting group. There is no particular restriction on the nature of the base to be used in this reaction, and any base conventionally used to facilitate removal of an base labile amine protecting group $Z^1$, may equally be used here, provided that it has no adverse effect on other parts of the molecule. Examples of suitable bases include: organic bases such as ammonia, piperidine, morpholine, ethanolamine and diethylamine.

This reaction can take place over a wide range of temperatures, and the precise reaction temperature is not critical to the invention. In general, we find it convenient to carry out the reaction at a temperature of from about 0° C. to about 150° C., preferably from room temperature to about 100° C, more preferably at about room temperature. The time required for the reaction may also vary widely, depending on many factors, notably the reaction temperature and the nature of the reagents. However, provided that the reaction is effected under the preferred conditions outlined above, a period of from 3 hours to 36 hours will usually suffice.

There is no particular restriction on the amine protecting group ($Z^1$) employed. However, amine protecting groups which allow removal of the protecting group and cyclization of the deprotected intermediate, without purification or isolation of intermediates, are preferred. Examples of amine protecting groups include both acid labile amine protecting groups and base labile protecting groups. Preferred acid labile amine protecting group include tert-butoxycarbonyl (BOC) and 2-(4-biphenylyl)-osopropoxy carbonyl (BPOC). Preferred base labile amine protecting group include 9-fluoroenylmethyl carbamate (FMOC).

Similarly, the synthesis of compounds of formula (LIII) can be carried out in solid phase using a resin bound isonitrile($R^{12}$—NC), for example, isonitrile functionalized polymer resin (IXa), 1-isocyanocyclohexene (IXb), or (XVIII).

General methodology for the preparation of hydration derivatives of general formula (LV)

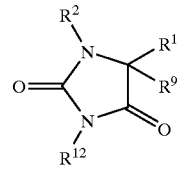

(LV)

Compounds of formula (LV) may be synthesized according to the present invention via a '3-step, 1-pot' procedure by the application or adaptation of known methods, by which is meant methods used heretofore or described in the literature, or by methods according to the present invention.

In general terms, hydantoin compounds of formula (LV) wherein $R^1$, $R^2$, $R^9$, and $R^{12}$, are hereinbefore defined, may be synthesized by generating the acid of formula (LI) in situ ($CO_2$ is bubbled through the reaction solution for 5 minutes at 0 C.), reacting the acid of formula (LI) with an isonitrile compound of formula (IX), wherein $R^{12}$, is hereinbefore defined, with compounds of formula (XV) wherein $R^1$ and $R^9$ are hereinbefore defined, an amine of formula (XVI) wherein $R^2$, is as hereinbefore defined; in a suitable solvent at about room temperature, to afford the intermediate compound (LVI). This reaction is illustrated in scheme 38 below:

Scheme 38

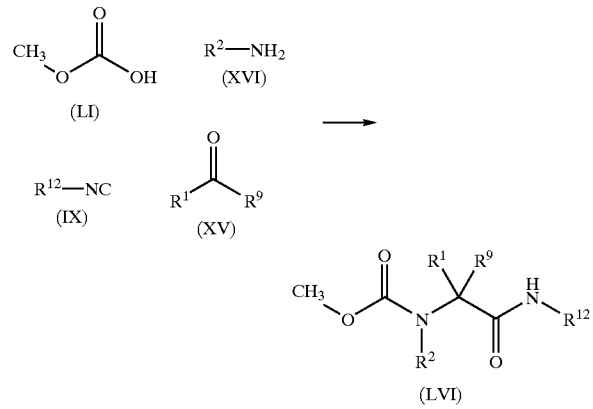

There is no restriction on the isonitrile used in the reaction scheme 38 above. Examples of suitable isonitriles include, benzyl isocyanide, n-butyl isocyanide, diethyl isocyanomethyl phosphonate, cyclohexyl isocyanide, 2,6-dimethylphenyl isocyanide, methyl isocyanoacetate, isopropyl isocyanide and 1,1,3,3-tetramethylbutyl isocyanide. Preferable isonitriles include benzyl isocyanide, n-butyl isocyanide, diethyl isocyanomethyl phosphonate. More preferred is 1-isocyanocyclohexene.

There is no particular restriction on the nature of the solvent to be employed, provided that it has no adverse effect on the reaction or on the reagents involved. Examples of suitable solvents include: alcohols, such as methanol, 1-butanol, phenol, trifluoroethanol, hexafluoro-2-propanol; hydrocarbons, such as benzene and toluene; amides, such as dimethyl acetamide, dimethylformamide; halides, such as dichloromethane, dichloroethane; and ethers, such as tetrahydrofuran and dioxane; other solvents include water, 1-methyl-2-pyrrolidine, diethyl phosphite, tetramethylsulphone, dimethyl sulphoxide, acetonitrile and pyridine. Of these solvents, the alcohols are preferred.

The reaction can take place over a wide range of temperatures, and the precise reaction temperature is not critical to the invention. In general, we find it convenient to carry out the reaction at a temperature of from about 0° C. to about 150° C., preferably from room temperature to about 100° C., more preferably at about room temperature. The time required for the reaction may also vary widely, depending on many factors, notably the reaction temperature and the nature of the reagents. However, provided that the reaction is effected under the preferred conditions outlined above, a period of from 3 hours to 36 hours will usually suffice.

The intermediate compound of formula (LVI) may be converted to a compound of formula (LV) by heating in a suitable solvent, to effect cyclization. This reaction is illustrated in scheme 39 below:

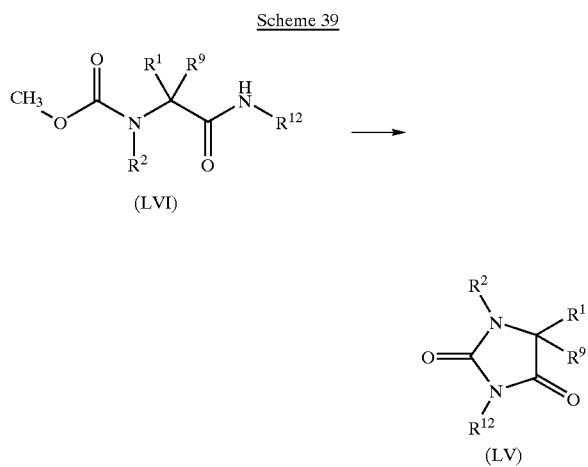

This reaction can take place over a wide range of temperatures, and the precise reaction temperature is not critical to the invention. In general, we find it convenient to carry out the reaction at a temperature of from about 0° C. to about 150° C., preferably from room temperature to about 100° C., more preferably at about room temperature. The time required for the reaction may also vary widely, depending on many factors, notably the reaction temperature and the nature of the reagents. However, provided that the reaction is effected under the preferred conditions outlined above, a period of from 3 hours to 36 hours will usually suffice.

Alternatively, the synthesis of compounds of formula (LV) can be carried out in solid phase using a resin bound isonitrile($R^{12}$—NC), for example, isonitrile functionalized polymer resin of formula (IXa), 1-isocyanocyclohexene of formula (IXb), or isonitrile functionalized polymer resin of formula (XVIII).

According to a further feature of the present invention, compounds of the invention may be prepared by interconversion of other compounds of the invention.

A compound of formula (I), (II), (III), (IV), (V), (VI), (VII), (VIII), (XLII), (L) (LIII), and (LV) including a group containing one or more nitrogen ring atoms, preferably imine (═N—), may be converted to the corresponding compound wherein one or more nitrogen ring atom of the group is oxidized to an N-oxide, preferably by reacting with a peracid, for example peracetic acid in acetic acid or m-chloroperoxybenzoic acid in an inert solvent such as dichloromethane, at a temperature from about room temperature to reflux, preferably at elevated temperature.

As an example of the interconversion process, compounds of formula (I), (II), (III), (IV), (V), (VI), (VII), (VIII), (XLII), (L) (LIII), and (LV), containing sulphoxide linkages may be prepared by the oxidation of corresponding compounds containing —S— linkages. For example, the oxidation may conveniently be carried out by means of reaction with a peroxyacid, e.g. 3-chloroperbenzoic acid, preferably in an inert solvent, e.g. dichloromethane, preferably at or near room temperature, or alternatively by means of potassium hydrogen peroxomonosulphate in a medium such as aqueous methanol, buffered to about pH 5, at temperatures between about 0° C. and room temperature. This latter method is preferred for compounds containing an acid-labile group.

As another example of the interconversion process, compounds of formula (I), (II), (III), (IV), (V), (VI), (VII), (VIII), (XLII), (L) (LIII), and (LV) containing sulphone linkages may be prepared by the oxidation of corresponding compounds containing —S— or sulphoxide linkages. For example, the oxidation may conveniently be carried out by means of reaction with a peroxyacid, e.g. 3-chloroperbenzoic acid, preferred is in an inert solvent, e.g. dichloromethane, preferably at or near room temperature.

It will be understood that designation of aromaticity with respect to carbocycles and heterocycles herein includes any highly resonant unsaturated ring structure. Alternatively, placement of double bonds, where indicated, represents one potential structure for the depicted compound but will be understood to include other resonant states of the compound as well as protonated and charged species, only one of which may be shown.

It will be appreciated that compounds of the present invention may contain asymmetric centers. These asymmetric centers may independently be in either the R or S configuration. It will be apparent to those skilled in the art that certain compounds of the invention may also exhibit geometrical isomerism. It is to be understood that the present invention includes individual geometrical isomers and stereoisomers and mixtures thereof, including racemic mixtures, of compounds of formula (I), (II), (III), (IV), (V), (VI), (VII), (VIII), (XLII), (L) (LIII), and (LV), hereinabove. Such isomers can be separated from their mixtures, by the application or adaptation of known methods, for example chromatographic techniques and recrystallization techniques, or they are separately prepared from the appropriate isomers of their intermediates.

For the propose herein it is understood that tautermeric forms are included in the recitation of a given group, e.g., thio/mercapto or oxo/hydroxyl.

Acid additional salts are formed with the compounds of the invention in which a basic function such as an amino, alkylamino, or dialkylamino group is present. The pharmaceutically acceptable, i.e., nontoxic, acid addition salts are preferred. The salts chosen are chosen optimally to be compatible with the customary pharmaceutical vehicles and adapted for oral or parenteral administration. Acid addition salts of the compounds of this invention may be prepared by reaction of the free base with the appropriate acid, by the application or adaptation of known methods. For example, the acid addition salts of the compounds of this invention may be prepared either by dissolving the free base in water or aqueous alcohol solution or other suitable solvents containing the appropriate acid and isolating the salt by evaporating the solution, or by reacting the free base and acid in an organic solvent, in which case the salt separates directly or can be obtained by concentration of the solution. Some suitable acids for use in the preparation of such salts are hydrochloric acid, hydrobromic acid, phosphoric acid, sulfuric acid, various organic carboxylic and sulfonic acids, such as acetic acid, citric acid, propionic acid, succinic acid, benzoic acid, tartaric acid, fumaric acid, mandelic acid, ascorbic acid, malic acid, methanesulfonic acid, toluenesulfonic acid, fatty acids, adipate, alginate, ascorbate, aspartate, benzenesulfonate, benzoate, cyclopentanepropionate, digluconate, dodecylsulfate, bisulfate, butyrate, lactate, laurate, lauryl sulfate, malate, hydroiodide, 2-hydroxy-ethanesulfonate, glycerophosphate, picrate, pivalate, pamoate, pectinate, persulfate, 3-phenylpropionate, thiocyanate, 2-naphthalenesulfonate, undecanoate, nicotinate, hemisulfate, heptonate, hexanoate, camphorate, camphersulfonate, and others.

The acid addition salts of the compounds of this invention can be regenerated from the salts by the application or adaptation of known methods. For example, parent compounds of the invention can be regenerated from their acid addition salts by treatment with an alkali, e.g. aqueous sodium bicarbonate solution or aqueous ammonia solution.

Compounds of this invention can be regenerated from their base addition salts by the application or adaptation of known methods. For example, parent compounds of the invention can be regenerated from their base addition salts by treatment with an acid, e.g. hydrochloric acid.

Base addition salts may be formed where the compound of the invention contains a carboxy group, or a sufficiently acidic bioisostere. The bases which can be used to prepare the base addition salts include preferably those which produce, when combined with the free acid, pharmaceutically acceptable salts, that is, salts whose cations are non-toxic to the patient in pharmaceutical doses of the salts, so that the beneficial inhibitory effects inherent in the free base are not vitiated by side effects ascribable to the cations. Pharmaceutically acceptable salts, including those derived from alkali and alkaline earth metal salts, within the scope of the invention include those derived from the following bases: sodium hydride, sodium hydroxide, potassium hydroxide, calcium hydroxide, aluminium hydroxide, lithium hydroxide, magnesium hydroxide, zinc hydroxide, ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, and the like.

Compounds of the present invention may be conveniently prepared, or formed during the process of the invention, as solvates (e.g. hydrates). Hydrates of compounds of the present invention may be conveniently prepared by recrystallization from an aqueous/organic solvent mixture, using organic solvents such as dioxan, tetrahydrofuran or methanol.

EXAMPLE 1

Solution Phase Synthesis of Compounds of Formula (I) via the '3-step, One Pot' Procedure, Employing the Ugi Multicomponent Reaction Equal amounts (0.1 ml) of 0.1 M solutions of the four appropriate components compound of formulae (XIV), (XV), (XVI) and (IXb), are employed generating a theoretical 10 $\mu$mol of final 1,4-benzodiazepine-2,5-dione product (I) for 100% conversion. The 4-component condensation is performed in methanol at room temperature and the solvent evaporated at 65° C. (using a SAVANT® evaporator for 2 hours). The deprotection/cyclization steps are performed using either a 10% solution of acetyl chloride in methanol, or a 10% solution of trifluoroacetic acid in dichloroethane. Solvents are then evaporated at 65° C. to afford the cyclized product compound of formula (I). Lc/ms analysis (liquid chromatography/mass spectrometry) is performed using a C18 Hypersil BDS 3m 4.6×50 mm column (UV 220 nm) with a mobile phase 0.1% TFA IN $H_2O/CH_3CN$ 10% to 100% 15 min, at a rate of 1 ml/min. Desired products are seen as (M+1).

Table 5 below shows the lc/ms A% yields taken from two 96 well plates using the experimental procedure described above and the Ugi components listed as 1–22 below:

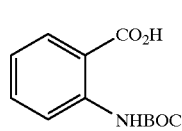

1

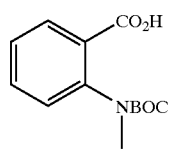

2

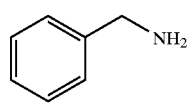

3

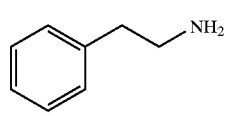

4

-continued

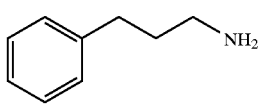
5

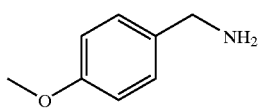
6

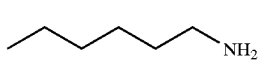
7

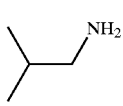
8

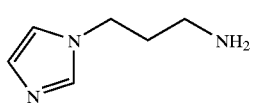
9

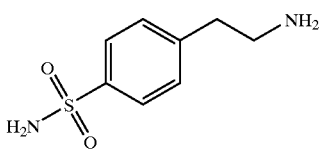
10

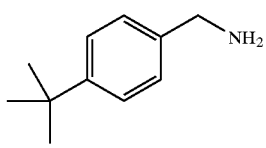
11

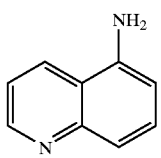
12

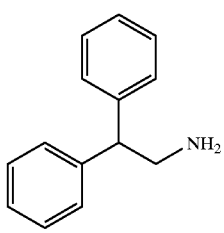
13

-continued

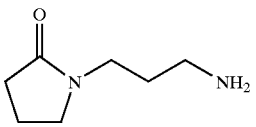
14

15

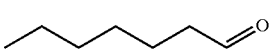
16

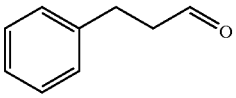
17

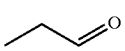
18

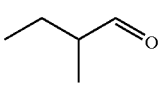
19

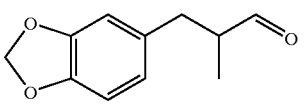
20

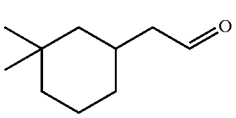
21

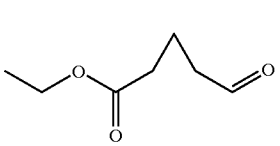
22

Table 1 contains hplc retention times of the desired products from anthranilic acid 1 using a C18 Hypersil BDS 3 m 4.6×50 mm column (UV 220 nm) with a mobile phase 0.1% TFA in $H_2O/CH_3CN$ 10% to 100%, 5 min, at a rate of 1 ml/min. For example, Table 1 indicates that anthranilic acid 1 reacted with amine 3 and aldehyde 15 affords the desired product with a retention time of 3.78, under the conditions mentioned above.

TABLE 1

|    | 3    | 4    | 5    | 6    | 7    | 8    | 9    | 10   | 11   | 12   | 13   | 14   |
|----|------|------|------|------|------|------|------|------|------|------|------|------|
| 15 | 3.78 | 3.92 | 4.18 | 3.79 | 3.52 | 4.14 | 2.82 | 3.26 | 4.63 | 2.86 | 4.36 | 3.04 |
| 16 | 4.71 | 4.84 | 5.15 | 4.67 | 4.58 | 4.97 | 3.70 | 4.14 | 5.46 | 3.61 | 5.15 | 4.01 |
| 17 | 4.31 | 4.40 | 4.67 | 4.27 | 4.14 | 4.58 | 3.35 | 3.79 | 5.02 | 3.30 | 4.75 | 3.61 |
| 18 | 3.61 | 3.79 | 4.05 | 3.65 | 3.35 | 4.01 | 2.55 | 3.04 | 4.53 | 2.46 | 4.27 | 2.82 |
| 19 | 4.01 | 4.14 | 4.01 | 4.01 | 3.83 | 4.36 | 3.04 | 3.48 | 4.80 | 4.58 | 3.26 | 4.27 |
| 20 | 4.27 | 4.40 | 4.62 | 4.27 | 4.14 | 4.53 | 3.04 | 3.83 | 4.97 | 3.43 | 4.75 | 3.65 |
| 21 | 5.11 | 5.20 | 5.50 | 5.02 | 4.97 | 5.33 | 4.05 | 4.49 | 5.86 | 3.92 | 5.55 | 4.36 |
| 22 | 3.43 | 3.74 | 3.91 | 3.48 | 3.34 | 3.87 | 2.64 | 3.08 | 4.31 | 2.95 | 4.18 | 2.86 |

Table 2 contains the molecular weight of the desired products from anthranilic acid 1. Desired products are seen as (M+1). For example, Table 2 indicates that anthranilic acid 1 reacted with amine 3 and aldehyde 15 affords the desired product with a molecule weight (M+1) of 308.4, under the conditions mentioned above.

TABLE 2

|    | 3     | 4     | 5     | 6     | 7     | 8     | 9     | 10    | 11    | 12    | 13    | 14    |
|----|-------|-------|-------|-------|-------|-------|-------|-------|-------|-------|-------|-------|
| 15 | 308.4 | 322.4 | 302.4 | 338.4 | 274.4 | 336.4 | 326.4 | 401.5 | 364.5 | 345.4 | 398.5 | 343.4 |
| 16 | 350.5 | 364.5 | 344.5 | 380.5 | 316.4 | 378.5 | 368.5 | 443.6 | 406.6 | 387.5 | 440.6 | 385.5 |
| 17 | 370.5 | 384.5 | 364.5 | 400.5 | 336.4 | 398.5 | 388.5 | 463.6 | 426.6 | 407.5 | 460.6 | 405.5 |
| 18 | 294.4 | 308.4 | 288.4 | 324.4 | 260.3 | 322.4 | 312.4 | 387.5 | 350.5 | 331.4 | 384.5 | 329.4 |
| 19 | 322.4 | 336.4 | 316.4 | 352.4 | 288.4 | 350.5 | 340.4 | 415.5 | 378.5 | 359.4 | 412.5 | 357.5 |
| 20 | 428.5 | 442.5 | 422.5 | 458.5 | 394.5 | 456.5 | 446.5 | 521.6 | 484.6 | 465.5 | 518.6 | 463.5 |
| 21 | 390.5 | 404.6 | 384.6 | 420.6 | 356.5 | 418.6 | 408.5 | 483.6 | 446.6 | 427.6 | 480.7 | 425.6 |
| 22 | 378.4 | 392.5 | 372.5 | 408.5 | 344.4 | 406.5 | 396.4 | 471.5 | 434.5 | 415.5 | 468.6 | 413.5 |

Table 3 contains hplc retention times of the desired products from anthranilic acid 2. For example, Table 3 indicates that anthranilic acid 2 reacted with amine 3 and aldehyde 15 affords the desired product with a retention time of 4.01, under the conditions mentioned above.

TABLE 3

|    | 3    | 4    | 5    | 6    | 7    | 8    | 9    | 10   | 11   | 12   | 13   | 14   |
|----|------|------|------|------|------|------|------|------|------|------|------|------|
| 15 | 4.01 | 4.09 | 4.45 | 4.01 | 3.79 | 4.36 | 2.95 | 3.30 | 4.84 | —    | 4.62 | 2.95 |
| 16 | 4.97 | 5.15 | 5.46 | 4.89 | 4.93 | 5.28 | 3.87 | 4.36 | 5.68 | 3.92 | 5.46 | 4.27 |
| 17 | 4.49 | 4.67 | 4.93 | 4.49 | 4.45 | 4.84 | 3.52 | 3.96 | 5.24 | 3.57 | 5.02 | 3.83 |
| 18 | 3.83 | 4.05 | 4.36 | 3.83 | 3.61 | 4.27 | 2.73 | 3.26 | 4.75 | 2.91 | 4.49 | 3.04 |
| 19 | 4.23 | 4.36 | 4.67 | 4.23 | 4.05 | 4.58 | 3.17 | 3.56 | 5.06 | —    | 4.80 | 3.48 |
| 20 | 4.36 | 4.62 | 4.84 | 4.36 | 4.40 | 4.71 | 3.43 | 3.92 | 5.06 | —    | 4.97 | 3.70 |
| 21 | 5.28 | 5.46 | 5.81 | 5.20 | 5.28 | 5.59 | 4.18 | 4.67 | 6.03 | 3.83 | 5.50 | 4.62 |
| 22 | 3.61 | 3.96 | 4.23 | 3.79 | 3.57 | 4.14 | 2.77 | 3.26 | 4.39 | 2.51 | 4.40 | 3.04 |

Table 4 contains molecular weight of the desired products from anthranilic acid 2. Desired products are seen as (M+1). For example, Table 4 indicates that anthranilic acid 2 reacted with amine 3 and aldehyde 15 affords the desired product with a molecule weight (M+1) of 322.4, under the conditions mentioned above.

TABLE 4

|    | 3     | 4     | 5     | 6     | 7     | 8     | 9     | 10    | 11    | 12    | 13    | 14    |
|----|-------|-------|-------|-------|-------|-------|-------|-------|-------|-------|-------|-------|
| 15 | 322.4 | 336.4 | 316.4 | 352.4 | 288.4 | 350.5 | 340.4 | 415.5 | 378.5 | 359.4 | 412.5 | 357.5 |
| 16 | 364.5 | 378.5 | 358.5 | 394.5 | 330.5 | 392.5 | 382.5 | 457.6 | 420.6 | 401.5 | 454.6 | 399.5 |
| 17 | 384.5 | 398.5 | 378.5 | 414.5 | 350.5 | 412.5 | 402.5 | 477.6 | 440.6 | 421.5 | 474.6 | 419.5 |
| 18 | 308.4 | 322.4 | 302.4 | 338.4 | 274.4 | 336.4 | 326.4 | 401.5 | 364.5 | 345.4 | 398.5 | 343.4 |
| 19 | 336.4 | 350.5 | 330.5 | 366.5 | 302.4 | 364.5 | 354.5 | 429.5 | 392.5 | 373.5 | 426.5 | 371.5 |
| 20 | 442.5 | 456.5 | 436.5 | 472.5 | 408.5 | 470.6 | 460.5 | 535.6 | 498.6 | 479.5 | 532.6 | 477.6 |
| 21 | 404.6 | 418.6 | 398.6 | 434.6 | 370.5 | 432.6 | 422.6 | 497.7 | 460.7 | 441.6 | 494.7 | 439.6 |
| 22 | 392.5 | 406.5 | 386.5 | 422.5 | 358.4 | 420.5 | 410.5 | 485.6 | 448.6 | 429.5 | 482.6 | 427.5 |

Table 5, Note: For A% yields x/y: The first yield "x" represents that for reactions with N-BOC anthranilic acid, 1. The second yield "y" represents that for N-Me-BOC anthranilic acid, 2. Row 15 represents yields of reactions with aldehyde 15. Column 3 represents yields of reactions with amine 3. For example, Table 5 indicates that anthranilic acid 1 reacted with amine 3 and aldehyde 15 affords the desired product with a yield 40%, under the conditions mentioned above.

TABLE 5

|    | 3     | 4     | 5     | 6     | 7     | 8     | 9     | 10    | 11    | 12    | 13    | 14    |
|----|-------|-------|-------|-------|-------|-------|-------|-------|-------|-------|-------|-------|
| 15 | 40/16 | 40/29 | 40/27 | 54/15 | 40/25 | 39/40 | 26/16 | 18/21 | 41/15 | 1/0   | 39/31 | 47/30 |
| 16 | 85/87 | 82/72 | 77/64 | 79/72 | 82/69 | 84/67 | 81/73 | 78/67 | 82/74 | 43/10 | 88/74 | 84/73 |
| 17 | 88/84 | 85/73 | 89/68 | 92/81 | 92/78 | 88/68 | 90/75 | 82/73 | 84/79 | 39/8  | 76/77 | 85/72 |
| 18 | 87/80 | 72/52 | 69/43 | 79/70 | 70/41 | 80/51 | 87/63 | 81/64 | 81/70 | 51/25 | 75/60 | 80/62 |
| 19 | 45/10 | 37/24 | 39/22 | 36/12 | 34/20 | 33/12 | 41/7  | 28/26 | 44/10 | 9/0   | 37/16 | 39/20 |
| 20 | 79/49 | 74/61 | 63/51 | 75/12 | 66/53 | 69/54 | 59/10 | 74/61 | 83/67 | 6/0   | 71/49 | 67/64 |
| 21 | 89/87 | 86/69 | 88/66 | 85/82 | 89/63 | 85/70 | 90/74 | 83/69 | 86/84 | 38/8  | 84/74 | 88/78 |
| 22 | 85/64 | 86/63 | 80/67 | 85/82 | 84/75 | 85/64 | 82/69 | 84/67 | 86/75 | 27/11 | 84/69 | 83/61 |

EXAMPLE 2

General Solid Phase Synthesis of Compounds of Formula (I) using the Ugi Reaction and Resin (IXa)

(60mg) of resin (IXa) is pre-swelled with THF. 0.5M solutions of the appropriate aldehyde (XV) (10 equiv.), amine (XVI) (10 equiv.) and carboxylic acid (XIV) (10 equiv.) in THF:MeOH (1:1) are added sequentially to the resin (IXa) and the reaction stirred at room temperature for 3 days. The resin is washed sequentially with $CH_2Cl_2$ THF, DMF, THF and MeOH dried under high vacuum to yield the resin bound Ugi product (IXa) Treatment with $BOC_2O$ (10 equiv.), $Et_3N$ (10 equiv.) and DMAP in $CH_2Cl_2$ (15 hours) afforded the activated resin (XX) for cleavage. Sodium methoxide (5 mg) in THF:MeOH, 1:1, is added to the resin and shaken for 20 hours. The solvent is evaporated in vacuo to give the desired methyl ester (XXI). The deprotection/cyclization steps are performed using either a 10% solution of acetyl chloride in methanol, or a 10% solution of trifluoroacetic acid in dichloroethane. The samples are then evaporated in a SAVANT at room temperature for 3 hours to give the crude product of formula (I). Examples of products (examples 23 to 28) synthesized using this general methodology are indicated below and purities are determined by lc/ms (liquid chromatography/mass spectrometry) ELSD (evaporative light scattering detector) A% and UV A%. Lc/ms analysis is performed using a Hypersil BDS 3 m C18 4.6×50 mm 0.1%TFA in $H_2O/CH_3N$ 10% to 100% $CH_3N$ 5 min, at a rate of 1 ml/min for 23–28. Desired products are seen as (M+1).

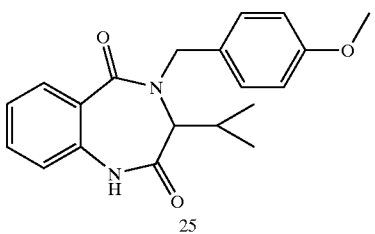

for R = H, 23 or $CH_3$, 24

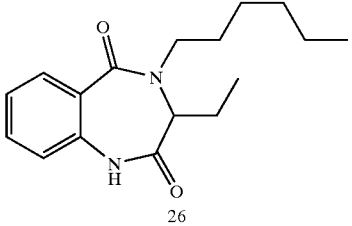

25

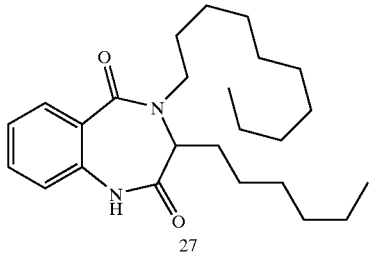

26

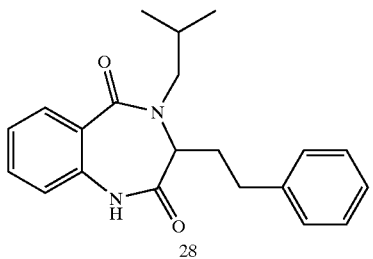

27

28

| Compound | Retention time | mass spec | ELSD A % | UV (220 nm) A % |
|----------|----------------|-----------|----------|-----------------|
| 23       | 3.36           | 388       | >90      | >90             |
| 24       | 3.62           | 402       | 90       | >90             |
| 25       | 3.93           | 338       | 90       | 80              |
| 26       | 4.27           | 288       | 90       | 91              |
| 27       | 6.48           | 400       | 95       | 91              |
| 28       | 4.36           | 336       | 89       | 80              |

EXAMPLE 3

Solution Phase Synthesis of Compounds of Formula (II) via the '3-step, one pot' Procedure Employing the Ugi Multicomponent Reaction Equal amounts (0.1 ml) of 0.1 M solutions of the four appropriate components compound of formulae (XXII), (XV), (XVI) and (IXb), are employed generating a theoretical 10 μmol of final diketopiperazine product (II) for 100% conversion. The 4-component condensation is performed in methanol at room temperature and the solvent evaporated at 65° C. (using a SAVANT® evaporator for 2 hours). The deprotection/cyclization steps are performed using either a 10% solution of acetyl chloride in methanol, or a 10% solution of trifluoroacetic acid in dichloroethane, and a 5% solution of diethylamine in dichloroethane [Note: 10–15 mg of N,N-(diisopropyl)amino-methylpolustyrene(PS-DIEA) is an excellent resin bound alternative to diethylamine]. Solvents are then evaporated at 65° C. to afford the cyclized products of formula(II).

EXAMPLE 4

General Solid Phase Synthesis of Compounds of Formula (II) Using the Ugi Reaction and Resin (IXa)

(60mg) of resin (IXa) is pre-swelled with THF. 0.5M solutions of the appropriate aldehyde (XV) (10 equiv.), amine (XVI) (10 equiv.) and carboxylic acid (XXII) (10 equiv.) in THF:MeOH (1:1) are added sequentially to the resin (IXa) and the reaction stirred at room temperature for 3 days. The resin is washed sequentially with CH$_2$Cl$_2$, THF, DMF, THF and MeOH dried under high vacuum to yield the resin bound Ugi product (XXIII). Treatment with BOC$_2$O (10 equiv.), Et$_3$N (10 equiv.) and DMAP in CH$_2$Cl$_2$ (15 hours) affords the activated resin bound product (XXIV) for cleavage. Sodium methoxide (5 mg) in THF:MeOH, 1:1, is added to the resin and shaken for 20 hours. The solvent is evaporated in vacuo to give the desired methyl ester (XXV). The deprotection/cyclization steps are performed using either a 10% solution of acetyl chloride in methanol, or a 10% solution of trifluoroacetic acid in dichloroethane, and a 5% solution of diethylamine in dichloroethane [Note: 10–15 mg of N,N-(diisopropyl)amino-methylpolystyrene (PS-DIEA) is an excellent resin bound alternative to diethylamine]. Solvents are then evaporated at 65° C. to afford the cyclized product of formula (II). Examples of products (examples 29 to 33) synthesized using this general methodology are indicated below and purities are determined by lc/ms (liquid chromatography/mass spectrometry) ELSD (evaporative light scattering detector) A% and UV A%. Lc/ms analysis is performed using a C18 Hypersil BDS 3 m C18 4.6×50mm 0.1%TFA in H$_2$O/CH$_3$N 10% to 100% CH$_3$N 5 min, at a rate of 1 ml/min for 29–33. Desired products are seen as (M+1).

29

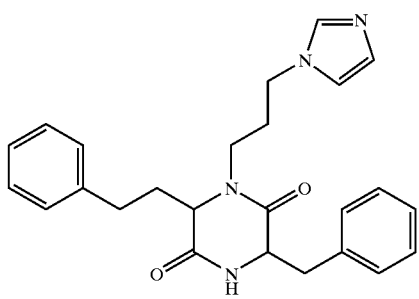

30

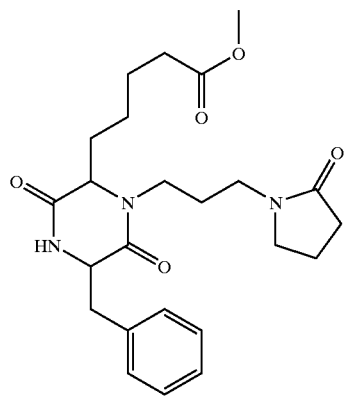

31

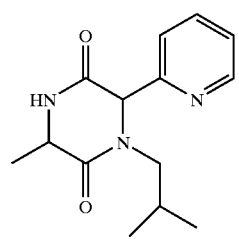

32

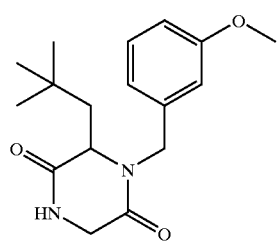

33a

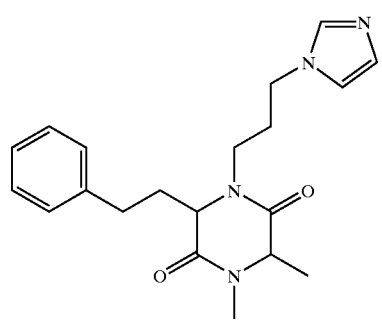

33b

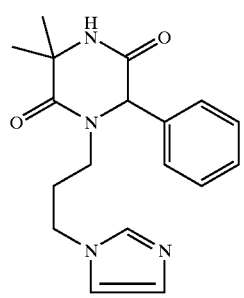

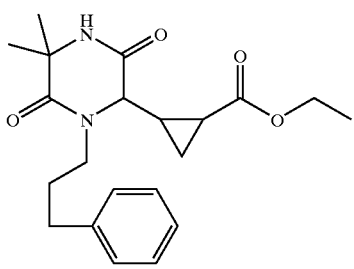

33c

| Compound | Retention time | Mass spec | ELSD A % | UV (220 nm) A % |
|---|---|---|---|---|
| 29 | 3.19 & 3.36 | 416 | 100 | 71 |
| 30 | 3.10 | 443 | 94 | 68 |
| 31 | 2.80 | 261 | 100 | 95 |
| 32 | 3.10 & 3.76 | 304 | 98 | 89 |
| 33 | 3.02 & 3.10 | 354 | 71 | 56 |

EXAMPLE 5

Solution Phase Synthesis of Compounds of Formula (III) via the '3-step, one pot' Procedure Employing the Ugi Multi-component Reaction Equal amounts (0.1 ml) of 0.1 M solutions of the four appropriate components compound of formulae (XXVI), (XXVII), (XV) and (IXb), are employed generating a theoretical 10 μmol of final product for 100% conversion. The 4-component condensation is performed in methanol at room temperature and the solvent evaporated at 65° C. (using a SAVANT® evaporator for 2 hours). The deprotection/cyclization steps are performed using either a 10% solution of acetyl chloride in methanol, or a 10% solution of trifluoroacetic acid in dichloroethane, and a 5% solution of diethylamine in dichloroethane [Note: 10–15 mg of N,N-(diisopropyl)amino-methylpolystrene (PS-DIEA) is an excellent resin bound alternative to diethylamine]. Solvents are then evaporated at 65° C. to afford the cyclized product of formula (III). Examples of products (examples 34 to 45) synthesized using this general methodology are indicated below and purities are determined by lc/ms (liquid chromatography/mass spectrometry) ELSD (evaporative light scattering detector) A% and UV A%. Lc/ms analysis is performed using a C 18 Hypersil BDS 3 m 2.1×50 mm column (UV 220 nm) with a mobile phase of 0.1% TFA in $CH_3CN/H_2O$, gradient from 10% $CH_3CN$ to 100% over 5 min. HPLC is interfaced with APCI techniques (Atmospheric Pressure Chemical Ionization). Desired products seen as (M+1).

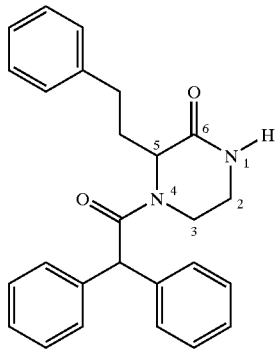

34

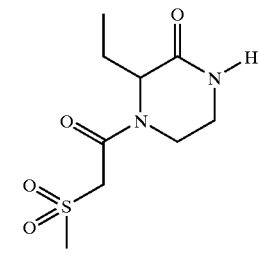

35

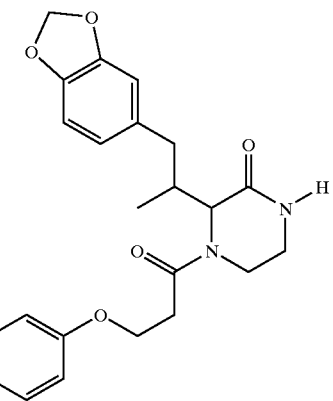

36

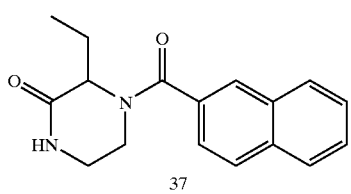

37

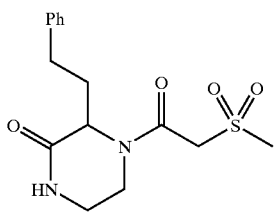

38

-continued
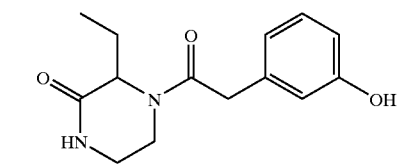
39
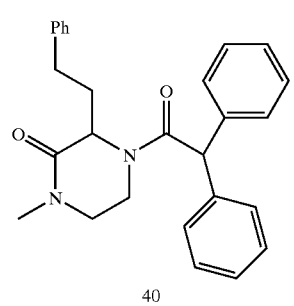
40
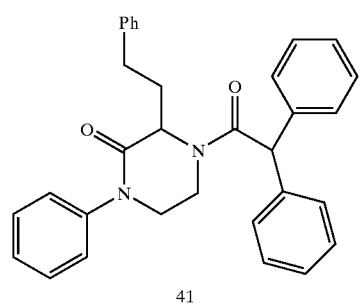
41
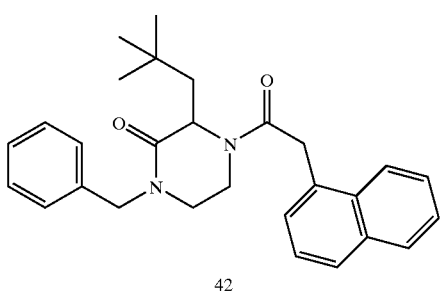
42
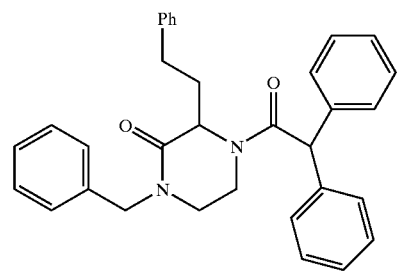
43
-continued
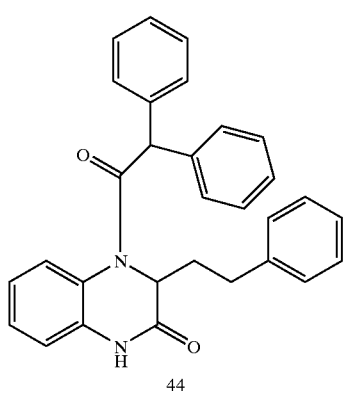
44
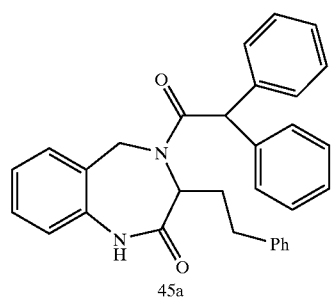
45a
| Compound | Retention time | Mass spec | UV (220 nm) A % |
| --- | --- | --- | --- |
| 34 | 6.66 | 398 | 77 |
| 35 | 1.06 | 248 | 97 |
| 36 | 4.09 | 394 | 92 |
| 37 | 3.35 | 282 | 77 |
| 38 | 2.91 | 324 | 77 |
| 39 | 2.38 | 262 | 69 |
| 40 | 4.14 | 412 | 83 |
| 41 | 5.07 | 474 | 70 |
| 42 | 4.60 | 428 | 80 |
| 43 | 5.26 | 488 | 85 |
| 44 | 5.19 | 446 | 66 |
| 45a | 5.14 | 460 | 30 |
The following compounds could potentially be made using the same protocol:
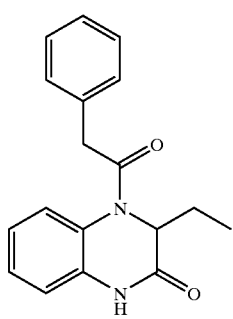
45b -continued

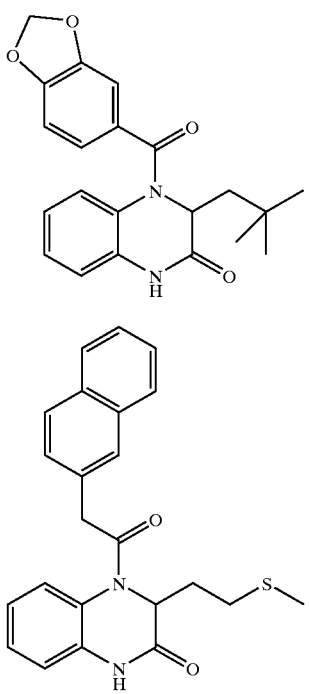

45c

45d

General Procedure and $^1$H for Compound 34

Stoichiometric amounts (2 ml) of 0.1 M solutions of the four appropriate Ugi components are combined and stirred at room temperature overnight. The solvent is evaporated in vacuo and the residue is dried under high vacuum. A 10% solution of AcCl in MeOH (8 ml) is added to the crude material and stirred at room temperature overnight. The solvent is evaporated in vacuo. A 5% solution of diethylamine in dichloroethane is then added to the crude material and the solution shaken overnight at room temperature. The solvent is evaporated in vacuo and crude material preabsorbed onto flash silica and purified by column chromatography to yield the desired ketopiperazine, 34, (44 mg, 55%) as a white solid: mp 188–190° C. For major conformer only: $^1$H(CDCl$_3$)7.90 (1H, s, NH), 7.10–7.40 (15H, m, C$_6$H$_5$×3), 5.60 (1H, s, CHC$_6$H$_5$), 4.78–4.83 (1H, m, CHCH$_2$), 4.05–4.12, 3.31–3.40 (2H, 2×m, CH$_2$N), 2.98–3.02, 2.80–2.88 (2H, 2×m, CH$_2$N), 2.50–2.60 (2H, m, CH$_2$C$_6$H$_5$), 1.90–2.00, 2.03–2.10 (2H, CH$_2$). For major conformer only: $^{13}$C (CDCl$_3$) 170.2, 168.7, 141.4, 139.8, 128.7, 128.4, 128.3, 126.7, 125.8, 54.5, 53.0, 39.2, 32.9, 31.7. IR (KBr disc) 3260m, 1641s, 1620s (selected peaks only). mspec (APCI) 399 (MH$^+$), 371. $^1$H and $^{13}$C assignments have been obtained from $^1$H, $^{13}$C, DEPT, COSY, HMQC and HMBC experiments. The $^1$H and $^{13}$C spectra show two sets of resonances throughout the spectrum. Exchange crosspeaks between major and minor forms are observed in a rotating frame Overhauser effect spectroscopy (ROESY). These resonances also show broadening at temperatures above 80° C. These experiments show that the two forms are in slow exchange under the present experimental conditions. HMBC spectrum showed correlation between the methylene protons(H$_2$ and H$_2$') with the carbonyl carbon C6 confirming the ring closure.

EXAMPLE 6
General Solid Phase Synthesis of Compounds of Formula (III) Using the Ugi Reaction and Resin (IXa)

(60 mg) of resin (IXa) is pre-swelled with THF. 0.5M solutions of the appropriate aldehyde (XV) (10 equiv.), diamine (XXVII) (10 equiv.) and carboxylic acid (XXVI) (10 equiv.) in THF:MeOH (1:1) are added sequentially to the resin (IXa) and the reaction stirred at room temperature for 3 days. The resin is washed sequentially with CH$_2$Cl$_2$, THF, DMF, THF and MeOH dried under high vacuum to yield the resin bound Ugi product (XXX). Treatment with BOC$_2$O (10 equiv.), Et$_3$N (10 equiv.) and DMAP in CH$_2$Cl$_2$ (15 hours) afford the activated the resin bound product (XXVII) for cleavage. Sodium methoxide (5 mg) in THF: MeOH, 1:1, is added to the resin and shaken for 20 hours. The solvent is evaporated in vacuo to give the desired methyl ester (XXXI). The deprotection/cyclization steps are performed using either a 10% solution of acetyl chloride in methanol, or a 10% solution of trifluoroacetic acid in dichloroethane. Solvents are then evaporated at 65° C. to afford the cyclized product of formula (III). Examples of products (examples 46 to 51) synthesized using this general methodology are indicated below and purities are determined by lc/ms (liquid chromatography/mass spectrometry) ELSD (evaporative light scattering detector) A% and UV A%. Lc/ms analysis is performed using a Hypersil BDS 3 m C18 4.6×50 mm 0.1 %TFA in H$_2$O/CH$_3$N 10% to 100% CH$_3$N 5 min, at a rate of 1 ml/min for 46–49 and 51. C18 Hypersil BDS 3 m C18 4.6×50 mm 0.1%TFA in H$_2$O/CH$_3$N 5% to 100% CH$_3$N 5 min, at a rate of 1 ml/min for 52. Desired products are seen as (M+1).

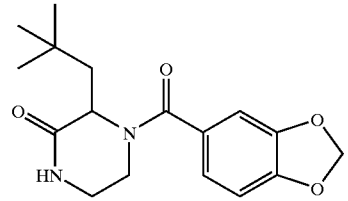

46

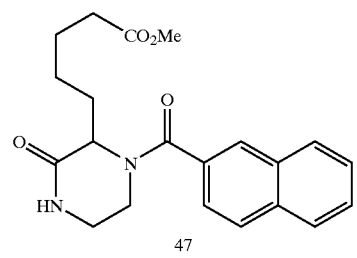

47

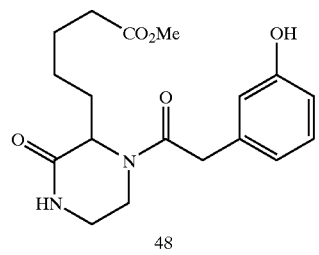

48

-continued

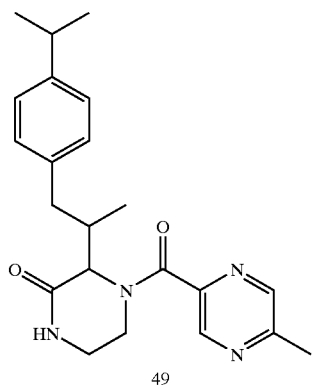

49

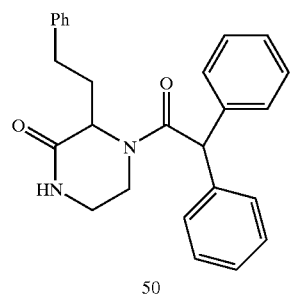

50

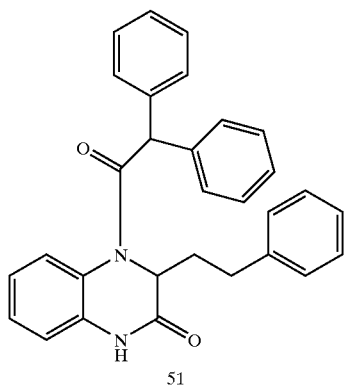

51

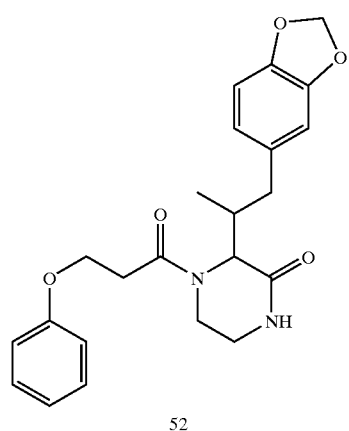

52

-continued

| Compound | Retention time | Mass spec | ELSD A % | UV (220 nm) A % |
|---|---|---|---|---|
| 46 | 3.54 | 318 | 100% | 100% |
| 47 | 3.63 | 368 | 100% | 100% |
| 48 | 2.80 | 348 | 100% | 94% |
| 49 | 4.19 | 380 | 100% | 100% |
| 50 | 7.55 | 398 | 100% | 77% |
| 51 | 5.19 | 446 | 80% | 86% |
| 52 | 4.06 | 410 | 100% | 90% |

EXAMPLE 7

General Solution Phase Synthesis of Compounds of Formula (IV) Via the '3-step One Pot' Procedure, Employing the Ugi Multi-component Reaction Equal amounts (0.1 ml) of 0.1 M solutions of the four appropriate components compounds of formulae (IX), (XV), (XVI) and (XXXIII) are employed generating a theoretical 10 µmol of dihydroimadazole product (IV) for 100% conversion. The 4-component condensation is performed in methanol at room temperature and the solvent evaporated at 65° C. (using a SAVANT® evaporator for 2 hours). The deprotection/cyclization steps are performed using either a 10% solution of acetyl chloride in methanol, or a 10% solution of trifluoroacetic acid in dichloroethane. Solvents are then evaporated at 65° C. to afford the cyclized product of formula (IV). The non-cyclized amines were removed via a solution phase scavenging step with the simultaneous addition of PS-DIEA or PS-tris(2-aminoethyl)amine (6 equiv.) and PS-NCO (3 equiv.) in dichloroethane. (Booth, R. J.; Hodges, J. C. *J. Am. Chem. Soc.* 1997, 119, 4882. Flynn, D. L.; Crich, J. Z.; Devraj, R. V.; Hockerman, S. L.; Parlow, J. J.; South, M. S.; Woodward, S. *J. Am. Chem. Soc.* 1997, 119, 4874. Purchased from Argonaut® technologies (PS-DIEA—polystyrene bound disopropylethylamine)). Examples of products (examples 53 to 61) synthesized using this general methodology are indicated below and purities are determined by lc/ms (liquid chromatography/mass spectrometry) ELSD (evaporative light scattering detector) A% and UV A%. Lc/ms analysis is performed using a C18 Hypersil BDS 3 m 4.6×50 mm column (UV 220 nm) with a mobile phase 0.1% TFA IN $H_2O/CH_3CN$ 10% to 100% 15 min, at a rate of 1 ml/min for 3, 6, 7, 9, 10 and 11. BDS Hyp. 3 m C18 4.6×50 mm 0.1% TFA IN $H_2O/CH_3CN$ 10% to 100% 5 min, at a rate of 1 ml/min for 4, 5, 8. HPLC is interfaced with APCI techniques (Atmospheric Pressure Chemical Ionization). Desired products are seen as (M+1).

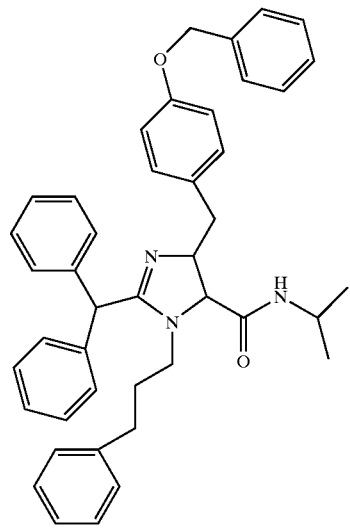
53
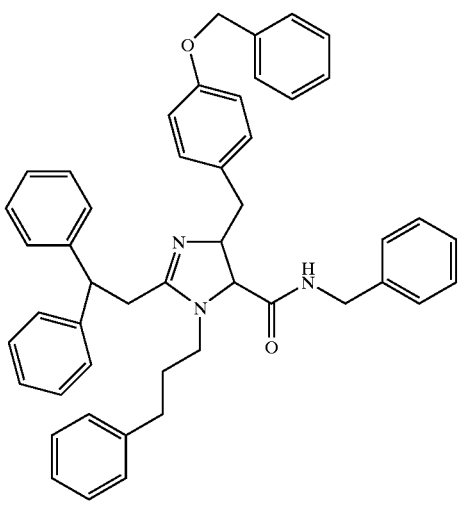
56
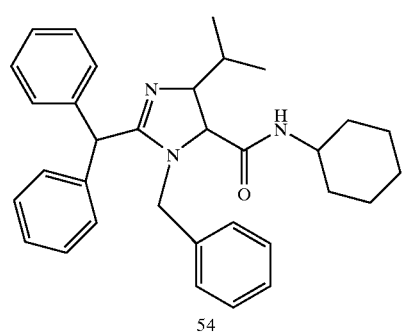
54
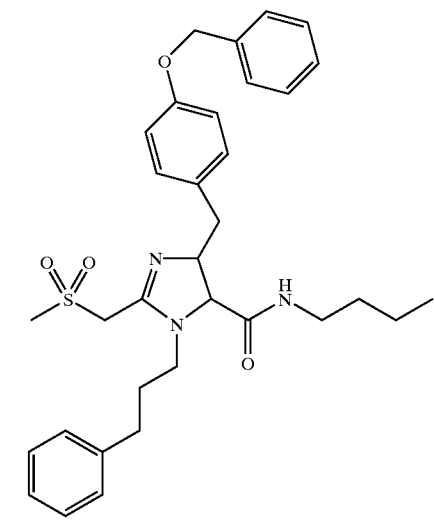
57
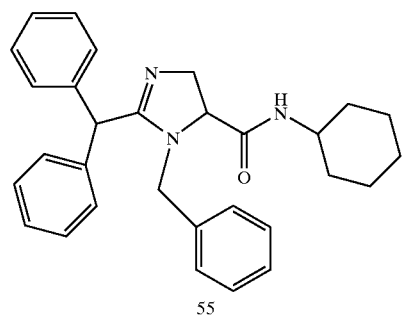
55
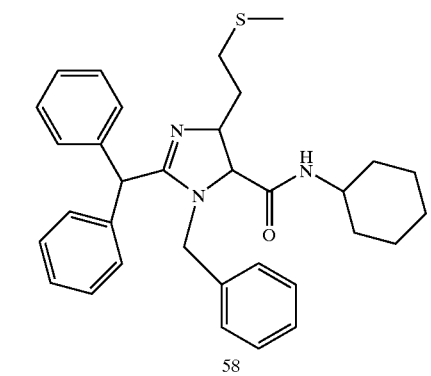
58

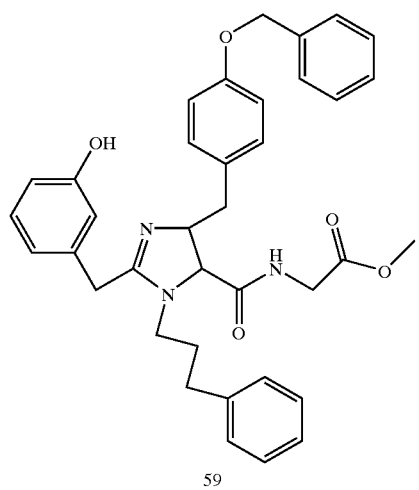

59

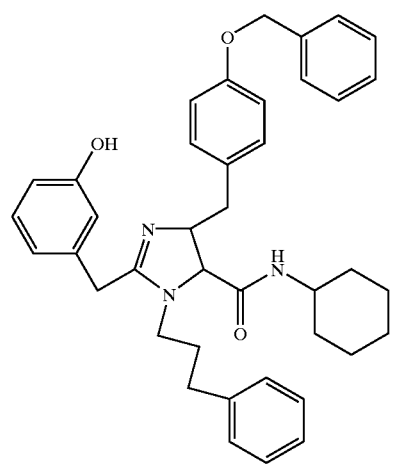

60

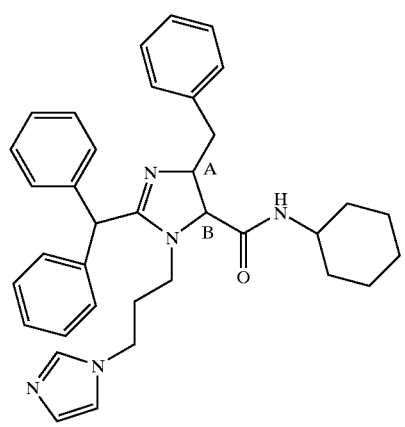

61

| Compound | Retention time | mass spec | UV (220 nm) A % |
|---|---|---|---|
| 53 | 7.36 & 8.05 | 625 | 40 |
| 54 | 4.87 & 5.08 | 493 | 66 |
| 55 | 4.58 | 451 | 60 |
| 56 | 11.26 & 1.57 | 697 | 67 |
| 57 | 6.36 & 6.84 | 565 | 59 |
| 58 | 4.86 & 5.03 | 525 | 79 |
| 59 | 8.53 | 605 | 56 |
| 60 | 10.0 & 10.22 | 615 | 48 |
| 61 | 8.05 & 8.88 | 665 | 71 |

EXAMPLE 8

General Solid Phase Synthesis of Compounds of Formula (V) Using the Ugi Reaction and Resin (XVIII)

(60 mg) of resin (XVIII) is pre-swelled with THF. 0.5M solutions of the appropriate aldehyde (XV) (10 equiv.), N-BOC-amino aldehyde (XXXV) (10 equiv.) and amine (XVI) (10 equiv.) in THF:MeOH (1:1) are added sequentially to the resin (XVIII) and the reaction stirred in methanol at room temperature and the solvent evaporated at 65° C. (using a SAVANT® evaporator for 2 hours). The resin is washed sequentially with $CH_2Cl_2$, THF, DMF, THF and MeOH dried under high vacuum to yield the resin bound Ugi product (XXXVI). The deprotection/cyclization steps are performed using either a 10% solution of acetyl chloride in methanol, or a 10% solution of trifluoroacetic acid in dichloroethane. Cyclization is then effected by base treatment with a 5% solution of diethylamine in dichloroethane [Note: 10–15 mg of N,N-(diisopropyl)amino-methylpolystyrene (PS-DIEA) is an excellent resin bound alternative to diethylamine]. Solvents are then evaporated at 65° C. to afford the cyclized products. Examples of products synthesized using this general methodology are indicated below. Lc/ms (liquid chromatography/mass spectrometry) analysis is performed using a C18 Hypersil BDS 3 m 4.6×50 mm column (UV 220 nm) with a mobile phase 0.1% TFA IN $H_2O/CH_3CN$ 10% to 100% 15 min, at a rate of 1 ml/min for 62. Hypersil BDS 3 m C18 4.6×50 mm 0.1% TFA IN $H_2O/CH_3CN$ 10% to 100% 5 min, at a rate of 1 ml/min for 63 to 72. HPLC is interfaced with APCI techniques (Atmospheric Pressure Chemical Ionization). Desired products are seen as (M+1).

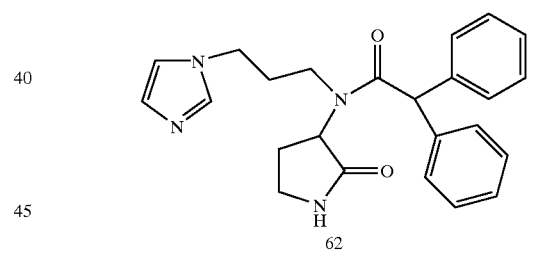

62

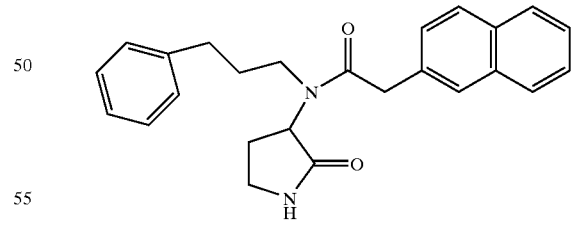

63

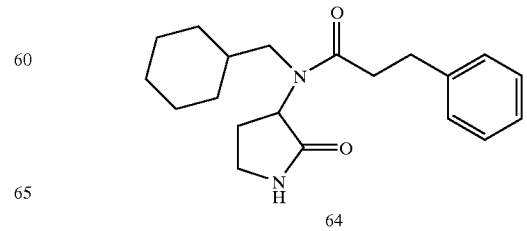

64

-continued

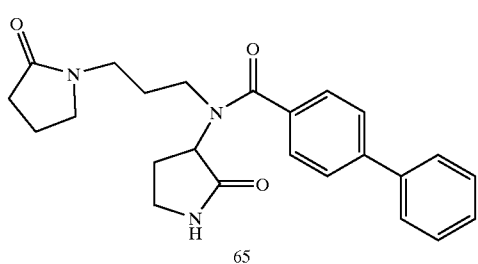
65

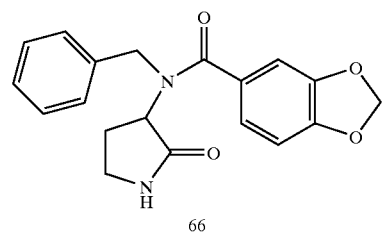
66

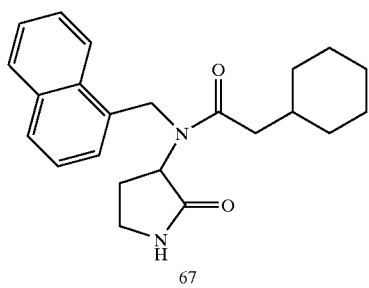
67

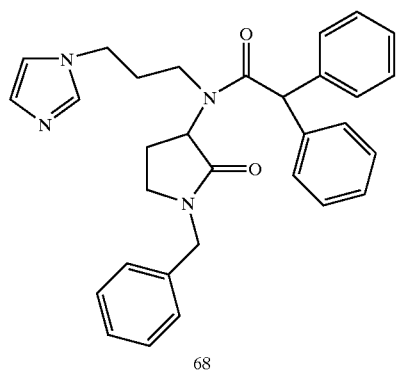
68

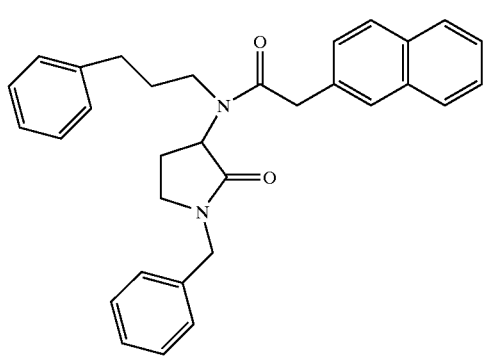
69

-continued

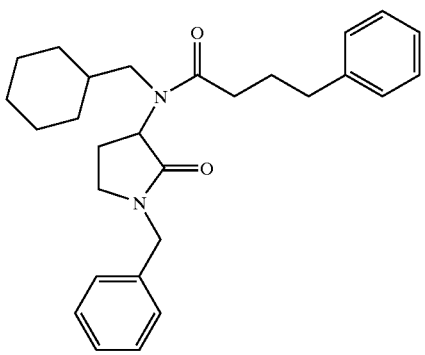
70

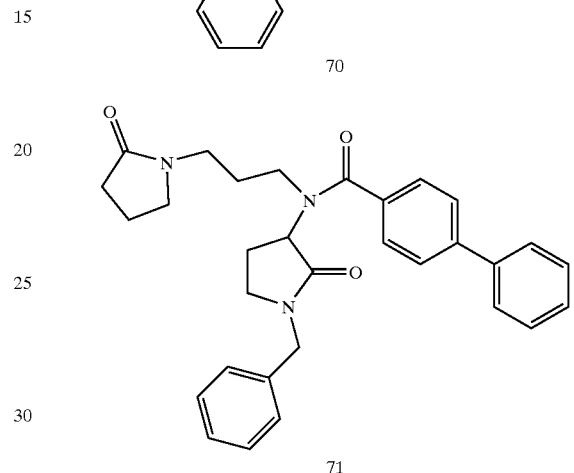
71

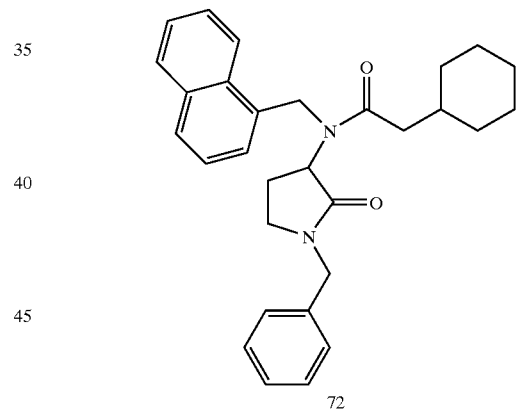
72

| Compound | Retention time | mass spec | Compound | Retention time | mass spec |
| --- | --- | --- | --- | --- | --- |
| 62 | 4.88 | 402 | 68 | 10.75 | 492 |
| 63 | 4.34 | 386 | 69 | 15.79 | 476 |
| 64 | 4.30 | 328 | 70 | 16.59 | 432 |
| 65 | 3.33 | 405 | 71 | 11.22 | 495 |
| 66 | 3.47 | 338 | 72 | 16.86 | 454 |
| 67 | 4.56 | 364 | | | |

EXAMPLE 9

General Solution Phase Synthesis of 1,4-benzodiazepine-2, 5-dione Compounds of Formula (VI) Via the '3-step, One Pot' Procedure, Employing the Ugi Multi-component Reaction Equal amounts (0.1 ml) of 0.1 M solutions of the four appropriate components, ethyl glyoxalate (XXXVII), compound of formulae (XIV), (XVI) and (IX), are employed generating a theoretical 10 μmol of final 1,4- benzodiazepine-2,5-dione product (VI) for 100% conversion. The 4-component condensation is performed in methanol at room temperature and the solvent evaporated at 65° C. (using a SAVANT® evaporator for 2 hours). The deprotection/cyclization steps are performed using either a 10% solution of acetyl chloride in methanol, or a 10% solution of trifluoroacetic acid in dichloroethane, and heat, to afford the cyclized products. Examples of products (examples 62 to 72) synthesized using this general methodology are indicated below and purities are determined by lc/ms (liquid chromatography/mass spectrometry) ELSD (evaporative light scattering detector) A%. Lc/ms (liquid chromatography/mass spectrometry) analysis is performed using a C18 Hypersil BDS 3 m 4.6×50 mm column (UV 220 nm) with a mobile phase 0.1% TFA IN H$_2$O/CH$_3$CN 10% to 100% 5 min, at a rate of 1 ml/min. HPLC is interfaced with APCI techniques (Atmospheric Pressure Chemical Ionization). Desired products are seen as (M+1).

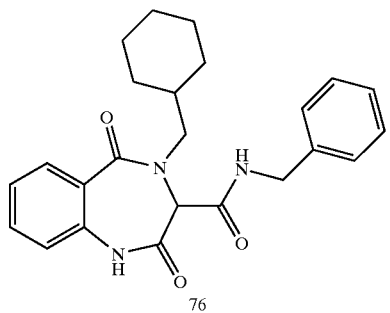

76

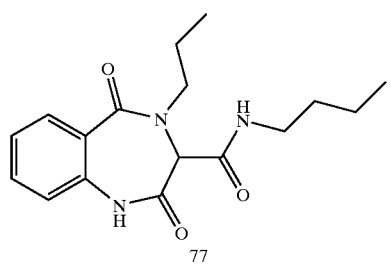

77

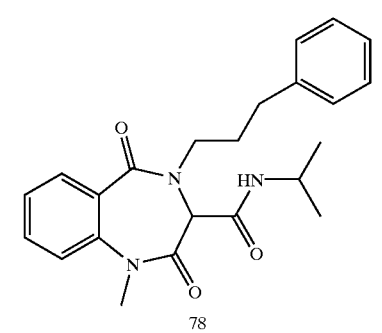

78

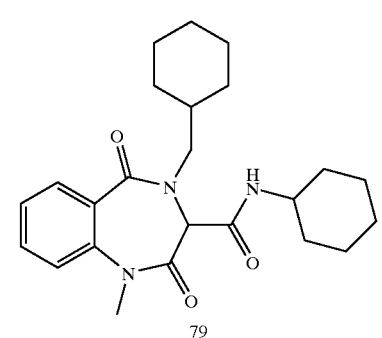

79

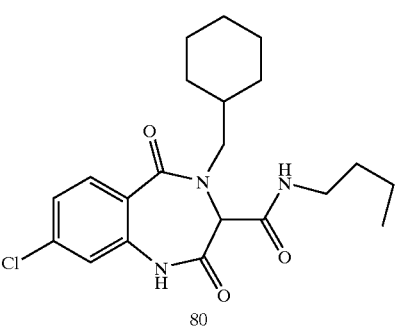

80

-continued

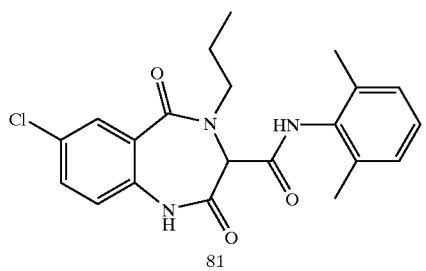

81

| Compound | Retention time | mass spec | ELSD A % |
|---|---|---|---|
| 73 | 4.26 | 419 | 82 |
| 74 | 4.93 | 449 | 83 |
| 75 | 4.10 | 427 | 90 |
| 76 | 4.06 | 405 | 89 |
| 77 | 3.16 | 317 | 39 |
| 78 | 4.00 | 393 | 27 |
| 79 | 4.47 | 411 | 63 |
| 80 | 4.30 | 455 | 60 |
| 81 | 3.97 | 399 | 84 |

EXAMPLE 10

General Solid Phase Synthesis of Compounds of Formula (VII) Using the Uai Reaction and Resin Bound Amine (XXXIX)

Wang bound Fmoc-amino acids (XXXIX) (100 mg: loading of 0.70 mmol/g) are treated with 20% piperidine in DMF (1 ml) at room temperature for one hour and washed with DMF (×3) and CH$_2$Cl$_2$ (×3). To each reaction vessel containing (XXXIX) is added 0.8 ml of CH$_2$Cl$_2$, followed by 0.1 M solutions in MeOH of the appropriate aldehydes (XV) (5 equiv.), isonitriles (IX) (5 equiv.) and anthranilic acid (XIV) (5 equiv.). The reactions are shaken overnight at room temperature and washed with methanol (×3) and CH$_2$Cl$_2$ (×3). Each resin is then treated with 10% TFA in CH$_2$Cl$_2$ at room temperature for 3 hours (1.3 ml), then washed with CH$_2$Cl$_2$ (×2). The samples are then evaporated in a SAVANT at room temperature for 3 hours to give the crude products. Examples of products (examples 82 to 93) synthesized using this general methodology are indicated below and purities are determined by lc/ms (liquid chromatography/mass spectrometry) ELSD (evaporative light scattering detector) A%. Lc/ms (liquid chromatography/ mass spectrometry) analysis is performed using a C18 Hypersil BDS 3 m 4.6×50 mm column (UV 220 nm) with a mobile phase 0.1% TFA IN H$_2$O/CH$_3$CN 20% to 100% 20 min, at a rate of 1 ml/min. HPLC is interfaced with APCI techniques (Atmospheric Pressure Chemical Ionization). Desired products are seen as (M+1).

The Following Specific Procedure is Followed for Compound 82

Wang bound Fmoc-Phenylalanine (100 mg: loading of 0.70 mmol/g) is treated with 20% piperidine in DMF (1 ml) at room temperature for one hour and washed with DMF (×3) and CH$_2$Cl$_2$ (×3). To each reaction vessel is added 0.8 ml of CH$_2$Cl$_2$, followed by 0.1M solutions in MeOH of phenpropionaldehyde (46 µl, 5 equiv.), benzyl isocyanide (43 µl, 5 equiv.) and N-BOC anthranilic acid (83 mg, 5 equiv.). The reactions are shaken overnight at room temperature and washed with methanol (×3) and CH$_2$Cl$_2$ (×3). Each resin is then treated with 10% TFA in CH2Cl$_2$ at room temperature for 3 hours (1.3 ml), then washed with CH$_2$Cl$_2$ (×2). The sample is then evaporated in a SAVANT at room temperature for 3 hours to give 20 mg of crude product.

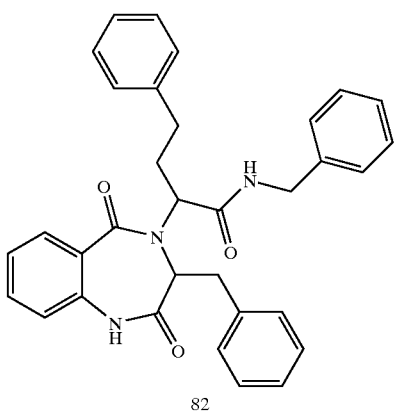

82

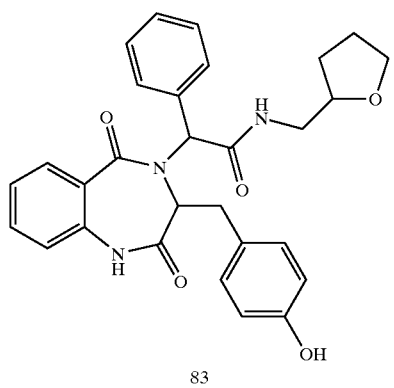

83

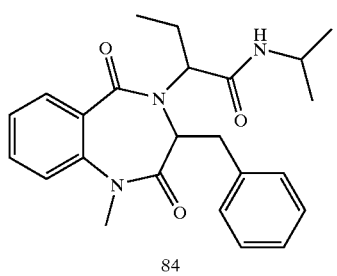

84

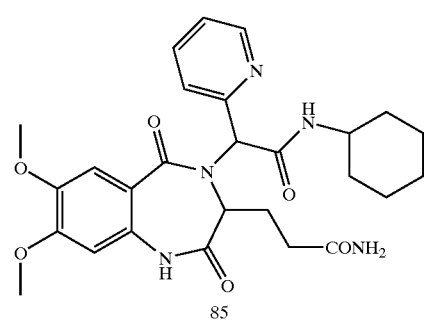

85

-continued
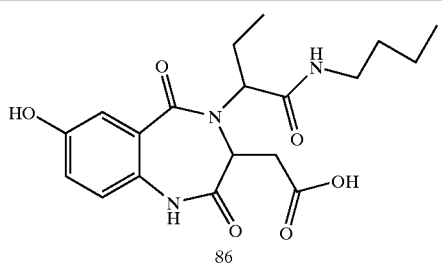
86
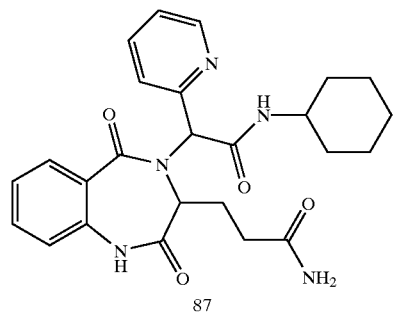
87
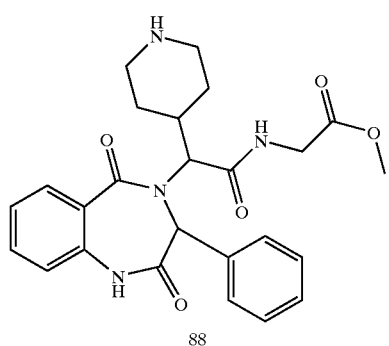
88
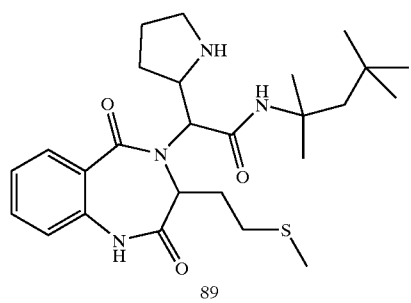
89
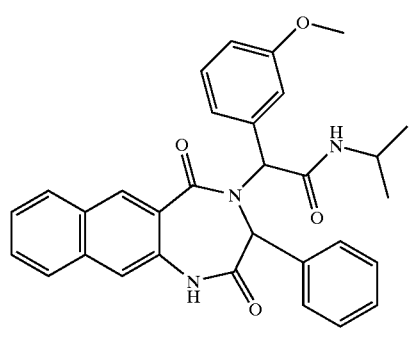
90
-continued
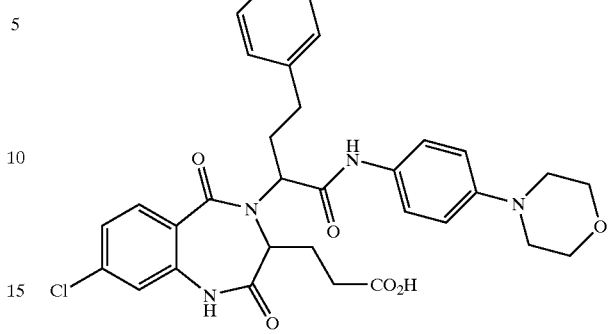
91
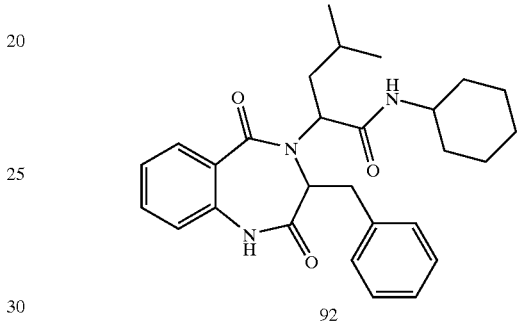
92
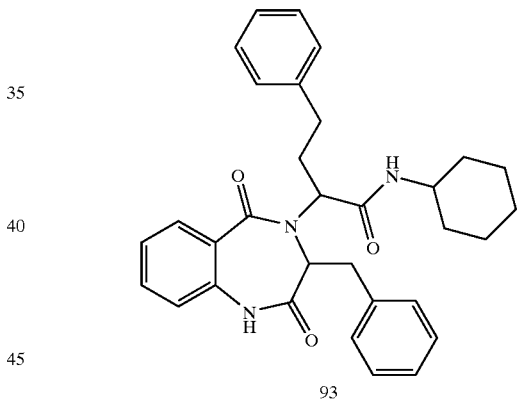
93
| Compound | Retention time | Mass spec | ELSD A % |
|---|---|---|---|
| 82 | 10.45 | 517 | 70 |
| 83 | 4.64 | 499 | 95 |
| 84 | 7.14, 7.37 | 407 | 97 |
| 85 | 3.83 | 523 | 95 |
| 86 | 3.50 | 391 | 50 |
| 87 | 4.14 | 463 | 100 |
| 88 | 3.80, 3.97 | 464 | 95 |
| 89 | 5.67 | 488 | 41 |
| 90 | 5.90, 6.10 | 507 | 44 |
| 91 | 5.10 | 605 | 44 |
| 92 | 5.36 | 461 | 100 |
| 93 | 9.38 & 10.35 | 481 | 100 |
EXAMPLE 11
General Solid Phase Synthesis of Acids by Hydroxide Clipping of Resin Bound Safety Catch Linker (IXa)
(60 mg) of resin (IXa) is pre-swelled with THF. 0.5M solutions of the appropriate aldehyde (XV) (10 equiv.), amine (2-(5-imidazole)ethylamine or 3-(1pyrrolidine)

propylamine) (10 equiv.) and carboxylic acid (XXVI) (10 equiv.) in THF:MeOH (1:1) are added sequentially to the resin (IXa) and the reaction stirred at room temperature for 3 days. The resin is washed sequentially with $CH_2Cl_2$, THF, DMF, THF and MeOH dried under high vacuum to yield the resin bound Ugi products. Treatment with $BOC_2O$ (10 equiv.), $Et_3N$ (10 equiv.) and DMAP in $CH_2Cl_2$ (15 hours) afford the activated the resin bound product. Sodium hydroxide (5 mg) in $THF:H_2O$, 1:1, is added to the resin and shaken for 20 hours. The solvent is evaporated in vacuo to afford the desired acid, where lc/ms (liquid chromatography/mass spectrometry) A% purities are judged by ELSD (evaporative light scattering detector) A%. Lc/ms analysis is performed using a Hypersil BDS 3 $\mu$C18 4.6×50 mm 0.1% TFA in $H_2O/CH_3N$ 5% to 100% $CH_3N$ 5 min, at a rate of 1 ml/min. Desired products are seen as (M+1). Examples of acids synthesized using this general methodology are:

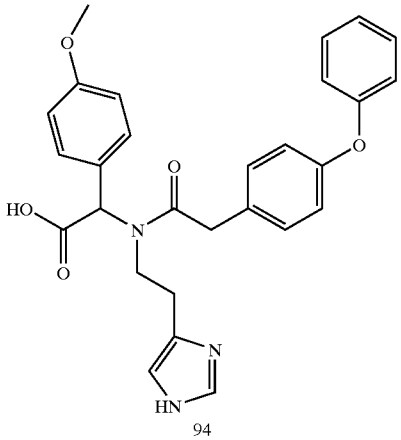

94

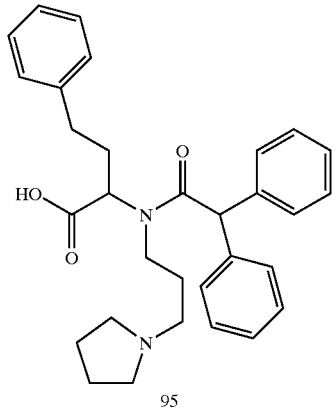

95

| Compound | Retention time | mass spec | ELSD A % |
|---|---|---|---|
| 94 | 4.80 | 485 | 100 |
| 95 | 4.23 | 484 | 89 |

EXAMPLE 12
General Solution Phase Synthesis of Diketopiperazine Compounds of Formula (VI) via the '3-step, One Pot' Procedure, Employing the Ugi Multi-component Reaction Equal amounts (0.1 ml) of 0.1 M solutions of the four appropriate components compound of formulae (XIV), (XXXVII), (XVI) and (IX), are employed generating a theoretical 10 $\mu$mol of final 1 Diketopiperazine product (VI) for 100% conversion. The 4-component condensation is performed in methanol at room temperature and the solvent evaporated at 65° C. (using a SAVANT® evaporator for 2 hours). The deprotection/cyclization steps are performed using either a 10% solution of acetyl chloride in methanol, or a 10% solution of trifluoroacetic acid in dichloroethane, and heat, to afford the cyclized products. Examples of products (examples 96 to 112) synthesized using this general methodology are indicated below and purities are determined by lc/ms (liquid chromatography/mass spectrometry) ELSD (evaporative light scattering detector) A% and UV A%. Lc/ms analysis is performed using a C18 Hypersil BDS 3 m 4.6×50 mm column (UV 220 nm) with a mobile phase 0.1% TFA IN $H_2O/CH_3CN$ 10% to 100% 5 min, at a rate of 1 ml/min (Examples 96 to 99), or a mobile phase 5 mM $NH_4OAC.H_2O/CH_3CN$ 10% to 100% 5 min, at a rate of 1 ml/min (Examples 100 to 112). HPLC is interfaced with APCI techniques (Atmospheric Pressure Chemical Ionization). Desired products are seen as (M+1).

| Compound | UV (220 nm) A % | ELSD A % | Retention Time (min) | Mass spec |
|---|---|---|---|---|
| 96 | 80 | 70 | 4.33 | 421 |
| 97 | 75 | 90 | 3.80 | 379 |
| 98 | 81 | 90 | 4.27/4.40 | 419 |
| 99 | 80 | 90 | 3.83 | 379 |
| 100 | 86 | 100 | 3.13 | 303 |
| 101 | 86 | 100 | 4.90 | 495 |
| 102 | 84 | 100 | 4.57/4.80 | 469 |
| 103 | 92 | 100 | 433 | 4.60 |
| 104 | 72 | 100 | 329 | 3.53 |
| 105 | 83 | 100 | 357 | 3.80 |
| 106 | 81 | 100 | 475 | 4.53/4.77 |
| 107 | 82 | 100 | 343 | 3.67 |
| 108 | 88 | 100 | 449 | 4.39/4.49 |
| 109 | 95 | 70 | 499 | 3.89/3.96 |
| 110 | 80 | 90 | 3.88/4.22 | 521 |
| 111 | 70 | 86 | 3.78/3.51 | 476 |
| 112 | 63 | 84 | 3.50/3/63 | 538 |

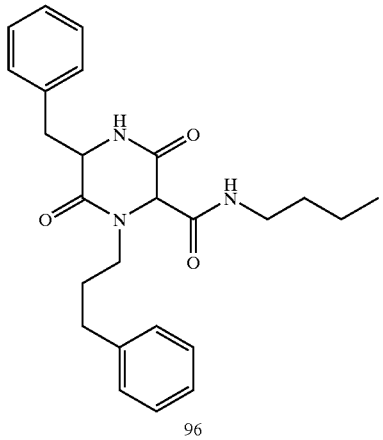

96

-continued
| Compound | UV (220 nm) A % | ELSD A % | Retention Time (min) | Mass spec |
|---|---|---|---|---|
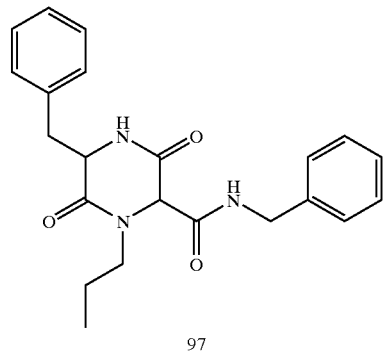
97
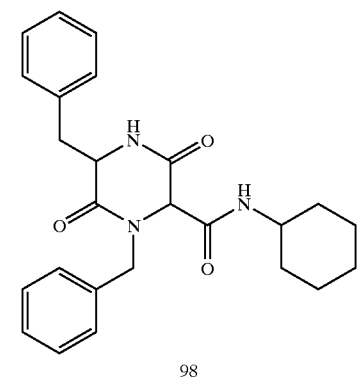
98
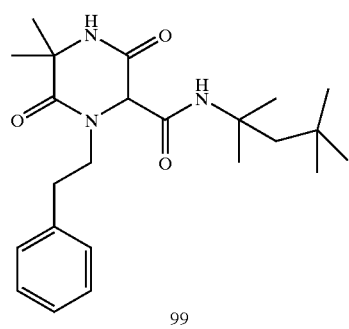
99
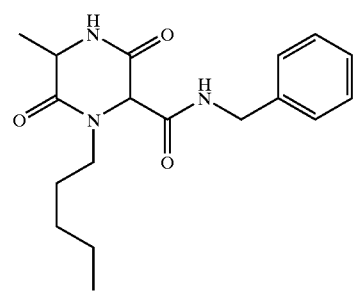
100
-continued
| Compound | UV (220 nm) A % | ELSD A % | Retention Time (min) | Mass spec |
|---|---|---|---|---|
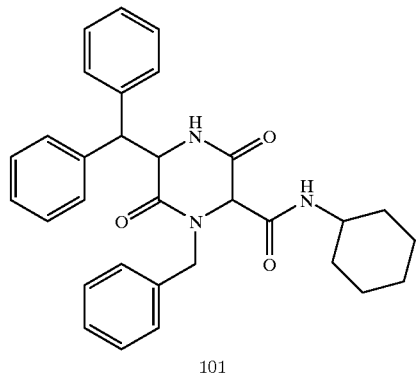
101
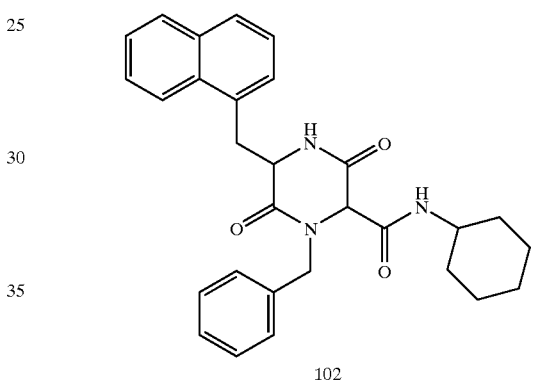
102
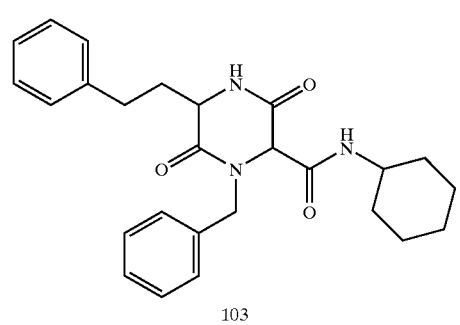
103
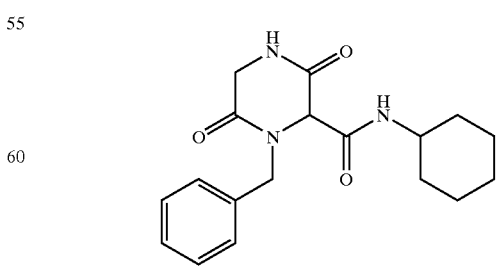
104

| Compound | UV (220 nm) A % | ELSD A % | Retention Time (min) | Mass spec |
|---|---|---|---|---|

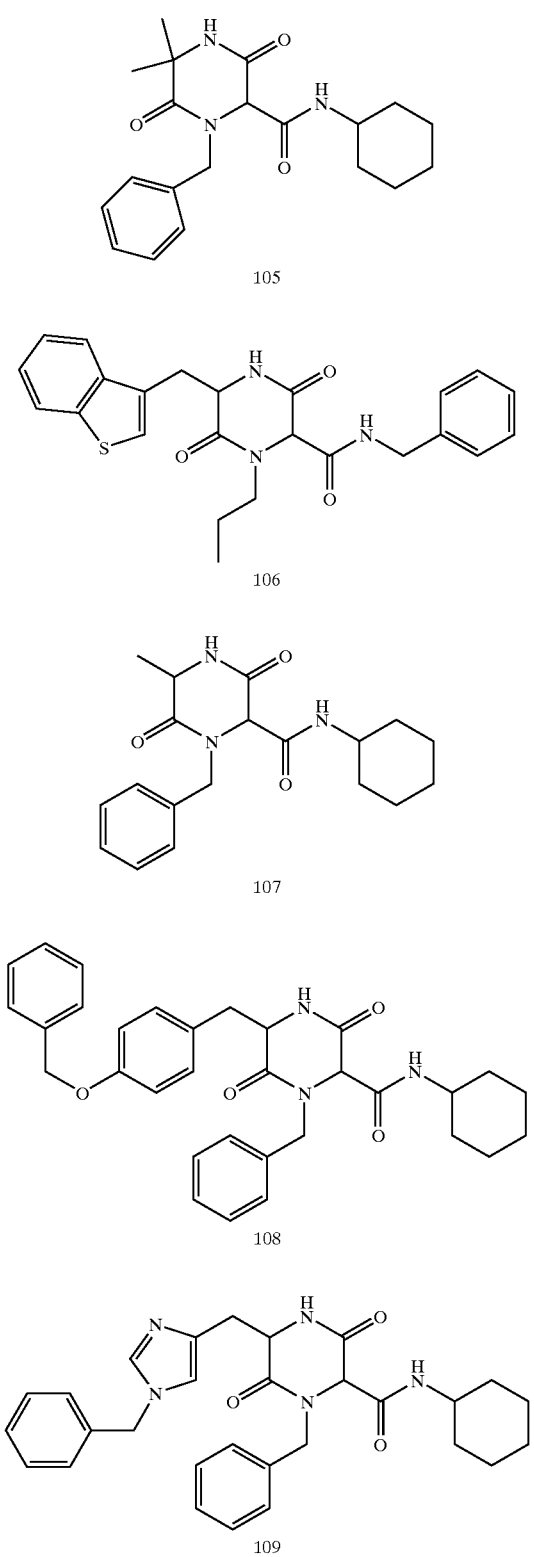

105

106

107

108

109

| Compound | UV (220 nm) A % | ELSD A % | Retention Time (min) | Mass spec |
|---|---|---|---|---|

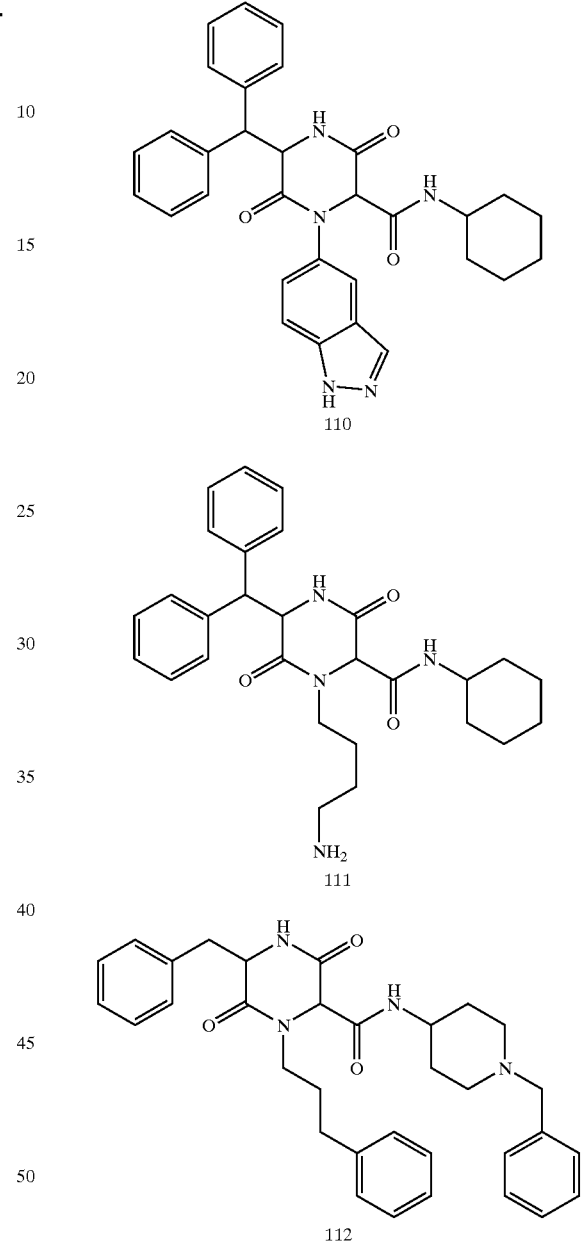

110

111

112

EXAMPLE 13

General Solution Phase Synthesis of Ketopiperazine Derivatives of Formula (VIII) via the '2-step. One Pot' Procedure, Employing the Ugi Multi-component Reaction Equal amounts (0.1 ml) of 0.1 M solutions of the four appropriate components of formulae (XXVI), (XXXVII), (XXVIIa) and (IX) are employed generating a theoretical 10 $\mu$mol of final product (VIII) for 100% conversion. The 4-component condensation is performed in methanol at room temperature followed by increased heating, to afford the cyclized products. Examples of products (examples 113 to 122) synthesized using this general methodology are indicated below and purities are determined by lc/ms (liquid chromatography/mass spectrometry) ELSD (evaporative light scattering detector) A% and UV A%. Lc/ms analysis is performed using a C18 Hypersil BDS 3 m 4.6×50 mm column (UV 220 nm) with a mobile phase 0.1% TFA IN H₂O/CH₃CN 10% to 100% 5 min, at a rate of 1 ml/min. HPLC is interfaced with APCI techniques (Atmospheric Pressure Chemical Ionization). Desired products are seen as (M+1).

| Compound | UV (220 nm) A % | ELSD A % | Mass spec | Retention Time (min) |
|---|---|---|---|---|
| 114 | 41% | 90% | 427 | 4.17 |
| 115 | 43% | 97% | 331 | 3.53 |
| 116 | 35% | 96% | 303 | 2.90 |
| 117 | 32% | 94% | 349 | 3.97 |
| 118 cis | 41% | 90% | 481 | 4.60 |
| 118 trans | 70% | 99% | 481 | 4.63 |
| 119 cis | 43% | 97% | 385 | 3.36/3.83 |
| 119 trans | 47% | 100% | 385 | 4.09 |
| 120 cis | 35% | 96% | 357 | 3.36/3.46 |
| 120 trans | 34% | 100% | 357 | 3.63 |
| 121 cis | 32% | 94% | 403 | 4.37/4.54 |
| 121 trans | 57% | 100% | 403 | 4.67 |
| 122 | 75% | 100% | 351 | 3.29 |

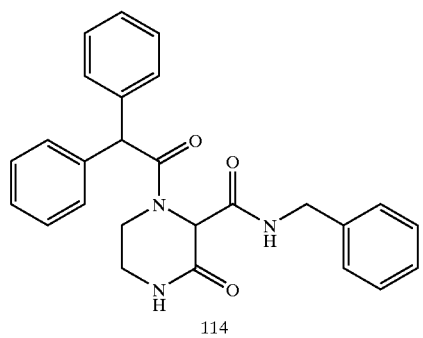

114

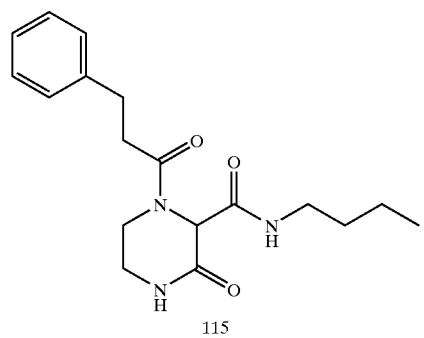

115

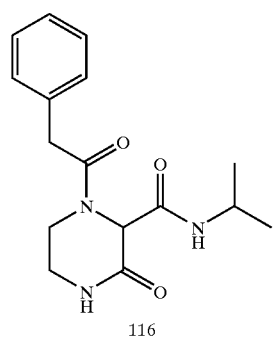

116

-continued

| Compound | UV (220 nm) A % | ELSD A % | Mass spec | Retention Time (min) |
|---|---|---|---|---|

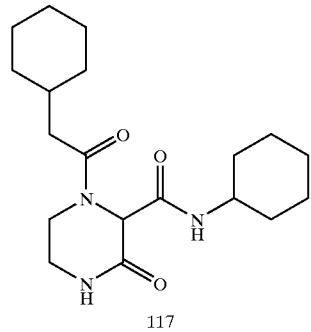

117

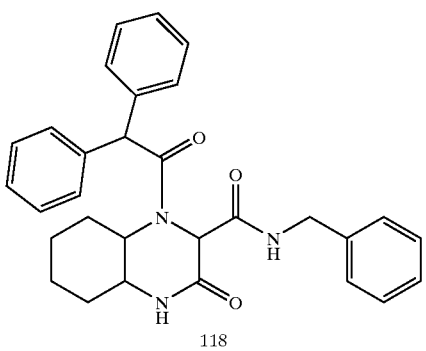

118

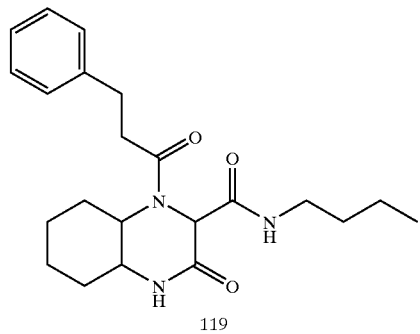

119

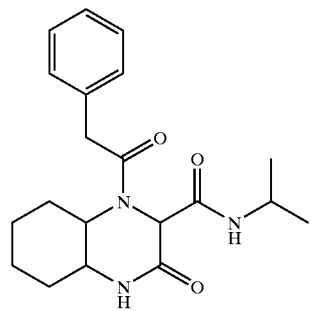

120

-continued

| Compound | UV (220 nm) A % | ELSD A % | Mass spec | Retention Time (min) |
|---|---|---|---|---|

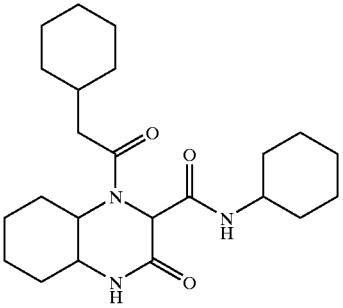

121

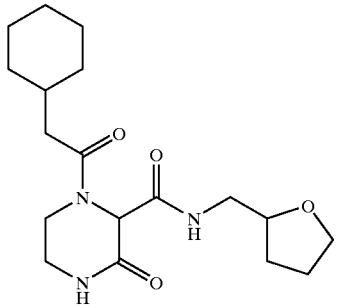

122

EXAMPLE 14
General Solution Phase Synthesis of Ketopiperazine Derivatives of Formula (VIII) via the '3-step One Pot' Procedure, Employing the Ugi Multi-component Reaction Equal amounts (0.1 ml) of 0.1 M solutions of the four appropriate components, compound of formulae (XXVI), (XXXVII), (XXVII) and (IX), are employed generating a theoretical 10 μmol of final Ketopiperazine product (VIII) for 100% conversion. The 4-component condensation is performed in methanol at room temperature and the solvent evaporated at 65° C. (using a SAVANT® evaporator for 2 hours). The deprotection/cyclization steps are performed using the intermediate (XLI) and either a 10% solution of acetyl chloride in methanol, or a 10% solution of trifluoroacetic acid in dichloroethane, and heat, to afford the acyclic products. MP-carbonate (3 equiv.) in dichloroethane (0.4 ml) is added to the crude product and stirred overnight. The resin is filtered and washed with dichloroethane and then the filtrate is evaporated at 65° C. for 2 hours. Examples of products (examples 123 to 129) synthesized using this general methodology are indicated below and purities are determined by lc/ms (liquid chromatography/mass spectrometry) ELSD (evaporative light scattering detector) A% and UV A%. Lc/ms analysis is performed using a C18 Hypersil BDS 3 m 4.6×50 mm column (UV 220 nm) with a mobile phase :—0.1% AQ/ACN 10% to 100%, 5 min. (Compounds 123 and 124); 0.1% AQ/ACN 0% to 100%, 10 min (compounds 125–128). HPLC is interfaced with APCI techniques (Atmospheric Pressure Chemical Ionization). Desired products are seen as (M+1).

| Compound | UV (220 nm) A % | ELSD A % | Mass spec | Retention Time (min) |
|---|---|---|---|---|
| 123 | 85 | 100 | 379 | 4.05 |
| 124 | 46 | 78 | 441 | 4.30 |
| 125 | 50 | 77 | 379 | 3.82 |
| 126 | 52 | 31 | 447 | 4.84 |
| 127 | 94 | 100 | 517 | 4.93 |
| 128 | 62 | 79 | 441 | 4.37 |

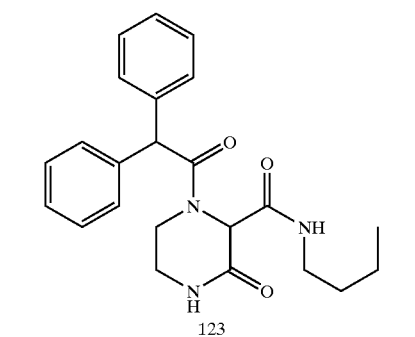

123

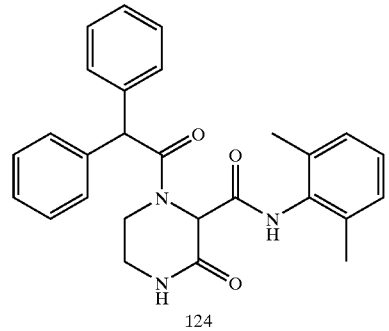

124

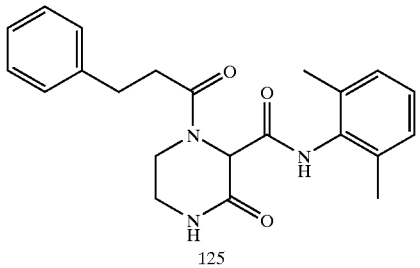

125

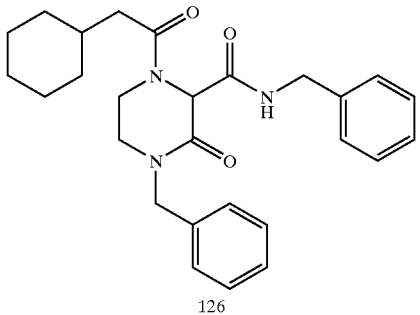

126

| Compound | UV (220 nm) A % | ELSD A % | Mass spec | Retention Time (min) |
|---|---|---|---|---|
| 129 | 30 | 28 | 467 | 5.17 |
| 130 | 40 | 43 | 367 | 3.03 |
| 131 | 30 | 20 | 405 | 4.04 |

EXAMPLE 15

General Solution Phase Synthesis of Dihydroquinoxalinone Derivatives of Formula (VIII) via the '3-step, One Pot' Procedure, Employing the Ugi Multi-component Reaction Equal amounts (0.1 ml) of 0.1 M solutions of the four appropriate components, compound of formulae (XXVI), (XXXVII), (XXVII) and (IX), are employed generating a theoretical 10 μmol of final Dihydroquinoxalinone product (VIII) for 100% conversion. The 4-component condensation is performed in methanol at room temperature and the solvent evaporated at 65° C. (using a SAVANT® evaporator for 2 hours). The deprotection/cyclization steps are performed using either a 10% solution of acetyl chloride in methanol, or a 10% solution of trifluoroacetic acid in dichloroethane, and heat, to afford the cyclized products. Examples of products synthesized and further examples of other products which could be formed using this general methodology are indicated below. Examples of products (examples 129 to 131) synthesized using this general methodology are indicated below and purities are determined by lc/ms (liquid chromatography/mass spectrometry) ELSD (evaporative light scattering detector) A% and UV A%. Lc/ms analysis is performed using a C18 Hypersil BDS 3 m 4.6×50 mm column (UV 220 nm) with a mobile 0.1% AQ/ACN 0% to 100%, 5 min. HPLC is interfaced with APCI techniques (Atmospheric Pressure Chemical Ionization). Desired products are seen as (M+1).

The following compounds can also be made by the same process:

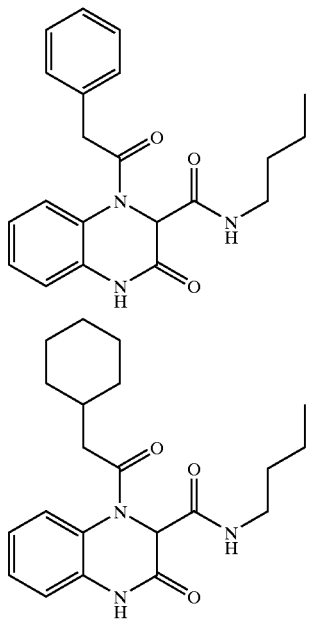

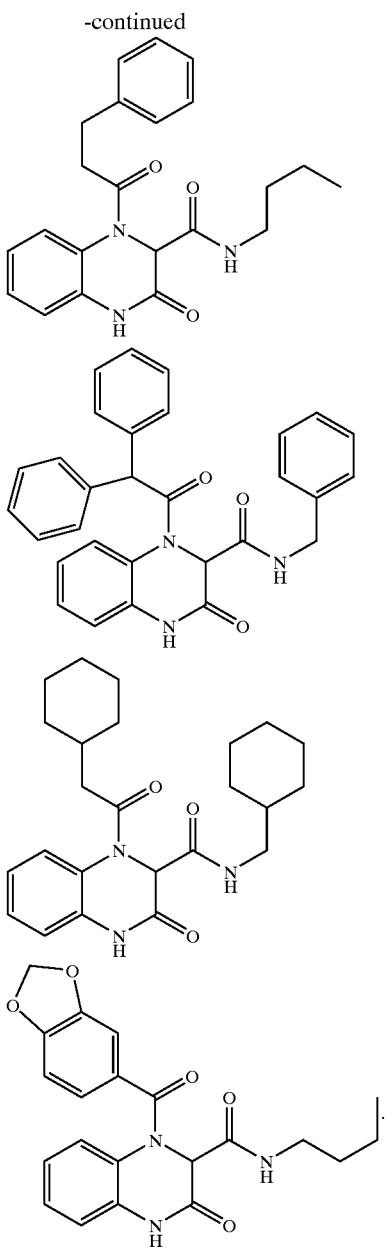

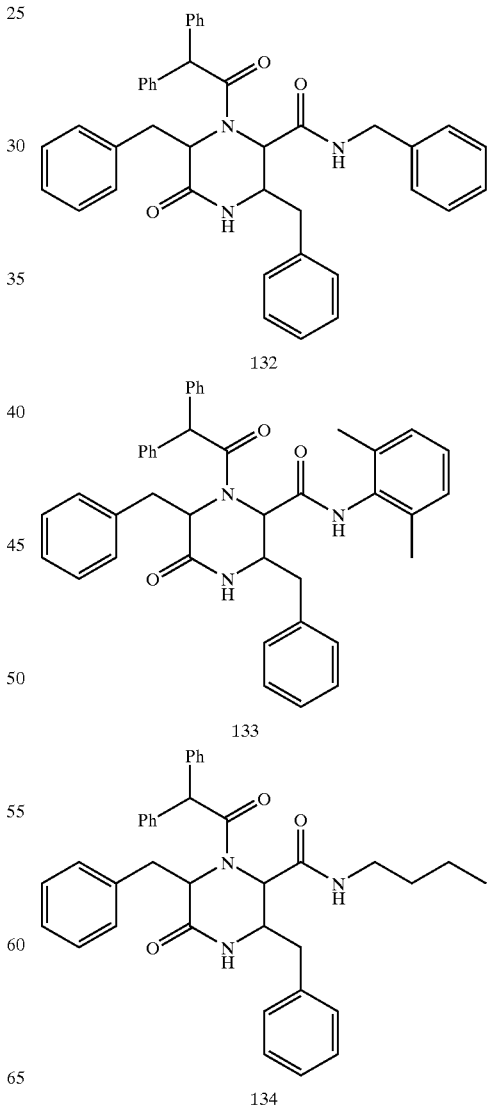

dichloroethane, and heat, to afford the cyclized products. Examples of products synthesized using this general methodology are indicated below. Examples of products (examples 132 to 139) synthesized using this general methodology are indicated below and purities are determined by lc/ms (liquid chromatography/mass spectrometry) ELSD (evaporative light scattering detector) A% and UV A%. Lc/ms analysis is performed using a C18 Hypersil BDS 3 m 4.6×50 mm column (UV 220 nm) with a mobile phase:— 0.1% AQ/ACN 10% to 100%, 5 min. HPLC is interfaced with APCI techniques (Atmospheric Pressure Chemical Ionization). Desired products are seen as (M+1).

| Compound | UV (220 nm) A% | ELSD A% | Mass Spec | Retention Time (Min) |
|---|---|---|---|---|
| 132 | 57 | 67 | 607 | 10.14 |
| 133 | 48 | 54 | 621 | 10.35/10.78 |
| 134 | 62 | 77 | 573 | 10.15 |
| 135 | 59 | 72 | 523 | 9.54 |
| 136 | 29 | 33 | 675 | 11.47 |
| 137 | 37 | 33 | 573 | 10.21 |
| 138 | 47 | 48 | 613 | 11.07 |
| 139 | 30 | 33 | 635 | 10.81 |

EXAMPLE 16

General Solid Phase Synthesis of Ketopiperazine Derivatives of Formula (XLII) via the '3-step, One Pot' Procedure, Employing the Ugi Multi-component Reaction Wang bound Fmoc-amino acids (XXXIX) (100 mg: loading of 0.70 mmol/g) is treated with 20% piperidine in DMF (1 ml) at room temperature for one hour and washed with DZMF (x3) and $CH_2Cl_2$ (x3). Equal amounts (0.1 ml) of 0.1 M solutions of the four appropriate components, compound of formulae (XXVI), (XXXIX), (XLIII) and (IX), are employed generating a theoretical 10 μmol of final Ketopiperazine product (XLII) for 100% conversion. The 4-component condensation is performed in methanol at room temperature and the solvent evaporated at 65° C. (using a SAVANT® evaporator for 2 hours). The deprotection/cyclization steps are performed using the intermediate (XLIX) and either a 10% solution of acetyl chloride in methanol, or a 10% solution of trifluoroacetic acid in -continued

| Compound | UV (220 nm) A% | ELSD A% | Mass Spec | Retention Time (Min) |
|---|---|---|---|---|

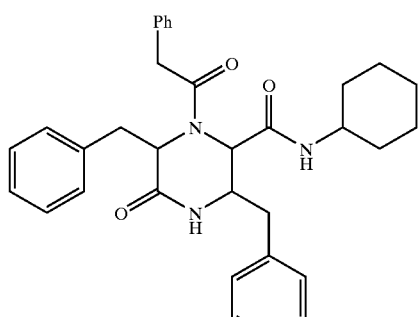

135

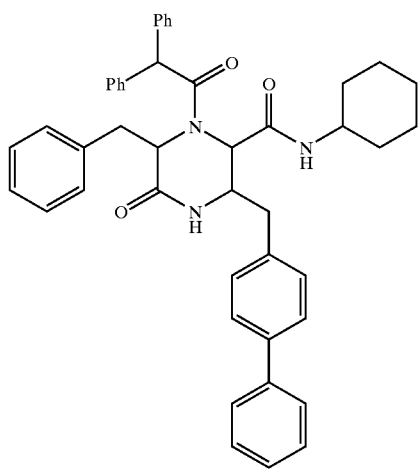

136

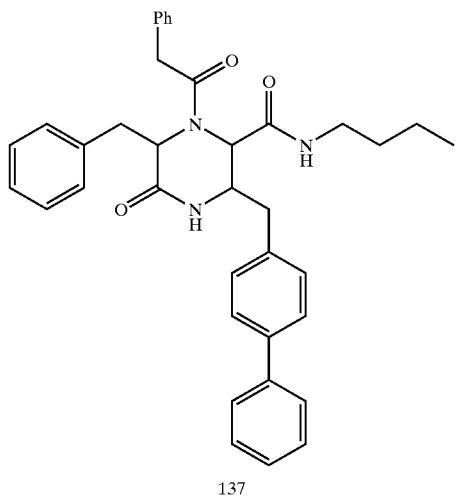

137

-continued

| Compound | UV (220 nm) A% | ELSD A% | Mass Spec | Retention Time (Min) |
|---|---|---|---|---|

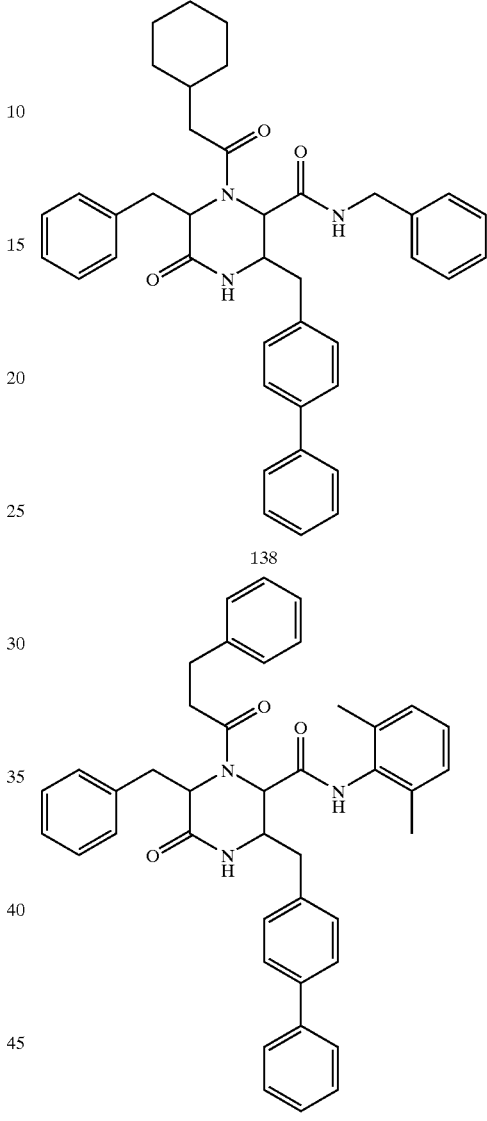

138

139

EXAMPLE 17

General Solid Phase Synthesis of Piperazinyl Derivatives of Formula (Ia), Using the Ugi Reaction and Resin (XVIII)

(25 mg) of resin (XVIII) is pre-swelled with THF. 0.5M solutions of the appropriate aldehyde (XVa) (10 equiv.), amine (XVIa) (10 equiv.), N-BOC anthranilic acid (XIV) (10 equiv.) in THF:MeOH (1:1) and NaHCO3 (10 equiv.) are added sequentially to the resin (XVIII) and the reaction stirred at room temperature for 3 days. The resin is washed sequentially with $CH_2Cl_2$, THF, DMF, THF and MeOH dried under high vacuum to yield the resin bound Ugi intermediate (XVIIa). A 10% solution of acetyl chloride in THF: MeOH (1:1, 900 ul) is added to the resin bound intermediate (XVIIa) and the reaction shaken for 24 hours. Solvents are then evaporated at 65° C. to afford the cyclized product of formula (Ia). Examples of products which are synthesized using this general methodology are indicated below.

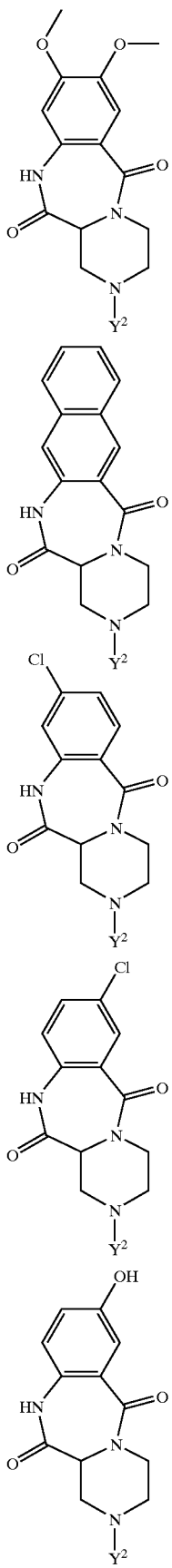

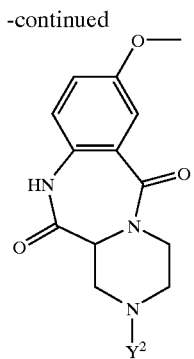

where $Y^2$=$CH_3$, $CH_2CH_3$, Phenyl, Benzyl, $CH_2CH(CH_3)_2$, $CH(CH_3)_2$.

EXAMPLE 18

General Solid Phase Synthesis of Piperazinyl Derivatives of Formula (Ia) Using the Ugi Reaction and Resin (XVIII)

(25 mg) of resin (XVIII) is pre-swelled with THF. 0.5M solutions of the appropriate aldehyde (XVa) (10 equiv.), amine (XVIa) (10 equiv.), N-BOC-a-amino acid (XXII) (10 equiv.) in THF:MeOH (1:1) and NaHCO3 (10 equiv.) are added sequentially to the resin (XVIII) and the reaction stirred at room temperature for 3 days. The resin is washed sequentially with $CH_2Cl_2$, THF, DMF, THF and MeOH dried under high vacuum to yield the resin bound Ugi intermediate (XXIIIa). A 10% solution of acetyl chloride in THF: MeOH (1:1, 900 ul) is added to the resin bound Ugi intermediate (XXIIIa) and the reaction shaken for 24 hours. Solvents are then evaporated at 65° C. to afford the cyclized product of formula (IIa). Examples of products which are synthesized using this general methodology are indicated below.

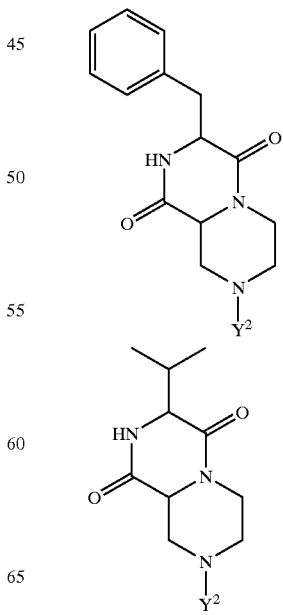

-continued
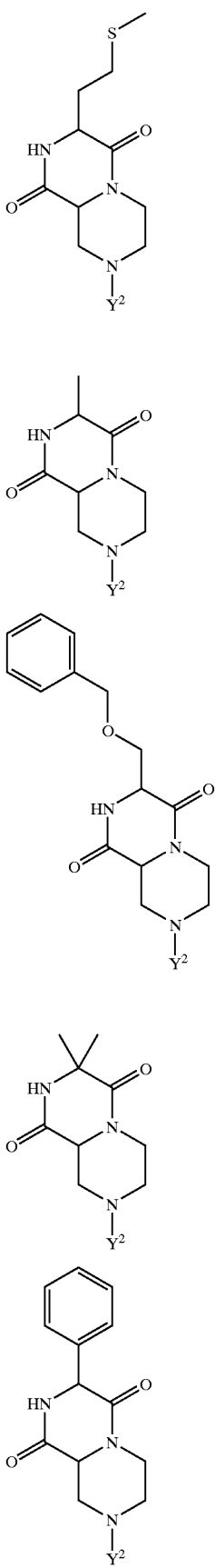
-continued
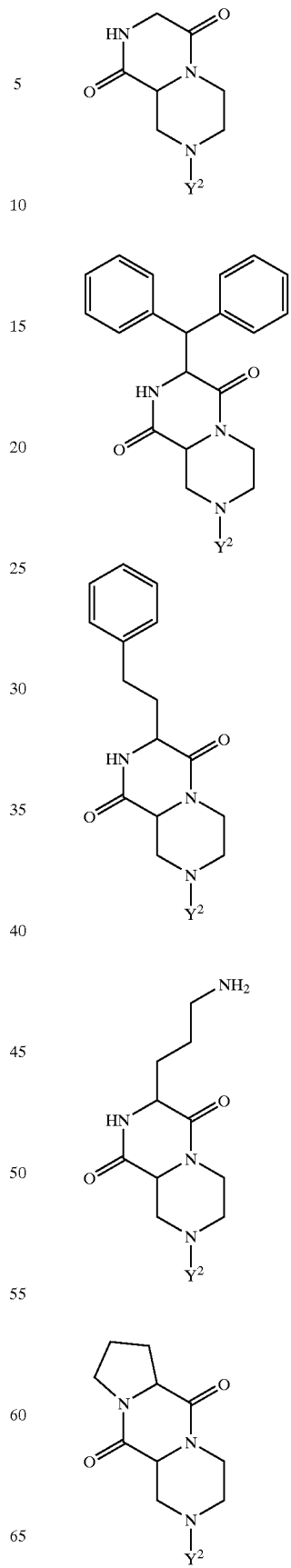

-continued

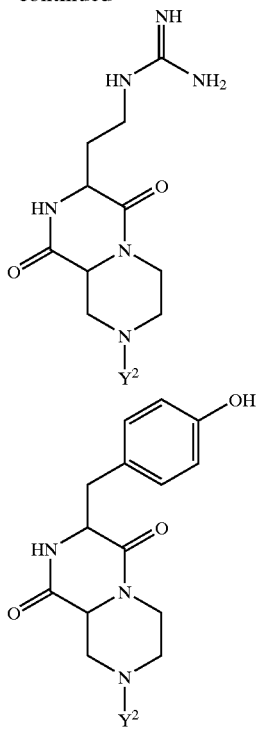

where $Y^2$=CH$_3$, CH$_2$CH$_3$, Phenyl, Benzyl, CH$_2$CH(CH$_3$)$_2$, CH(CH$_3$)$_2$.

EXAMPLE 19
General Solid Phase Synthesis of Lactam Derivatives of Formula (IIIa) Using the Ugi Reaction and Resin (XVIII)

(25 mg) of resin (XVIII) is pre-swelled with THF. 0.5M solutions of the acid (XXVIa) (10 equiv.), amine (XXVII) (10 equiv.), in THF:MeOH (1:1) are added sequentially to the resin (XVIII) and the reaction stirred at room temperature for 3 days. The resin is washed sequentially with CH$_2$Cl$_2$, THF, DMF, THF and MeOH dried under high vacuum to yield the resin bound Ugi intermediate (XXVIIIa). A 10% solution of acetyl chloride in THF:MeOH (1:1, 900 ul) is added to the resin bound intermediate (XXVIIIa) and the reaction shaken for 24 hours. Solvents are then evaporated at 65° C. to afford the intermediate salt. The intermediate salt is dissolved in dichloroethane and MP-carbonate (5 equiv.) added. The reaction is shaken at room temperature for three days and the solvent evaporated in vacuo at 65° C. to afford the desired cyclic products of general formula (IIIa). Examples of products which are synthesized using this general methodology are indicated below.

-continued

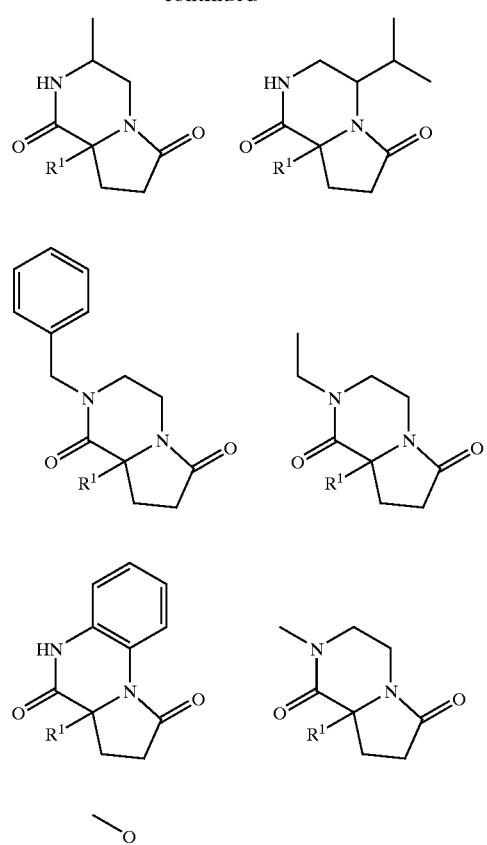

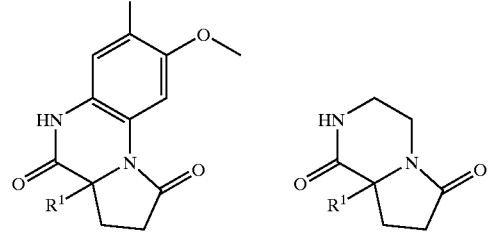

For R$^1$ = HC$_3$ or H

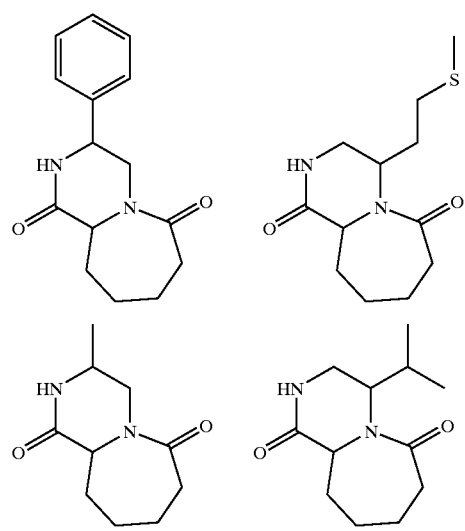

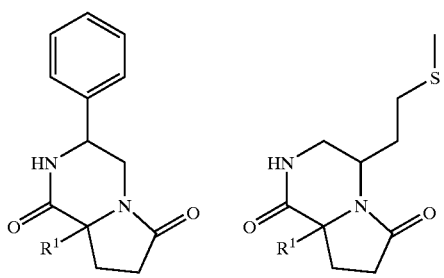

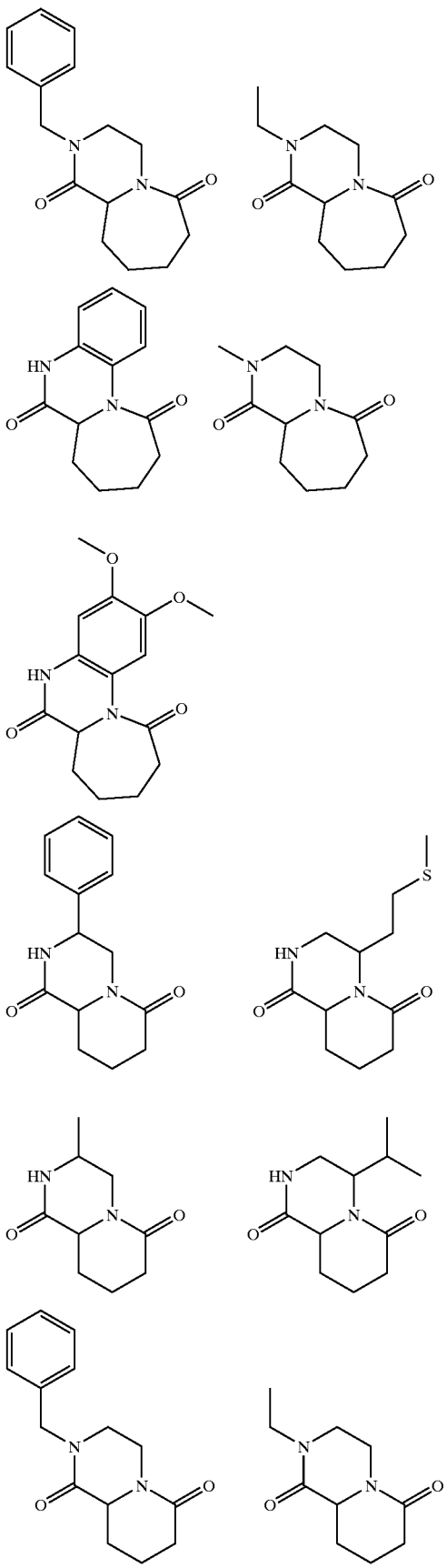

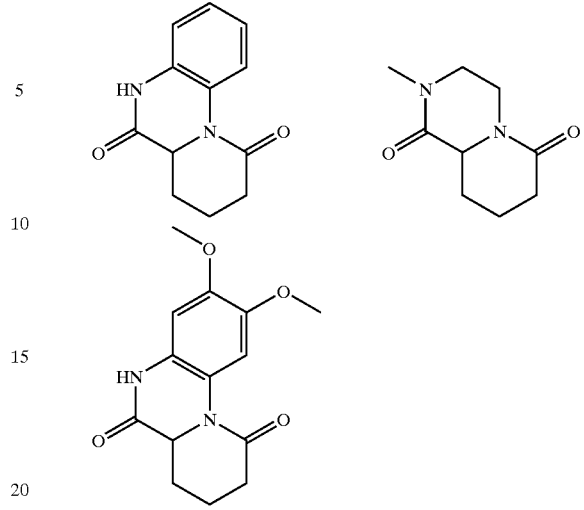

EXAMPLE 20

General Solution Phase Synthesis of 1,4-benzodiazepine-2,5-dione Compounds of Formula (VI) via the '3-step, One Pot' Procedure, Employing the Ugi Multi-component Reaction Equal amounts (0.1 ml) of 0.1M solutions of the four appropriate components, ethyl glyoxalate (XXXVII), an isonitrile of formula (XVI), an amine (XVI) and di-BOC protected N-mono-BOC arginine (XIV), are employed generating a theoretical 10 μmol of final diketopiperazine product (VI) for 100% conversion. The 4-component condensation is performed in methanol at room temperature and the solvent evaporated at 65° C. (using a SAVANT® evaporator for 2 hours) The deprotection/cyclization steps are performed using either a 10% solution of acetyl chloride in methanol, or a 10% solution of trifluoroacetic acid in dichloroethane, and heat, to afford the cyclized products. Examples of products (examples 140 to 160) synthesized using this general methodology are indicated below and purities are determined by lc/ms (liquid chromatography/mass spectrometry) ELSD (evaporative light scattering detector) A%. Lc/ms (liquid chromatography/mass spectrometry) analysis is performed using a C18 Hypersil BDS 3 m 4.6×50 mm column (UV 220 nm) with a mobile phase 0.1% TFA IN H$_2$O/CH$_3$CN 10% to 100% 5 min, at a rate of 1 ml/min. HPLC is interfaced with APCI techniques (Atmospheric Pressure Chemical Ionization). Desired products are seen as (M+1).

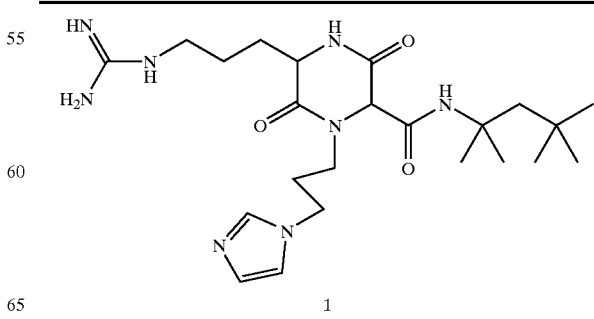

1

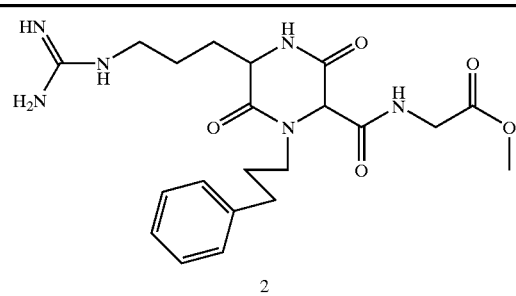
2
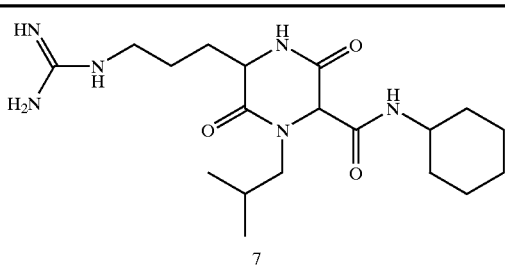
7
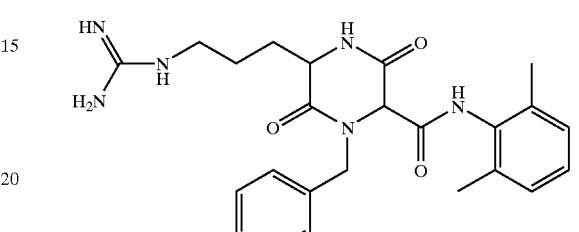
8
3
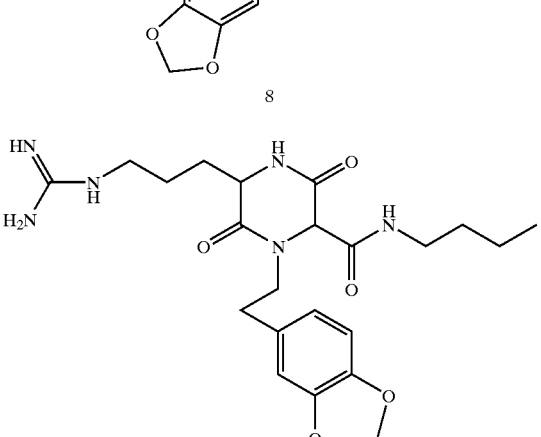
9
4
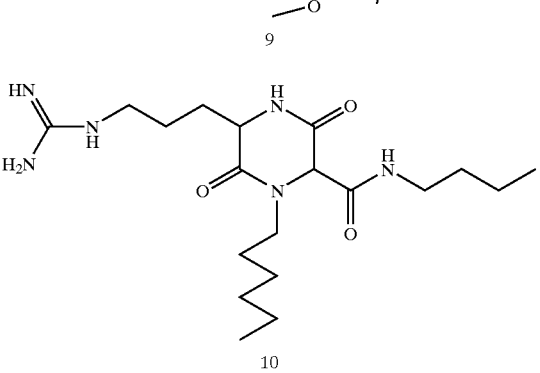
10
5
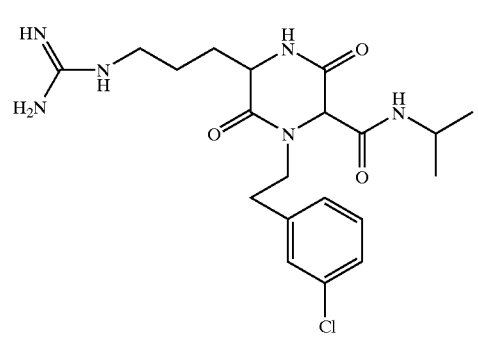
11
6

US 6,492,553 B1
-continued
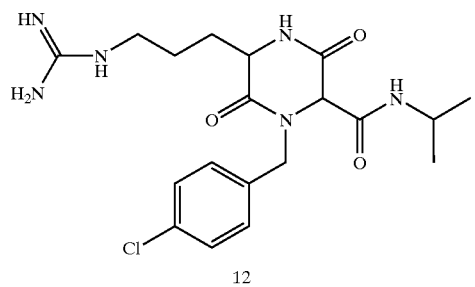
12
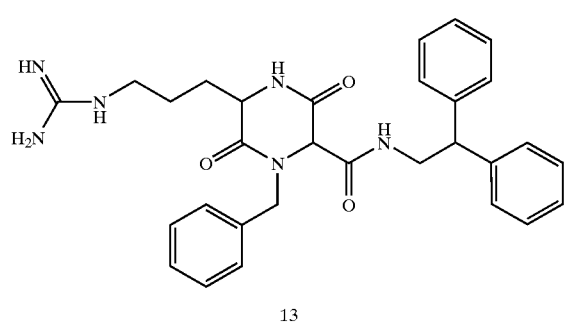
13
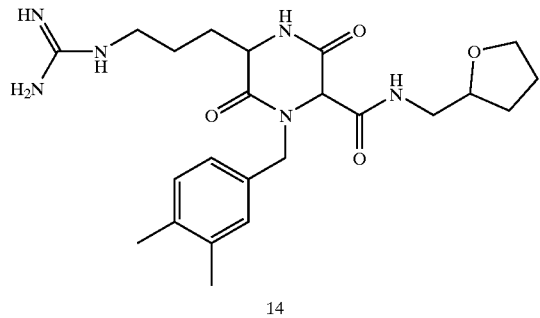
14
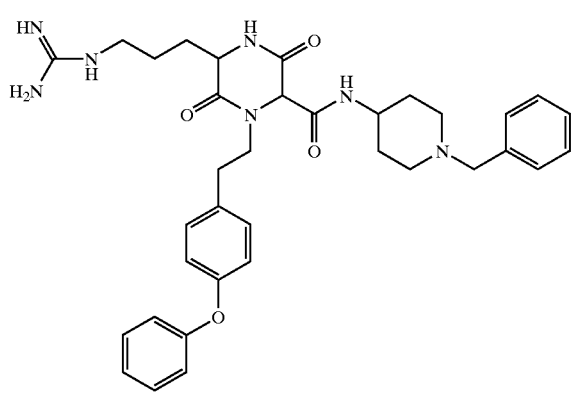
15
-continued
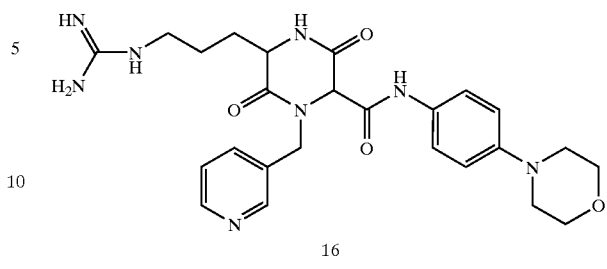
16
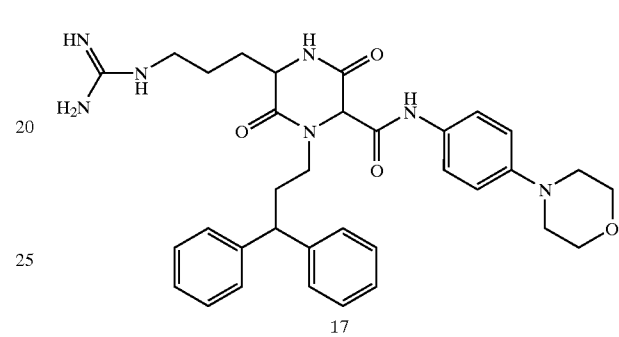
17
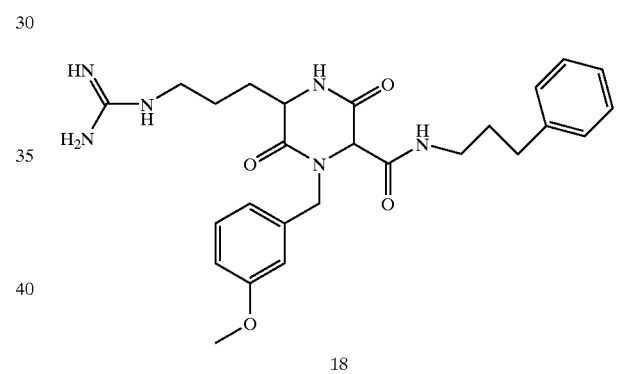
18
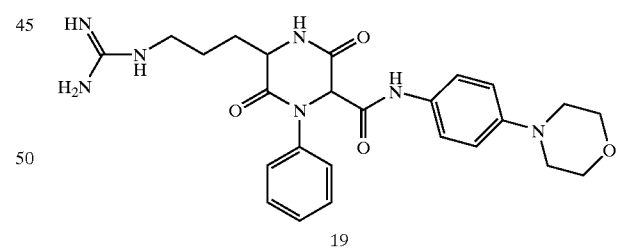
19
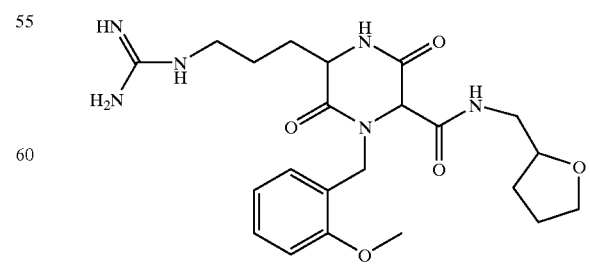
20

-continued

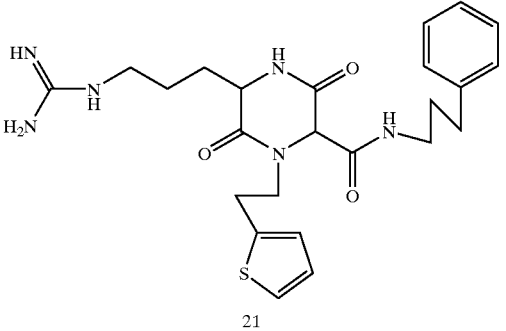

21

| Structure | Mw | ELSD A% | UV 220 | R.T |
|---|---|---|---|---|
| 1 | 476 | 100 | 43 | 2.84; 2.95 |
| 2 | 446 | 92 | 70 | 2.87 |
| 3 | 354 | 100 | 100 | 2.66 |
| 4 | 434 | 100 | 60 | 3.38 |
| 5 | 432 | 100 | 59 | 2.76 |
| 6 | 512 | 100 | 87 | 3.48 |
| 7 | 394 | 100 | 58 | 2.97 |
| 8 | 494 | 97 | 84 | 3.21 |
| 9 | 446 | 100 | 82 | 3.06 |
| 10 | 396 | 100 | 100 | 3.23 |
| 11 | 436 | 100 | 88 | 3.13 |
| 12 | 422 | 100 | 53 | 3.11 |
| 13 | 526 | 84 | 74 | 3.55 |
| 14 | 458 | 100 | 88 | 2.97 |
| 15 | 625 | 91 | 81 | 3.38 |
| 16 | 508 | 97 | 66 | 1.92 |
| 17 | 611 | 100 | 90 | 3.28 |
| 18 | 512 | 100 | 86 | 3.41 |
| 19 | 493 | 100 | 76 | 2.47 |
| 20 | 460 | 95 | 83 | 2.74 |
| 21 | 484 | 92 | 86 | 3.35 |

EXAMPLE 21

Solid Phase Preparation of Cyclic Ureas of General Formula (L)

The aldehyde (XV) (5 ml, 0.3M solution in MeOH), the amine (XXVII) (5 ml, 0.15M solution in MeOH) and the isocyanide (IX) (5 ml, 0.15M solution in MeOH) are added sequentially to the reaction flask and the acid (LI) (generated in situ in the reaction flask by bubbling $CO_2$ through MeOH at 0° C. five minutes), the reaction flask capped and the reaction allowed to warm to room temperature. The solution is then stirred at room temperature for 24 hours under an atmosphere of $CO_2$. The solution is evaporated under high vacuum at high temperature. The crude material is re-dissolved in dichloroethane and PS-TsNHNH$_2$ (5 mmol) is added to scavenge excess aldehyde. The solvent is evaporated under high vacuum. A 10% TFA solution in dichloroethane (10 ml) is added to the crude reaction and the reaction stirred for 24 hours at room temperature. The solution is then evaporated under high vacuum. An immobilized proton scavenger (e.g. MP-carbonate, PS-morpholine) is added (5 equiv.) in dichloroethane and the suspension shaken at room temperature for 3 days. The resin is then filtered and the solvent evaporated at high temperature to yield the desired cyclic product (L). Below is are examples of compounds which are synthesized by this process.

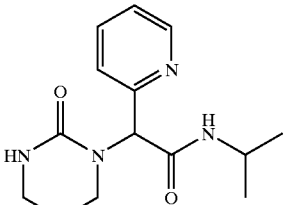
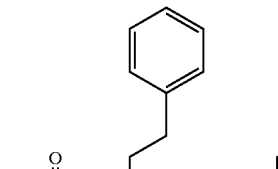
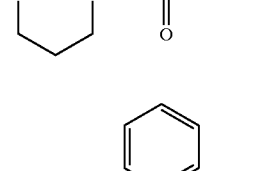
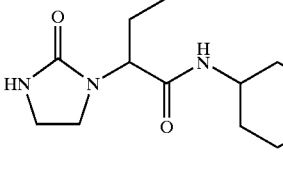
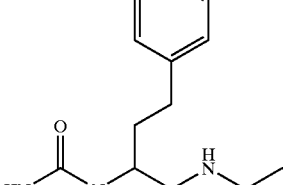
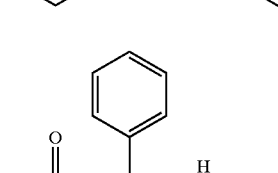
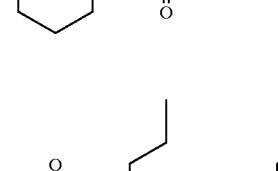
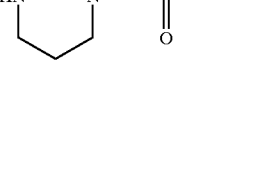

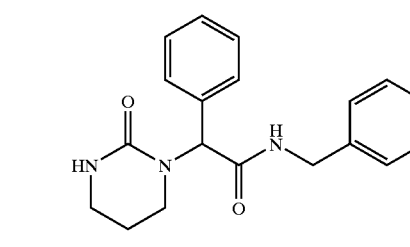
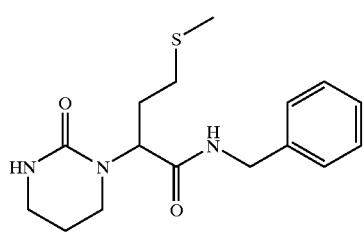
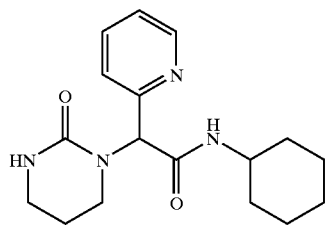
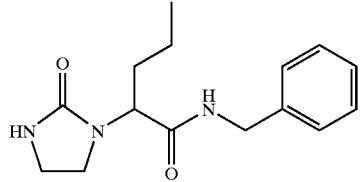
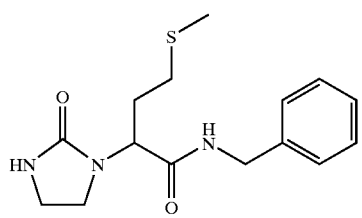
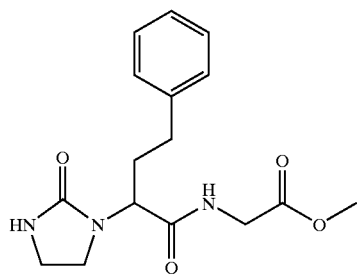
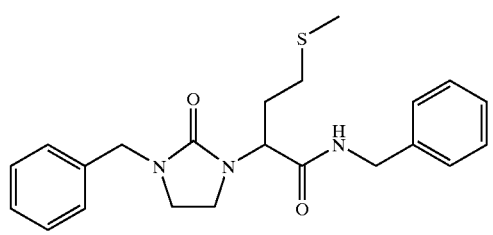
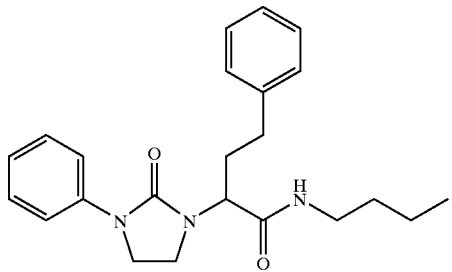
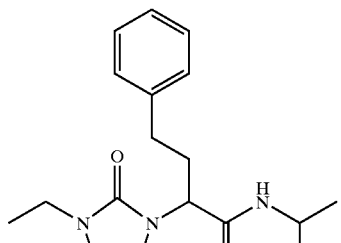
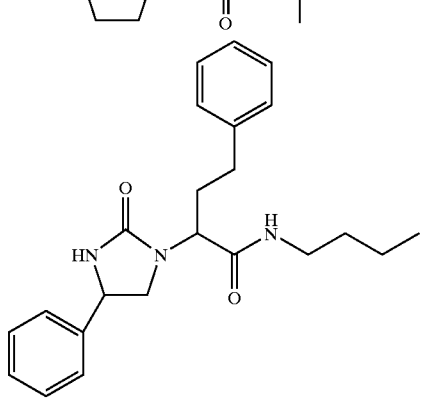
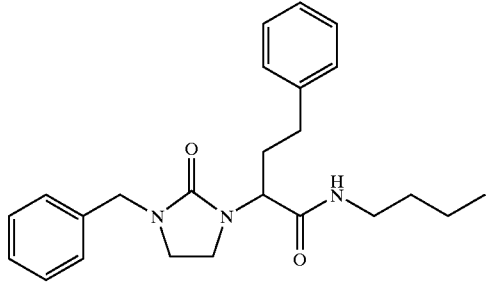
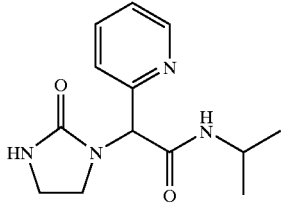
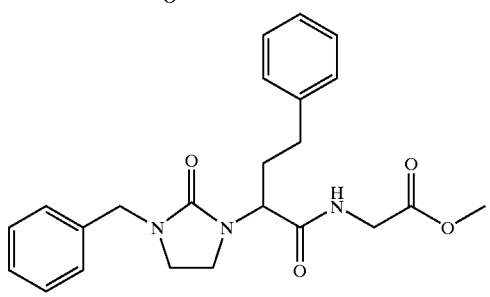

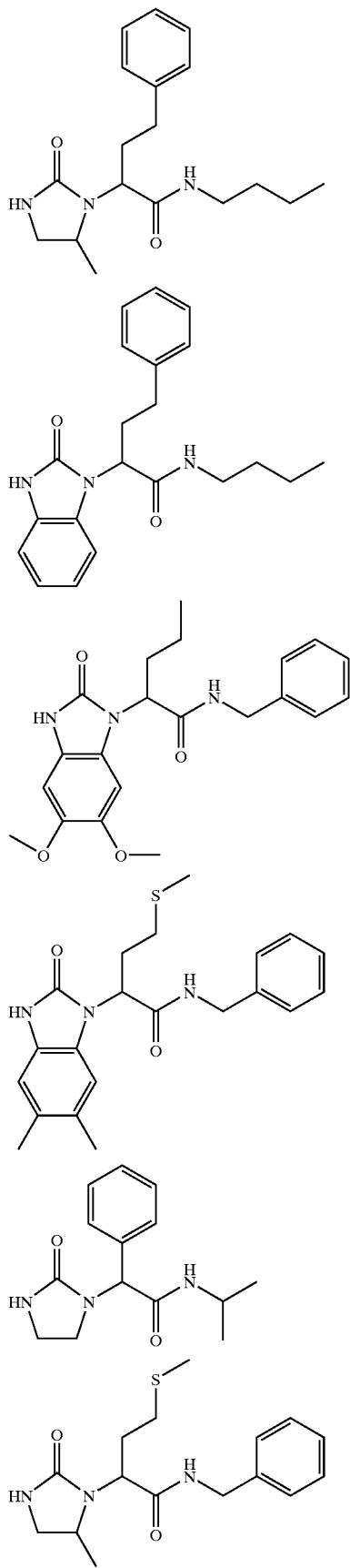
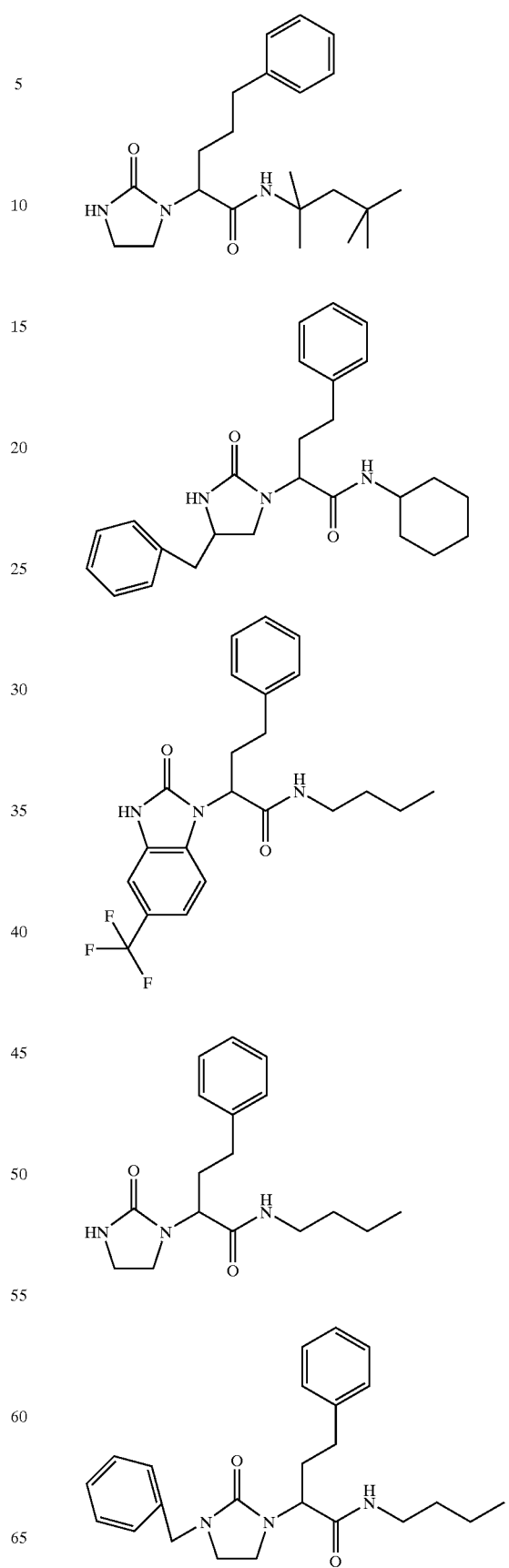

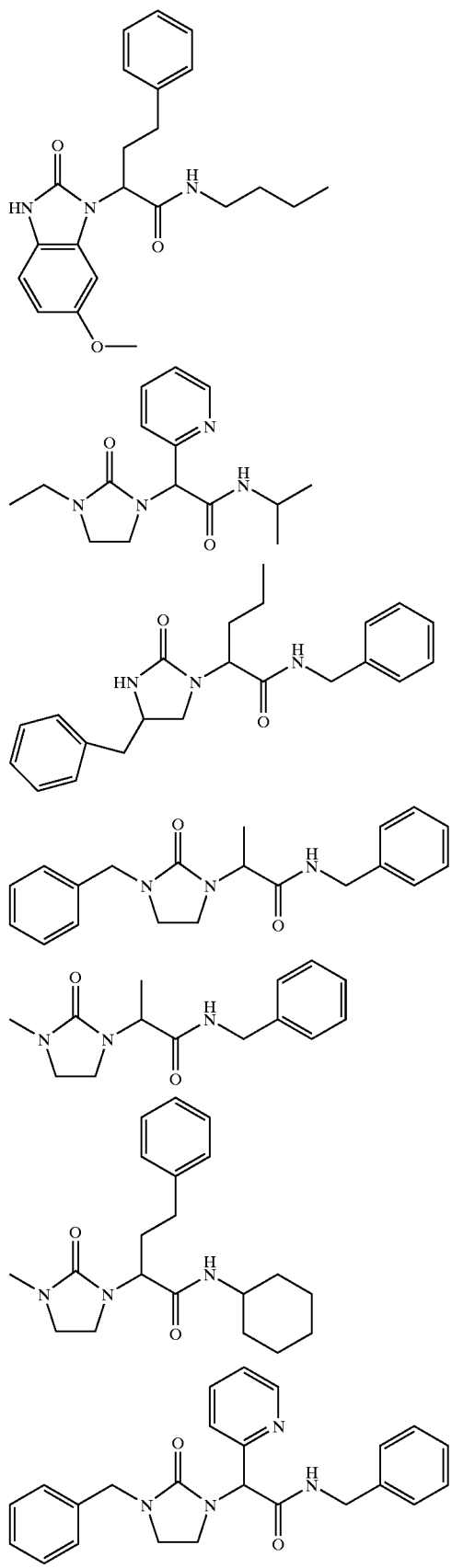

EXAMPLE 22

Solid Phase Preparation of Cyclic Ureas of General Formula (LIII)

The aldehyde (XXXIII)(5 ml, 0.3M solution in MeOH), the amine (XVI)(5 ml, 0.15M solution in MeOH) and the isocyanide (IX) (5 ml, 0.15M solution in MeOH) are added sequentially to the reaction flask and stirred at 0° C. The acid (LI) is generated in the reaction flask by bubbling through the solution for five minutes, the reaction flask capped and the reaction allowed to warm to room temperature. The solution is then stirred at room temperature for 24 hours under an atmosphere of $CO_2$. The solution is evaporated under high vacuum at high temperature to afford the intermediate (LIV). The crude material is re-dissolved in dichloroethane and PS-TsNHNH$_2$ (5 mmol) is added to scavenge excess aldehyde. The solvent is evaporated under high vacuum. A 10% TFA solution in dichloroethane (10 ml) is added to the crude reaction and the reaction stirred for 24 hours at room temperature. The solution is then evaporated under high vacuum. An immobilized proton scavenger (eg MP-carbonate, PS-morpholine) is added (5 equiv.) in dichloroethane and the suspension shaken at room temperature for 3 days. The resin is then filtered and the solvent evaporated at high temperature to yield the desired cyclic product of general formula (LIV). Examples of the products formed by this process are listed below.

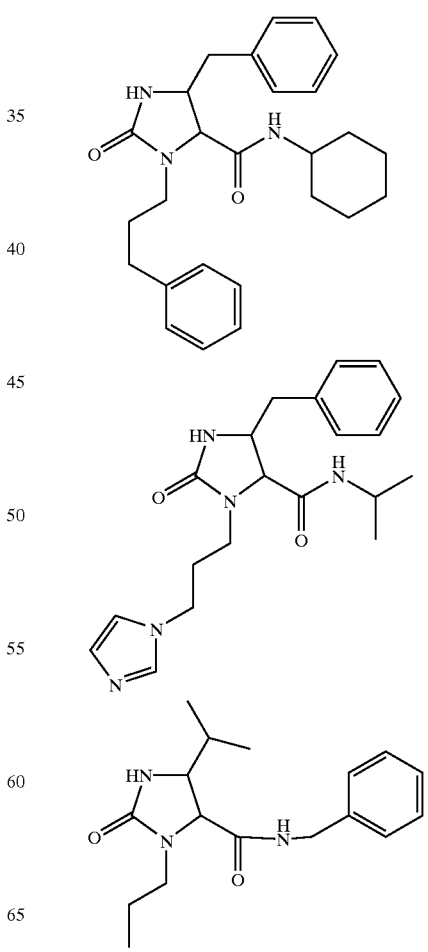

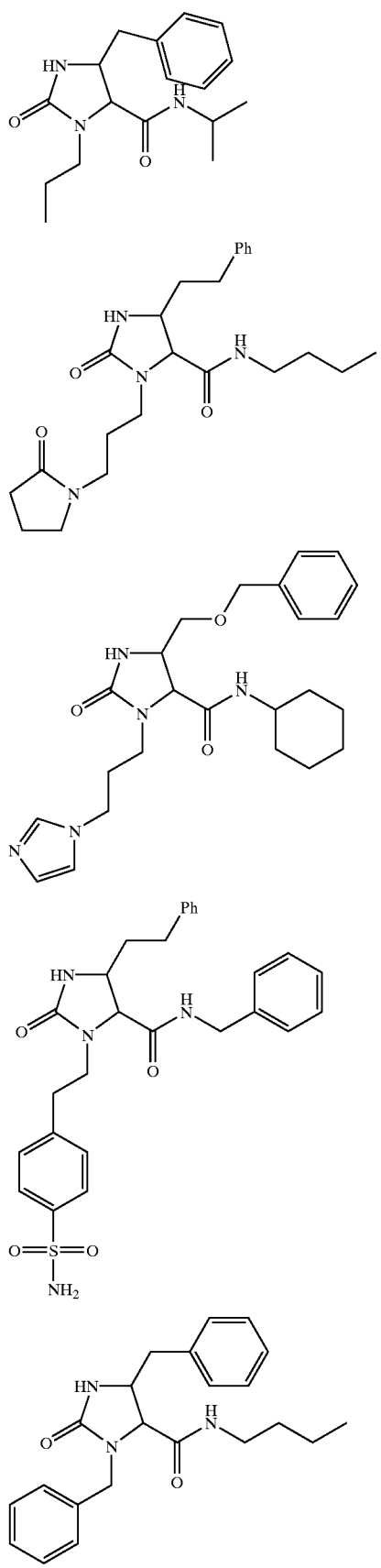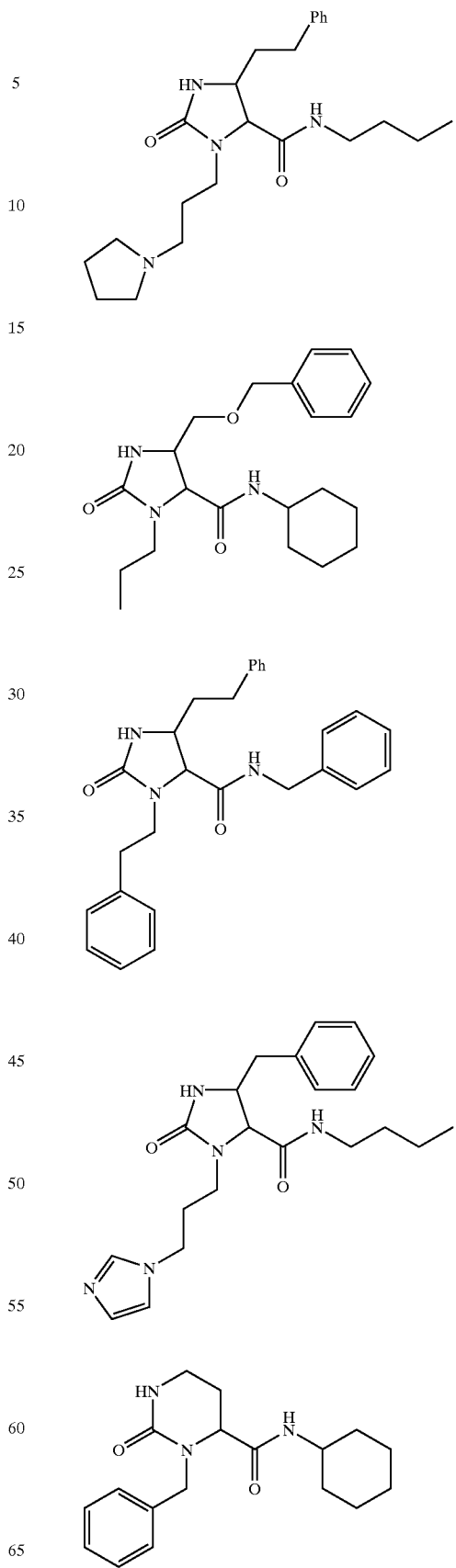

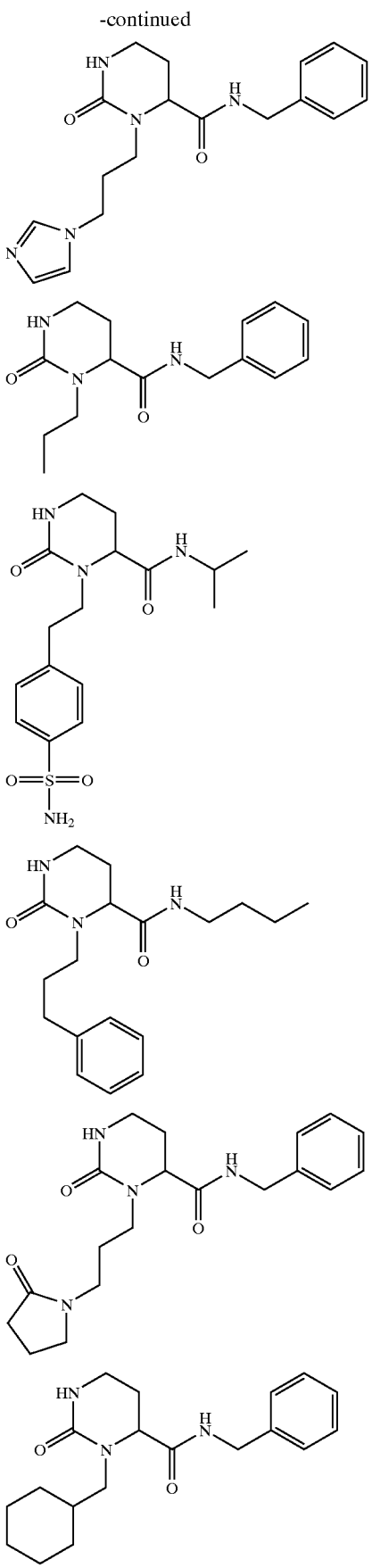

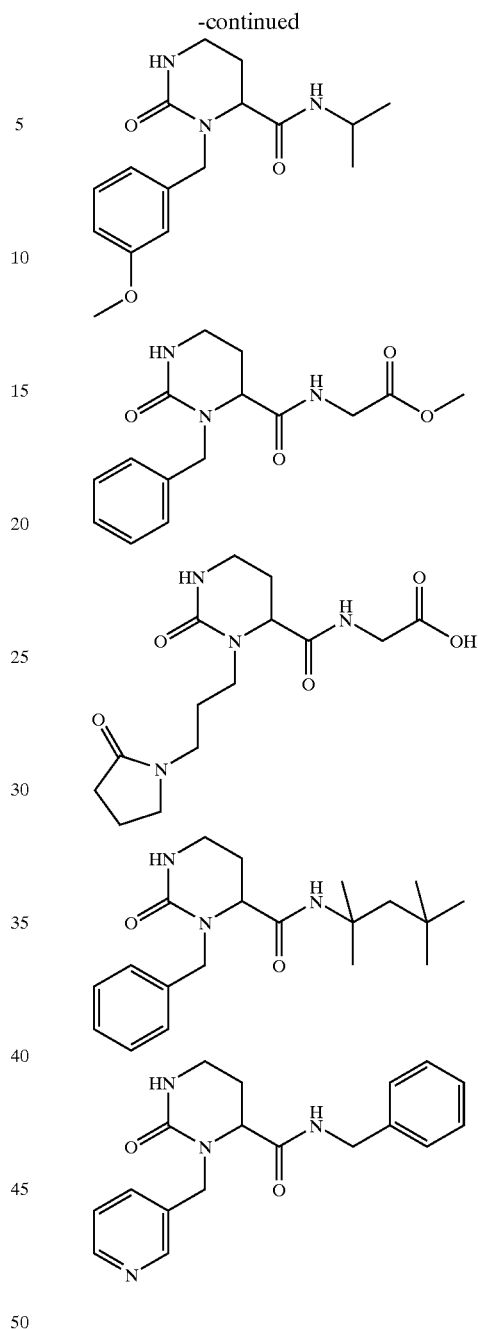

EXAMPLE 23

Solution Phase Preparation of Hydanoins of General Formula (LV)

Phenpropionaldehyde (XV) (5 ml, 0.3M solution in MeOH), para-methoxybenzyl amine (XV (5 ml, 0.15M solution in MeOH) and cyclohexylisocyanide (IX) (5 ml, 0.15M solution in MeOH) a added sequentially to the reaction flask and stirred at 0° C. The acid (LI) is generated in the reacti flask by bubbling through the solution for five minutes, the reaction flask capped and the reacti allowed to warm to room temperature. The solution is then stirred at room temperature for 24 hou under an atmosphere of $CO_2$. The solution is evaporated under high vacuum at high temperature. A 1 solution of KOH in MeOH was added to the crude material and the reaction shaken overnight at roo temperature. The solvent was then evaporated at 65° C. under high vacuum to afford the product 161.

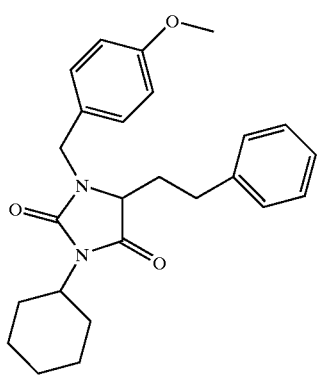
FAB 407 (MH+), 13C (CDCl$_3$) 25.06, 25.86, 25.89, 29.15, 29.38, 29.54, 30.34, 44.38, 55.31, 57.74, 114.32, 126.23, 127.96, 127.96, 128.37, 128.49, 156.72, 159.41, 172.75 Similarly, the following compounds can be made using the above methodology and the appropriate acid (LI), aldehyde (XXXIII) amine (XVI) and isocyanide (IX)
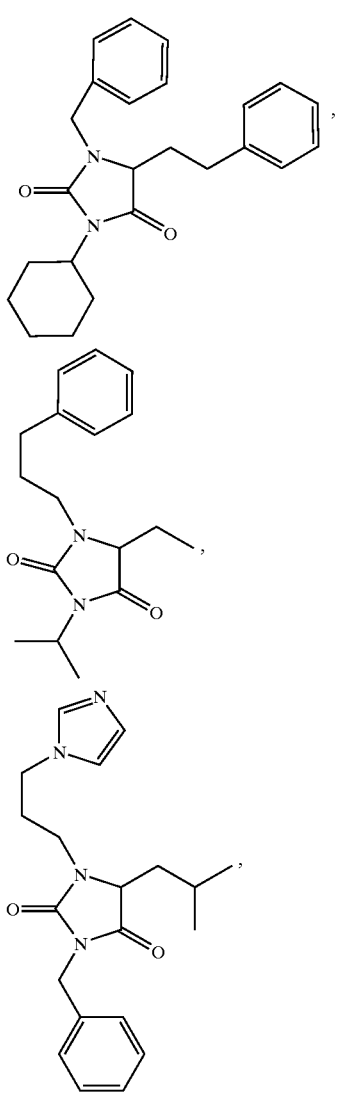
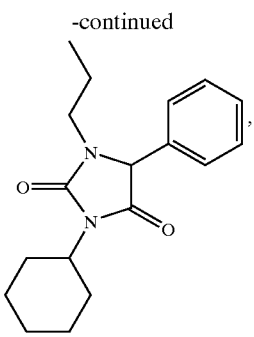
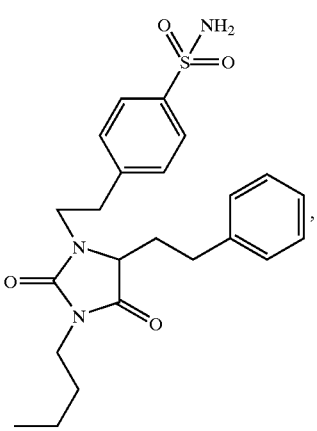
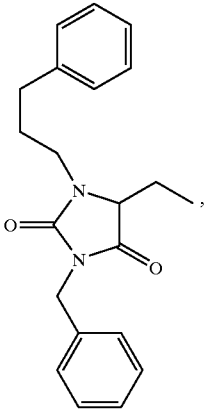
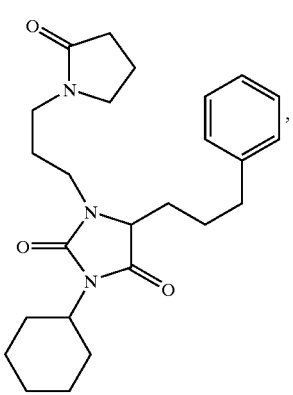

-continued
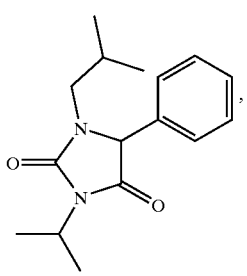
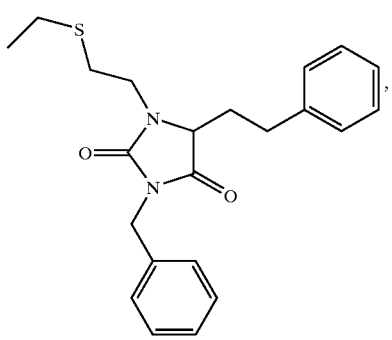
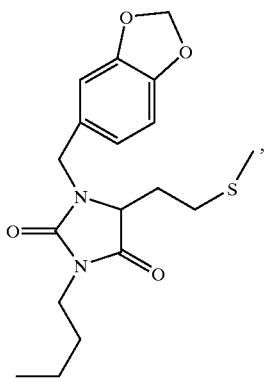
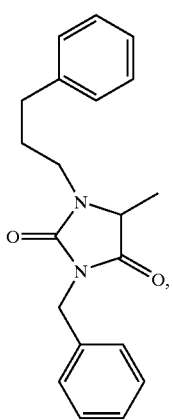
-continued
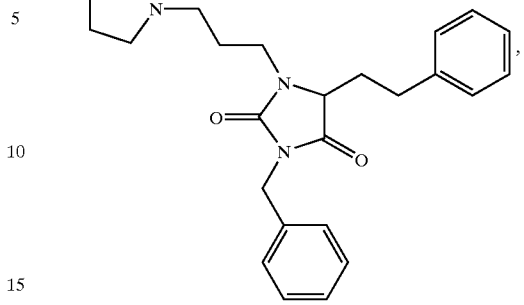
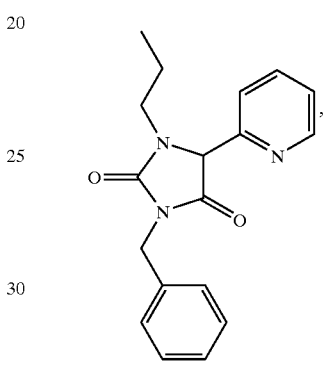
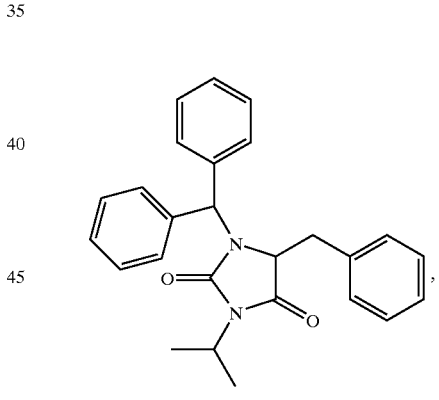
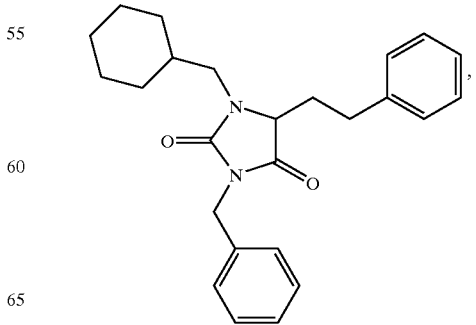

EXAMPLE 24

Solution Phase Preparation of Compounds 162 and 163

100 microliters of 0.1M solutions of the N-BOC anthranilic acid, phenpropionaldehyde, cyclohexylisonitrile and the methyl ester of phenylalanine in MeOH were stirred at room temperature for 2 days. The solvent was evaporated in vacuo at 65 C. to give Ugi intermediate, 162. The product was treated with 400 ul of 10% AcCl in methanol solution (alternatively a 10% TFA solution in 1,2-dichloroethane could be used). The reaction was stirred for 24 hours and the solvent evaporated in vacuo to give the product, 163.

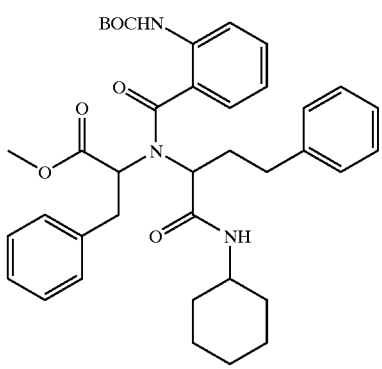

162

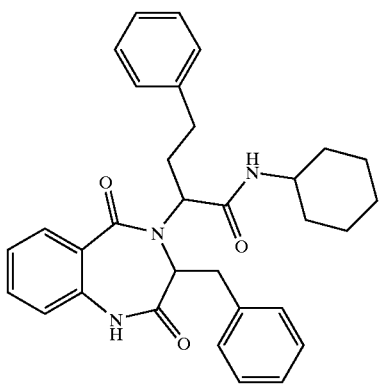

163

EXAMPLE 25

Solution Phase Preparation of Compounds 164, 165, 166 and 167

100 microliters of 0.1M solutions of the N-BOC a-amino aldehyde, diphenylacetic acid, cyclohexylisonitrile and the methyl ester of phenylalanine in MeOH were stirred at room temperature for 2 days. The solvent was evaporated in vacuo at 65 C. to give Ugi intermediates, 164. The product was treated with 400 ul of 10% AcCl in methanol solution (alternatively a 10% TFA solution in 1,2-dichloroethane could be used). The reaction was stirred for 24 hours and the solvent evaporated in vacuo to give the products, 165–167.

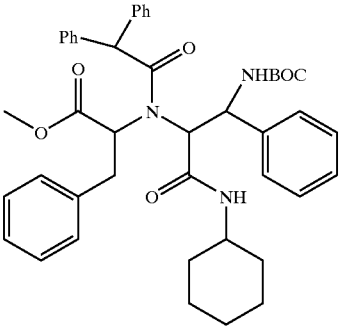

164

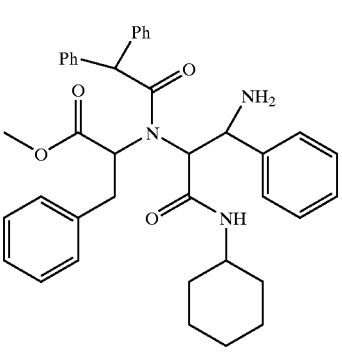

165

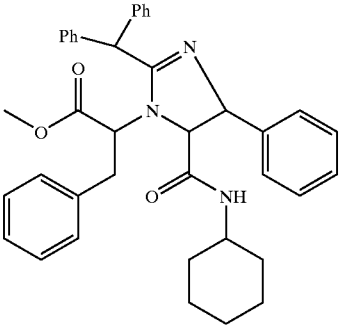

166

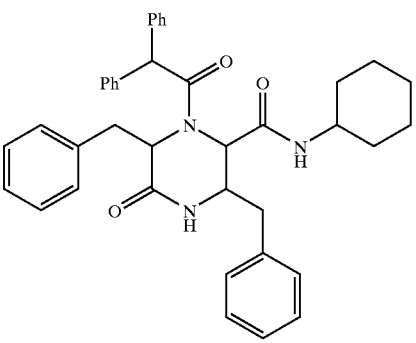

167

The present invention may be embodied in other specific forms without departing from the spirit or essential attributes thereof.

What is claimed is:

1. A method for preparing an N-[(aliphatic or aromatic) carbonyl)]-2-aminoacetamide compound of the formula

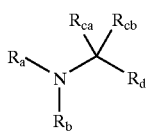 (A)

wherein

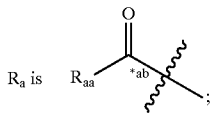

$R_{aa}$ is hydrogen, alkoxy, an optionally substituted aliphatic moiety or an optionally substituted aromatic moiety;

$R_b$ is hydrogen, an optionally substituted aliphatic moiety or an optionally substituted aromatic moiety;

$R_{ca}$ and $R_{cb}$ are independently hydrogen, an optionally substituted aliphatic moiety or an optionally substituted aromatic moiety;

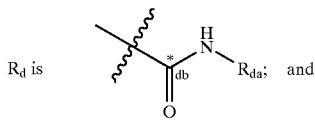

$R_{da}$ is an optionally substituted aliphatic moiety or an optionally substituted aromatic moiety, this method comprising reacting:

(i) a carbonyl compound of formula

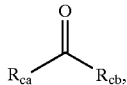 (B)

with (ii) an amine compound of formula

 [C], (iii) an isonitrile compound of formula

 (D), and (iv) an acid compound of formula

 (E)

wherein said carbonyl compound, amine compound, isonitrile compound and acid compound are selected so that either $R_{aa}$ is an aliphatic or aromatic moiety that is substituted with a primary or secondary protected amine that, upon deprotection, can react with the *ab or *db carbon, or with at least one $R_b$, $R_{ca}$ and $R_{cb}$, which is substituted with an activated carboxylic acid, to form a 5–7 membered cyclic ring; or $R_b$ is an aliphatic or aromatic moiety that is substituted with a primary or secondary protected amine that, upon deprotection, can react with the *ab or *db carbon, or with at least one $R_{aa}$, $R_{ca}$ and $R_{cb}$, which is substituted with an activated carboxylic acid, to form a 5–7 membered cyclic ring; or at least one of $R_{ca}$ and $R_{cb}$ is an aliphatic or aromatic moiety that is substituted with a primary or secondary protected amine that, upon deprotection, can react with the *ab or *db carbon, or with at least one $R_{aa}$, $R_b$, $R_{ca}$, $R_{cb}$ and $R_{da}$, which is substituted with an activated carboxylic acid, to form a 5–7 membered cyclic ring; or $R_{da}$ is an aliphatic or aromatic moiety that is substituted with a primary or secondary protected amine that, upon deprotection, can react with at least one of $R_{ca}$ and $R_{cb}$, which is substituted with an activated carboxylic acid, to form a 5–7 membered cyclic ring, provided that, when $R_{aa}$ is substituted with a primary or secondary protected amine that, upon deprotection, can react with $R_b$ (substituted with an activated carboxylic acid), then $R_{aa}$ is a substituted aromatic moiety.

2. The method according to claim 1 wherein $R_{aa}$ is substituted with a primary or secondary protected amine that, upon deprotection, can react with the *db carbon, or with at least one of $R_{ca}$ or $F_{cb}$ which is substituted with an activated carboxylic acid, to form a 5–7 membered cyclic ring.

3. The method according to claim 1 wherein $R_{aa}$ is substituted with a primary or secondary protected amine that upon deprotection can react with $R_b$, which is substituted with an activated carboxylic acid, to form a 5–7 membered cyclic ring.

4. The method according to claim 1 wherein $R_b$ is substituted with a primary or secondary protected amine that, upon deprotection, can react with the *db carbon, or with at least one of $R_{ca}$ or $R_{cb}$, which is substituted with an activated carboxylic acid, to form a 5–7 membered cyclic ring.

5. The method according to claim 1 wherein at least one of $R_{ca}$ and $R_{cb}$ is substituted with a primary or secondary protected amine that, upon deprotection, can react with the *ab or *db carbon, or with $R_b$, which is substituted with an activated carboxylic acid, to form a 5–7 membered cyclic ring.

6. The method according to claim 1 further comprising deprotecting and cyclizing the N-[(aliphatic or aromatic) carbonyl)]-2-aminoacetamide compound of formula (A) to afford a cyclized compound having a formula selected from the group consisting of:

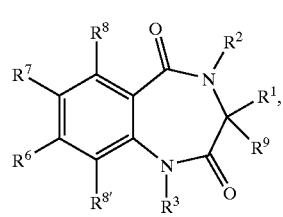 (I)

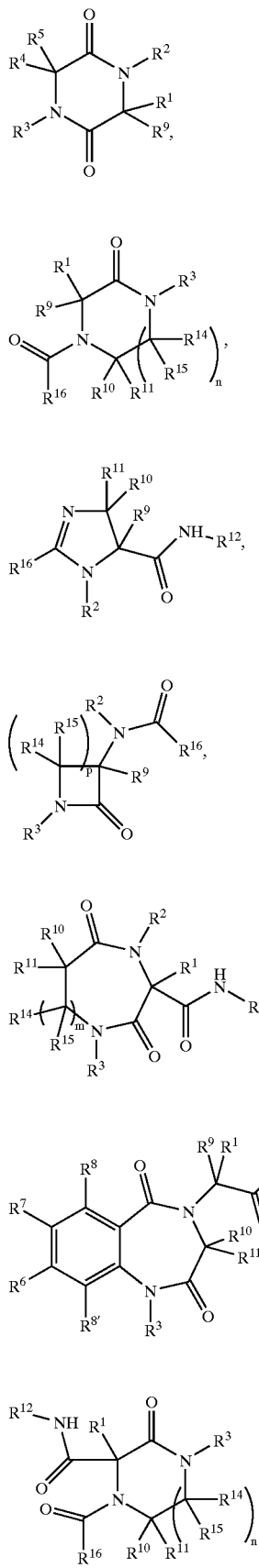

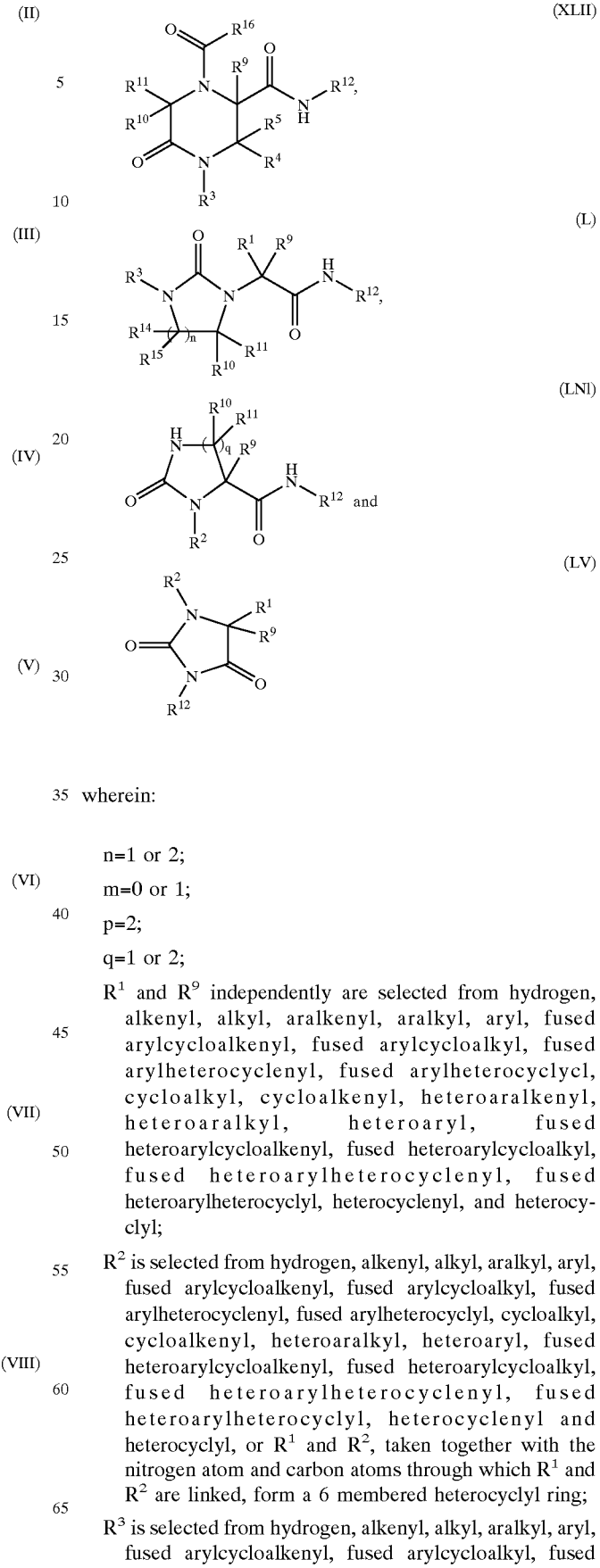

wherein:

n=1 or 2;

m=0 or 1;

p=2;

q=1 or 2;

$R^1$ and $R^9$ independently are selected from hydrogen, alkenyl, alkyl, aralkenyl, aralkyl, aryl, fused arylcycloalkenyl, fused arylcycloalkyl, fused arylheterocyclenyl, fused arylheterocyclyl, cycloalkyl, cycloalkenyl, heteroaralkenyl, heteroaralkyl, heteroaryl, fused heteroarylcycloalkenyl, fused heteroarylcycloalkyl, fused heteroarylheterocyclenyl, fused heteroarylheterocyclyl, heterocyclenyl, and heterocyclyl;

$R^2$ is selected from hydrogen, alkenyl, alkyl, aralkyl, aryl, fused arylcycloalkenyl, fused arylcycloalkyl, fused arylheterocyclenyl, fused arylheterocyclyl, cycloalkyl, cycloalkenyl, heteroaralkyl, heteroaryl, fused heteroarylcycloalkenyl, fused heteroarylcycloalkyl, fused heteroarylheterocyclenyl, fused heteroarylheterocyclyl, heterocyclenyl and heterocyclyl, or $R^1$ and $R^2$, taken together with the nitrogen atom and carbon atoms through which $R^1$ and $R^2$ are linked, form a 6 membered heterocyclyl ring;

$R^3$ is selected from hydrogen, alkenyl, alkyl, aralkyl, aryl, fused arylcycloalkenyl, fused arylcycloalkyl, fused arylheterocyclenyl, fused arylheterocyclyl, cycloalkyl, cycloalkenyl, heteroaralkyl, heteroaryl, fused heteroarylcycloalkenyl, fused heteroarylcycloalkyl, fused heteroarylheterocyclenyl, fused heteroarylheterocyclyl, heterocyclenyl and heterocyclyl;

$R^4$ and $R^5$ independently are selected from hydrogen, alkenyl, alkyl, aryl, alkynyl, aralkenyl, aralkynyl, fused arylcycloalkenyl, fused arylcycloalkyl, fused arylheterocyclenyl, fused arylheterocyclyl, heteroaralkenyl, heteroaralkynyl, fused heteroarylcycloalkenyl, fused heteroarylcycloalkyl, fused heteroarylheterocyclenyl, fused heteroarylheterocyclyl, heteroaryl, aralkyl, heteroaralkyl, cycloalkyl, cycloalkenyl, heterocyclyl and heterocyclenyl, or $R^4$ and $R^5$, taken together with the carbon atom through which $R^4$ and $R^5$ are linked, form a 3 to 7 membered cycloalkyl or cycloalkenyl ring;

$R^6$, $R^7$, $R^8$ and $R^{8'}$ independently are selected from hydrogen, alkenyl, alkenyloxy, alkoxy, alkyl, aryl, alkylsulfinylcarbamoyl, alkynyl, alkynyloxy, aralkenyl, aralkylsulfonyl, aralkynyl, fused arylcycloalkenyl, fused arylcycloalkyl, fused arylheterocyclenyl, fused arylheterocyclyl, aryloxycarbonyl, cycloalkyloxy, heteroaralkenyl, heteroaralkyloxy, heteroaralkynyl, heteroaroyl, fused heteroarylcycloalkenyl, fused heteroarylcycloalkyl, fused heteroarylheterocyclenyl, fused heteroarylheterocyclyl, heteroarylsulphonylcarbamoyl, heterocyclyloxy, heteroaryl, aralkyl, heteroaralkyl, hydroxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, aryldiazo, heteroaryldiazo, amidino, $Y^1Y^2N-$, $Y^1Y^2NCO-$ and $Y^1Y^2NSO_2-$, wherein $Y^1$ and $Y^2$ are independently hydrogen, alkyl, aryl, aralkyl or heteroaralkyl, or, where the substituent is $Y^1Y^2N-$, then one of $Y^1$ and $Y^2$ is acyl or aroyl and the other of $Y^1$ and $Y^2$ is as defined previously, or, where the substituent is $Y^1Y^2NCO-$ or $Y^1Y^2NSO_2-$, $Y^1$ and $Y^2$, taken together with the N atom through which $Y^1$ and $Y^2$ are linked, form a 4 to 7 membered heterocyclyl or heterocyclenyl ring, or $R^3$ and $R^{8'}$, taken together with the nitrogen atom and carbon atoms through which $R^3$ and $R^{8'}$ are linked, form a 5 to 7 membered heterocyclyl or heterocyclenyl ring, or two adjacent substituents selected from the substituents $R^6$, $R^7$, $R^{8'}$ and $R^8$, taken together with the aryl carbon atoms through which the two adjacent substituents are linked, form a 5 to 7 membered cycloalkyl or a cycloalkenyl, heterocyclyl or heterocyclenyl, or 6 membered aryl or 5 or 6 membered heteroaryl ring;

$R^{14}$, $R^{15}$, $R^{10}$ and $R^{11}$ independently are selected from hydrogen, alkenyl, alkyl, aryl, alkynyl, aralkenyl, aralkynyl, fused arylcycloalkenyl, fused arylcycloalkyl, fused arylheterocyclenyl, fused arylheterocyclyl, heteroaralkenyl, heteroaralkynyl, fused heteroarylcycloalkenyl, fused heteroarylcycloalkyl, fused heteroarylheterocyclenyl, fused heteroarylheterocyclyl, heteroarylsulphonylcarbamoyl, heteroaryl,, aralkyl, heteroaralkyl, cycloalkyl, cycloalkenyl, heterocyclyl, heterocyclenyl, or, when n=1, and $R^{11}$ and $R^{14}$ are absent, $R^{10}$ and $R^{15}$, taken together with the adjacent carbon atoms through which they are linked, form a 6 membered aryl or 5 or 6 membered heteroaryl ring;

or, when n=1, and $R^{11}$ and $R^{14}$ are present, $R^{10}$ and $R^{15}$, taken together with the adjacent carbon atoms through which they are linked, form a 5 to 7 membered cycloalkyl or a cycloalkenyl, heterocyclyl or heterocyclenyl ring;

or, when n=2, and adjacent $R^{11}$ and $R^{14}$ are absent, $R^{10}$ and adjacent $R^{15}$, taken together with the adjacent carbon atoms through which they are linked, form a 6 membered aryl or 5 to 6 membered heteroaryl ring;

or when n=2, and $R^{11}$ and $R^{14}$ are present, $R^{10}$ and adjacent $R^{15}$, taken together with the adjacent carbon atoms through which they are linked, form a 5 to 7 membered cycloalkyl or a cycloalkenyl, heterocyclyl or heterocyclenyl ring;

or when n or p=2, and the adjacent $R^{14}$ and $R^{14}$ are absent, the adjacent $R^{15}$ and $R^{15}$, taken together with the adjacent carbon atoms through which they are linked, form a 6 membered aryl or 5 or 6 membered heteroaryl ring;

or when n or p=2, and the adjacent $R^{14}$ and $R^{14}$ are present, adjacent $R^{15}$ and $R^{15}$, taken together with the adjacent carbon atoms through which they are linked, form a 5 to 7 membered cycloalkyl or a cycloalkenyl, heterocyclyl or heterocyclenyl ring;

or, when m=1, and $R^{11}$ and $R^{14}$ are absent, $R^{10}$ and $R^{15}$, taken together with the adjacent carbon atoms through which they are linked, form a 6 membered aryl or 5 or 6 membered heteroaryl ring;

or, when m=1, and $R^{11}$ and $R^{14}$ are present, $R^{10}$ and $R^{15}$, taken together with the adjacent carbon atoms through which they are linked, form a 5 to 7 membered cycloalkyl or a cycloalkenyl, heterocyclyl or heterocyclenyl ring;

$R^{12}$ is selected from alkenyl, alkyl, aralkyl, aryl, fused arylcycloalkenyl, fused arylcycloalkyl, fused arylheterocyclenyl, fused arylheterocyclyl, cycloalkyl, cycloalkenyl, heteroaralkyl, heteroaryl, fused heteroarylcycloalkenyl, fused heteroarylcycloalkyl, fused heteroarylheterocyclenyl, fused heteroarylheterocyclyl, heterocyclenyl and heterocyclyl; and $R^{16}$ is selected from hydrogen, alkenyl, alkyl, aralkyl, aryl, fused arylcycloalkenyl, fused arylcycloalkyl, fused arylheterocyclenyl, heteroaralkenyl, fused arylheterocyclyl, cycloalkyl, cycloalkenyl, heteroaralkyl, heteroaryl, fused heteroarylcycloalkenyl, fused heteroarylcycloalkyl, fused heteroarylheterocyclenyl, fused heteroarylheterocyclyl, heterocyclenyl and heterocyclyl, or $R^9$ and $R^{16}$, together with the carbon atoms and nitrogen atom though which they are linked, form a 5–8 membered heterocyclyl ring.

7. The method according to claim 6, wherein the acid compound is of formula

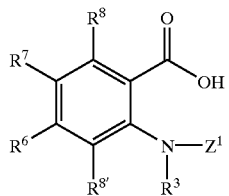

wherein $Z^1$ is a suitable amine protecting group;

the carbonyl compound is of formula

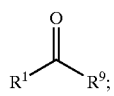
(XV)

the isonitrile compound is of formula

(IX);

and the amine compound is of formula

(XVI).

8. The method according to claim 7 wherein the N-[(aliphatic or aromatic)carbonyl)]-2-aminoacetamide compound is of the formula

XVII

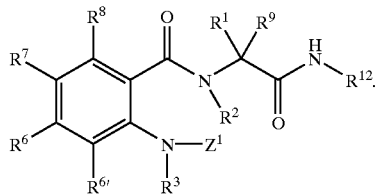

9. The method according to claim 6 wherein the cyclized product is (I)

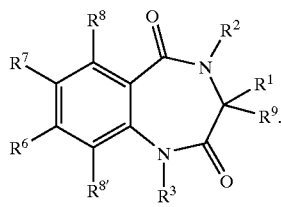

10. The method according to claim 6, wherein the acid compound is of formula

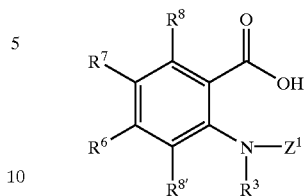

wherein $Z^1$ is a suitable amine protecting group;

the carbonyl compound is of formula (XV)

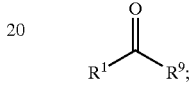

the isonitrile compound is selected from the group of formulae (IXa)

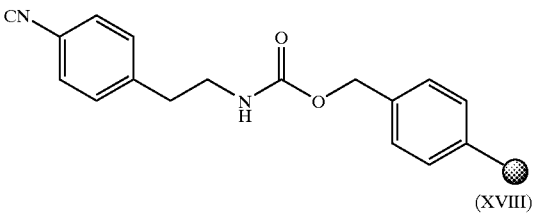

and

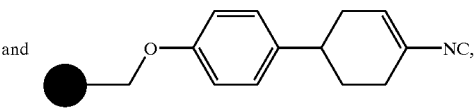
(XVIII)

solid support resin; and the amine compound is of formula

(XVI).

11. The method according to claim 6 wherein the N-[(aliphatic or aromatic)carbonyl)]-2-aminoacetamide compound is of the formula (XXI)

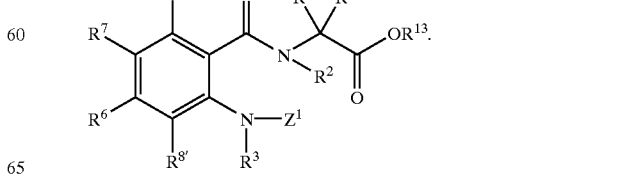

12. The method according to claim 11 wherein the cyclized compound is of the formula

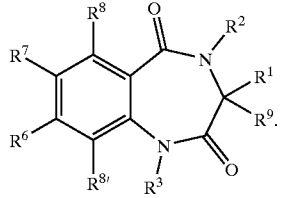 (I)

13. The method according to claim 6, wherein the acid compound is of formula

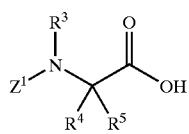 (XXII)

wherein $Z^1$ is a suitable amine protecting group;
the carbonyl compound is of formula

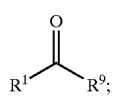 (XV)

the isonitrile compound is of formula $R^{12}$—NC (IX);

and the amine compound is of formula $R^2$—$NH_2$ (XVI).

14. The method as claimed in claim 13 wherein the N-[(aliphatic or aromatic)carbonyl)]-2-aminoacetamide compound is of the formula

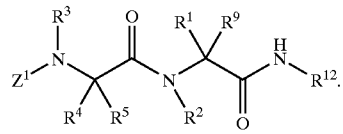 (XXIII)

15. The method according to claim 14, wherein the cyclized compound is of the formula

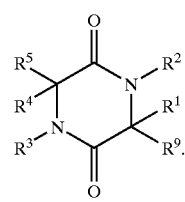 (II)

16. The method according to claim 6, wherein the acid compound is of formula

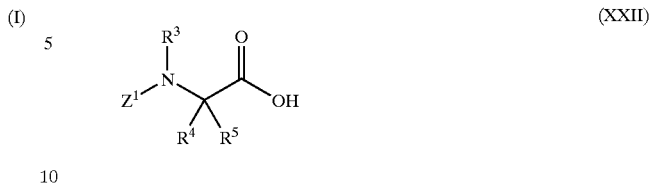 (XXII)

wherein $Z^1$ is a suitable amine protecting group;
the carbonyl compound is of formula

 (XV)

the isonitrile compound is of formula

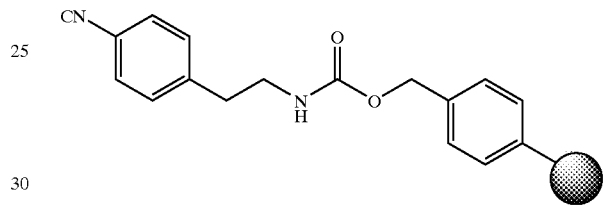 (IXa)

and the amine compound is of formula $R^2$—$NH_2$ (XVI).

17. The method as claimed in claim 16 wherein the N-[(aliphatic or aromatic)carbonyl)]-2-aminoacetamide compound is of the formula

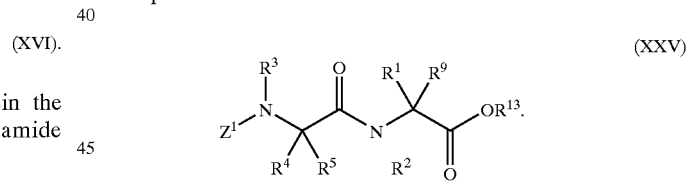 (XXV)

18. The method according to claim 6, wherein the acid compound is of formula

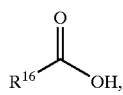 (XXVI)

the carbonyl compound is of formula

 (XV)

the isonitrile compound is of formula $R^{12}$—NC (IX)

and the amine compound is of formula

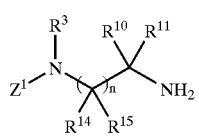 (XXVII)

wherein $Z^1$ is a suitable amine protecting group.

19. The method as claimed in claim 18 wherein the N-[(aliphatic or aromatic)carbonyl)]-2-aminoacetamide compound is of the formula

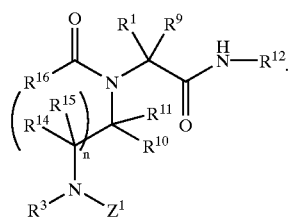 (XXVIII)

20. The method according to claim 19, wherein the cyclized compound is of the formula

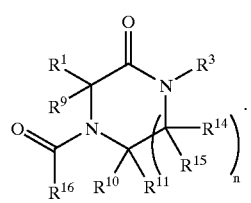 (III)

21. The method according to claim 6, wherein the acid compound is of formula

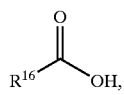 (XXVI)

the carbonyl compound is of formula

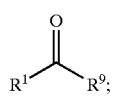 (XV)

the isonitrile compound is of formula

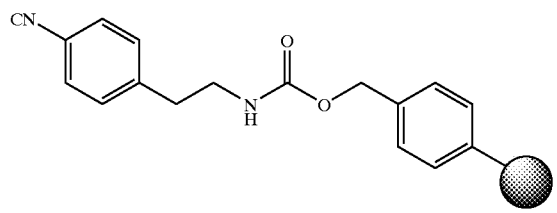 (IXa)

and the amine compound is of formula

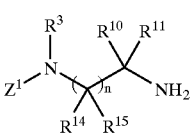 (XXVII)

wherein $Z^1$ is a suitable amine protecting group.

22. The method according to claim 21 wherein the N-[(aliphatic or aromatic)carbonyl)]-2-aminoacetamide compound is of the formula

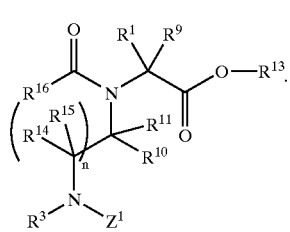 (XXXI)

23. The method according to claim 6, wherein the acid compound is of formula

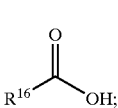 (XXVI)

the carbonyl compound is of the formula

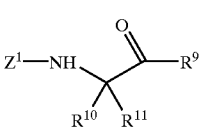 (XXXIII)

wherein $Z^1$ is a suitable amine protecting group;

the isonitrile compound is of the formula $R^{12}$—NC   (IX)

and the amine compound is of the formula $R^2$—NH$_2$   (XVI).

24. The method according to claim 23 wherein the N-[(aliphatic or aromatic)carbonyl)]-2-aminoacetamide compound is of the formula

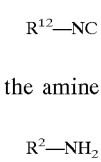 (XXXIV)

25. The method according to claim 24, wherein the cyclized compound is of the formula

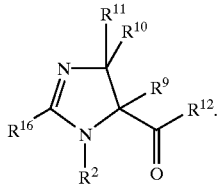

(IV)

26. The method according to claim 6, wherein the acid compound is of formula

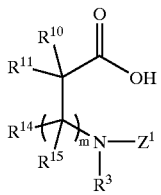

(XIV)

wherein $Z^1$ is a suitable amine protecting group;

the carbonyl compound is of formula

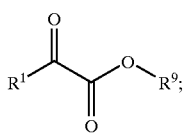

(XXXVII)

the isonitrile compound is of formula $R^{12}$—NC    (IX);

and the amine compound is of formula $R^2$—$NH_2$    (XVI).

27. The method according to claim 26 wherein the N-[(aliphatic or aromatic)carbonyl)]-2-aminoacetamide compound is of the formula

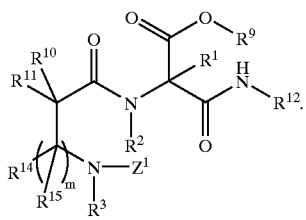

(XXXVIII)

28. The method according to claim 27, wherein the cyclized compound is of the formula

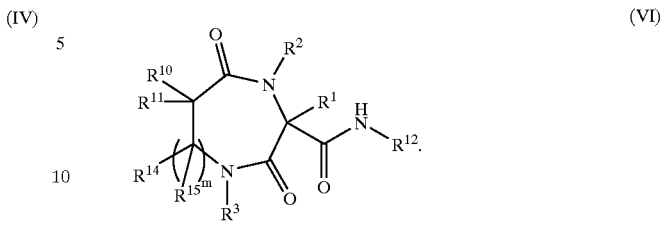

(VI)

29. The method according to claim 6, wherein the acid compound is of formula

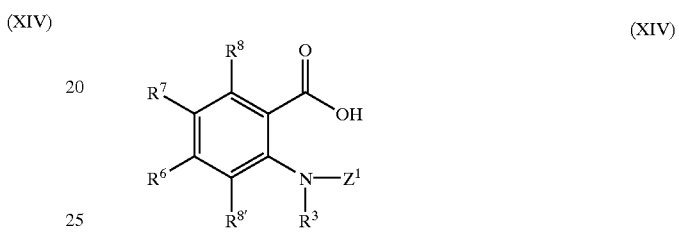

(XIV)

wherein $Z^1$ is a suitable amine protecting group;

the carbonyl compound is of formula

(XV)

the isonitrile compound is of formula $R^{12}$—NC    (IX);

and the amine compound is of formula $R^2$—$NH_2$    (XVI).

30. The method as claimed in claim 29 wherein the N-[(aliphatic or aromatic)carbonyl)]-2-aminoacetamide compound is of the formula

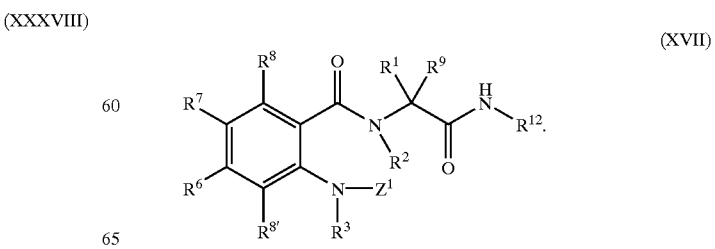

(XVII)

31. The method according to claim 6, wherein the acid compound is of formula

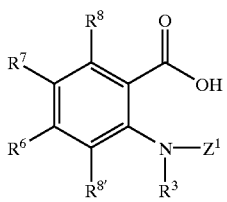 (XIV)

wherein $Z^1$ is a suitable amine protecting group; the carbonyl compound is of formula

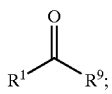 (XV)

the isonitrile compound is selected from

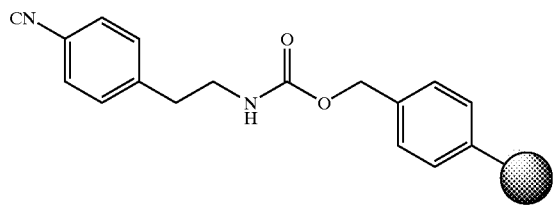

and

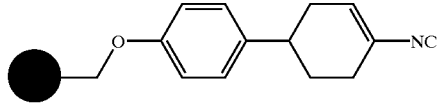 (XVIII)

wherein  is a solid support resin; and
the amine compound is of formula $R^2$—$NH_2$  (XVI).

32. The method according to claim 31 wherein the N-[(aliphatic or aromatic)carbonyl)]-2-aminoacetamide compound is of the formula

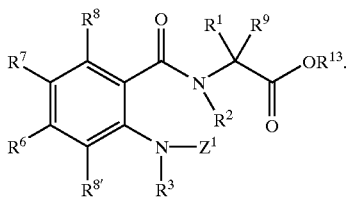 (XXI)

33. The method according to claim 6, wherein the acid compound is of formula

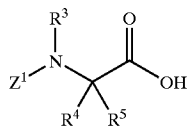 (XXII)

wherein $Z^1$ is a suitable amine protecting group;

the carbonyl compound is of formula;

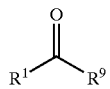 (XV)

the isonitrile compound is selected from the group of formulae

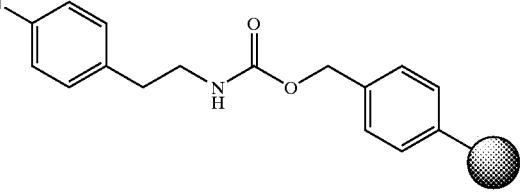 (IXa)

and

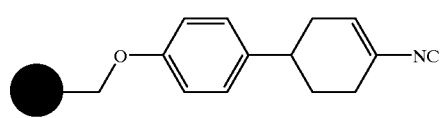 (XVIII)

wherein  is a solid support resin; and the amine compound is of formula $R^2$—$NH_2$  (XVI).

34. The method as claimed in claim 33 wherein the N-[(aliphatic or aromatic)carbonyl)]-2-aminoacetamide compound is of the formula

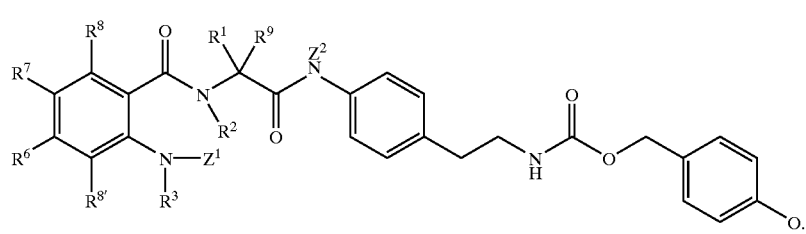

(XX)

35. The method according to claim 6, wherein the acid compound is of formula

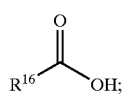

(XXVI)

the carbonyl compound is of formula

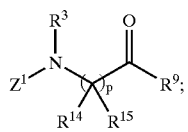

(XXXV)

wherein $Z^1$ is a suitable amine protecting group;

the isonitrile compound is selected from (IXa)

(XVIII)

and the amine compound is of formula $R^2$—$NH_2$ (XVI).

36. The method according to claim 35 wherein the N-[(aliphatic or aromatic)carbonyl)]-2-aminoacetamide compound is selected from compounds of formulae

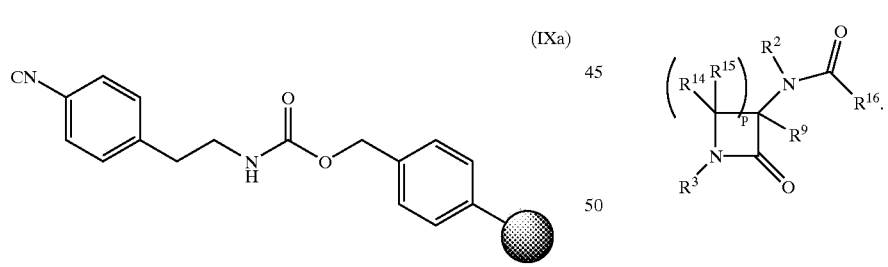

and

37. The method according to claim 36 wherein the cyclized product is

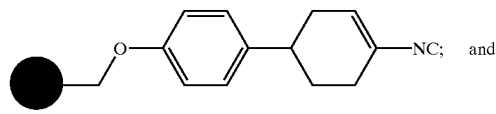

(V)

38. The method according to claim 6, wherein the acid compound is of formula

(XIV)

the carbonyl compound is of formula

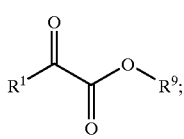   (XXXVII)

the isonitrile compound is of formula $R^{12}$—NC   (IX);

and
the amine compound is of formula $R^2$—$NH_2$   (XVI).

39. The method according to claim 38 wherein the N-[(aliphatic or aromatic)carbonyl)]-2-aminoacetamide compound is of the formula

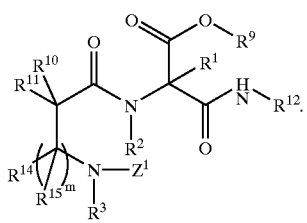   (XXXVIII)

40. The method according to claim 6, wherein the acid compound is of formula

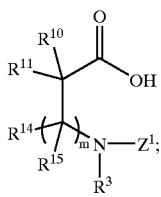   (XIV)

the carbonyl compound is of formula

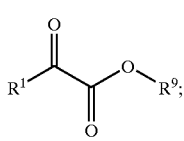   (XXXVII)

the isonitrile compound is of formula

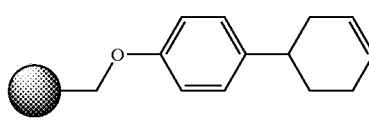   (XVIII)

the amine compound is of formula $R^2$—$NH_2$   (XVI).

41. The method according to claim 40 wherein the N-[(aliphatic or aromatic)carbonyl)]-2-aminoacetamide compound is of the formula

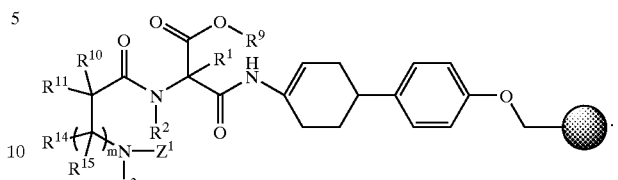

42. The method according to claim 6, wherein the acid compound is of formula

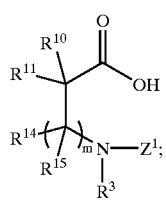   (XIV)

the carbonyl compound is of formula (XV)

$R^1$ $R^9$;

the isonitrile compound is of formula $R^{12}$—NC   (IX);

and
the amine compound is of formula (XXXIX)

43. The method according to claim 42 wherein the N-[(aliphatic or aromatic)carbonyl)]-2-aminoacetamide compound is of the formula (XL)

44. The method according to claim 43 wherein cyclized product is

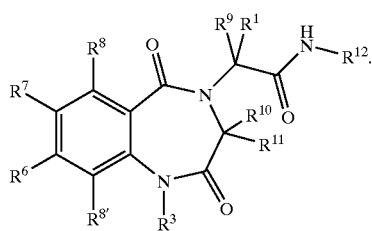
(VII)

45. The method according to claim 6, wherein the acid compound is of formula

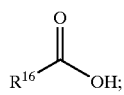
(XXVI)

the carbonyl compound is of formula

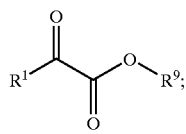
(XXXVII)

the isonitrile compound is of formula $R^{12}$—NC    (IX);

and the amine compound is of formula

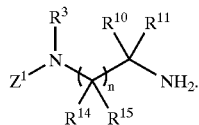
(XXVII)

46. The method according to claim 45 wherein the N-[(aliphatic or aromatic)carbonyl)]-2-aminoacetamide compound is of the formula

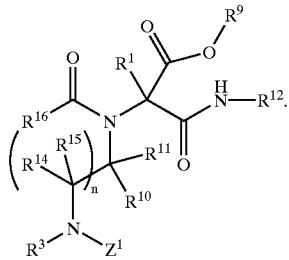
(XLI)

47. The method according to claim 46 wherein cyclized product is

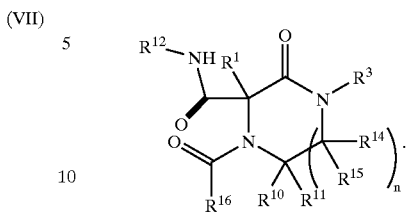
(VIII)

48. The method according to claim 6, wherein the acid compound is of formula

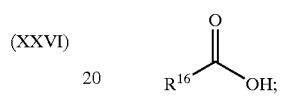
(XXVI)

the carbonyl compound is of formula

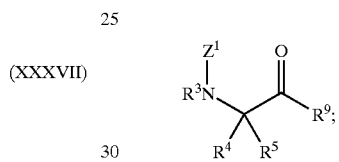
(XLIII)

the isonitrile compound is of formula $R^{12}$—NC    (IX);

and the amine compound is of formula

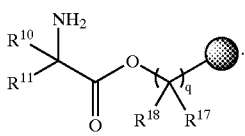
(XXXIX)

49. The method according to claim 48 wherein the N-[(aliphatic or aromatic)carbonyl)]-2-aminoacetamide compound is of the formula

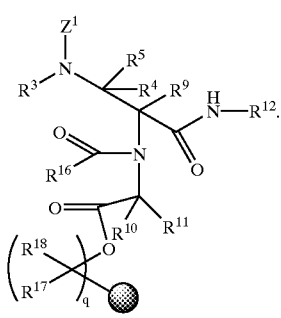
(XLIX)

50. The method according to claim 49 wherein the cyclized product is of formula
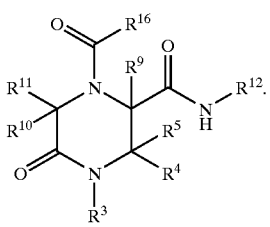
(XLII)
51. The method according to claim 6 wherein the cyclized product is selected from the group of formulae consisting of:
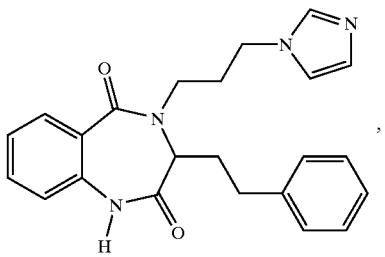
,
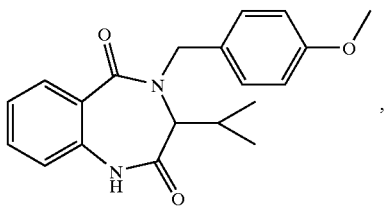
,
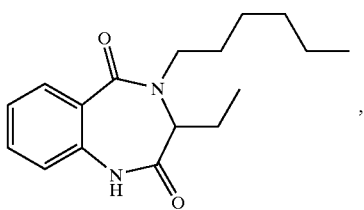
,
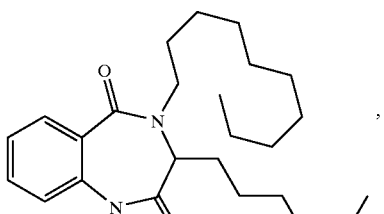
,
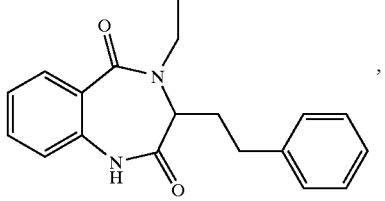
,
-continued
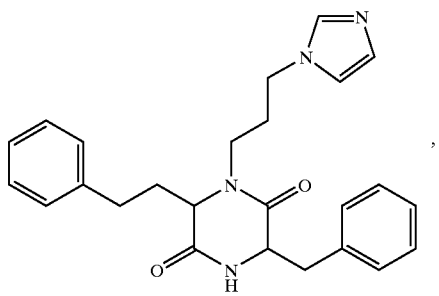
,
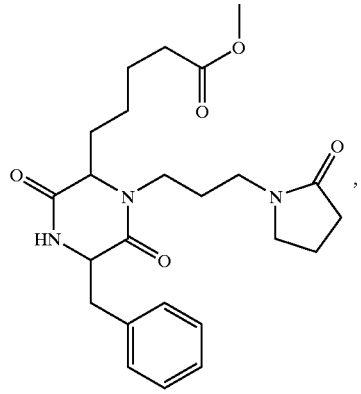
,
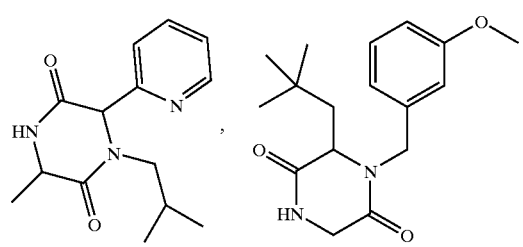
,
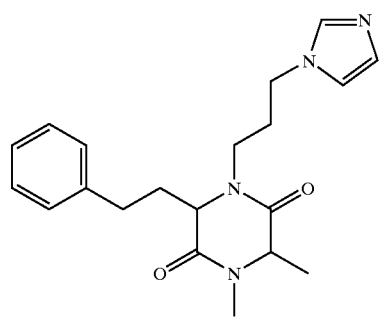
,
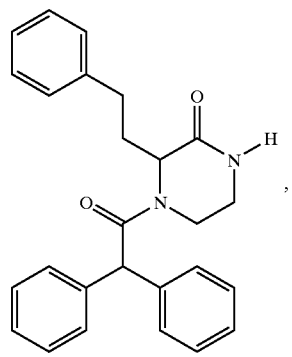
,

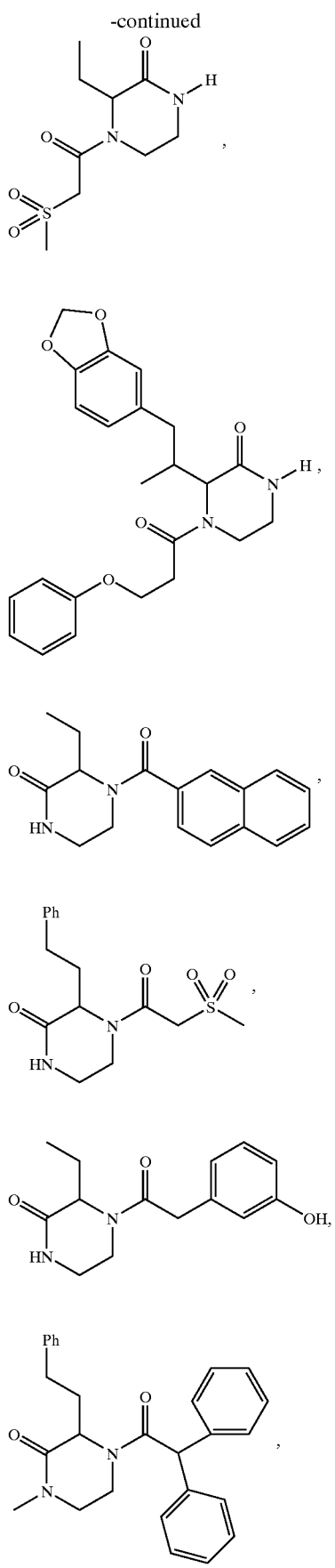

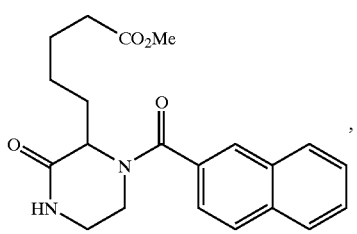,
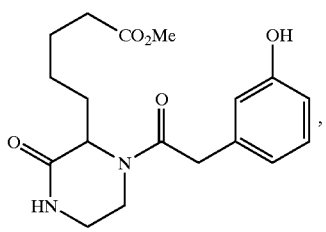,
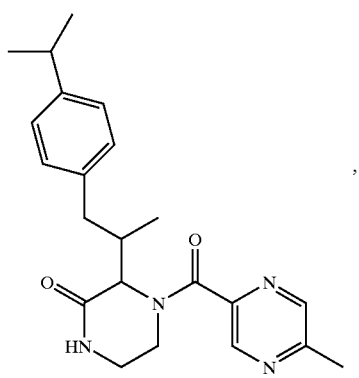,
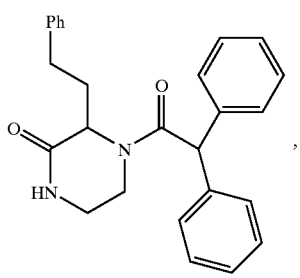,
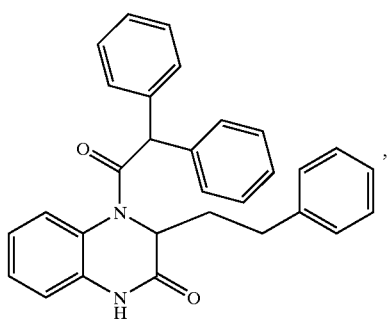,
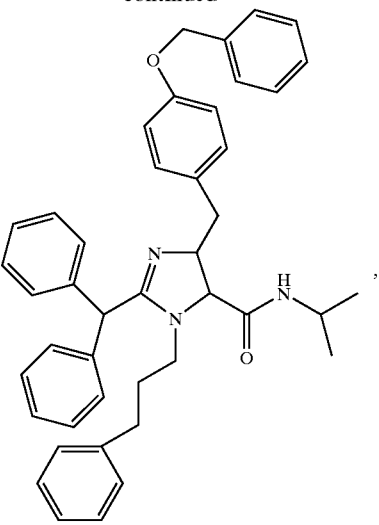,
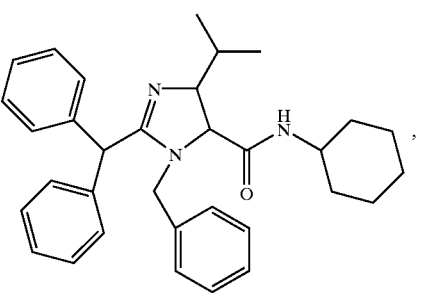,
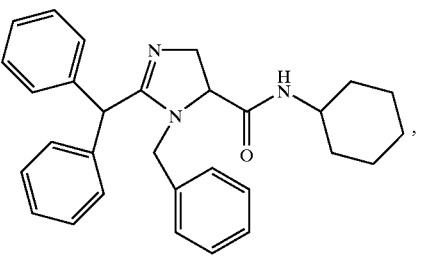,
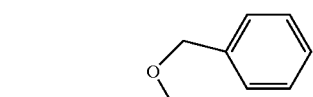
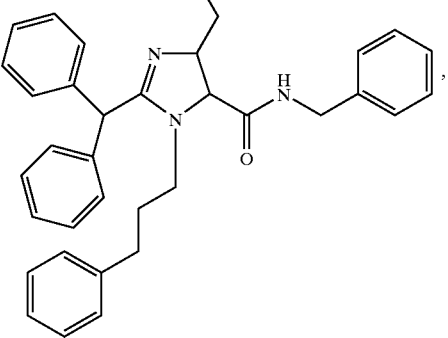, 219
-continued
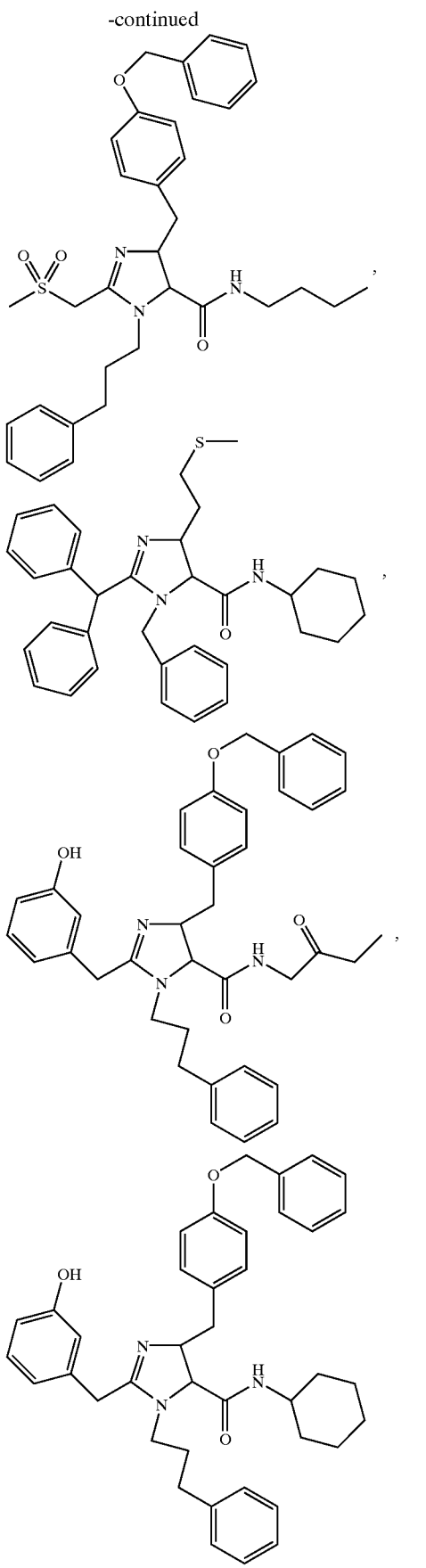
220
-continued
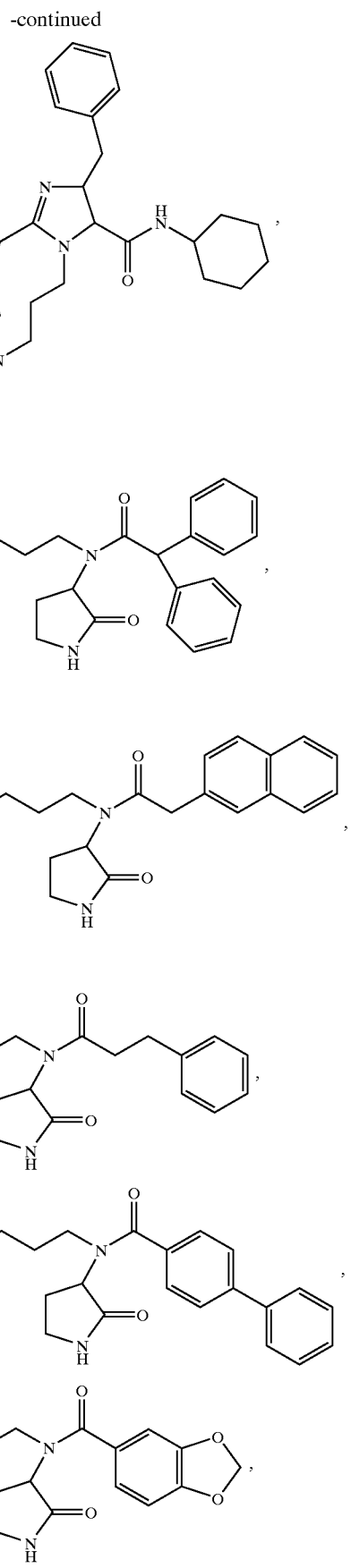

221
-continued
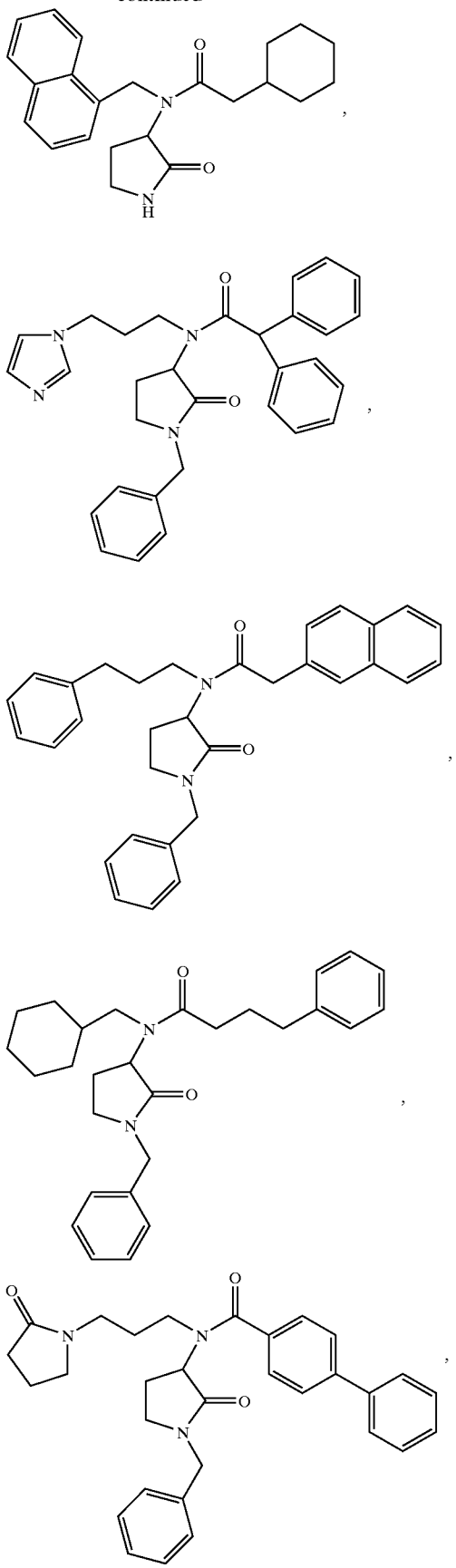
222
-continued
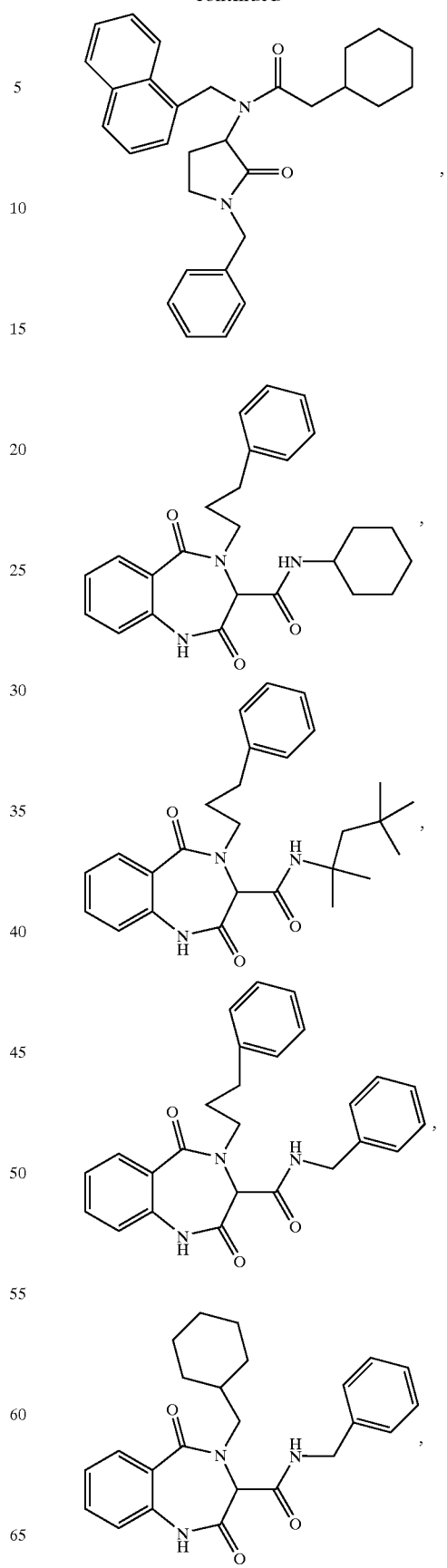

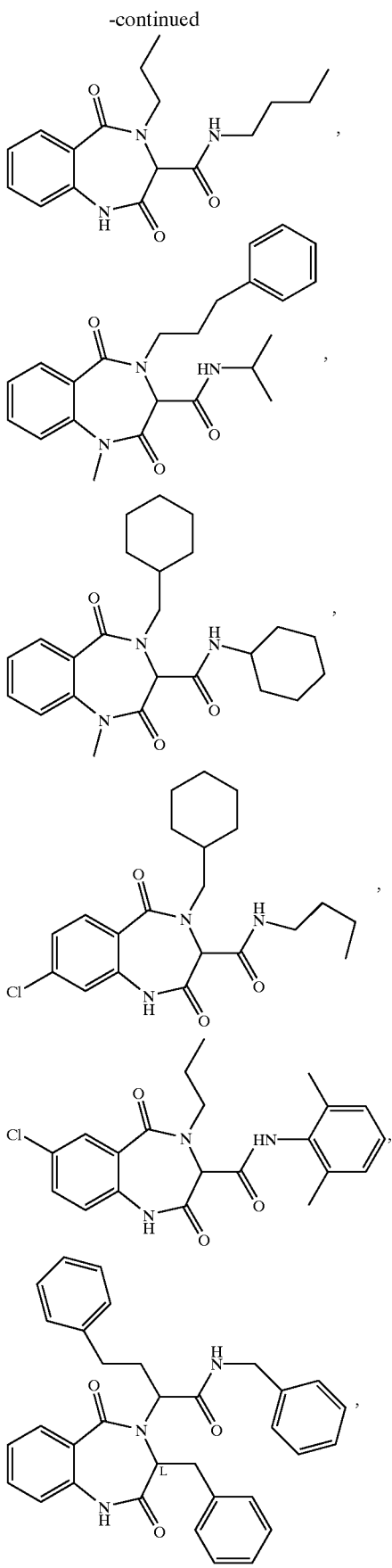

225
-continued
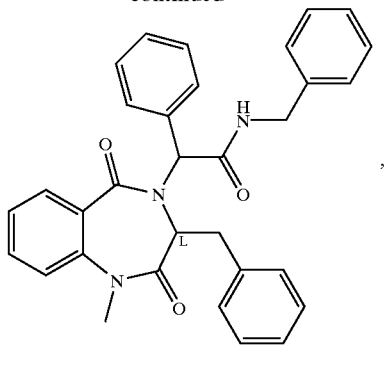
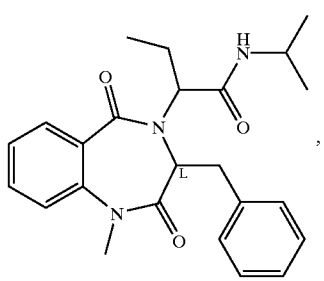
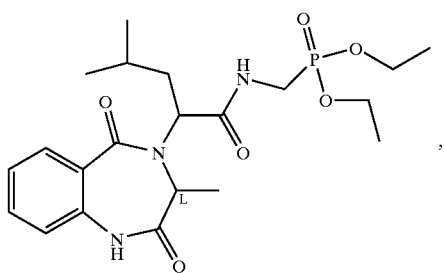
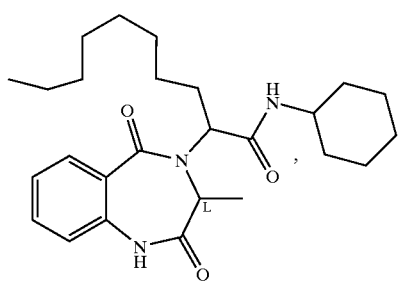
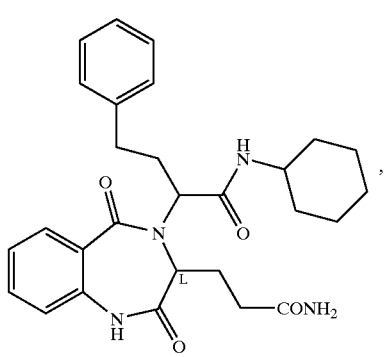
226
-continued
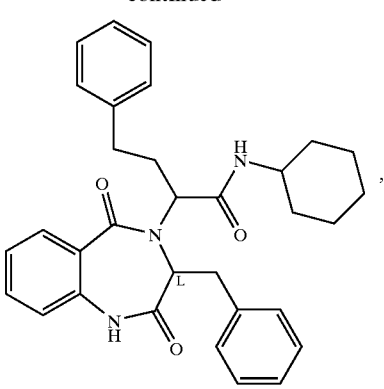
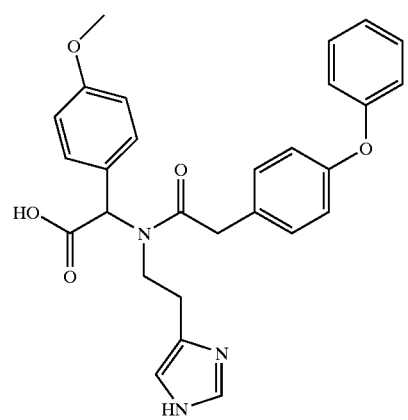
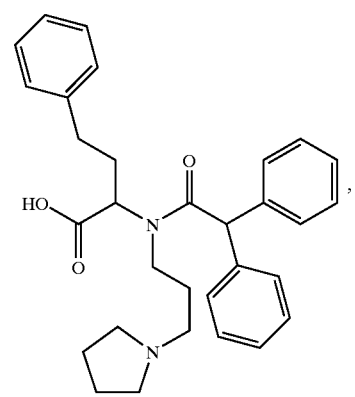
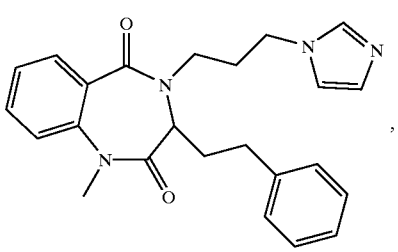

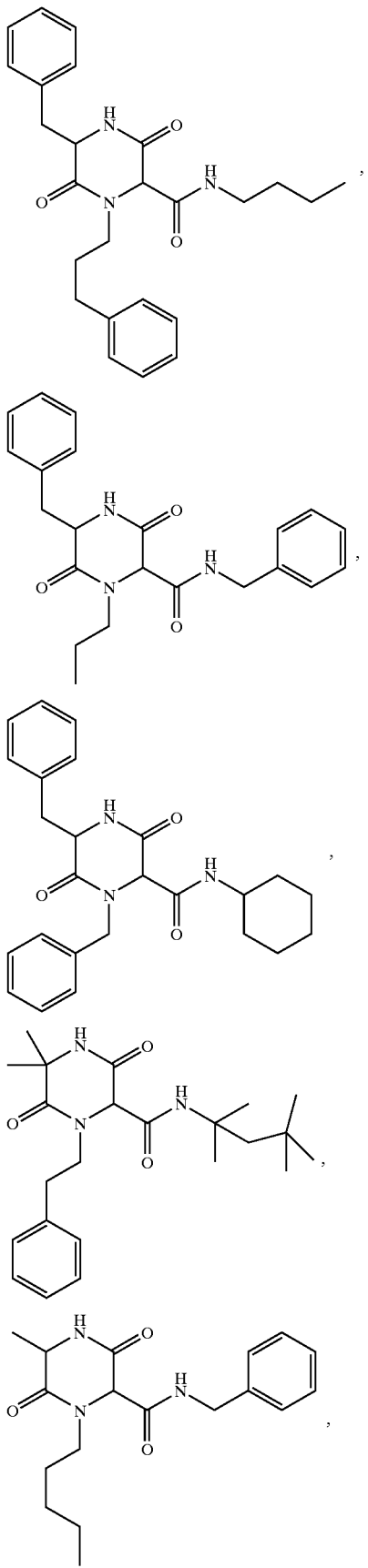
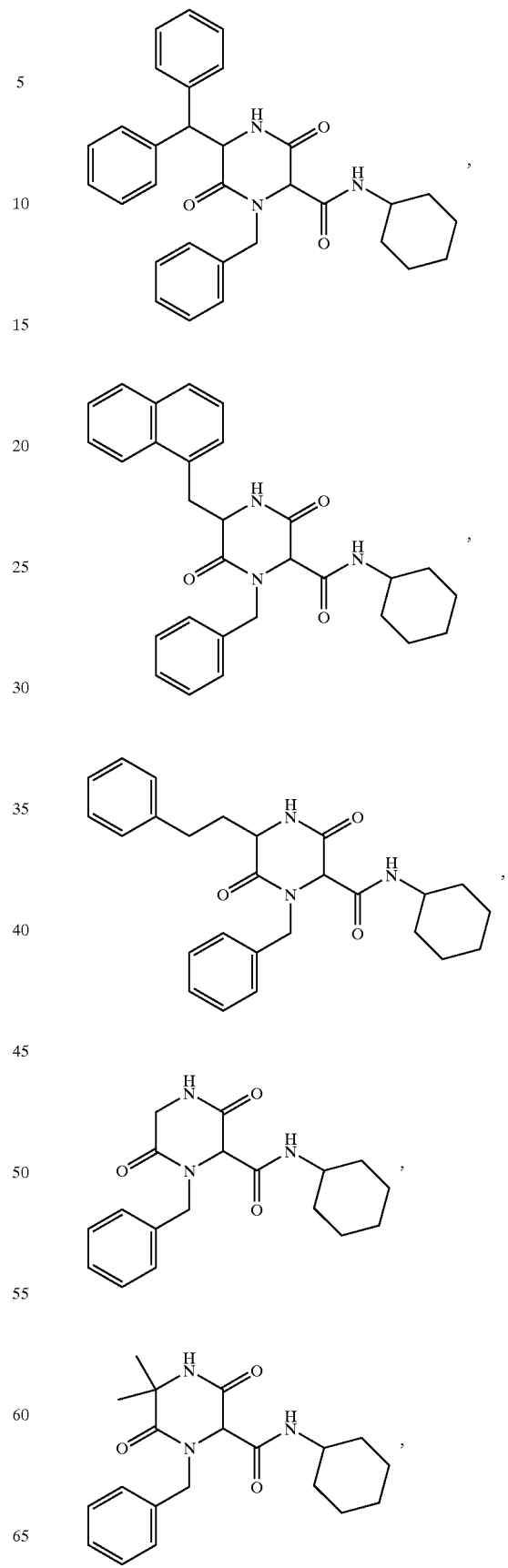

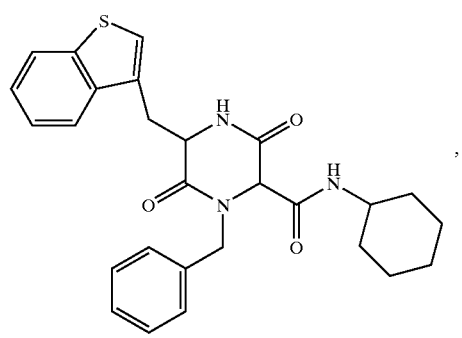
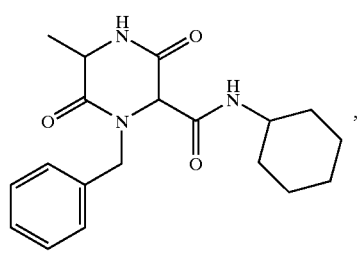
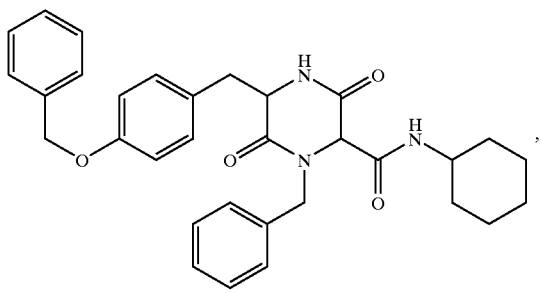
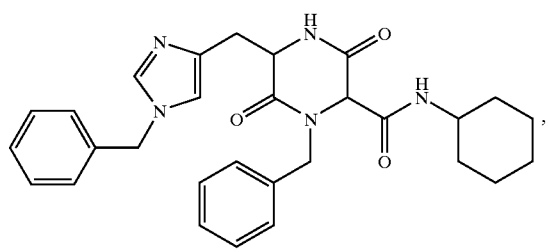
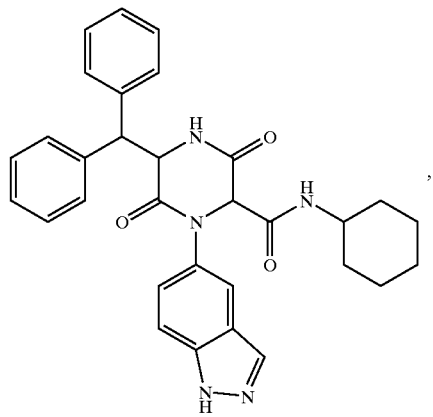
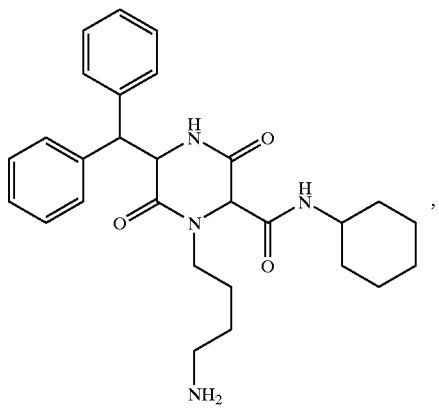
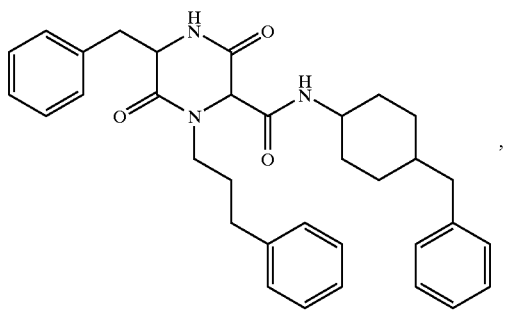
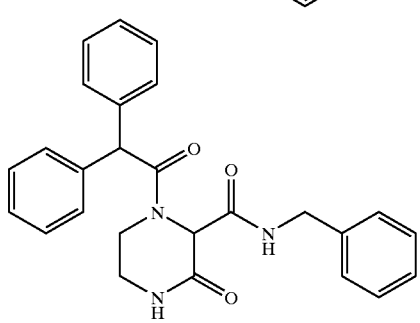
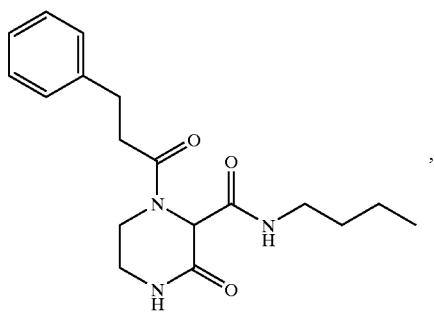
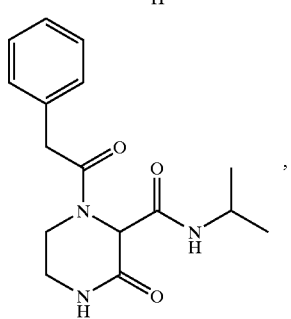

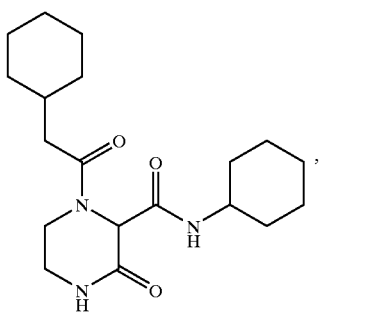
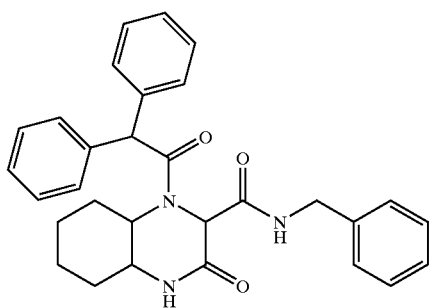
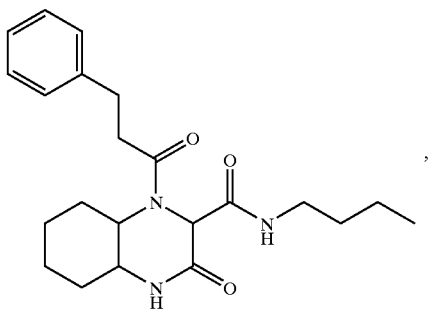
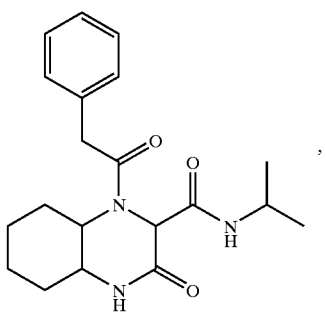
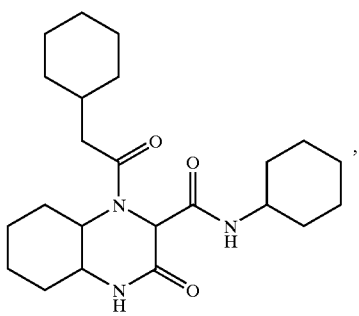
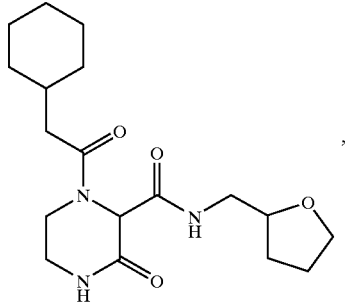
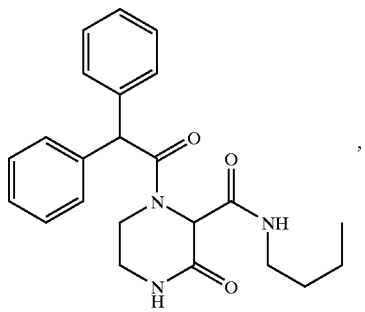
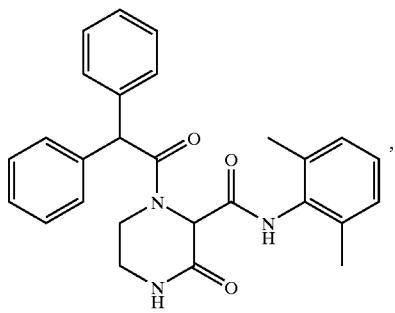
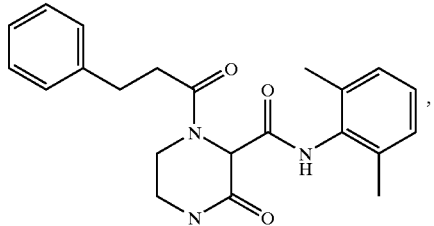
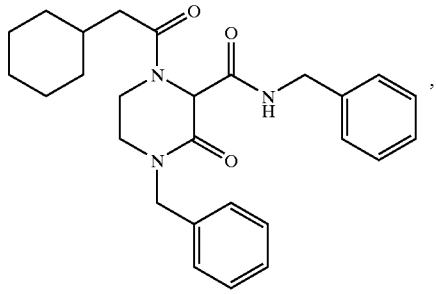
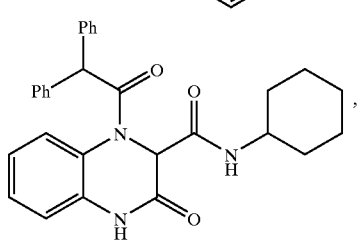

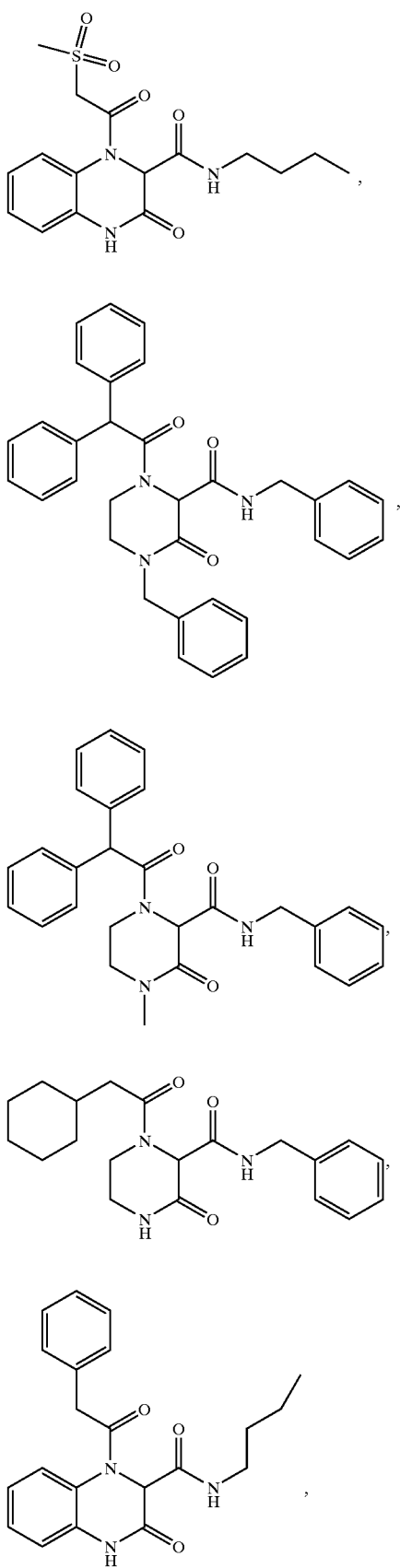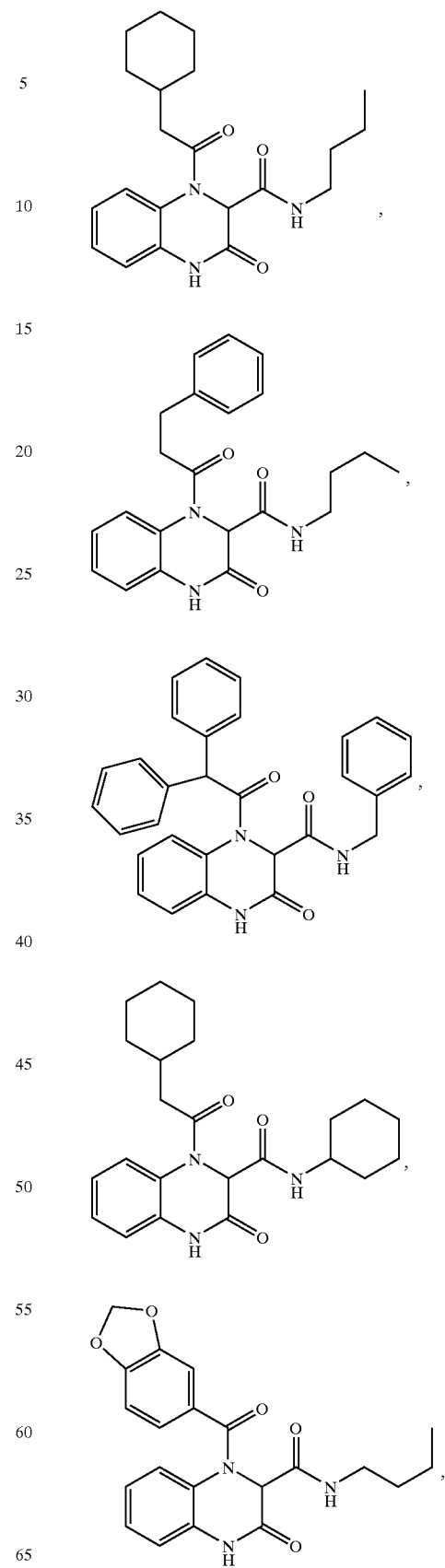

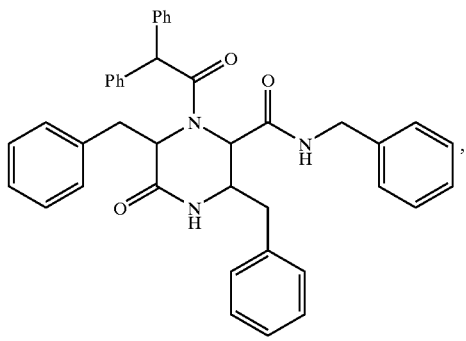
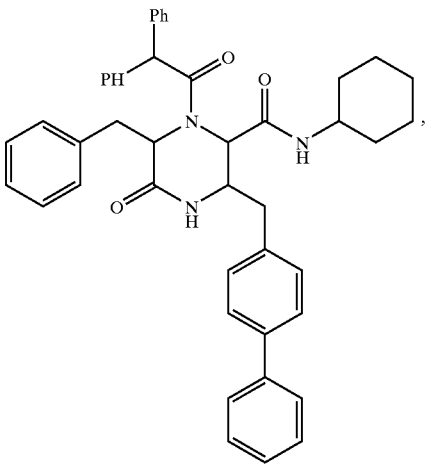
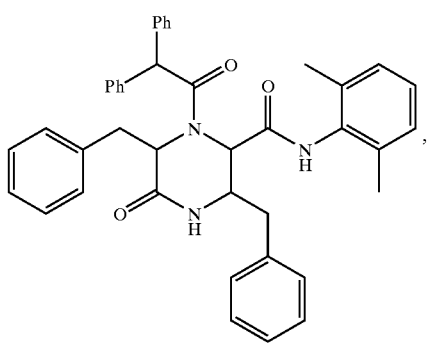
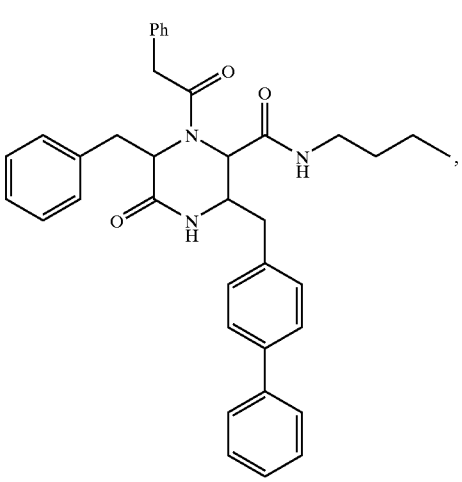
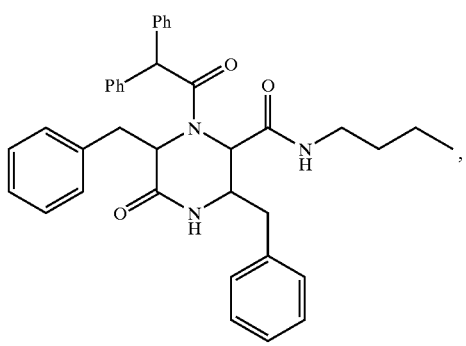
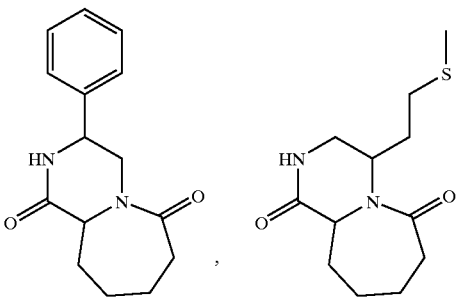
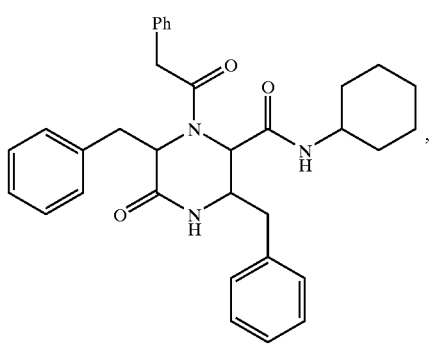
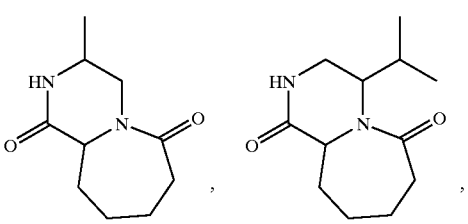

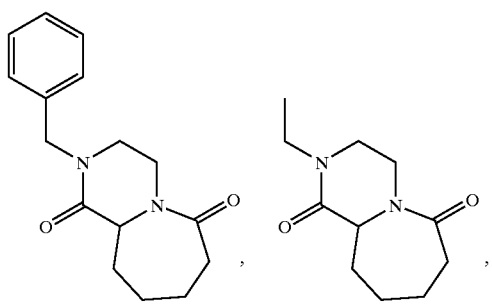
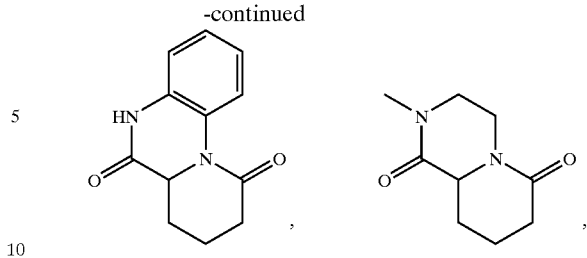
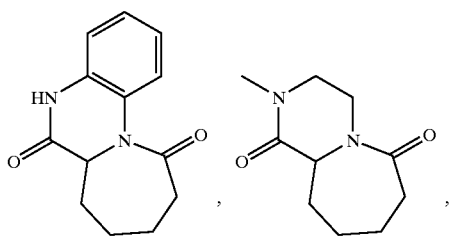
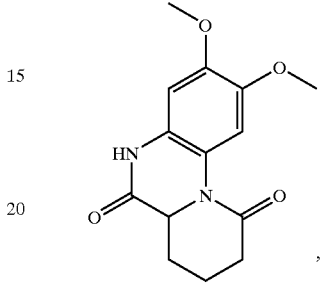
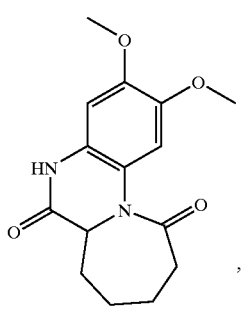
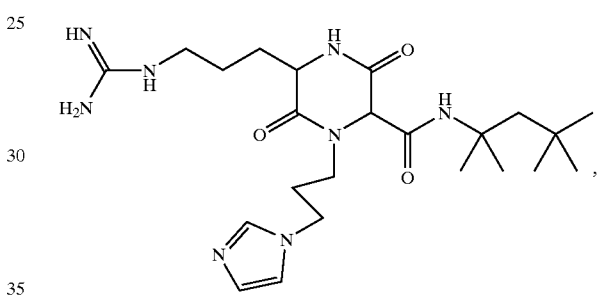
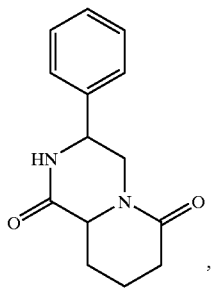
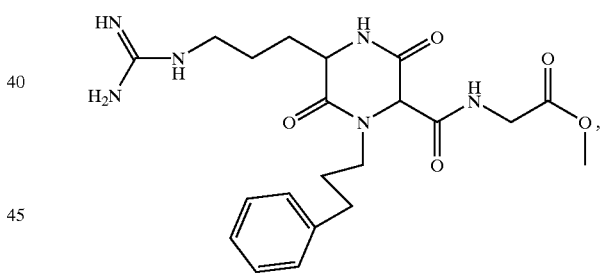
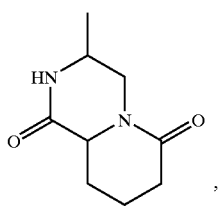
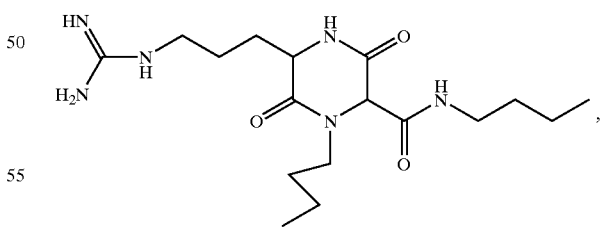
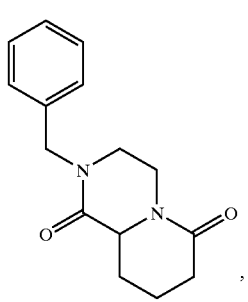
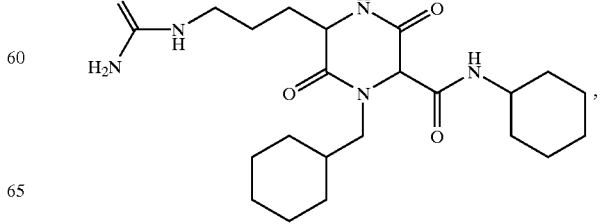

-continued
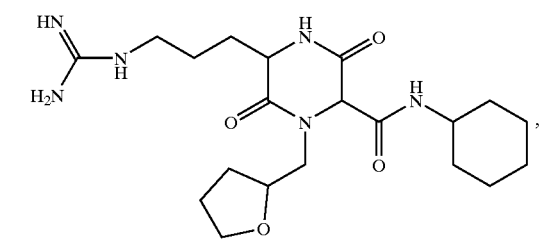
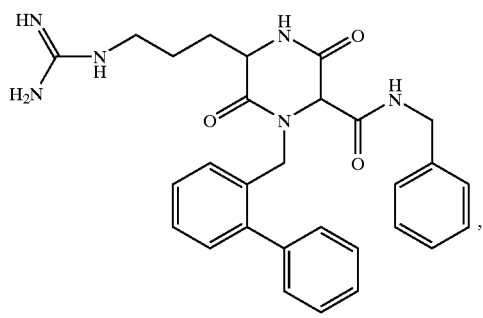
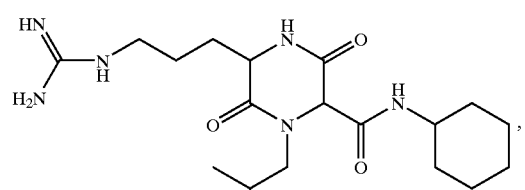
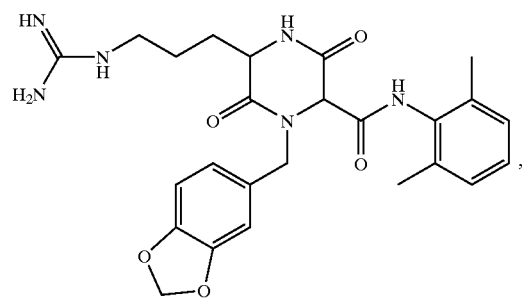
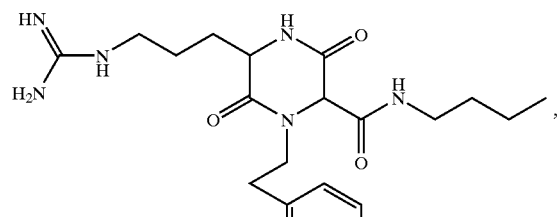
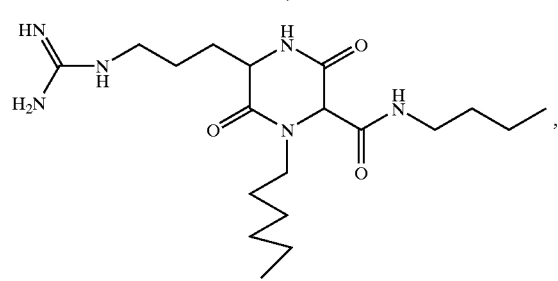
-continued
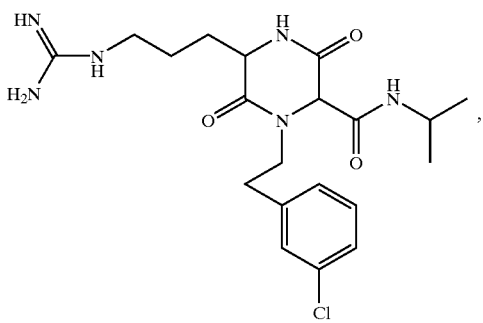
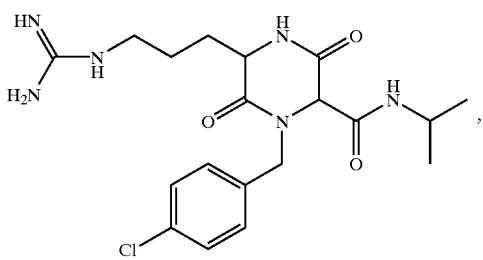
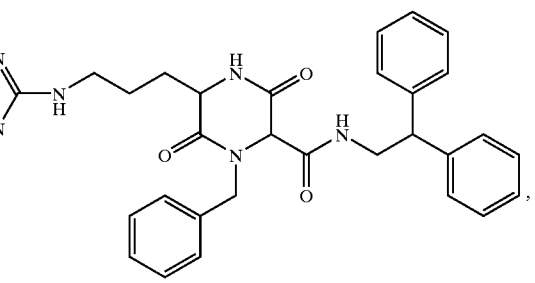
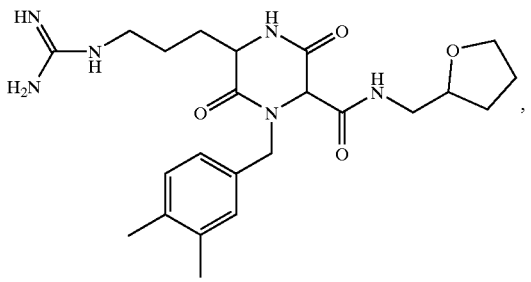
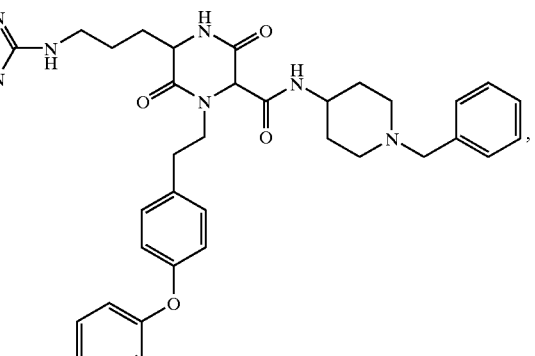

241
-continued
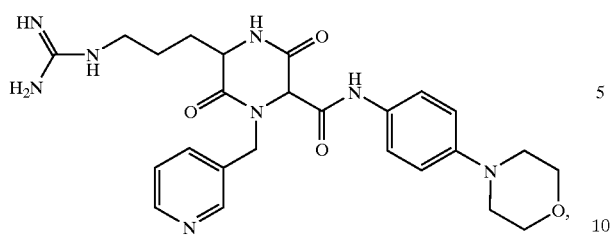
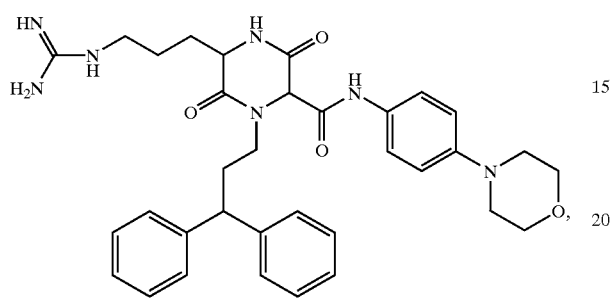
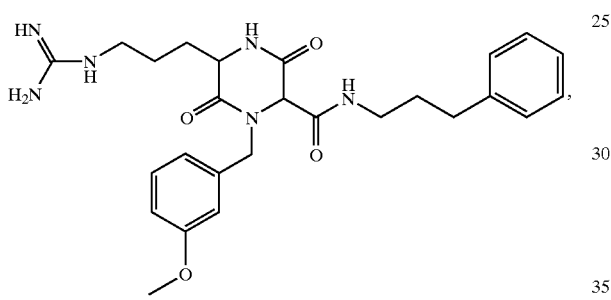
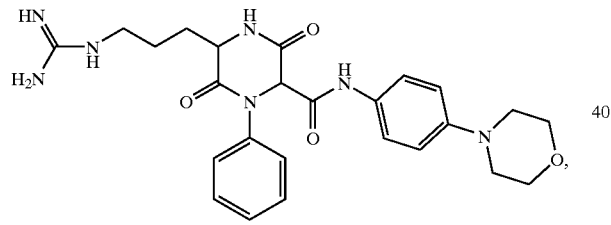
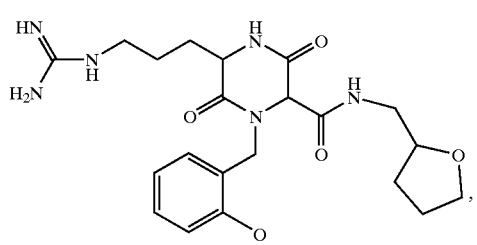
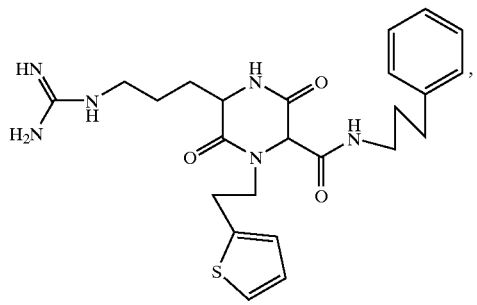
242
-continued
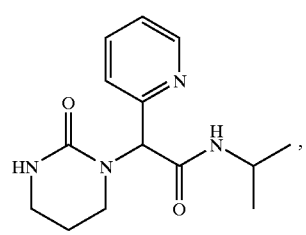
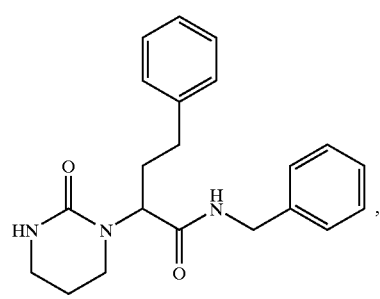
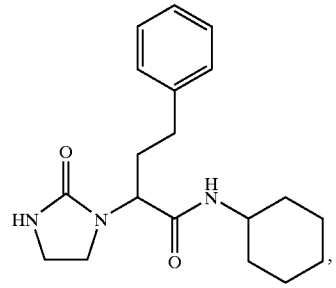
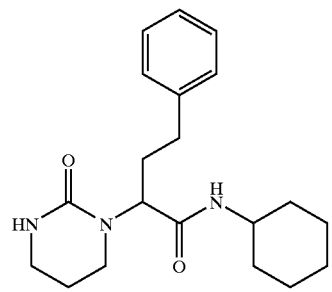
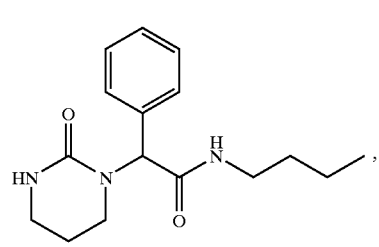
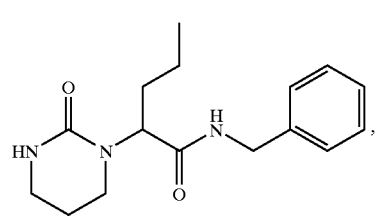

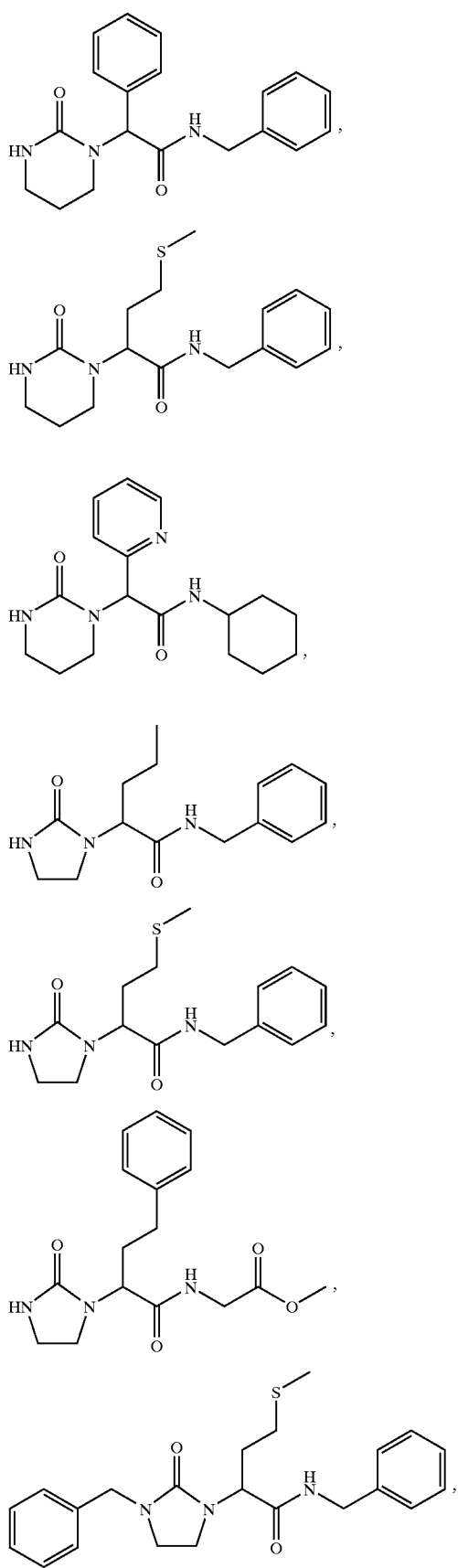
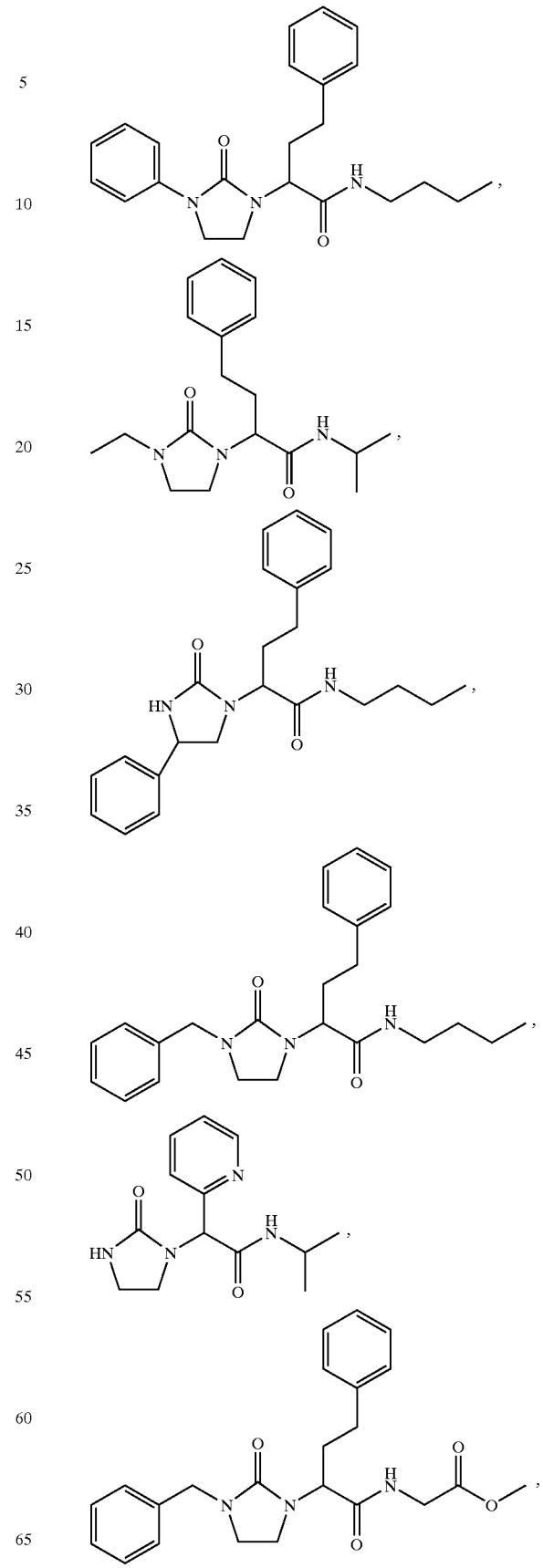

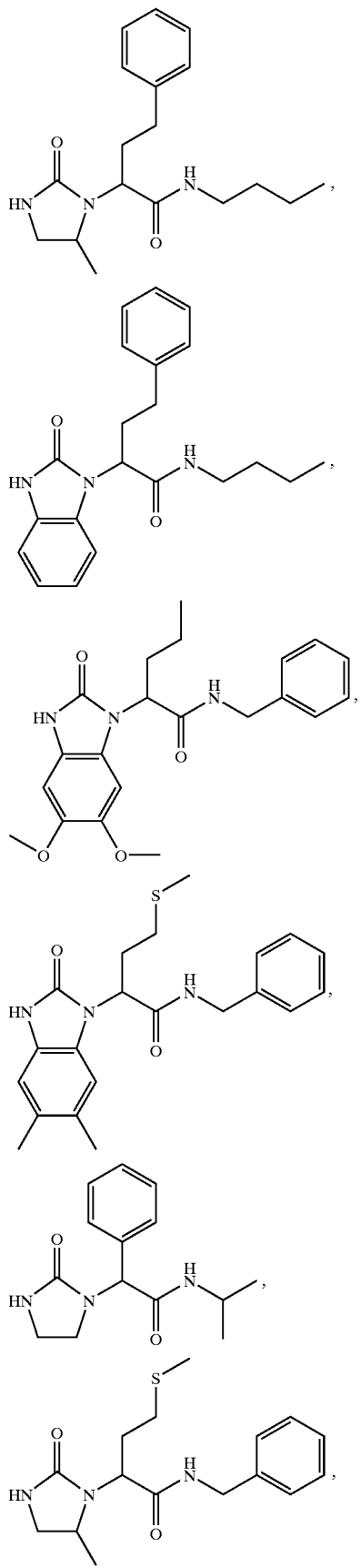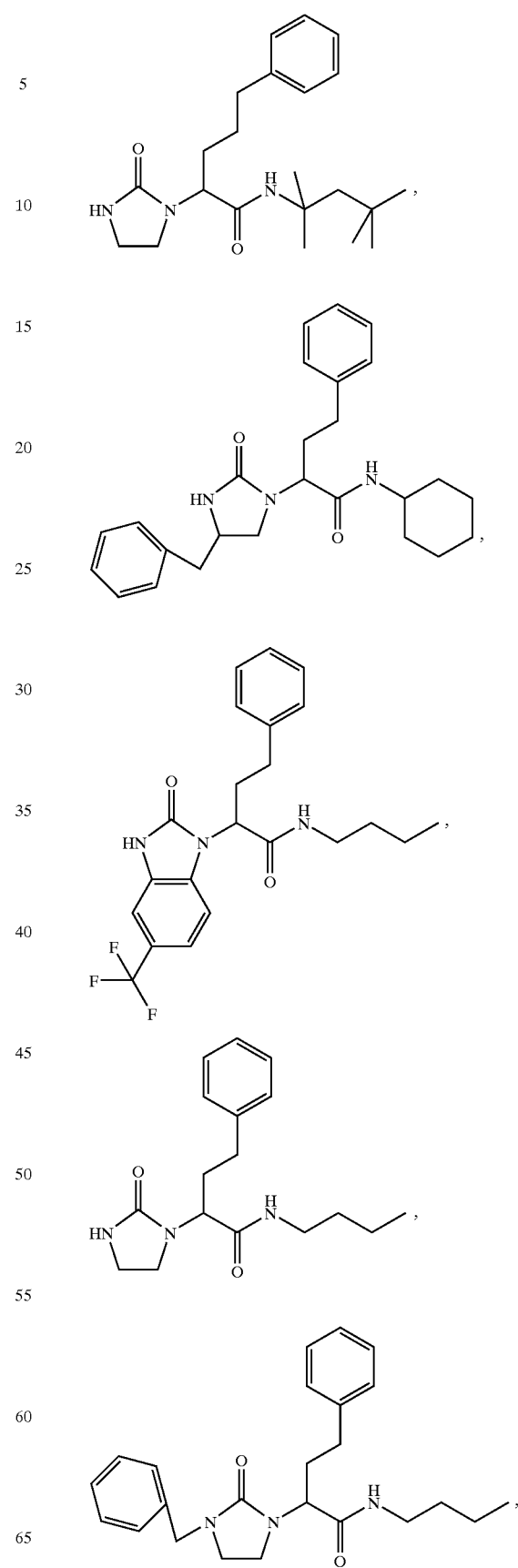

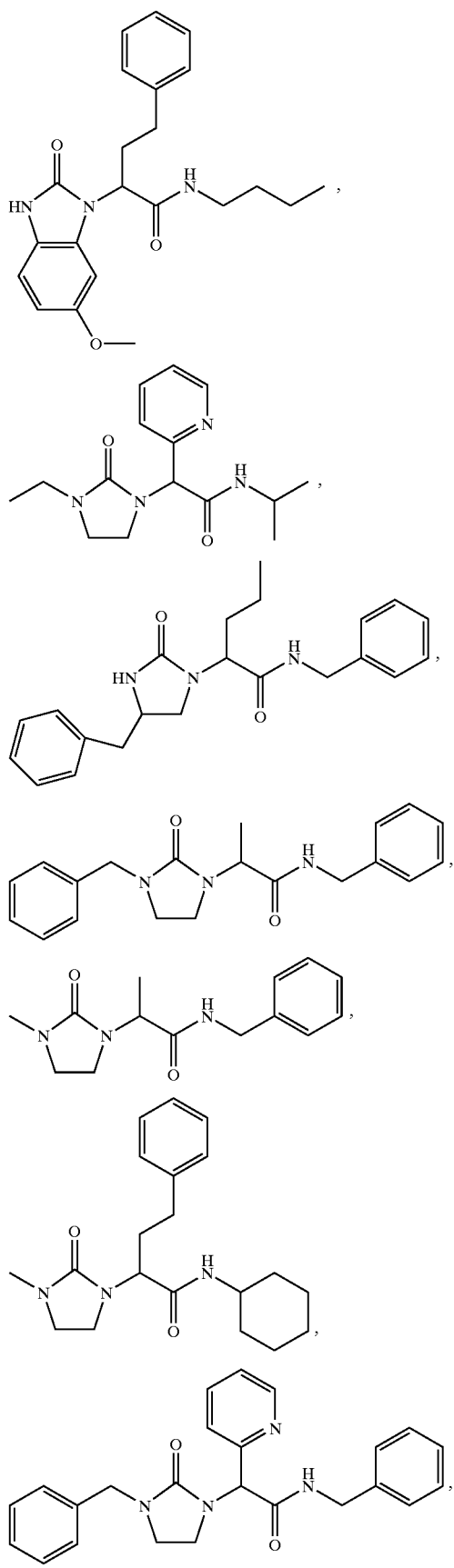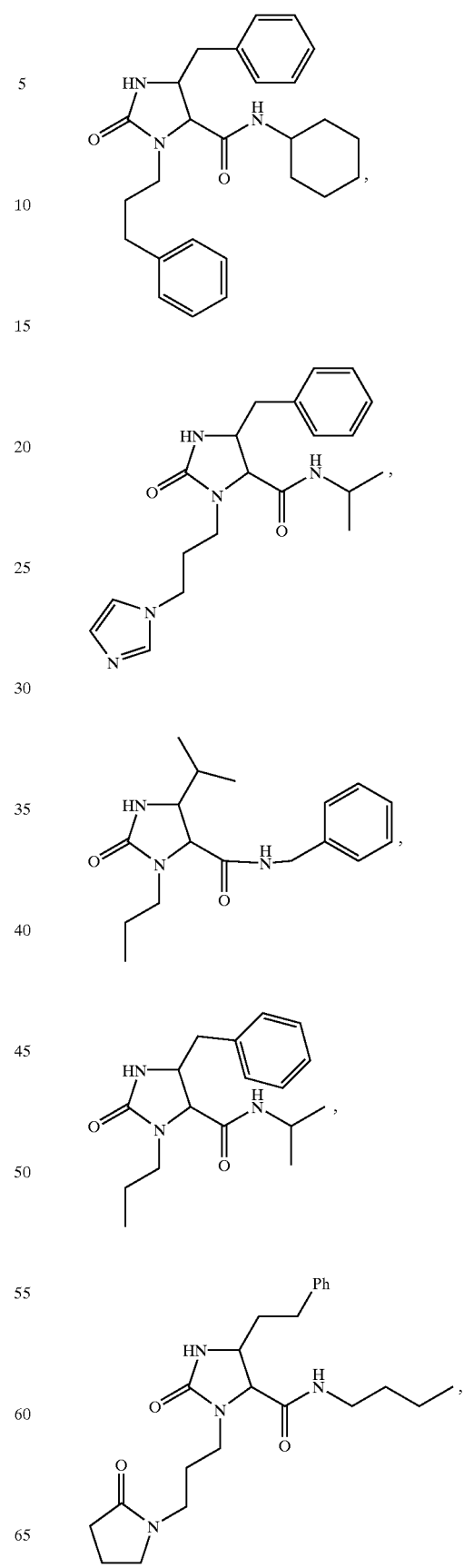

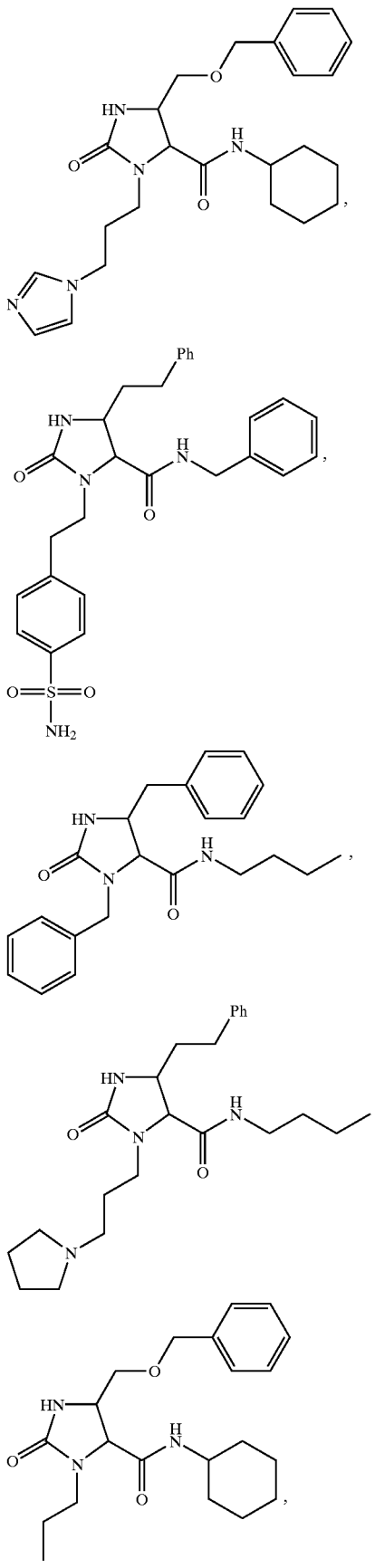
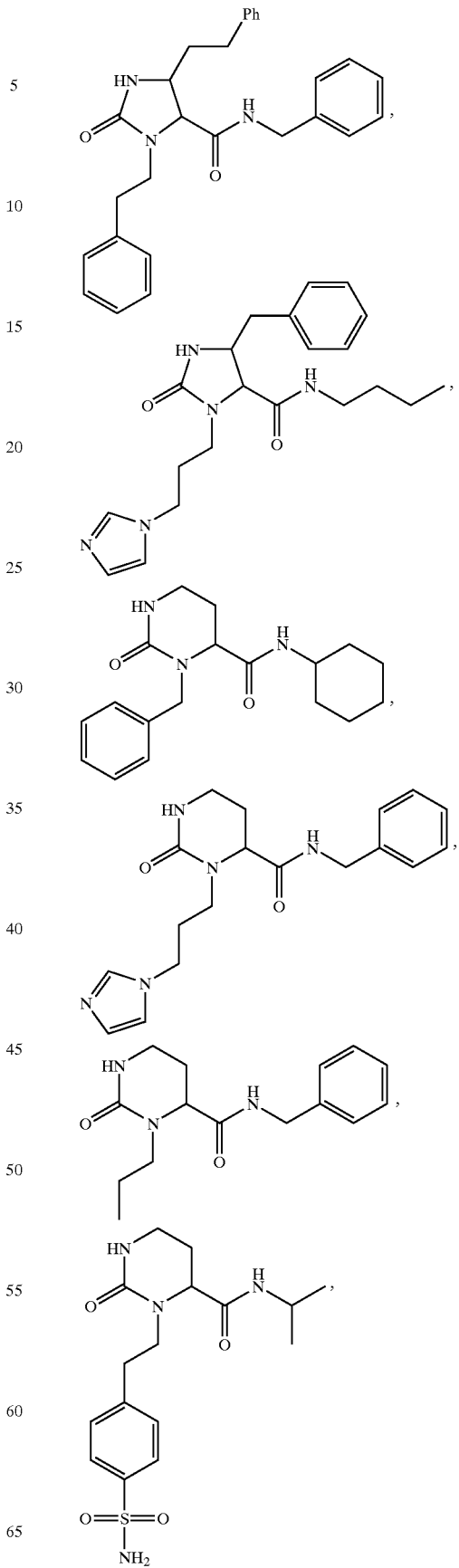

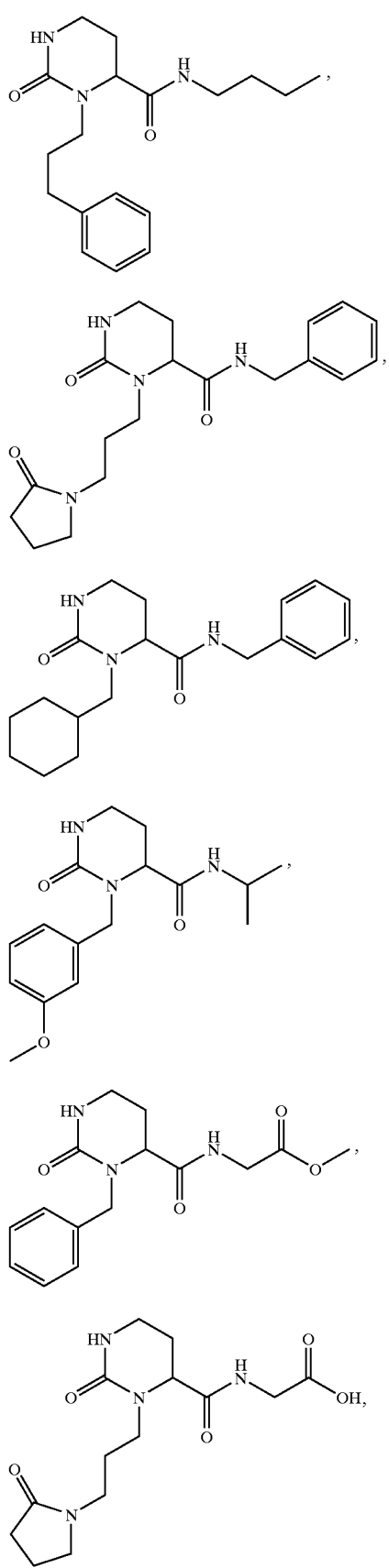
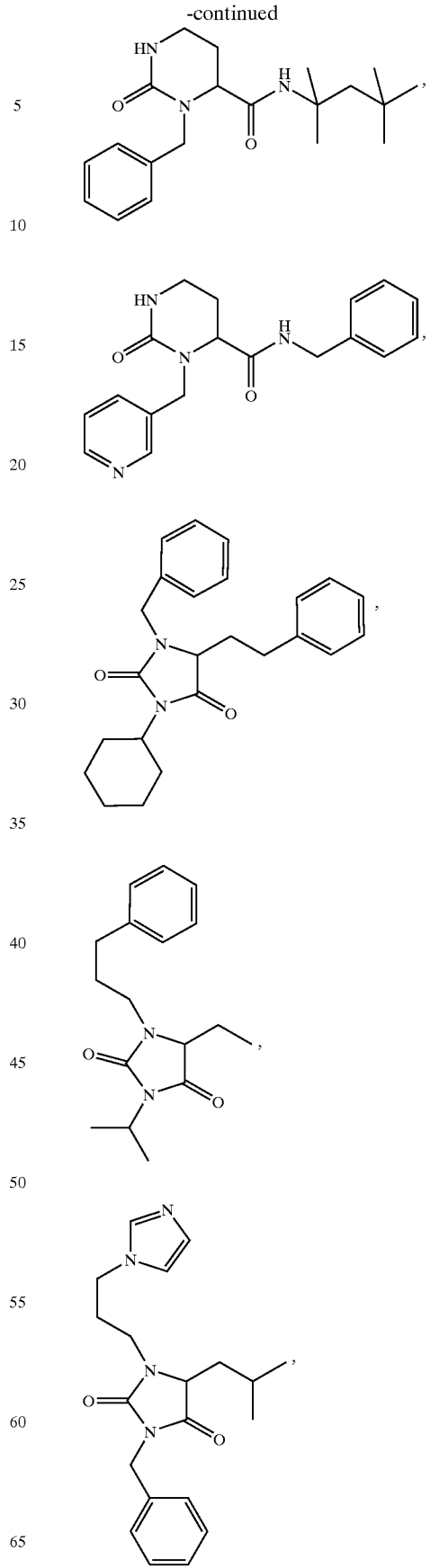

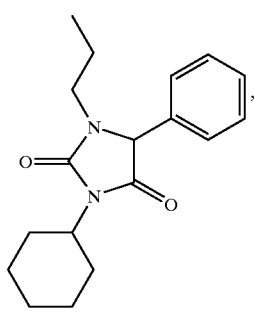
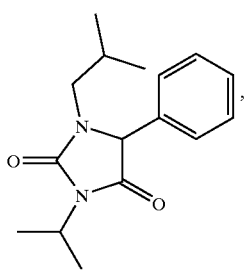
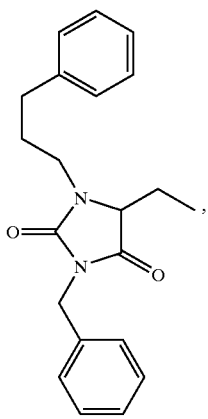
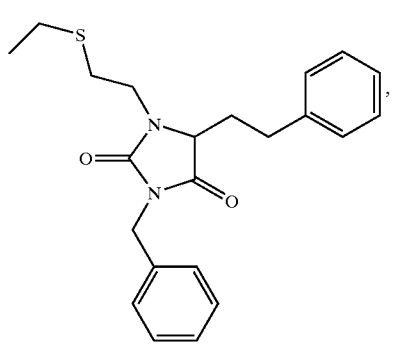
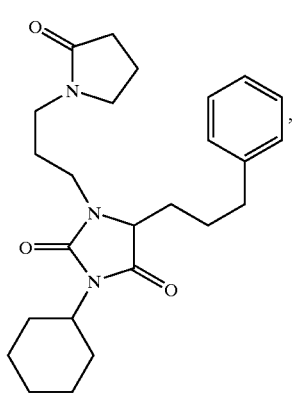
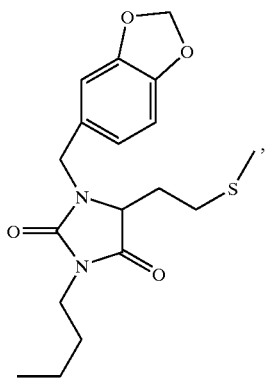

-continued
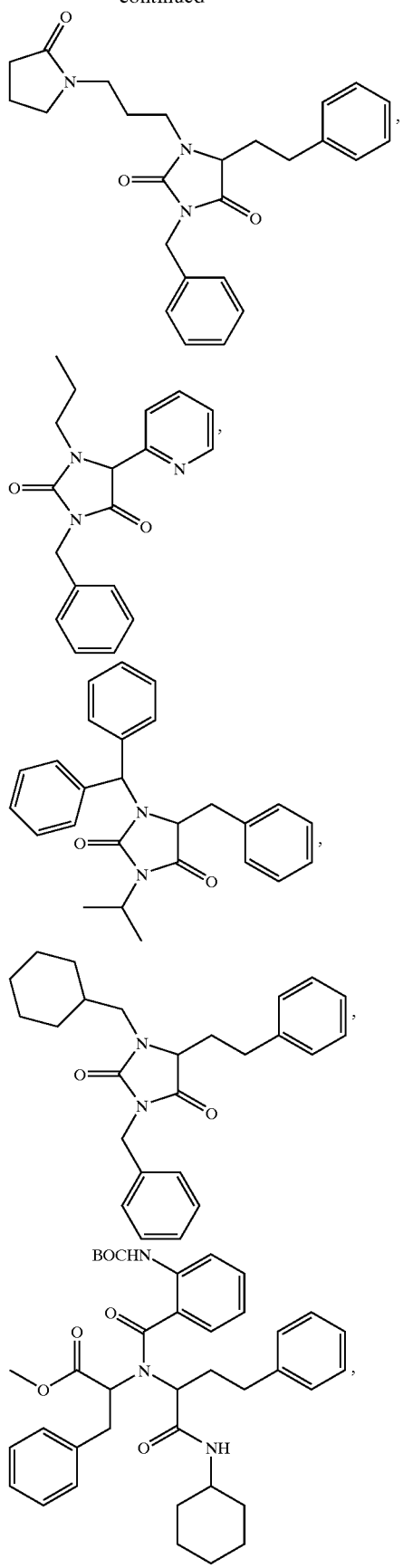
-continued
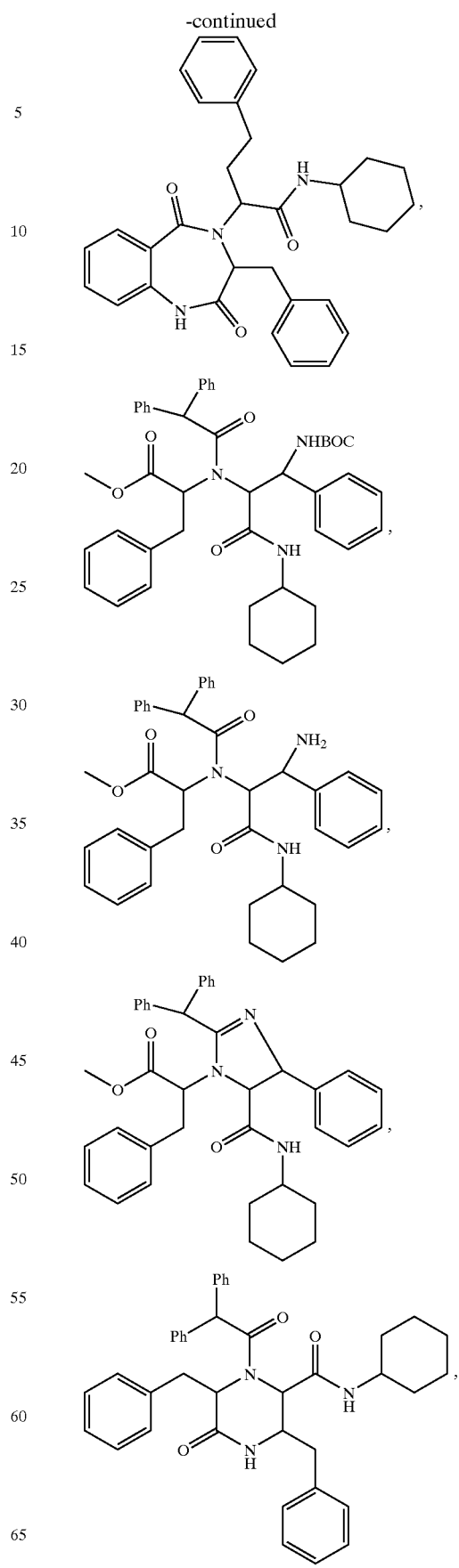

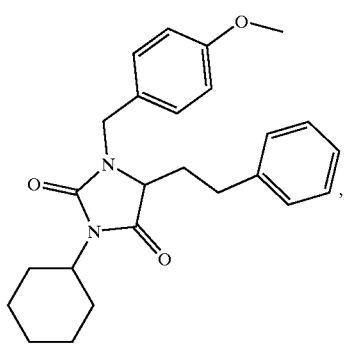
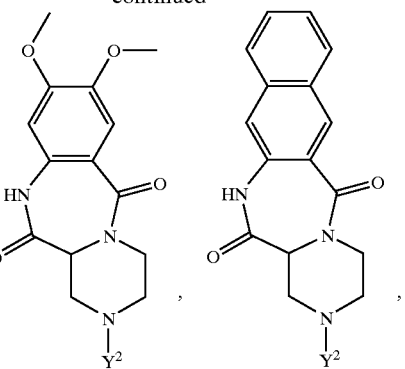
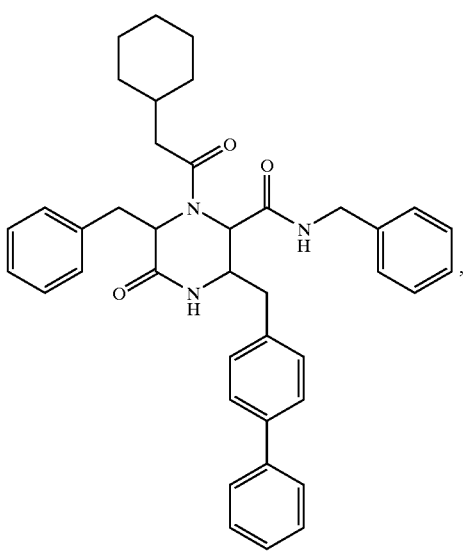
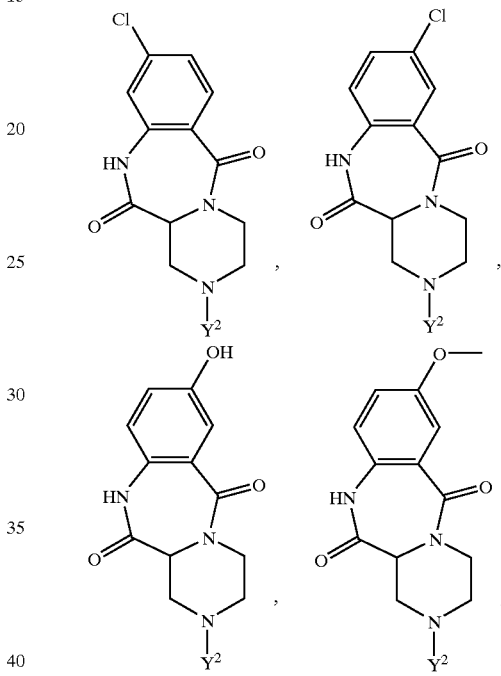
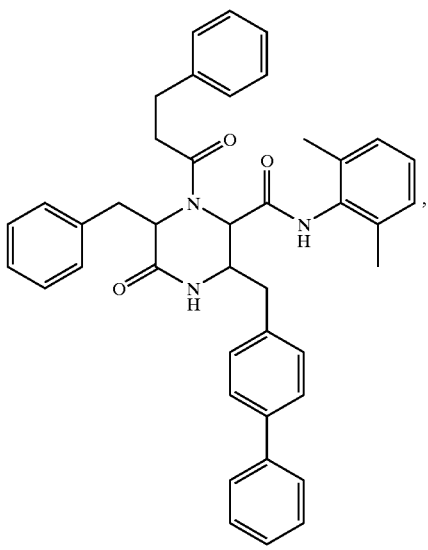
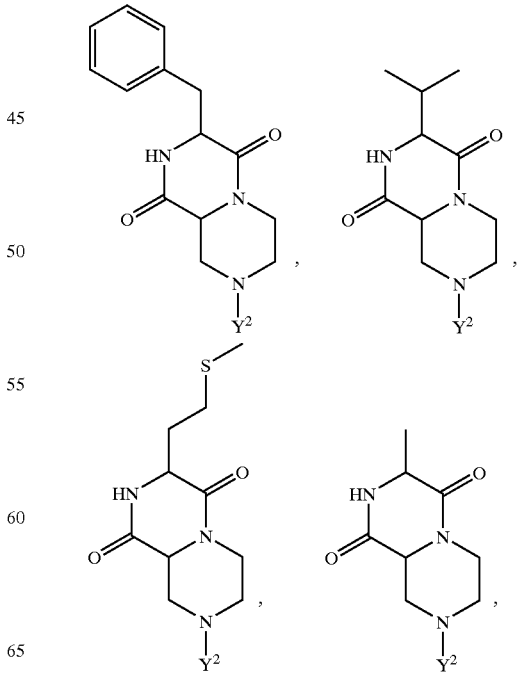

-continued

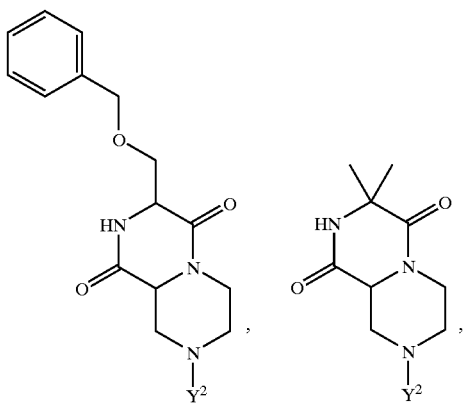

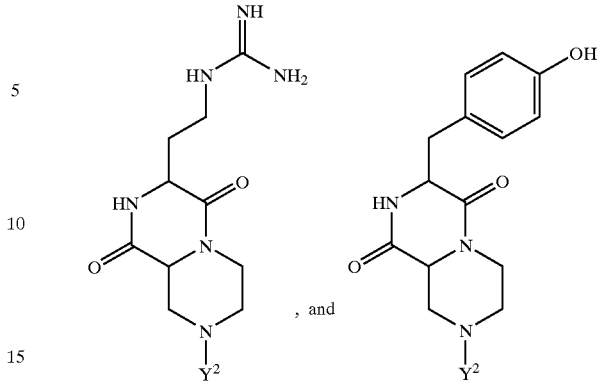

, and wherein $Y^2$ is selected from $CH_3$, $CH_2CH_2CH_3$, Phenyl, Benzyl, $CH_2CH(CH_3)_2$, and $CH(CH_3)_2$.

52. A resin bound isonitrile selected from

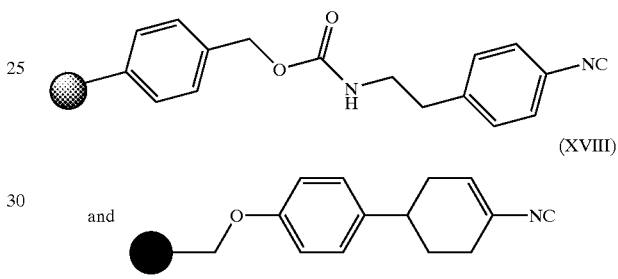

(IXa)

(XVIII)

wherein ⬤ is a solid support resin.

53. A resin bound amine compound of formula

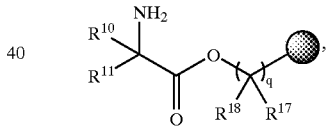

(XXXIX)

wherein
$R^{10}$ and $R^{11}$ independently are selected from hydrogen, alkenyl, alkyl, aryl, alkynyl, aralkenyl, aralkynyl, fused arylcycloalkenyl, fused arylcycloalkyl, fused arylheterocyclenyl, fused arylheterocyclyl, heteroaralkenyl, heteroaralkynyl, fused heteroarylcycloalkenyl, fused heteroarylcycloalkyl, fused heteroarylheterocyclenyl, fused heteroarylheterocyclyl, heteroarylsulphonylcarbamoyl, heteroaryl, aralkyl, heteroaralkyl, cycloalkyl, cycloalkenyl, heterocyclyl, heterocyclenyl;
$R^{17}$ and $R^{18}$ independently represent hydrogen, alkoxycarbonyl, alkyl, aralkoxycarbonyl, aralkyl, aroyl, aryl, fused arylcycloalkyl, fused arylheterocyclyl, aryloxy, aryloxycarbonyl, cycloalkyl, heteroaralkyl, heteroaroyl, heteroaryl, fused heteroarylcycloalkyl, fused heteroarylheterocyclyl, or heterocyclyl; and
q is 1, 2 or 3.

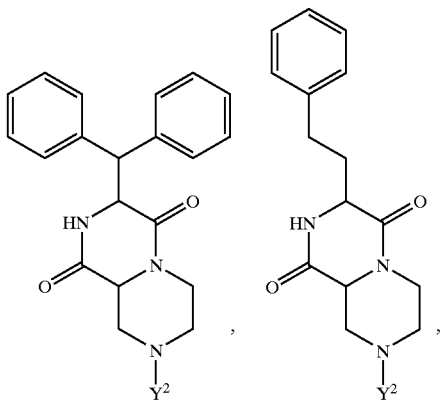

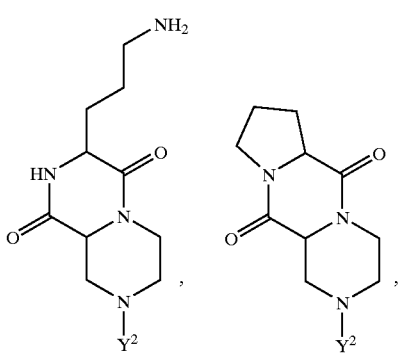

* * * * *